US009388422B2

(12) United States Patent
Shen et al.

(10) Patent No.: US 9,388,422 B2
(45) **Date of Patent: *Jul. 12, 2016**

(54) CELLULOSIC PROCESSING TRAIT DEVELOPMENT USING A THERMOREGULATED, INTEIN-MODIFIED XYLANASE

(75) Inventors: Binzhang Shen, Boston, MA (US); James Apgar, Somerville, MA (US); Oleg Bougri, Boise, ID (US); R. Michael Raab, Arlington, MA (US)

(73) Assignee: Agrivida, Inc., Medford, MA (US)

(*) Notice: Subject to any disclaimer, the term of this patent is extended or adjusted under 35 U.S.C. 154(b) by 493 days.

This patent is subject to a terminal disclaimer.

(21) Appl. No.: 13/818,928

(22) PCT Filed: Aug. 23, 2011

(86) PCT No.: PCT/US2011/048847

§ 371 (c)(1),
(2), (4) Date: Apr. 4, 2013

(87) PCT Pub. No.: WO2012/027395

PCT Pub. Date: Mar. 1, 2012

(65) Prior Publication Data

US 2013/0203125 A1 Aug. 8, 2013

Related U.S. Application Data

(60) Provisional application No. 61/377,759, filed on Aug. 27, 2010.

(51) Int. Cl.

| | |
|---|---|
| ***C12N 9/24*** | (2006.01) |
| ***A01H 5/00*** | (2006.01) |
| ***A01H 5/10*** | (2006.01) |
| ***C12N 15/82*** | (2006.01) |
| ***C12N 15/05*** | (2006.01) |
| ***C12P 19/14*** | (2006.01) |

(52) U.S. Cl.

CPC ............ *C12N 15/8243* (2013.01); *C12N 9/248* (2013.01); *C12N 9/2482* (2013.01); *C12N 15/8216* (2013.01); *C12N 15/8246* (2013.01); *C12P 19/14* (2013.01); *C12Y 302/01008* (2013.01)

(58) Field of Classification Search

None

See application file for complete search history.

(56) References Cited

U.S. PATENT DOCUMENTS

| | | | | |
|---|---|---|---|---|
| 6,238,905 | B1 | 5/2001 | McHenry et al. | |
| 8,420,387 | B2 * | 4/2013 | Shen et al. | 435/320.1 |
| 2005/0125860 | A1 * | 6/2005 | Raab | 800/298 |
| 2006/0211003 | A1 | 9/2006 | Peters et al. | |
| 2011/0111442 | A1 * | 5/2011 | Shen et al. | 435/18 |

FOREIGN PATENT DOCUMENTS

| | | | |
|---|---|---|---|
| WO | 2005/112597 | A2 | 12/2005 |
| WO | 2011057163 | A2 | 5/2011 |

OTHER PUBLICATIONS

Guo et al (2004), Proc. Natl. Acad. Sci. USA vol. 101 pp. 9205-9210.*

Ngo et al. in The Protein Folding Problem and Tertiary Structure Prediction, 1994, Merz et al. (ed.), Birkhauser, Boston, MA, pp. 491-495.*

Maniatis et al. (Molecular Cloning: A Laboratory Manual, Cold Spring Harbor Laboratory, 1982; pp. 324-389.*

Elleuche et al, Appl Microbiol Biotechnol (2010) 87:479-489.*

Amitai et al, PNAS (2009) 106: 11005-11010.*

Jonathan Caspi, et al., "Distribution of split DnaE inteins in cyanobacteria," Molecular Microbiology, 2003, 50 (5):1569-1577.

Bernhard Borkhardt, et al., "Autohydrolysis of plant xylans by apoplastic expression of thermophilic bacterial endo-xylanases," Plant Biotechnology Journal, 2010, 8:363-374.

Uniprot Direct Submission Accession Q72GP2. DNA polymerase III alpha subunit (EC 2.7.7.7). [online]. Jul. 5, 2004 [retrieved on Dec. 27, 2011]. Retrieved from the Internet; <URL:http://www.uniprot.org/uniprot/Q72GP2.txt?version=8>, pp. 1-2.

Uniprot Direct Submission Accession P77853. BETA-1,4-XYLANASE 229B (EC 3.2.1.8) (1,4-BETA-D-XYLAN XYLANOHYDROLASE). [online]. Oct. 1, 2000 [retrieved on Dec. 27, 2011]. Retrieved from the Internet; <URL:http://www.uniprot.org/uniprot/P77853.txt?version=10>, p. 1.

Uniprot Direct Submission Accession Q5SLW3. DNA polymerase III alpha subunit. [online]. Jun. 13, 2006 [retrieved on Dec. 27, 2011]. Retrieved from the Internet; <URL:http://www.uniprot.org/uniprot/Q5SLW3.txt?version=10>, pp. 1-2.

GenBank Accession AM181054. Thermus thermophilus HB8 partial dnaE-1 gene including Tth-HB8 DnaE-1 intein. [online]. Jan. 9, 2006 [retrieved on Mar. 12, 2013]. Retrieved from the Internet; <URL: http//www.ncbi.nlm.nih.gov/nuccore/AM181054>, pp. 1-2.

Morris et al., "Cloning of the XynB gene from Dictyoglomus thermophilum Rt46B.1 and action of the gene product on Kraft pulp," Applied and Environmental Microbiology, 1998, vol. 64, pp. 1759-1765.

Patent Examination Report from the Australian Patent Office, Mar. 14, 2014.

European Search Report, Feb. 14, 2014.

* cited by examiner

*Primary Examiner* — Amjad Abraham
*Assistant Examiner* — Ryan H Brown
(74) *Attorney, Agent, or Firm* — Volpe and Koenig, P.C.

(57) ABSTRACT

In planta consolidated bioprocessing has the advantages of decreasing biomass pretreatment costs, utilizing excess plant protein production capacity for enzyme production, and decreasing mass transfer resistance of enzyme diffusion to its substrate. However, in planta expression of cell wall degrading (CWD) enzymes often leads to detrimental plant phenotypes that impact crop yield. To provide in planta CWD enzyme activity without any adverse phenotype, a thermostable xylanase, XynB (EC 3.2.1.8), was engineered with a thermoregulated intein, Tth-HB27 DnaE-1 (Tth intein), that controls its hydrolytic activity through conditional intein splicing. Maize plants expressing the heat inducible Tth intein-modified XynB developed normally, yet possessed enhanced post harvest glucose production from dried corn stover. Expression of CWD enzymes as dormant, intein-modified proteins that can be activated by heat treatment after harvest provides the basis for developing a novel cellulosic processing trait in plants.

7 Claims, 18 Drawing Sheets

```
...RPPGA CLAEGSLV LDAATGQR VPIEKVRP GMEVFSLG PDYRLYRV
...RVNQP
          51                    71                 88
PVLEVLES GVREVVRL RTRSGRTL VLTPDHPL LTPEGWKP LCDLPLGT

                                                  136
PIAVPAEL PVAGHLAP PEERVTLL ALLLGDGN TKLSGRRG TRPNAFFY

                                                  184
SKDPELLA AYRRCAEA LGAKVKAY VHPTTGVV TLATLAPR PGAQDPVK

                                                  232
RLVVEAGM VAKAEEKR VPEEVFRY RREALALF LGRLFSTD GSVEKKRI

                                                  280
SYSSASLG LAQDVAHL LLRLGITS QLRSRGPR AHEVLISG REDILRFA

                                                  328
ELIGPYLL GAKRERLA ALEAEARR RLPGQGWH LRLVLPAV AYRVSEAK

                                                  376
RRSGFSWS EAGRRVAV AGSCLSSG LNLKLPRR YLSRHRLS LLGEAFAD

                                                 423
PGLEALAE GQVLWDPI VAVEPAGK ARTFDLRV PPFANFVS EDLVVHNT134
                                                      S158

SLGQ...
IVGT...
```

FIG. 2A

CELLULOSIC PROCESSING TRAIT DEVELOPMENT USING A THERMOREGULATED, INTEIN-MODIFIED XYLANASE

CROSS REFERENCE TO RELATED APPLICATIONS

This application is a 35 U.S.C. 371 National Stage Application of International Application No. PCT/US2011/048847, filed Aug. 23, 2011, which claims priority from U.S. provisional application 61/377,759, filed Aug. 27, 2010, which are all incorporated herein by reference as if fully set forth.

The Sequence listing filed with this application, titled "Sequence Listing," having a file size of 380,147 bytes, and created on Feb. 22, 2013 is incorporated herein by reference as if fully set forth. The Substitute Sequence listing titled "Substitute Sequence Listing" filed Apr. 4, 2013, having a file size of 381,574 bytes, and created Apr. 4, 2013 is incorporated herein by reference as if fully set forth.

The sequence listing filed herewith title "Sequence Listing," having a file size of 380,200 bytes and created on Aug. 23, 2011 is incorporated herein by reference as if fully set forth.

FIELD

This application relates to cellulosic processing trait development.

BACKGROUND

Dwindling fossil resources and concerns about greenhouse gas emissions are driving the development of alternative fuels (Hill, et. al. 2006). Cellulosic biofuels are among the leading alternative fuels because of their potential for high capacity, ability to be produced from non-food biomass, and relatively low feedstock cost (Klass, D. L., 2004). Today's cellulosic biofuels may have high production costs, particularly those associated with biomass pretreatment and enzymatic hydrolysis (Lynd, et. al., 2008; Himmel et. al., 2007). Enzyme loading requirements for cellulosic processing remain a challenge for the industry due to high costs and limited production capacity (Hood et. al., 2007). In contrast to microbial consolidated bioprocessing (Lynd, et. al., 2005), which relies on the availability of fermentable sugars for co-production of enzymes and biofuels, in planta consolidation is predicted to be more cost efficient because it does not require the diversion of fermentable sugars to microbial enzyme production (Sairam, et. al., 2008; Sainz 2009).

In spite of this advantage, in planta expression of cell wall degrading (CWD) enzymes may lead to detrimental plant phenotypes, including stunted plant stature, poor seed set and quality, reduced fertility, and increased susceptibility to disease (Harholt, et. al., 2010; Hood et. al., 2003; Taylor et. al., 2008); all of which can impact yield.

Inteins are self-splicing peptides found within host polypeptides (exteins) in many organisms (Perler et. al., 1994). Upon excision, inteins ligate the bordering extein polypeptide sequences back together with a peptide bond in a splicing reaction (Saleh and Perler, 2006). A cysteine, serine, or threonine at the junction site between the carboxy terminus of the intein and the carboxy extein of the target protein is often present (Xu, et. al., 1993).

Xylanases are a major class of cell wall degrading enzymes required for complete hydrolysis of plant cell walls into fermentable sugars. Xylanases hydrolyze hemicellulose polymers and play key roles in making cellulose more accessible to enzymatic hydrolysis (Selig et. al., 2008; Selig et. al., 2009; Dylan & Cann, 2009). Because of their catalytic properties, cellulases and xylanases that are able to function over a wide pH range and at high temperatures may be suitable in the production of biofuels and chemicals from lignocellulosic feedstocks. Process consolidation using in planta enzyme production has the potential to significantly reduce enzyme costs and production capacity, if it does not impact biomass yields.

SUMMARY

In an aspect, the invention relates to a transgenic plant having an autohydrolytic trait. The transgenic plant includes an expression vector having a sequence that encodes an intein-modified xylanase. The intein-modified xylanase has the intein internally fused within the xylanase sequence. The intein-modified xylanase has decreased activity relative to the xylanase lacking the intein.

In an aspect, the invention relates to a method of obtaining a sugar. The method includes providing a transgenic plant having an expression vector, or a part of the transgenic plant. The expression vector includes a sequence that encodes a xylanase. The method also includes subjecting the transgenic plant to enzymatic hydrolysis.

In an aspect, the invention relates to a method of obtaining a sugar. The method includes providing a transgenic plant having an expression vector, or a part of the transgenic plant. The expression vector includes a sequence that encodes an intein-modified xylanase. The intein-modified xylanase has the intein internally fused within the xylanase sequence, and decreased activity relative to the xylanase lacking the intein. The method also includes subjecting the transgenic plant to enzymatic hydrolysis.

In an aspect, the invention relates to a method of producing a transgenic plant having an autohydrolytic trait and seed with a decreased germination rate relative to seed that does not have the autohydrolytic trait. The method includes providing an expression vector having a sequence that encodes a xylanase and transforming a plant or part thereof with the expression construct.

In an aspect, the invention relates to a method of producing a transgenic plant having an autohydrolytic trait. The method includes providing an expression vector having a sequence that encodes an intein-modified xylanase. The intein-modified xylanase has the intein internally fused within the xylanase sequence. The method also includes transforming a plant or part thereof with the expression construct. The intein-modified xylanase has decreased activity relative to the xylanase lacking the intein.

In an aspect, the invention relates to a transgenic plant having an autohydrolytic trait and seed with a decreased germination rate relative to seed that does not have the autohydrolytic trait. The transgenic plant includes an expression vector having a sequence that encodes a xylanase.

In an aspect, the invention relates to an intein modified xylanase having a sequence with at least 90% identity to one of SEQ ID NOS: 2, 4, 6, 8, 10, 12, 14, 16, 17 21, 29, 30, 60, 62, or 64.

In an aspect, the invention relates to an isolated nucleic acid having a sequence that hybridizes to a reference nucleic acid consisting of the sequence of SEQ ID NOS: 1, 3, 5, 7, 9, 11, 13, 15, 18, 35, 36, 37, 38, 59, 61, or 63 or the complement thereof under conditions of moderate stringency.

In an aspect, the invention relates to an isolated nucleic acid having a sequence that hybridizes to a reference nucleic acid consisting of the sequence of SEQ ID NOS: 1, 3, 5, 7, 9, 11, 13, 15, 18, 35, 36, 37, 38, 59, 61, or 63 or the complement thereof under conditions of high stringency.

In an aspect, the invention relates to an isolated nucleic acid including a sequence that encodes an intein modified xylanase having a sequence with at least 90% identity to one of SEQ ID NOS: 2, 4, 6, 8, 10, 12, 14, 16, 17, 21, 29, 30, 60, 62, or 64.

In an aspect, the invention relates to an intein having a sequence with at least 90% identity to one of SEQ ID NOS: 22, 23, 24, 25, 26, 27, or 28.

In an aspect, the invention relates to an isolated nucleic acid encoding an intein having a sequence with at least 90% identity to one of SEQ ID NOS: 22, 23, 24, 25, 26, 27, or 28.

In an aspect, the invention relates to seed from a transgenic plant. The transgenic plant has an autohydrolytic trait and seed with a decreased germination rate relative to seed that does not have the autohydrolytic trait. The transgenic plant includes an expression vector having a sequence that encodes a xylanase.

In an aspect, the invention relates to seed from a transgenic plant. The transgenic plant has an autohydrolytic trait. The transgenic plant includes an expression vector having a sequence that encodes an intein-modified xylanase. The intein-modified xylanase has the intein internally fused within the xylanase sequence. The intein-modified xylanase has decreased activity relative to the xylanase lacking the intein.

BRIEF DESCRIPTION OF THE DRAWINGS

The following detailed description of the preferred embodiment of the present invention will be better understood when read in conjunction with the appended drawings. For the purpose of illustrating the invention, there are shown in the drawings embodiments which are presently preferred. It is understood, however, that the invention is not limited to the precise arrangements and instrumentalities shown. In the drawings:

FIG. 1A shows candidate screening on agar plates. FIG. 1B shows thermoregulated assessment of iXynB activity. FIG. 1C shows time dependent, thermoregulated activity of iXynB candidates. FIG. 1D shows an intein splicing time course.

FIGS. 2A-B illustrate identification and mapping of key amino acids in Tth iXynB that modulate temperature sensitive intein splicing. FIG. 2A shows some mutations in the sequence. In FIG. 2*a*, a segment of XynB-modified with a Tth sequence at position T134 (SEQ ID NO: 40) starts with the first five bold, underlined amino acids and continues through the non-bold, non-underlined amino acids then through the final four bold, underlined amino acids. A segment of XynB modified with a Tth sequence at position S158 (SEQ ID NO: 41) starts with the first five non-bold, underlined amino acids and continues through the non-bold, non-underlined text then through the final non-bold, underlined amino acids. FIG. 2B shows a structural mapping of amino acid residues.

FIG. 4A shows data regarding seed development, FIG. 4B shows data regarding xylanase activity in seeds, FIG. 4C shows data regarding seed biomass, FIG. 4D shows data regarding seed germination, and FIG. 4E illustrates seed morphology.

FIG. 5A shows data regarding xylanase activity in corn stover, and FIG. 5B shows data regarding glucose release from corn stover.

DETAILED DESCRIPTION OF THE PREFERRED EMBODIMENTS

Figure 1A:
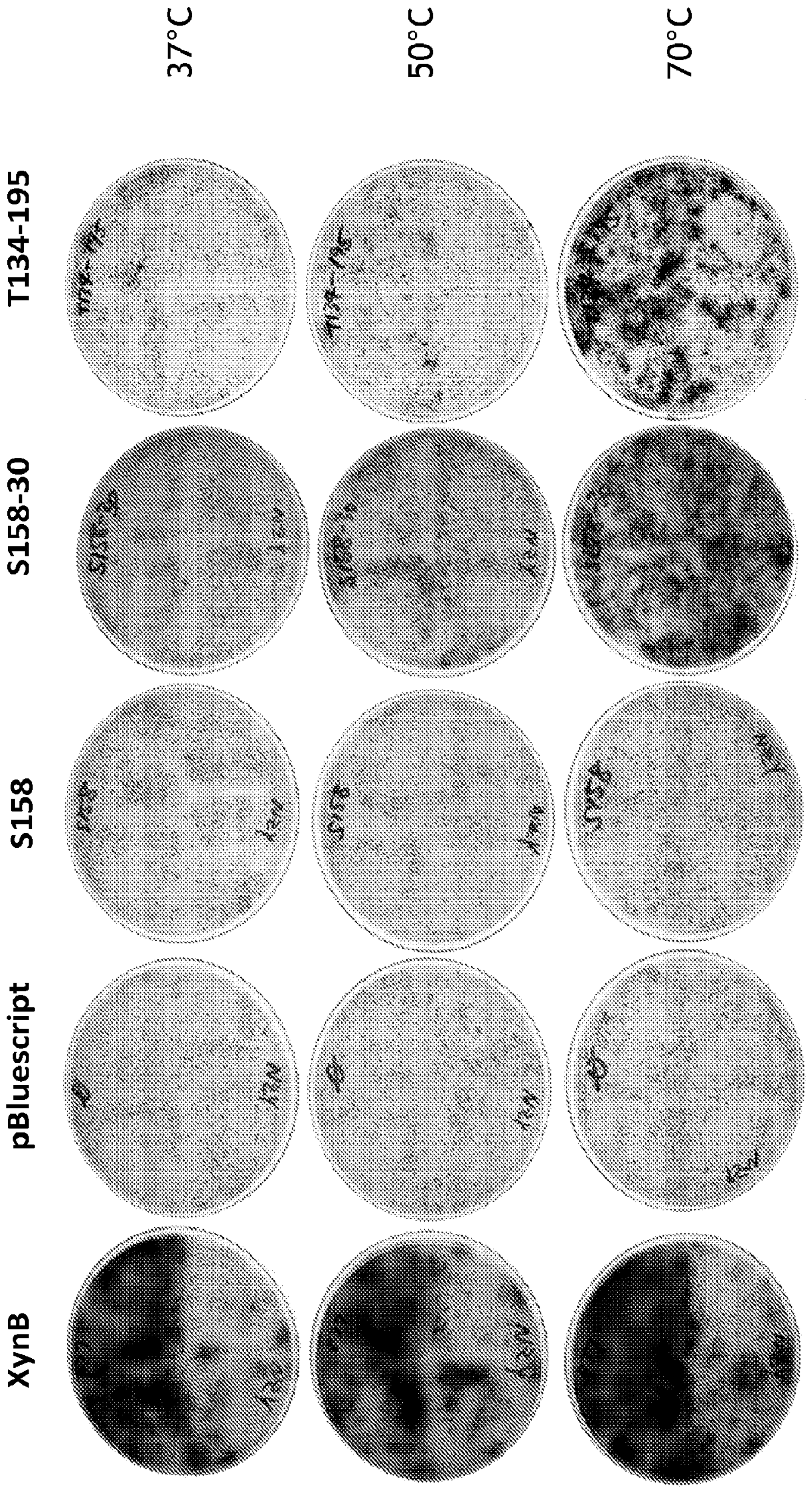
FIGS. 1A-D illustrate development of temperature regulated, intein-modified XynB.

Certain terminology is used in the following description for convenience only and is not limiting. The words "right," "left," "top," and "bottom" designate directions in the drawings to which reference is made.

The words "a" and "one," as used in the claims and in the corresponding portions of the specification, are defined as including one or more of the referenced item unless specifically stated otherwise. The phrase "at least one" followed by a list of two or more items, such as "A, B, or C," means any individual one of A, B, or C as well as any combination thereof.

"Isolated nucleic acid," "isolated polynucleotide," "isolated oligonucleotide," "isolated DNA," or "isolated RNA" as used herein refers to a nucleic acid, polynucleotide, oligonucleotide, DNA, or RNA separated from the organism from which it originates or from the naturally occurring genome, location, or molecules with which it is normally associated. An isolated nucleic acid, isolated polynucleotide, isolated oligonucleotide, isolated DNA, or isolated RNA may be a nucleic acid that was made through a synthetic process. An isolated nucleic acid, isolated polynucleotide, isolated oligonucleotide, isolated DNA, or isolated RNA may have covalent bonds to moieties other than found in its natural location, or may lack covalent bonds to moieties that it is associated with in its natural location.

"Isolated protein," "isolated polypeptide," "isolated oligopeptide," "isolated peptide," or "isolated amino acid sequence" as used herein refers to a protein, polypeptide, oligopeptide, peptide, or amino acid sequence separated from the organism from which it originates or from the naturally occurring location, or molecules with which it is normally associated. An isolated protein, isolated polypeptide, isolated oligopeptide, isolated peptide, or isolated amino acid sequence may be made through a synthetic process. An isolated protein, isolated polypeptide, isolated oligopeptide, isolated peptide, or isolated amino acid sequence may have covalent bonds to moieties other than found in its natural location, or may lack covalent bonds to moieties that is associated with in its natural location.

As used herein, "variant" refers to a molecule that retains a biological activity that is the same or substantially similar to that of the original sequence. The variant may be from the same or different species or be a synthetic sequence based on a natural or prior molecule. In the context of enzyme activity, substantially similar means that the variant has at least 50% of the activity of the native enzyme or a enzyme having a particular reference sequence herein. The enzymatic activity may be hydrolysis of plant material. The enzymatic activity may be xylanase activity. The enzymatic activity may be hydrolysis of hemicellulose, cellulose, cellobiose, or lignin. A variant intein may have substantially similar splicing activity compared to the native intein or an intein having a particular reference sequence herein, where substantially similar means the variant has at least 50% splicing activity of the native intein or intein having the particularly reference sequence. A variant may have mutations and/or a different length than the original sequence. Tests for assaying enzymatic activity or intein splicing provided below may be used to analyze variants. A liquid assay or diagnostic agar plate assay as described in Example 1 may be used as a test.

Nucleic acids, nucleotide sequences, proteins or amino acid sequences referred to herein can be isolated, purified, synthesized chemically, or produced through recombinant DNA technology. All of these methods are well known in the art.

As used herein, "operably linked" refers to the association of two or more biomolecules in a configuration relative to one another such that the normal function of the biomolecules can be performed. In relation to nucleotide sequences, "operably linked" refers to the association of two or more nucleic acid sequences in a configuration relative to one another such that the normal function of the sequences can be performed. For example, the nucleotide sequence encoding a presequence or secretory leader is operably linked to a nucleotide sequence for a polypeptide if it is expressed as a preprotein that participates in the secretion of the polypeptide; a promoter or enhancer is operably linked to a coding sequence if it affects the transcription of the coding sequence; and a nucleic acid ribosome binding site is operably linked to a coding sequence if it is positioned so as to facilitate binding of the ribosome to the nucleic acid.

An embodiment provides an engineered temperature regulated (thermoregulated) intein splicing as a conditional switch that can be used to control enzyme activity in plants. An embodiment provides a method of controlling enzyme activity in plants by utilizing thermoregulated intein splicing. An embodiment provides transgenic plants engineered to contain an intein modified enzyme. An embodiment provides transgenic plants engineered to contain a cell wall degrading enzyme. An embodiment provides transgenic plants engineered to contain a cell wall degrading enzyme and an intein modified cell wall degrading enzyme. An embodiment provides a method of increasing autohydrolysis in a plant by providing a cell wall degrading enzyme and/or an intein modified cell wall degrading enzyme in the plant. The increased autohydrolysis may be provided by including an intein-modified cell wall degrading protein in the plant. The increased autohydrolysis may be provided by including a cell wall degrading protein in the plant. The increased autohydrolysis may be provided by including at least one of a xylanse or an intein-modified xylanase in the plant.

An embodiment provides a transgenic plant having increased autohydrolysis and normal seed germination rates, or germination rates similar to those of the same type of seed lacking increased autohydrolysis. The transgenic plant of this embodiment may include an intein-modified cell wall degrading protein in the plant. The intein-modified cell wall degrading protein may be an intein-modified xylanase.

An embodiment provides a transgenic plant with increased autohydrolysis and lower germination rates. The increased autohydrolysis may be provided by including hemicellulose or cellulose hydrolysis traits in the transgenic plant. The increased autohydrolysis may be provided by including a cell wall degrading protein in the transgenic plant. The increased autohydrolysis may be provided by including a xylanase in the transgenic plant.

As used herein, "autohydrolysis" refers the constituents of a plant being hydrolyzed by at least one heterologous agent produced by the plant. Heterologous agents produced by the plant may include enzymes, intein-modified enzymes, proteins, RNA sequences, or other agents. An embodiment provides plants with increased autohydrolyis and methods of making the same. The heterologous agent in the plant or incorporated in the methods may be an enzyme, intein-modified enzyme, protein, RNA sequence, or other agent.

A method, composition, transgenic plant or part thereof, nucleic acid, or amino acid sequence herein may include one or more of the nucleic acid or amino acid sequences referred to anywhere herein or a variant thereof, a protein encoded by a nucleic acid referred to herein or a variant thereof, or a nucleic acid encoding a protein referred to herein or a variant thereof. Subsequences of the nucleic acids or proteins herein may be provided, where a subsequence may be selected from every sequence in the range of 5 to X nucleotides or amino acid residues long, taken anywhere along the length of the nucleic acid or protein sequence, where X=any integer from 5 to N, and where N=the full length of the nucleic acid or protein sequence. When the starting point of the subsequence is a position other than position 1 in the nucleic acid or protein sequence, X is chosen so that the total length of the subsequence does not exceed the length from the starting point to N. As a non-limiting example, a sequence may have 350 nucleotides, and any 5 to X length fragment of the 350 nucleotide sequence may be provided as a subsequence herein. In this example, if nucleotide position 100 is chosen as the starting point, the subsequence may be chosen from positions 100-105, 100-106, 100-107 . . . 100-350; if nucleotide position 50 is chosen as the starting point, the subsequence may be chosen from positions 50-55, 50-56, 50-57 . . . 50-350; etc. The sequences and subsequences, and variants thereof may be provided in forms including but not limited to isolated nucleic acids, isolated amino acid sequences, in a vector, in an expression vector, or in a transgenic plant. Subsequences may be provided in a vector, expression vector or transgenic plant. A subsequence may be a hybridization probe or a primer. The sequences or subsequences in an expression vector may be operably linked to a promoter. The expression vectors may be provided in a transgenic plant. Nucleic acid and amino acid sequences that are provided in embodiments herein include but are not limited to those in Example 18, below, and the accompanying sequence listing.

"Percent identity," as used herein means that a sequence has a given percent of identity along its length to an equal length of a reference sequence. A sequence herein may be provided having 75, 80, 85, 90, 91, 92, 93, 94, 95, 96, 97, 98, 99, or 100% identity to one of the sequences or subsequences thereof herein, or any single integer percent identity from 75% to 100%. Percent identity to a sequence can be measured by the Smith-Waterman algorithm (Smith T F, Waterman M S (1981), "Identification of Common Molecular Subsequences," *Journal of Molecular Biology* 147: 195-197, which is incorporated herein by reference as if fully set forth.).

An isolated nucleic acid may be provided for a method or composition herein having a sequence as set forth in any one of the nucleic acids listed herein or the complement thereof. In an embodiment, an isolated nucleic acid having a sequence that hybridizes to a nucleic acid having the sequence of one of the nucleic acid listed herein or the complement thereof is provided. In an embodiment, the hybridization conditions are low stringency conditions. In an embodiment, the hybridization conditions are moderate stringency conditions. In an embodiment, the hybridization conditions are high stringency conditions. Examples of hybridization protocols and methods for optimization of hybridization protocols are described in the following books: Molecular Cloning, T. Maniatis, E. F. Fritsch, and J. Sambrook, Cold Spring Harbor Laboratory, 1982; and, Current Protocols in Molecular Biology, F. M. Ausubel, R. Brent, R. E. Kingston, D. D. Moore, J. G. Seidman, J. A. Smith, K. Struhl, Volume 1, John Wiley & Sons, 2000, which are incorporated by reference in their entirety as if fully set forth. By way of example, but not limitation, procedures for hybridization conditions of moderate stringency are as follows: filters containing DNA are pretreated for 2-4 h at 68° C. in a solution containing 6×SSC (Amresco, Inc., Solon, Ohio), 0.5% SDS (Amersco, Inc., Solon, Ohio), 5×Denhardt's solution (Amersco, Inc., Solon, Ohio), and 100 ug/mL denatured, salmon sperm DNA (Invitrogen Life Technologies, Inc., Carlsbad, Calif.). Approximately 0.2 mL of pretreatment solution are used per square centimeter of membrane used. Hybridizations are carried out in the same solution with the following modifications: 0.01 M EDTA (Amersco, Inc., Solon, Ohio), 100 μg/ml salmon sperm DNA, and $5-20\times10^6$ cpm $^{32}$P-labeled or fluorescently labeled probes can be used. Filters are incubated in hybridization mixture for 16-20 h at 68° C. and then washed for 15 minutes at room temperature (within five degrees of 25° C.) in a solution containing 2×SSC and 0.1% SDS, with gentle agitation. The wash solution is replaced with a solution containing 0.1×SSC and 0.5% SDS, and incubated an additional 2 h at 68° C., with gentle agitation. Filters are blotted dry and exposed for development in an imager or by autoradiography. If necessary, filters are washed for a third time and re-exposed for development. By way of example, but not limitation, low stringency refers to hybridizing conditions that employ low temperature for hybridization, for example, temperatures between 37° C. and 60° C. By way of example, but not limitation, high stringency refers to hybridizing conditions as set forth above but with modification to employ high temperatures, for example, hybridization at a temperature over 68° C.

In an embodiment, a method of producing a transgenic plant having an autohydrolytic trait and seed with a decreased germination rate relative to seed that does not have the autohydrolytic trait is provided. The method may include providing an expression vector having a sequence that encodes a xylanase and transforming a plant or part thereof with the expression construct. The expression construct may include a promoter operably linked to the sequence that encodes a xylanase. The operably linked promoter may be an inducible promoter. The operably linked promoter may be a constitutive promoter. Constitutive promoters that may be provided include but are not limited to ubiquitin promoters, actin promoters, the phosphoenolpyruvate promoter (PEPC), or the cauli flower mosaic virus (CMV) promoter The method may include expressing the xylanase. If the expression vector is configured to express the xylanase at all or most times, the xylanase may accumulate without any further steps being taken. If the expression vector is configured to express the xylanase by inducing of expression, the method may include expressing the xylanase by providing conditions conducive for induction. Examples of promoters and steps for providing conditions conducive for induction that may be provided include but are not limited to the rice pathogenesis related protein 1a promoter that can be induced by applying exogenous salicyclic acid to the plant, the rice Sag39 promoter that is induced when the plant enters senescence, and the rice glutelin promoter that is induced during seed development in the plant. The xylanase may be but is not limited to a *Dictyoglomus* xylanase or a variant thereof. The xylanase may but is not limited to one having an amino acid sequence having at least 75, 80, 85, 90, 91, 92, 93, 94, 95, 96, 97, 98, 99, or 100% identity with the sequence of SEQ ID NO: 19. The xylanase may be subsequence of SEQ ID NO: 19 that is a variant of SEQ ID NO: 19. A xylanase having less than 100% identity with the sequence of SEQ ID NO: 19 may be a variant of the sequence having 100% identity to SEQ ID NO: 19. The sequence encoding the xylanase may include a nucleic acid that hybridizes to a reference nucleic acid consisting of the sequence of SEQ ID NO: 20 or the complement thereof under conditions of one of low stringency, alternatively moderate stringency, or alternatively high stringency. The sequence encoding the xylanase may include a nucleic acid having at least 75, 80, 85, 90, 91, 92, 93, 94, 95, 96, 97, 98, 99, or 100% identity to the sequence of SEQ ID NO: 20 or the complement thereof. The sequence encoding the xylanase may include a nucleic acid encoding an amino acid sequence having at least 75, 80, 85, 90, 91, 92, 93, 94, 95, 96, 97, 98, 99, or 100% identity to a reference amino acid sequence consisting of the sequence of SEQ ID NO: 19, or a subsequence of the amino acid sequence that is at least 20 amino acids. The plant or part thereof may be but is not limited to a maize plant or part thereof, a switchgrass plant or part thereof, or a sorghum plant or part thereof. The method may include at least one of growing the transgenic plant, propogating the plant, propogating the plant, obtaining progeny from the transgenic plant, or obtaining seed from, the transgenic plant or its progeny.

In an embodiment, a method of producing a transgenic plant having an autohydrolytic trait is provided. The method includes providing an expression vector having a sequence that encodes an intein-modified xylanase. The intein may be internally fused within the xylanase. The method may include transforming a plant or part thereof with the expression construct. The intein-modified xylanase may have decreased activity relative to the xylanase lacking the intein. The expression construct may include a promoter operably linked to the sequence that encodes an intein-modified xylanase. The operably linked promoter may be an inducible promoter. The operably linked promoter may be a constitutive promoter. Constitutive promoters that may be provided include but are not limited to ubiquitin promoters (for example promoters such as maize ubiquitin, rice ubiquitin, or panicum ubiquitin promoters), actin promoters, the phosphoenolpyruvate promoter (PEPC), or the cauli flower mosaic virus (CMV) promoter. The method may include expressing the intein-modified xylanase. If the expression vector is configured to express the intein-modified xylanase at all or most times, the intein-modified xylanase may accumulate without any further steps being taken. If the expression vector is configured to express the intein-modified xylanase by inducing of expression, the method may include expressing the intein-modified xylanase by providing conditions conducive for induction. Examples of promoters and steps for providing conditions conducive for induction that may be provided include but are not limited to the rice pathogenesis related protein 1a promoter that can be induced by applying exogenous salicyclic acid to the plant, the rice Sag39 promoter that is induced when the plant enters senescence, and the rice glutelin promoter that is induced during seed development in the plant. The xylanase portions of the intein-modified xylanase when considered as a contiguous sequence may be a *Dictyoglomus* xylanase or a variant thereof. The xylanase portions of the intein-modified xylanase when considered as a contiguous sequence may have an amino acid sequence having at least 75, 80, 85, 90, 91, 92, 93, 94, 95, 96, 97, 98, 99, or 100% identity with the sequence of SEQ ID NO: 19. The xylanase portions of the intein-modified xylanase when considered as a contiguous sequence may be subsequence of SEQ ID NO: 19 that is a variant of SEQ ID NO: 19. The xylanase portions of the intein-modified xylanase when considered as a contiguous sequence and having less than 100% identity with the sequence of SEQ ID NO: 19 may be a variant of the sequence having 100% identity to SEQ ID NO: 19. The sequence encoding the xylanase portions of the intein-modified xylanase when considered as a contiguous sequence may include a nucleic acid that hybridizes to a reference nucleic acid consisting of the sequence of SEQ ID NO: 20 or the complement thereof under conditions of one of low, or alternative moderate stringency, or alternatively high stringency. The sequence encoding the xylanase of the intein-modified xylanase when considered as a contiguous sequence may include a nucleic acid having at least 75, 80, 85, 90, 91, 92, 93, 94, 95, 96, 97, 98, 99, or 100% identity to the sequence of SEQ ID NO: 20 or the complement thereof. The sequence encoding the xylanase when considered as a contiguous sequence may include a nucleic acid encoding an amino acid sequence having at least 75, 80, 85, 90, 91, 92, 93, 94, 95, 96, 97, 98, 99, or 100% identity to a reference amino acid sequence consisting of the sequence of SEQ ID NO: 19. The intein-modified xylanase may have an amino acid sequence having at least 75, 80, 85, 90, 91, 92, 93, 94, 95, 96, 97, 98, 99, or 100% identity with a sequence selected from SEQ ID NOS: 2, 4, 6, 8, 10, 12, 14, 16, 17, 21, 29, 30, 60, 62, or 64. The sequence that encodes the intein-modified xylanase may be an isolated nucleic acid that hybridizes to a reference nucleic acid consisting of the sequence of one of SEQ ID NOS: 1, 3, 5, 7, 9, 11, 13, 15, 18, 35, 36, 37, 38, 59, 61, or 63 or the complement thereof under conditions of low stringency, alternatively moderate stringency, or alternatively high stringency. The sequence that encodes the intein-modified xylanase may be an isolated nucleic acid having at least 75, 80, 85, 90, 91, 92, 93, 94, 95, 96, 97, 98, 99, or 100% identity to the sequence of one of SEQ ID NOS: 1, 3, 5, 7, 9, 11, 13, 15, 18, 35, 36, 37, 38, 59, 61, or 63 or the complement thereof. The sequence that encodes the intein-modified xylanase may be an isolated nucleic acid that encodes an amino acid sequence having at least 75, 80, 85, 90, 91, 92, 93, 94, 95, 96, 97, 98, 99, or 100% identity to a reference amino acid sequence consisting of the sequence of one of SEQ ID NOS: 2, 4, 6, 8, 10, 12, 14, 16, 17, 21, 29, 30, 60, 62, or 64. The intein in the intein-modified xylanase may have a sequence having at least 75, 80, 85, 90, 91, 92, 93, 94, 95, 96, 98, 97, 99, or 100% identity with a sequence selected from SEQ ID NOS: 22-28. The plant or part thereof may be but is not limited to a maize plant or part thereof, a switchgrass plant or part thereof, or a sorghum plant or part thereof. The method may include providing conditions to induce splicing of the intein. The conditions to induce splicing of the intein may be but are not limited to a temperature above the temperature at which the transgenic plant is grown. The conditions to induce splicing of the intein may be but are not limited to a temperature of 50° C. to 70° C. The conditions to induce splicing of the intein may be but are not limited to any one temperature in any one range between any two integer values from 50° C. to 70° C. The transgenic plant or part thereof may be but is not limited to a maize plant or part thereof, a switchgrass plant or part thereof, or a sorghum plant or part thereof. The method may include at least one of growing the transgenic plant, propogating the plant, obtaining progeny from the transgenic plant, or obtaining seed from, the transgenic plant or its progeny.

In an embodiment, a transgenic plant having an autohydrolytic trait and seed with a decreased germination rate relative to seed that does not have the autohydrolytic trait, or a part thereof is provided. The transgenic plant may be the plant originally developed after transformation or a progeny thereof. The transgenic plant may include an expression vector having a sequence that encodes a xylanase. The expression construct may include a promoter operably linked to the sequence that encodes a xylanase. The operably linked promoter may be an inducible promoter. The operably linked promoter may be a constitutive promoter. Constitutive promoters that may be provided include but are not limited to ubiquitin promoters (for example promoters such as maize ubiquitin, rice ubiquitin, or panicum ubiquitin promoters), actin promoters, the phosphoenolpyruvate promoter (PEPC), or the cauli flower mosaic virus (CMV) promoter. The transgenic plant may be configured to allow expressing the xylanase. If the expression vector is configured to express the xylanase at all or most times, the xylanase may accumulate without any further steps being taken. If the expression vector is configured to express the xylanase by inducing of expression, expressing the xylanase may be accomplished by providing conditions conducive for induction. Examples of promoters and steps for providing conditions conducive for induction that may be provided include but are not limited to the rice pathogenesis related protein 1a prmoter that can be induced by applying exogenous salicyclic acid to the plant, the rice Sag39 promoter that is induced when the plant enters senescence, and the rice glutelin promoter that is induced during seed development in the plant. The xylanase may be but is not limited to a *Dictyoglomus* xylanase or a variant thereof. The xylanase may but is not limited to one having an amino acid sequence having at least 75, 80, 85, 90, 91, 92, 93, 94, 95, 96, 97, 98, 99 or 100% identity with the sequence of SEQ ID NO: 19. The xylanase may be subsequence of SEQ ID NO: 19 that is a variant of SEQ ID NO: 19. A xylanase having less than 100% identity with the sequence of SEQ ID NO: 19 may be a variant of the sequence having 100% identity to SEQ ID NO: 19. The sequence encoding the xylanase may include a nucleic acid that hybridizes to a reference nucleic acid consisting of the sequence of SEQ ID NO: 20 or the complement thereof under conditions of one of low, or alternatively moderate stringency, or alternatively high stringency. The sequence encoding the xylanase may include a nucleic acid encoding an amino acid sequence having at least 75, 80, 85, 90, 91, 92, 93, 94, 95, 96, 97, 98, 99, or 100% identity to a reference amino acid sequence consisting of the sequence of SEQ ID NO: 19, or a subsequence of the amino acid sequence that is at least 20 amino acids. The sequence encoding the xylanase may include a nucleic acid having at least 75, 80, 85, 90, 91, 92, 93, 94, 95, 96, 97, 97, 99 or 100% identity to the sequence of SEQ ID NO: 20 or the complement thereof. The transgenic plant or part thereof may be but is not limited to a transgenic maize plant or part thereof, a transgenic switchgrass plant or part thereof, or a transgenic sorghum plant or part thereof.

In an embodiment, a transgenic plant having an autohydrolytic trait, or a part thereof is provided. The transgenic plant may be the plant originally developed after transformation or a progeny thereof. The transgenic plant may include an expression vector having a sequence that encodes an intein-modified xylanase. The intein-modified xylanase may have an intein internally fused within the xylanase. The intein-modified xylanase may have decreased activity relative to the xylanase lacking the intein. The expression construct may include a promoter operably linked to the sequence that encodes an intein-modified xylanase. The operably linked promoter may be an inducible promoter. The operably linked promoter may be a constitutive promoter. Constitutive promoters that may be provided include but are not limited to ubiquitin promoters (for example promoters such as maize ubiquitin, rice ubiquitin, or panicum ubiquitin promoters), actin promoters, the phosphoenolpyruvate promoter (PEPC), or the cauli flower mosaic virus (CMV) promoter. The transgenic plant may be configured to allow expressing the intein-modified xylanase. If the expression vector is configured to express the intein-modified xylanase at all or most times, the intein-modified xylanase may accumulate without any further steps being taken. If the expression vector is configured to express the intein-modified xylanase by inducing of expression, expressing the intein-modified xylanase may include providing conditions conducive for induction. Examples of promoters and steps for providing conditions conducive for induction that may be provided include but are not limited to the rice pathogenesis related protein 1a prmoter that can be induced by applying exogenous salicyclic acid to the plant, the rice Sag39 promoter that is induced when the plant enters senescence, and the rice glutelin promoter that is induced during seed development in the plant. The xylanase portions of the intein-modified xylanase when considered as a contiguous sequence may be a *Dictyoglomus* xylanase or a variant thereof. The xylanase portions of the intein-modified xylanase when considered as a contiguous sequence may have an amino acid sequence having at least 75, 80, 85, 90, 91, 92, 93, 94, 95, 96, 97, 98, 99 or 100% identity with the sequence of SEQ ID NO: 19. The xylanase portions of the intein-modified xylanase when considered as a contiguous sequence may be subsequence of SEQ ID NO: 19 that is a variant of SEQ ID NO: 19. The xylanase portions of the intein-modified xylanase when considered as a contiguous sequence and having less than 100% identity with the sequence of SEQ ID NO: 19 may be a variant of the sequence having 100% identity to SEQ ID NO: 19. The sequence encoding the xylanase portions of the intein-modified xylanase when considered as a contiguous sequence may include a nucleic acid encoding an amino acid sequence having at least 75, 80, 85, 90, 91, 92, 93, 94, 95, 96, 97, 98, 99, or 100% identity to a reference amino acid sequence consisting of the sequence of SEQ ID NO: 19. The sequence encoding the xylanase portions of the intein-modified xylanase may include a nucleic acid that hybridizes to a reference sequence consisting of the sequence of SEQ ID NO: 20 or the complement thereof under conditions of low stringency, or alternatively moderate stringency, or alternatively high stringency. The sequence encoding the xylanase of the intein-modified xylanase may include a nucleic acid having at least 75, 80, 85, 90, 91, 92, 93, 94, 95, 96, 97, 98, 99, or 100% identity to the sequence of SEQ ID NO: 20 or the complement thereof. The intein-modified xylanase may have an amino acid sequence having at least 75, 80, 85, 90, 91, 92, 93, 94, 95, 96, 97, 98, 99, or 100% identity with a sequence selected from SEQ ID NOS: 2, 4, 6, 8, 10, 12, 14, 16, 17, 21, 29, 30, 60, 62, or 64. The sequence that encodes the intein-modified xylanase may be an isolated nucleic acid that hybridizes to a reference nucleic acid consisting of the sequence of one of SEQ ID NOS: 1, 3, 5, 7, 9, 11, 13, 15, 18, 35, 36, 37, 38, 59, 61, or 63 or the complement thereof under conditions of low stringency, alternatively moderate stringency, or alternatively high stringency. The sequence that encodes the intein-modified xylanase may be an isolated nucleic acid that encodes an amino acid sequence having at least 75, 80, 85, 90, 91, 92, 93, 94, 95, 96, 97, 98, 99, or 100% identity to a reference amino acid sequence consisting of the sequence of one of SEQ ID NOS: 2, 4, 6, 8, 10, 12, 14, 16, 17, 21, 29, 30, 60, 62, or 64. The sequence that encodes the intein-modified xylanase may be an isolated nucleic acid having at least 75, 80, 85, 90, 91, 92, 93, 94, 95, 96, 97, 98, 99, or 100% identity to the sequence of one of SEQ ID NOS: 1, 3, 5, 7, 9, 11, 13, 15, 18, 35, 36, 37, 38, 59, 61, or 63 or the complement thereof. The intein in the intein-modified xylanase may have a sequence having at least 75, 80, 85, 90, 91, 92, 93, 94, 95, 96, 97, 98, 99 or 100% identity with a sequence selected from SEQ ID NOS: 22-28. The transgenic plant may be configured to include an intein that splices upon exposure to induction conditions. The conditions to induce splicing of the intein may be but are not limited to a temperature above the temperature at which the transgenic plant is grown. The conditions to induce splicing of the intein may be but are not limited to a temperature of 50° C. to 70° C. The conditions to induce splicing of the intein may be but are not limited to any one temperature in any one range between any two integer values from 50° C. to 70° C. The transgenic plant or part thereof may be but is not limited to a transgenic maize plant or part thereof, a transgenic switchgrass plant or part thereof, or a transgenic sorghum plant or part thereof.

In an embodiment, a method of obtaining a sugar is provided. The method may include providing a transgenic plant or part of the transgenic plant. The transgenic plant includes an expression vector having a sequence that encodes a xylanase. The method also includes subjecting the transgenic plant or part thereof to enzymatic hydrolysis. The method may also include expressing the xylanase. The method may also include milling and/or pre-processing with a pretreatment procedure. Non-limiting examples of hydrolysis, milling, and pre-processing with a pretreatment procedure are provided below. The transgenic plant may include an expression vector having a sequence that encodes a xylanase. The expression construct may include a promoter operably linked to the sequence that encodes a xylanase. The operably linked promoter may be an inducible promoter. The operably linked promoter may be a constitutive promoter. Constitutive promoters that may be provided include but are not limited to ubiquitin promoters (for example promoters such as maize ubiquitin, rice ubiquitin, or panicum ubiquitin promoters), actin promoters, the phosphoenolpyruvate promoter (PEPC), or the cauli flower mosaic virus (CMV) promoter. The transgenic plant may be configured to allow expressing the xylanase. If the expression vector is configured to express the xylanase at all or most times, the xylanase may accumulate without any further steps being taken. If the expression vector is configured to express the xylanase by inducing of expression, the method may include expressing the xylanase by providing conditions conducive for induction. Examples of promoters and steps for providing conditions conducive for induction that may be provided include but are not limited to the rice pathogenesis related protein 1a prmoter that can be induced by applying exogenous salicyclic acid to the plant, the rice Sag39 promoter that is induced when the plant enters senescence, and the rice glutelin promoter that is induced during seed development in the plant. The xylanase may be but is not limited to a *Dictyoglomus* xylanase or a variant thereof. The xylanase may but is not limited to one having an amino acid sequence having at least 75, 80, 85, 90, 91, 92, 93, 94, 95, 96, 97, 98, 99 or 100% identity with the sequence of SEQ ID NO: 19. The xylanase may be subsequence of SEQ ID NO: 19 that is a variant of SEQ ID NO: 19. A xylanase having less than 100% identity with the sequence of SEQ ID NO: 19 may be a variant of the sequence having 100% identity to SEQ ID NO: 19. The sequence encoding the xylanase may include a nucleic acid that hybridizes to a reference sequence consisting of the sequence of SEQ ID NO: 20 or the complement thereof under conditions of low stringency, or alternatively moderate stringency, or alternatively high stringency. The sequence encoding the xylanase may include a nucleic acid encoding an amino acid sequence having at least 75, 80, 85, 90, 91, 92, 93, 94, 95, 96, 97, 98, 99, or 100% identity to a reference amino acid sequence consisting of the sequence of SEQ ID NO: 19, or a subsequence of the amino acid sequence that is at least 20 amino acids, or a subsequence of the amino acid sequence that is at least 20 amino acids. The sequence encoding the xylanase may include a nucleic acid having at least 75, 80, 85, 90, 91, 92, 93, 94, 95, 96, 97, 98, 99, or 100% identity to the sequence of SEQ ID NO: 20 or the complement thereof. The transgenic plant or part thereof may be but is not limited to a transgenic maize plant or part thereof, a transgenic switchgrass plant or part thereof, or a transgenic sorghum plant or part thereof. The method may include at least one of growing the transgenic plant, propogating the transgenic plant, obtaining progeny from the transgenic plant, or obtaining seed from, the transgenic plant or its progeny.

In an embodiment, a method of obtaining a sugar is provided. The method may include providing a transgenic plant or part of the transgenic plant. The transgenic plant may have an expression vector including a sequence that encodes an intein-modified xylanase. The method also includes subjecting the transgenic plant or part thereof to enzymatic hydrolysis. The method may also include expressing the xylanase. The method may also include milling and/or pre-processing with a pretreatment procedure. Non-limiting examples of hydrolysis, milling, and pre-processing with a pretreatment procedure are provided below. The intein may be internally fused within the xylanase, and the intein-modified xylanase may have decreased activity relative to the xylanase lacking the intein. The expression construct may include a promoter operably linked to the sequence that encodes an intein-modified xylanase. The operably linked promoter may be an inducible promoter. The operably linked promoter may be a constitutive promoter. Constitutive promoters that may be provided include but are not limited to ubiquitin promoters (for example promoters such as maize ubiquitin, rice ubiquitin, or panicum ubiquitin promoters), actin promoters, the phosphoenolpyruvate promoter (PEPC), or the cauli flower mosaic virus (CMV) promoter. The transgenic plant may be configured to allow expressing the intein-modified xylanase. If the expression vector is configured to express the intein-modified xylanase at all or most times, the intein-modified xylanase may accumulate without any further steps being taken. If the expression vector is configured to express the intein-modified xylanase by inducing of expression, the method may include expressing the intein-modified xylanase by providing conditions conducive for induction. Examples of promoters and steps for providing conditions conducive for induction that may be provided include but are not limited to the rice pathogenesis related protein 1a prmoter that can be induced by applying exogenous salicyclic acid to the plant, the rice Sag39 promoter that is induced when the plant enters senescence, and the rice glutelin promoter that is induced during seed development in the plant. The xylanase portions of the intein-modified xylanase when considered as a contiguous sequence may be a *Dictyoglomus* xylanase or a variant thereof. The xylanase portions of the intein-modified xylanase when considered as a contiguous sequence may have an amino acid sequence having at least 75, 80, 85, 90, 91, 92, 93, 94, 95, 96, 97, 98, 99 or 100% identity with the sequence of SEQ ID NO: 19. The xylanase portions of the intein-modified xylanase when considered as a contiguous sequence may be subsequence of SEQ ID NO: 19 that is a variant of SEQ ID NO: 19. The xylanase portions of the intein-modified xylanase when considered as a contiguous sequence and having less than 100% identity with the sequence of SEQ ID NO: 19 may be a variant of the sequence having 100% identity to SEQ ID NO: 19. The sequence encoding the xylanase portion of the intein-modified xylanase when considered as a contiguous sequence may include a nucleic acid encoding an amino acid sequence having at least 75, 80, 85, 90, 91, 92, 93, 94, 95, 96, 97, 98, 99, or 100% identity to a reference amino acid sequence consisting of the sequence of SEQ ID NO: 19. The sequence encoding the xylanase portions of the intein-modified xylanase when considered as a contiguous sequence may include a nucleic acid that hybridizes to a reference nucleic acid consisting of the sequence of SEQ ID NO: 20 or the complement thereof under conditions of one of low, alternatively moderate stringency, or alternatively high stringency. The sequence encoding the xylanase of the intein-modified xylanase may include a nucleic acid having at least 75, 80, 85, 90, 91, 92, 93, 94, 95, 96, 97, 98, 99, or 100% identity to the sequence of SEQ ID NO: 20 or the complement thereof. The intein-modified xylanase may have an amino acid sequence having at least 75, 80, 85, 90, 91, 92, 93, 94, 95, 96, 97, 98, 99, or 100% identity with a sequence selected from SEQ ID NOS: 2, 4, 6, 8, 10, 12, 14, 16, 17, 21, 29, 30, 60, 62, or 64. The sequence that encodes the intein-modified xylanase may be an isolated nucleic acid that hybridizes to a reference nucleic acid consisting of the sequence of one of SEQ ID NOS: 1, 3, 5, 7, 9, 11, 13, 15, 18, 35, 36, 37, 38, 59, 61, or 63 or the complement thereof under conditions of low stringency, alternatively moderate stringency, or alternatively high stringency. The sequence that encodes the intein-modified xylanase may be an isolated nucleic acid having at least 75, 80, 85, 90, 91, 92, 93, 94, 95, 96, 97, 97, 99 or 100% identity to the sequence of one of SEQ ID NOS: 1, 3, 5, 7, 9, 11, 13, 15, 18, 35, 36, 37, 38, 59, 61, or 63 or the complement thereof. The sequence that encodes the intein-modified xylanase may be an isolated nucleic acid that encodes an amino acid sequence having at least 75, 80, 85, 90, 91, 92, 93, 94, 95, 96, 97, 98, 99, or 100% identity to a reference amino acid sequence consisting of the sequence of one of SEQ ID NOS: 2, 4, 6, 8, 10, 12, 14, 16, 17, 21, 29, 30, 60, 62, or 64. The intein in the intein-modified xylanase may have a sequence having at least 75, 80, 85, 90, 91, 92, 93, 94, 95, 96, 97, 97, 99 or 100% identity with a sequence selected from SEQ ID NOS: 22-30. The transgenic plant may be configured to include an intein that splices upon exposure to induction conditions, and the method may further include providing a condition for inducing intein splicing. The conditions to induce splicing of the intein may be but are not limited to a temperature above the temperature at which the transgenic plant is grown. The conditions to induce splicing of the intein may be but are not limited to a temperature of 50° C. to 70° C. The conditions to induce splicing of the intein may be but are not limited to any one temperature in any one range between any two integer values from 50° C. to 70° C. The transgenic plant or part thereof may be but is not limited to a transgenic maize plant or part thereof, a transgenic switchgrass plant or part thereof, or a transgenic sorghum plant or part thereof.

In an embodiment, an intein modified xylanase is provided. The intein modified xylanase may have a sequence with at least 75, 80, 85, 90, 91, 92, 93, 94, 95, 96, 97, 97, 99 or 100% identity to one of SEQ ID NOS: 2, 4, 6, 8, 10, 12, 14, 16, 21, 29, 30, 60, 62, or 64. The identity may be 100%.

In an embodiment, an isolated nucleic acid having a sequence that hybridizes to a reference nucleic acid consisting of the sequence of SEQ ID NOS: 1, 3, 5, 7, 9, 11, 13, 15, 18, 35, 36, 37, 38, 59, 61, or 63 or the complement thereof under conditions of low stringency is provided. In an embodiment, an isolated nucleic acid having a sequence that hybridizes to a reference nucleic acid consisting of the sequence of SEQ ID NOS: 1, 3, 5, 7, 9, 11, 13, 15, 18, 35, 36, 37, 38, 59, 61, or 63 or the complement thereof under conditions of moderate stringency is provided. In an embodiment, an isolated nucleic acid having a sequence that hybridizes to a reference nucleic acid consisting of the sequence of SEQ ID NOS: 1, 3, 5, 7, 9, 11, 13, 15, 18, 35, 36, 37, 38, 59, 61, or 63 or the complement thereof under conditions of high stringency is provided. In an embodiment, a nucleic acid encoding an amino acid sequence with at least 75, 80, 85, 90, 91, 92, 93, 94, 95, 96, 97, 97, 99 or 100% identity to a reference amino acid sequence consisting of one of SEQ ID NOS: 2, 4, 6, 8, 10, 12, 14, 16, 21, 29, 30, 60, 62, or 64 is provided. The percent identity may be 100%.

In an embodiment, an isolated nucleic acid including a sequence that encodes an intein modified xylanase having a sequence with at least 75, 80, 85, 90, 91, 92, 93, 94, 95, 96, 97, 97, 99 or 100% identity to one of SEQ ID NOS: 2, 4, 6, 8, 10, 12, 14, 16, 21, 29, 30, 60, 62, or 64 is provided. The percent identity may be 100%

In an embodiment, an intein having a sequence with at least 75, 80, 85, 90, 91, 92, 93, 94, 95, 96, 97, 97, 99 or 100% identity to one of SEQ ID NOS: 22, 23, 24, 25, 26, 27, or 28 is provided. The percent identity may be 100%.

In an embodiment, an isolated nucleic acid encoding an intein having a sequence with at least 90% identity to one of SEQ ID NOS: 22, 23, 24, 25, 26, 27, or 28 is provided. The percent identity may be 100%.

As described above, a xylanase may be provided having less than 100% identity to a reference sequence. The xylanase may be provided as a contiguous sequence or as part of an intein-modified xylanase. The xylanase having less than 100% identity to a reference sequence may have xylanase activity when provided as a contiguous sequence. The xylanase having less than 100% identity to a reference sequence may have xylanase activity after splicing when provided as sequences in an intein-modified xylanase. The amount of xylanase activity may be that of a variant. The xylanase provided having less than 100% identity to a reference sequence and xylanase activity may be in a method, transgenic plant or amino acid sequence embodiment herein. A nucleic acid may be provided that encodes the xylanase having less than 100% identity to a reference sequence and xylanase activity may be provided. The nucleic acid may be provided in a method, transgenic plant or nucleic acid sequence embodiment herein.

As described above, an intein-modified xylanase or an intein may be provided where the intein sequence has less than 100% identity to a reference sequence. The intein may have splicing activity. The amount of splicing activity may be that of a variant. An intein having less that 100% identity to a reference sequence and having splicing activity may be provided in a method, transgenic plant or amino acid sequence embodiment herein. A nucleic acid may be provided that encodes the intein having less than 100% identity to a reference sequence and having splicing activity. The nucleic acid may be provided in a method, transgenic plant or nucleic acid sequence embodiment herein.

In an embodiment, seed from a transgenic plant is provided. The transgenic plant from which the seed is provided may be any transgenic plant herein, or a progeny thereof; or derived from any method herein. An embodiment includes making seed from a transgenic plant including making any one transgenic plant herein and harvesting seed from the transgenic plant or progeny thereof.

One or more mutation in a xylanase sequence or intein sequence in the examples below may be present in any one xylanase, xylanase portions of an intein modified enzyme, intein in an intein modified xylanase, or intein in any of the preceding embodiments. One or more mutation in a xylanase sequence or intein sequence in the examples below may be present in any xylanase, xylanase portions of an intein modified enzyme, intein in an intein modified xylanase, or intein encoded by any one nucleic acid in any of the preceding embodiments.

Introduction of intein-modified cell wall degrading enzymes into plants may be used to create valuable cellulosic processing traits that help address pretreatment costs, enzyme costs, and enzyme production capacity challenges, while enabling the production of biofuels from non-food biomass. As shown herein, plants expressing an iXynB enzyme did not have the shriveled seed phenotype found in transgenic maize plants expressing the wild-type, native XynB (SEQ ID NOS 20). After plant harvest, the intein modified enzymes still provided activity levels following a heat treatment that were high enough to significantly improve corn stover hydrolysis, with or without the use of external xylanase, compared to wild-type (A×B) corn stover. Such plant processing traits may be particularly valuable if they can reduce or eliminate enzyme costs (estimated at over $0.50/gal) (Lebler, 2010), reduce pretreatment costs (estimated at $0.30/gal) (Mosier et. al., 2005), and help reduce the required build-out of enzyme production capacity that would be necessary to meet the cellulosic renewable fuels standard.

Additional embodiments include those formed by reading any dependent claim in the claim listing below as being dependent on any one or more preceding claim up to and including its base independent claim.

Additional embodiments herein include those that may be formed by supplementing any one embodiment with one or more element from any one or more other embodiment herein.

EXAMPLES

The following non-limiting examples are provided to illustrate particular embodiments. The embodiments throughout may be supplemented with one or more detail from any one or more example below.

XynB position numbers referred to herein are in reference to the native sequence, which includes a 24 amino acid signal peptide (SEQ ID NO: 39); position 1 in SEQ ID NO: 19 is counted as position 25. By this numbering S158, shown by underlining below, appears at position 134 of SEQ ID NO: 19:

(SEQ ID NO: 19)

```
QTSITLTSNASGTFDGYYYELWKDTGNTTMTVYTQGRFSCQWSNINNALFRTGKKYNQNWQSL

GTIRITYSATYNPNGNSYLCIYGWSTNPLVEFYIVESWGNWRPPGATSLGQVTIDGGTYDIYR

TTRVNQPSIVGTATFDQYWSVRTSKRTSGTVTVTDHFRAWANRGLNLGTIDQITLCVEGYQSS
```

-continued

GSANITQNTFSQGSSSGSSGGSSGSTTTTRIECENMSLSGPYVSRITNPFNGIALYANGDTAR

ATVNFPASRNYNFRLRGCGNNNNLARVDLRIDGRTVGTFYYQGTYPWEAPIDNVYVSAGSHTV

EITVTADNGTWDVYADYLVIQ.

Tth intein mutation position numbers referred to herein are numbered based on the native Tth intein sequence (SEQ ID NO: 34) even when in the context of a larger intein modified protein context. For example, a mutation at R51 refers to a mutation at Arg 51 of SEQ ID NO: 34 even when the Tth intein sequence or a portion thereof is within another protein.

Example 1

To improve the digestibility of corn stover, an intein-modified xylanase was developed. The thermostable xylanase (xynB) from *Dictyoglomus thermophilum* was cloned into a lambda expression vector. To generate a XynB with a regulated, dormant hydrolytic activity, the thermostable, *Thermus thermophilus* intein, Tth-HB27 DnaE-1 (Tth), coding sequence was inserted into xynB directly upstream of selected cysteine (C), serine (S), or threonine (T) codons. In total, the Tth intein coding sequence was inserted into 23 individual sites (one C, eight S, and 14 T) in xynB, resulting in 23 different Tth intein-modified xynB genes. These sites were selected among the 82 possible C, S, T sites in XynB because they spanned the catalytic domain of the enzyme and resided primarily between the catalytic residues in the primary sequence of the enzyme (E118 and E208). Referring to FIG. 1*a*, *E. coli* cells transfected with lambda phage encoding xynB were grown on diagnostic agar plates containing an insoluble xylan substrate (AZCL-xylan, Megazyme). Blue halos that developed in and around the plaques were indicative of xylanase hydrolytic activity. Four serial, 10× dilutions of phage expressing native XynB, no xylanase (pBluescript, pBS), iXynB S158, iXynB S158-30, or iXynB T134-195, were used to transfect XL1-Blue MRF' *E. coli* cells and plated in quadrants on NZY plates containing IPTG and AZCL-xylan. Tth iXynB S158 was derived by inserting the Tth intein (SEQ ID NO: 34) into XynB (SEQ ID NO: 19) adjacent to S158.

Tth iXynB S158-30 is a mutant derived from iXynB S158, while iXynB T134-195 is a mutant derived from inserting the Tth intein into XynB before T134. Replicate plates were incubated overnight at 37° C., and each followed by 2 hours of incubation either at 37° C. or 50° C. or 70° C. Plaques expressing these genes were screened for thermoregulated activity. Depending on the insertion site, the Tth intein differentially affected XynB activity and the plaques were scored according to their activity, as evidenced by blue color development (plaque "phenotype"). Plaques were defined as "permissive" if they turned blue spontaneously with no heat treatment (37° C. or lower), "switching" if they turned blue only after incubating the plaques at an elevated temperature (50° C., 60° C., 65° C., or 70° C.), or "non-permissive" if the plaques remained clear under all conditions. Plaques expressing intein-modified XynB (iXynB) were classified according to the intein +1 insertion site as follows: permissive (S63, S112, S135, S170, S174, S178, C206), non-permissive (T113, T140, T145, T151, T152, T164, T180, T182, T184, T199 and T204) and switching (S124, T134, S158, T173, T177). Tth intein insertion before a cysteine or serine most often resulted in a permissive or switching phenotype, whereas insertion before a threonine most often created a non-permissive phenotype, suggesting that a C+1 or S+1 residue favors Tth intein splicing in XynB.

To develop a thermoregulated iXynB with robust temperature regulated activity, mutagenized Tth iXynB libraries at insertion sites T134 and S158 were screened, using the diagnostic agar plate screen, described above. These sites were selected because of their switching plaque phenotype with the wild-type Tth intein and because they produced a stable iXynB that was readily detected on a western blot. Approximately $2.5\times10^6$ plaques representing three independently mutagenized libraries were screened at the T134 site. At the S158 site, an estimated $3.5\times10^6$ plaques representing four independently mutagenized libraries were screened. The frequency of plaques with a reproducible improvement in switching phenotype was about 0.01% at the T134 site, and 0.004% at the S158 site. Phagemids from plaques that reproducibly resulted in a switching phenotype were rescued and tested in an activity assay to measure how temperature pretreatment affected the activity of isolated Tth iXynB mutants. In these assays, cell lysates were heat treated at various temperatures (25° C.-65° C.) in the absence of xylan substrate, cooled on ice, and then assayed for hydrolytic activity at 37° C. using AZCL-xylan. The initial heat treatment performed in the absence of substrate decoupled the effect of the heat treatment on intein splicing from the effect that elevated temperature would have had on the specific activity of the enzyme.

Figure 1B:
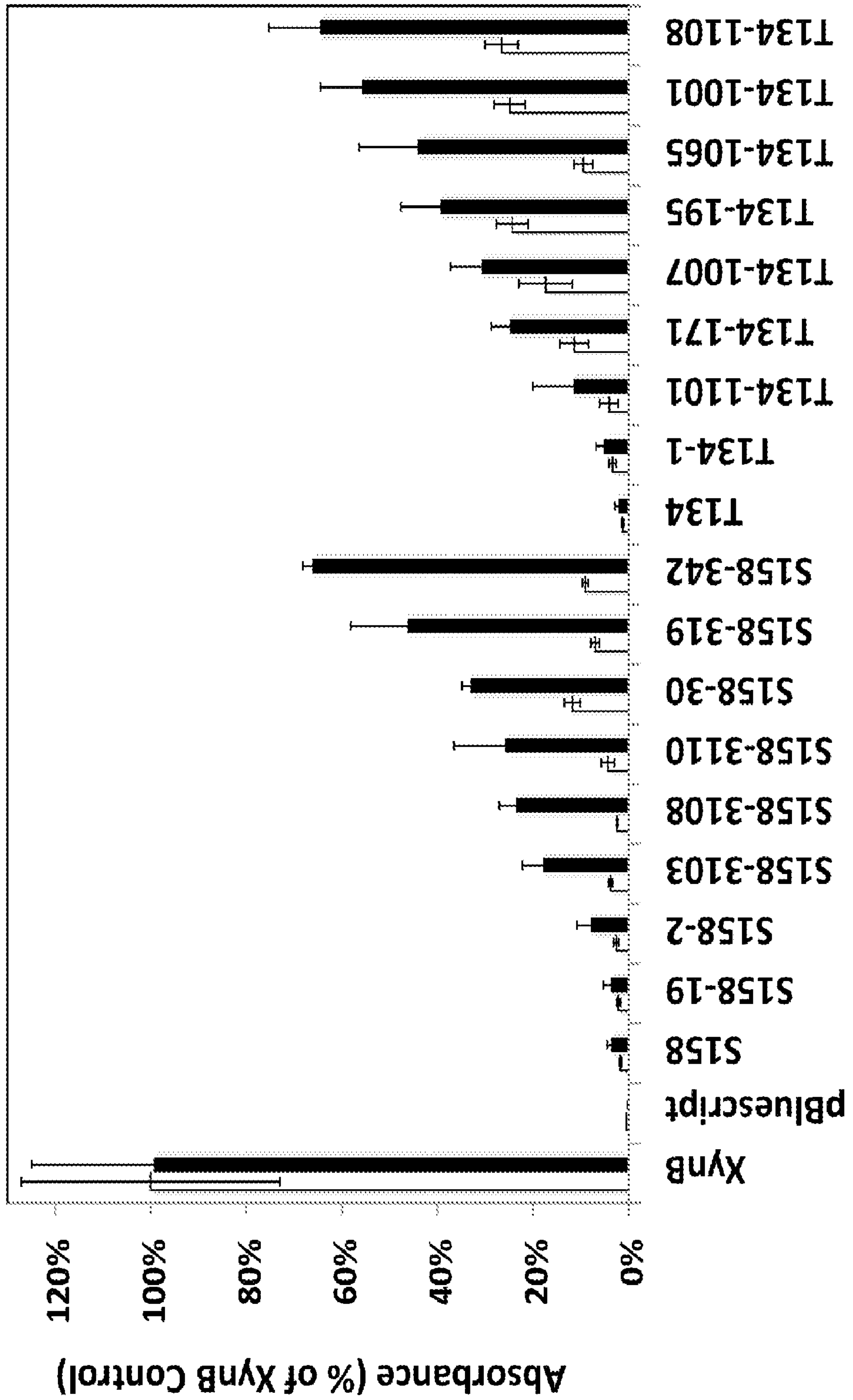

For each clone evaluated, the fold-induction, FI, was calculated as the ratio of the heated activity divided by the unheated activity; an FI of one would mean no induction occurred, FI<1 would indicate a decrease of enzyme activity following heating, FI>1 would indicate an increase in thermoregulated activity by heat treatment. The FI of wild-type XynB did not significantly differ from unity, while increases in FI were observed in the iXynB mutants, demonstrating that the insertion of the Tth intein was responsible for thermoregulation, and this property was not inherent in the native XynB. To evolve improved thermoregulated activity, clones were selected based on FI and used these in multiple rounds of mutagenesis. Referring FIG. 1*b*, the themoregulation of different mutants in the screening program was compared. The activity was measured and compared between high (59° C. for four hours) and low (37° C. for four hours) heat-treated samples, Mutagenized Tth iXynB candidates were assessed with a switching assay in which aliquots of lysate were heated for 4 hours at 37° C. (left bar in each pair of bars above each sample label) or 59° C. (right bar in each pair of bars above each sample label) without substrate, cooled on ice and incubated with AZCL-xylan at 37° C. for 2 hours. Hydrolyzed product was measured as absorbance at 590 nm. Lysate from cells transformed with pBS, and from cells expressing XynB were used as controls. For selected Tth iXynB candidates, the calculated FI ranged from 1.5-9, while that for the wild type XynB enzyme was 0.8-1.2.

Figure 1C:
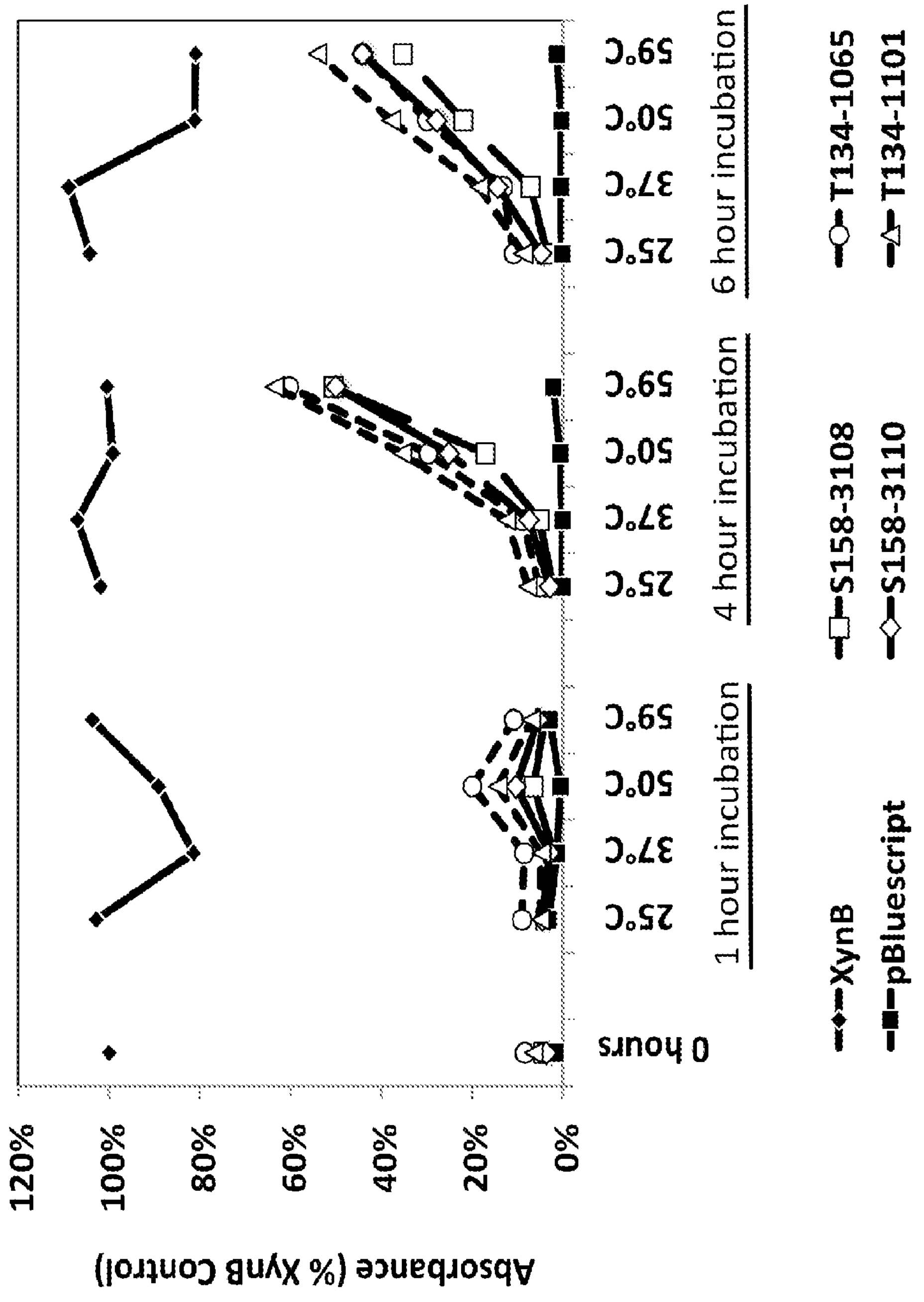

Referring to FIG. 1*c*, the heat treatment temperature and time that yielded the maximum FI was established by following the time course of intein splicing using the activity assay. Bacterial cell lysates from several candidates were either unheated (control samples at 25° C.) or heated at 37° C., 50° C. and 59° C. for 1, 4 and 6 hours without substrate. Samples were cooled on ice and then incubated with AZCL-xylan at 37° C. for 2 hours. Hydrolyzed product was measured as 590 nm absorbance. Lysate from cells transformed with pBS and native XynB were used as controls. In the one hour panel, the samples appear from top to bottom as XynB, T134-1065, T134-1101, S158-3110, S158-3108, and pBluescript. In the four hour panel, the samples appear from top to bottom as XynB, T134-1101, T134-1065, S158-3110, S158-3108, and pBluescript. In the six hour panel at 50° C., the samples appear from top to bottom as XynB, T134-1101, T134-1065, S158-3110, S158-3108, and pBluescript. As shown in FIG. 1*c*, most candidates achieved a peak activity at approximately 4 hours and 59° C. In some candidates, the maximum recovered activity from iXynB reached ≥60% that of the native XynB, whereas the baseline activity (37° C., 4 hours heat treated) was ≤10%. Heat treatment beyond the optimal heating time or temperature often reduced activity below the optimum fold induction (FI).

Figure 1D:
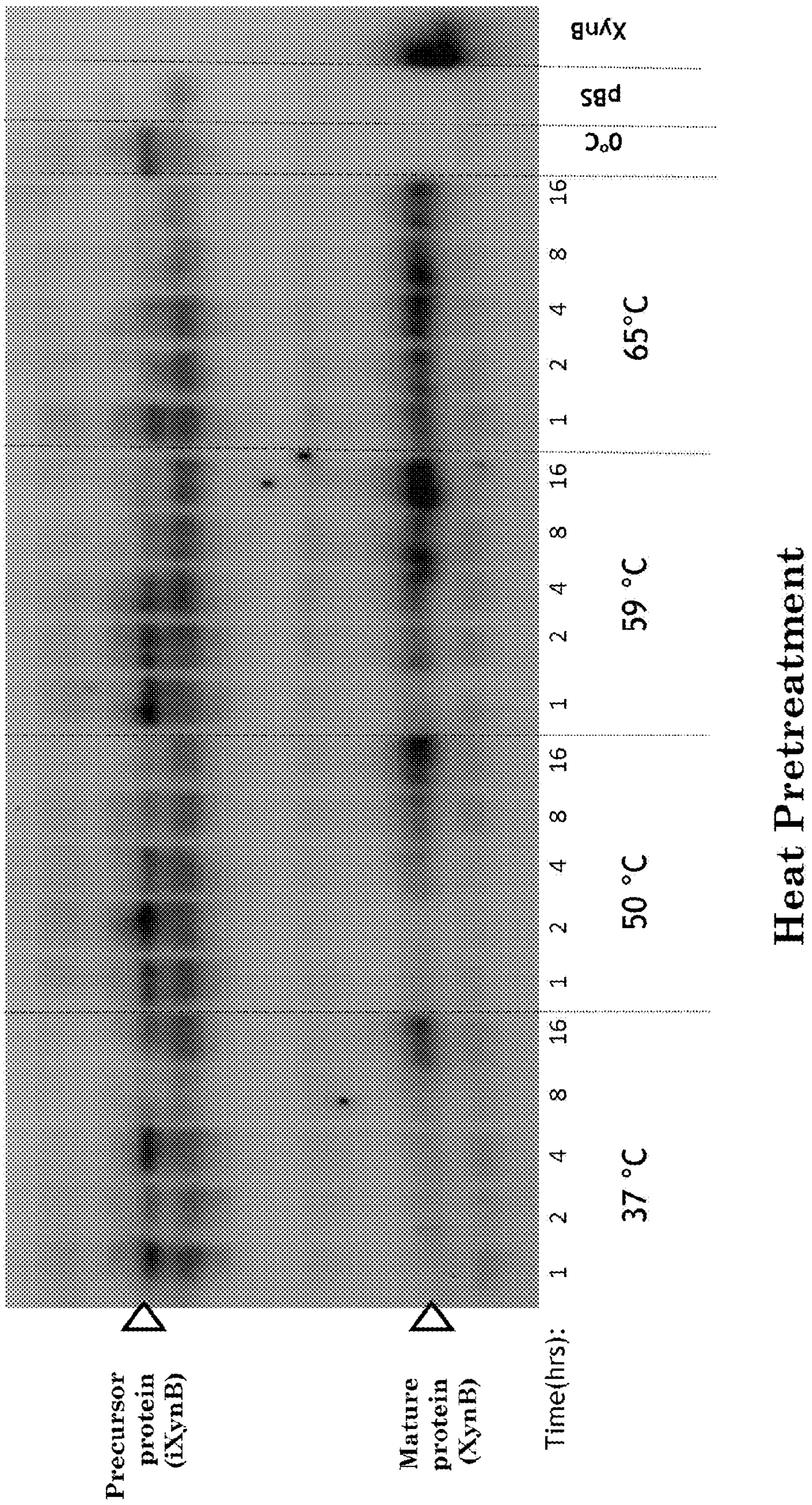

Referring to FIG. 1*d*, the time course of FI was correlated with the time course of intein splicing in selected candidates to investigate whether intein splicing may cause the thermoregulated xylanase activity. A western blot was used to assess intein splicing of Tth iXynB candidates. FIG. 1D illustrates a representative blot of S158-3103 following heat treatment of lysate at 37° C., 50° C., 59° C. and 65° C. for 1, 2, 4, 8, and 16 hours. Unheated sample and lysate from cells transformed with pBluescript (pBS) and native XynB were used as controls. Arrows indicate the S158-3103 iXynB candidate (precursor protein) and intein spliced, mature XynB (mature protein). Cell lysates were heated for different times and temperatures, and analyzed by western blot using anti-XynB antibody. FIG. 1D shows progressive accumulation of the mature protein during heat treatment and a proportional decrease of the Tth iXynB precursor, which is consistent with heat inducible splicing. Of 103 candidates tested, 76 showed heat inducible splicing that correlated with the heat inducible enzyme activity under the conditions tested.

Sequences were examined to better understand the molecular basis of the thermoregulated activity and splicing in the Tth iXynB clones. The sequence of 67 candidates with an FI≥3 that displayed detectable precursor protein from unheated samples and spliced mature XynB from heated samples on a western blot was examined. Referring to FIG. 2*a*, multiple mutations were observed, but all of these candidates shared mutations in one of four amino acids. Four amino acids were recovered at high frequency in the mutated candidates and each was sufficient for temperature sensitive intein splicing. Two mutations (R51 and P71) occur within the intein and two mutations (S135 and P136) occur in the C-extein near the intein insertion site. Mutation R51 was recovered only in candidates in which the Tth intein was inserted before S158 of XynB, the other three mutations were recovered only in candidates in which Tth was inserted in front of T134 of XynB. The T134 extein sequences are underlined and bolded, the S158 extein sequences are underlined, and key mutations are underlined, bolded and italicized (the first R in GVREVVRL, the second P in VLTPDHPL, and the S in SLGQ). The numbering 1-423 corresponds to the intein, with the first cysteine amino acid as number one, and the last asparagine as number 423. The insertion site amino acids, T134 and S158, are denoted by superscripts indicating the amino acid number in native XynB. Mutations observed in the intein, as referenced from the first amino acid of the Tth intein, were R51G (recovered 16 times or 16×) or R51S (4×) when inserted at site S158; while P71L (7×), P71T (2×), or P71Q (1×) were found when the Tth intein was inserted at site T134. The rest of the mutations, S135V (11×), S135G (1×), S135R (1×), or P136 insertions (24×), were found on the C-extein (+2 and +3 position, respectively) when the Tth intein was inserted at T134 site of XynB. As a control to see whether any of these mutations occurred in candidates that did not show thermoregulated splicing, more than 30 random clones with FI<2 were sequenced and although other mutations were identified, none of the random clones had mutations at R51, P71, S135, or a P136 insertion. Furthermore, candidates carrying mutations in one of the four conserved positions were recovered independently from seven distinct mutagenized intein stocks used to make iXynB libraries, arguing against potential biases due to PCR amplification and cloning effects.

Site-directed mutagenesis was conducted to further test the importance of these amino acids in the thermoregulation of Tth iXynB activity and splicing. When each of the R51G, R51S, P71L, and P136 (insertion) mutations were inserted into an otherwise non-mutagenized iXynB, increased thermoregulated activity (FI≥2) and intein splicing was observed. Among all combinations of mutations tested, the only single mutations that showed FI≥3 were mutation R51G when Tth was inserted at S158, and the P136 insertion when Tth was inserted at T134.

Figure 2B:
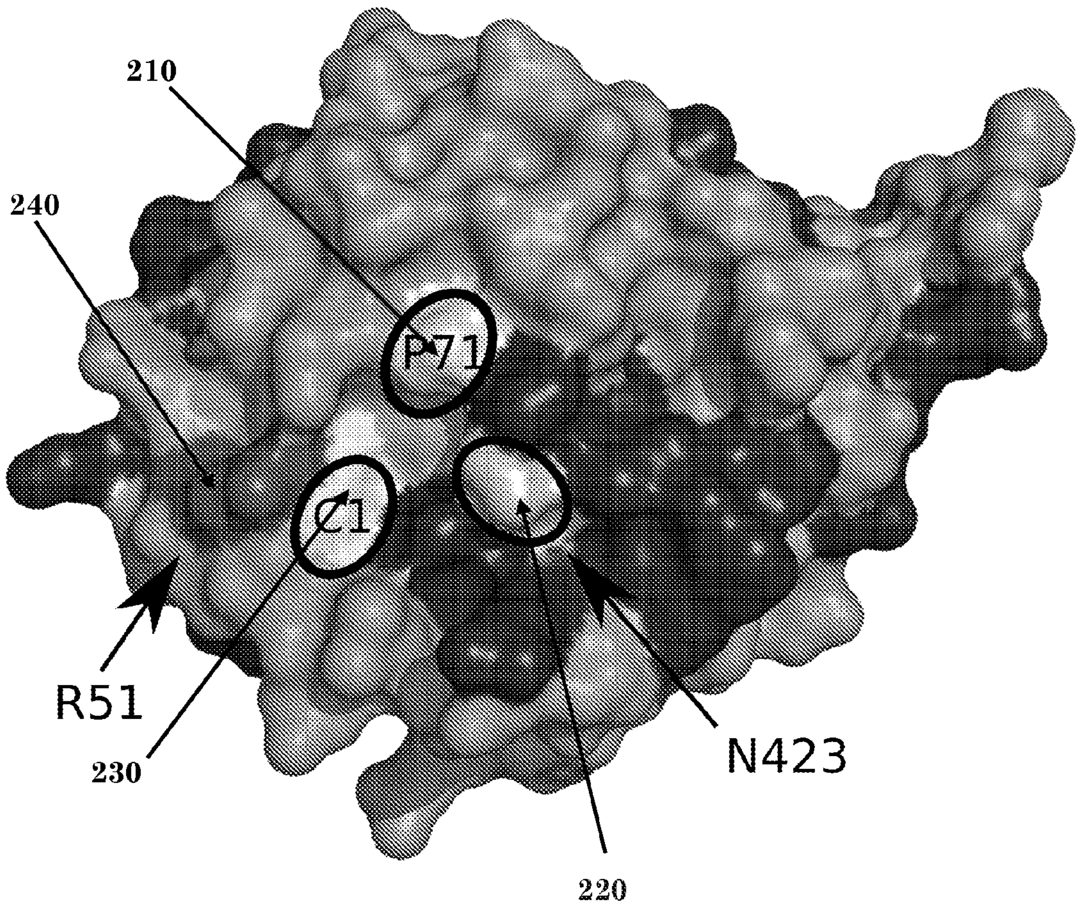

For Tth iXynB candidates that possessed thermoregulated activity and intein splicing using the T134 insertion site, the S135 and P136 mutations occur in the C-extein adjacent to the splice junction (+2 and +3 position, respectively), consistent with the finding that neighboring extein amino acids affect intein activity (Amitai et. al., 2009). Conversely, R51 and P71 mutations reside within the intein, distant from their splice sites in the primary protein chain (FIG. 2A). Referring to FIG. 2B, which shows a predicted intein secondary structure, R51 and P71 both map in close proximity to the intein-extein junction with R51 within 3.3 angstroms of the amino-terminal residue of the inserted intein, while P71 lies within 5.6 angstroms of the carboxy-terminal residue of the intein. In FIG. 2B, a structural model of the Tth intein shows the position of the key amino acids in relation to the splicing junction. R51 (reference 240, left of center in the figure) is in close proximity to C1 (reference 230, to the right of R51 in the figure) the first amino acid of the Tth intein. P71 (reference character 210, above center in the figure) is in close proximity to N423 (reference 220, near center in the figure) and the last C-terminal amino acid of Tth. Both R51 and P71 are aligned close to the amino acids that are directly involved in intein splicing. The spatial positioning of these mutations in the predicted folded structure of the iXynB precursors may enable them to interact with the junction site amino acids in a thermoregulated manner. Placing the R51G mutation in the Tth intein inserted at the T134 position, or introducing the P71L mutation in the Tth intein inserted at the S158 site resulted in the loss of heat inducible switching and splicing (data not shown), suggesting that intein mutations and functionality are context specific. Combining two mutations, R51G and P71L, in one intein also resulted in loss of heat inducible switching and splicing at both sites.

Figure 3:
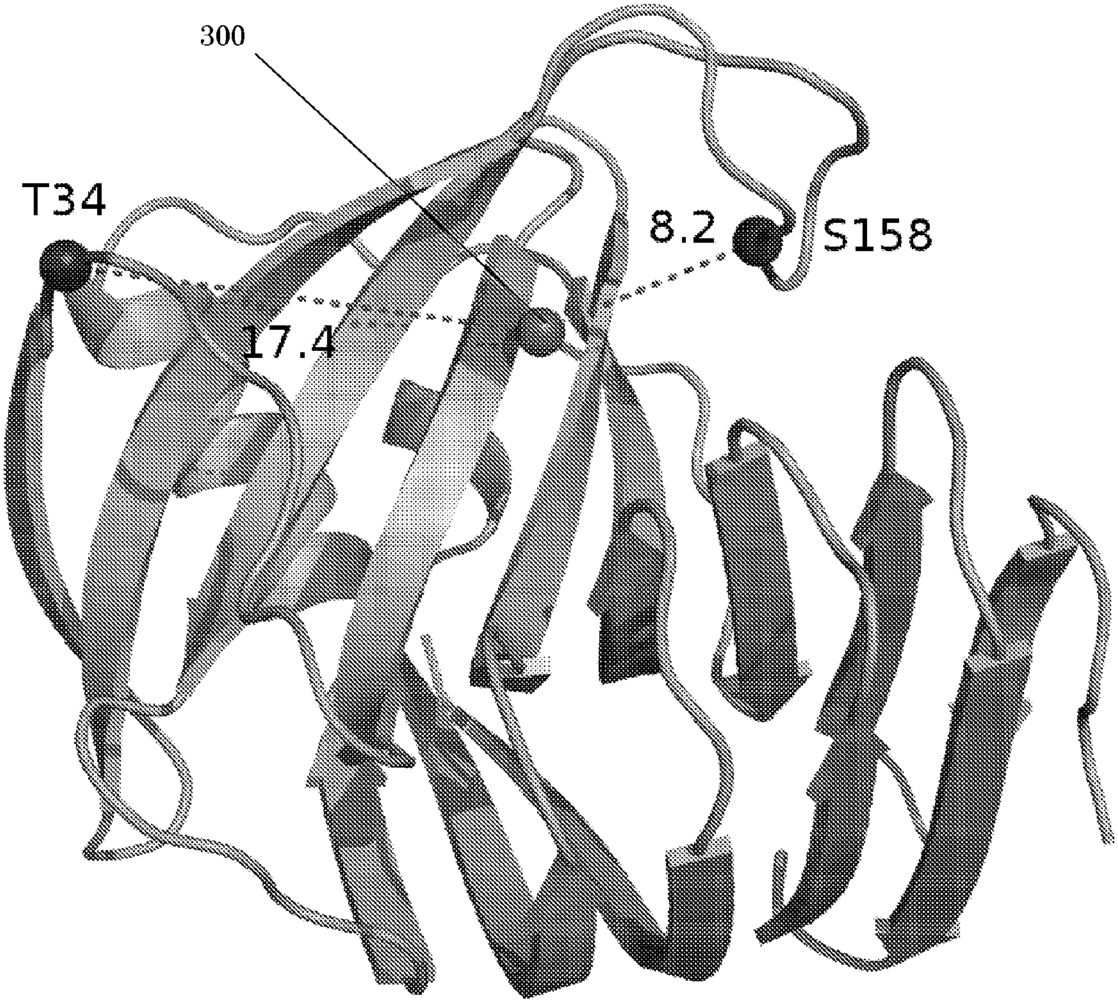
FIG. 3 illustrates Tth intein insertion sites S158 and T134 relative to the nearest active site groove amino acid of XynB.

Referring to FIG. 3, further analysis of the XynB crystal structure reveals that the T134 residue is located at the surface, approximately 17.4 angstroms from the groove of the closest active site residue of XynB, while the S158 residue is located directly on the top of the groove and only 8.2 angstroms away from the active site. In FIG. 3, balls T34 and S158 represents the Tth intein insertion sites in XynB, while ball 300 denotes the closest active site residue of XynB. Note substrate binding site in XynB. The distance of the T134 residue to the active site suggests that an intein insertion may only partially block substrate binding, whereas insertion before the S158 residue could impose a nearly complete block to substrate binding. The much lower baseline activities of S158 candidates compared to those of the T134 candidates (FIG. 1B) is consistent with this hypothesis.

Figure 4A:
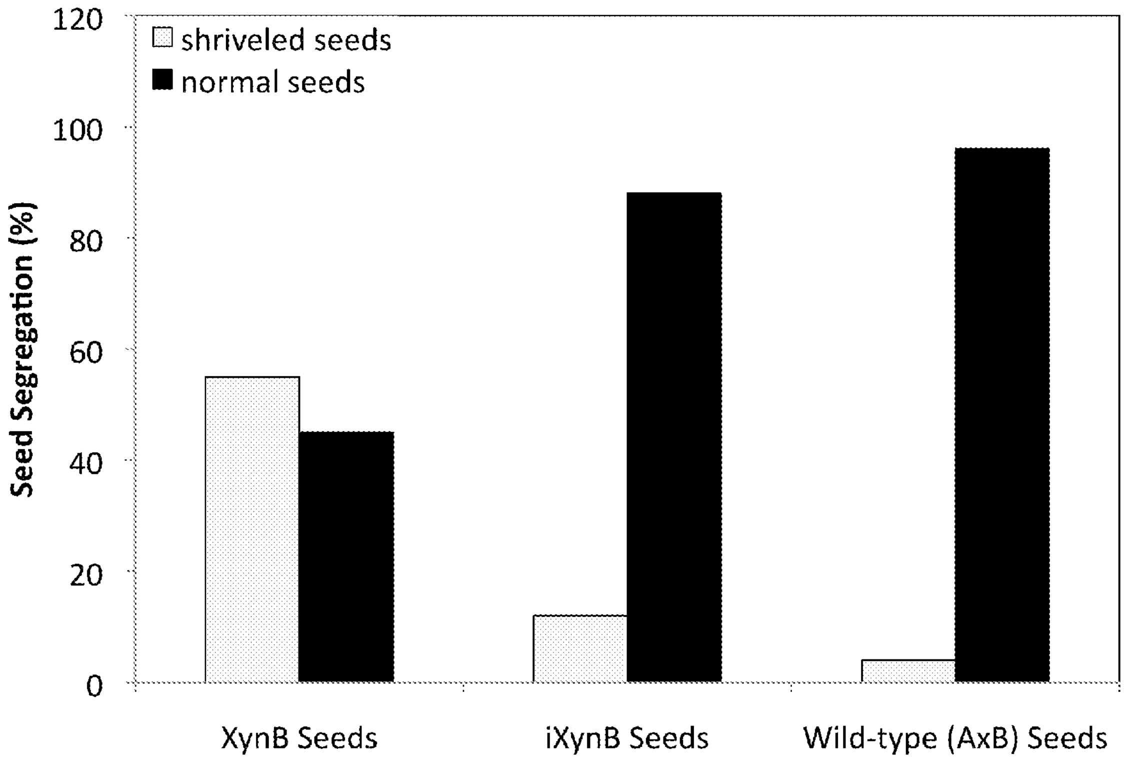
FIGS. 4A-E illustrate effects of native XynB and iXynB on seed development, activity, and germination.

To test the utility of the thermoregulated iXynB as a cellulosic processing trait, the dormant iXynB precursor enzyme was expressed in maize, fused to the barley alpha amylase signal sequence (BAASS) for cell wall targeting (Rogers, 1985), from the constitutive rice Ubi3 gene promoter (Sivamani and Qu, 2006). In transgenic plants expressing native XynB, a severe shriveled seed phenotype was observed, whereas no such phenotype was found in plants expressing iXynB. Transgenic plants expressing the native XynB and the iXynB were crossed with wild-type (A×B) maize lines. Referring to FIG. 4*a*, cobs from plants expressing native XynB were poorly developed, bearing kernels that segregated with shriveled (55.3% of grain, 57±28 mg per grain) and normal (44.7% of grain, 184±39 mg per grain) phenotypes. This phenotype segregated with the presence of the transgene in 83% of cases as determined by PCR based genotyping. FIG. 4A illustrates experiments where Seeds from transgenic plants expressing native XynB (n=535) and Tth iXynB (n=610), and wild-type (A×B, n=269) were scored as normal or shriveled. The fraction of normal and shriveled seeds, over total number of seeds was calculated.

Figure 4B:
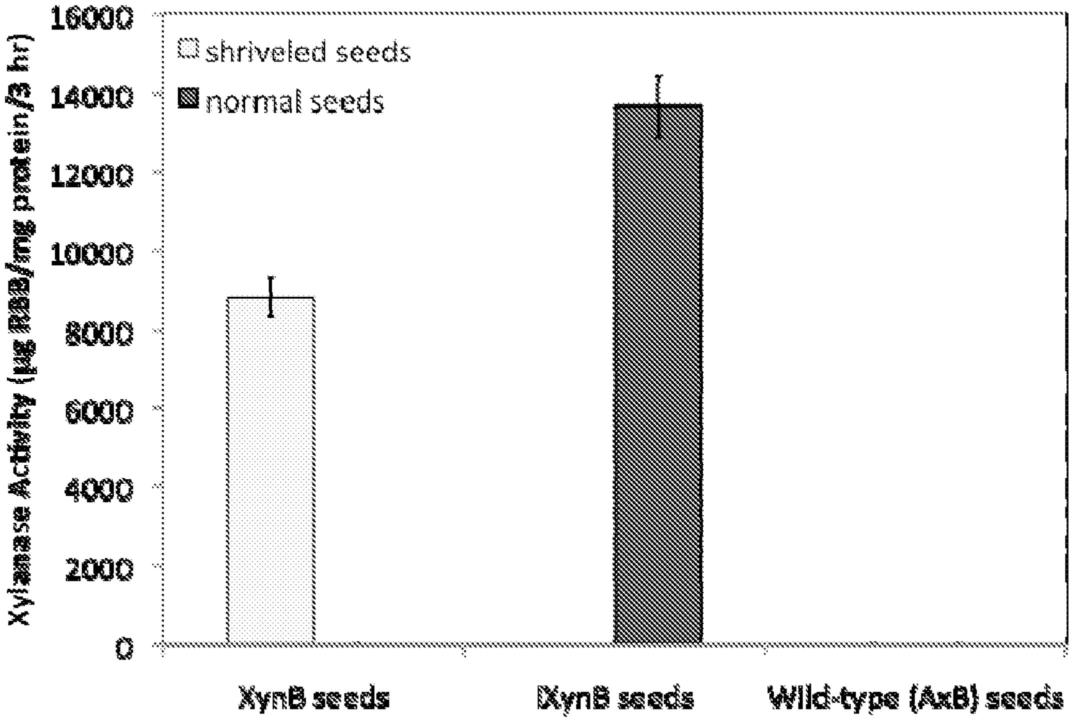
Figure 4C:
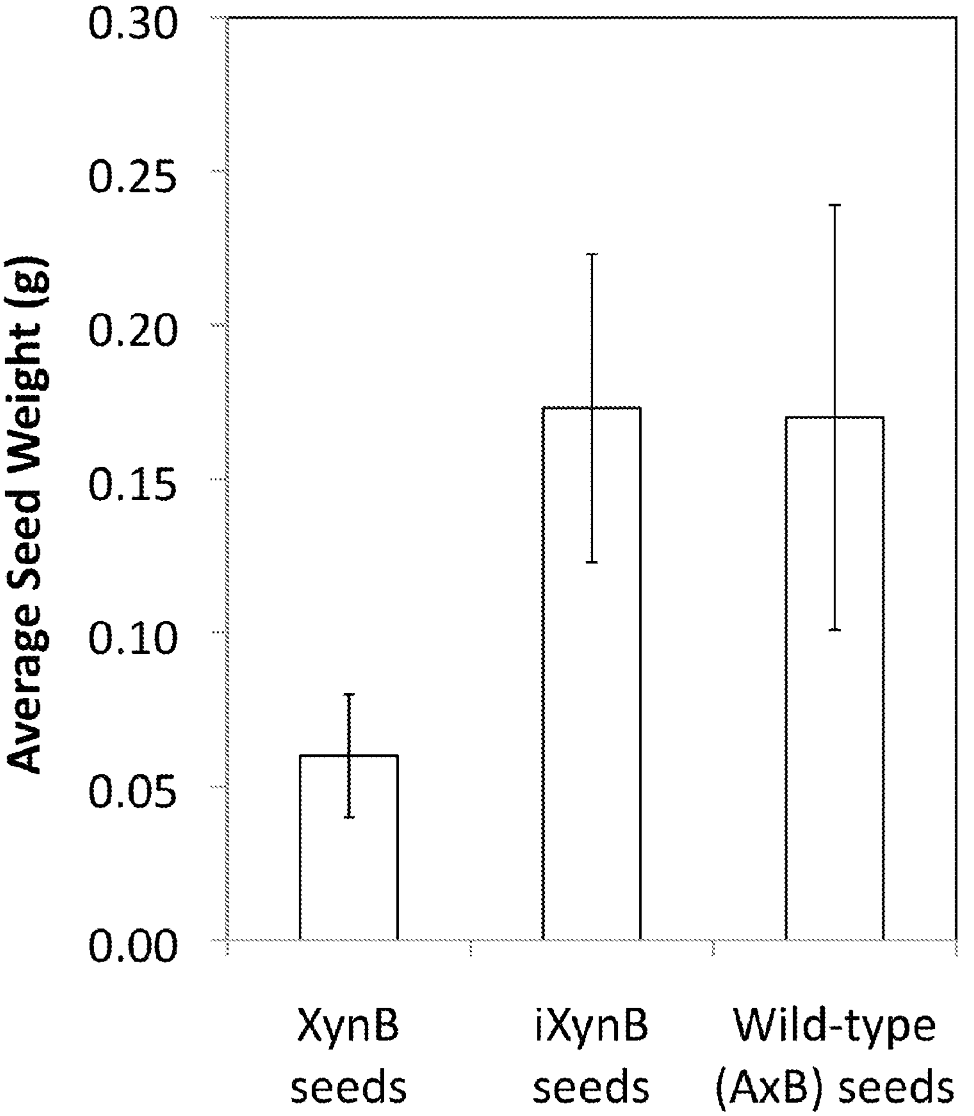
Figure 4D:
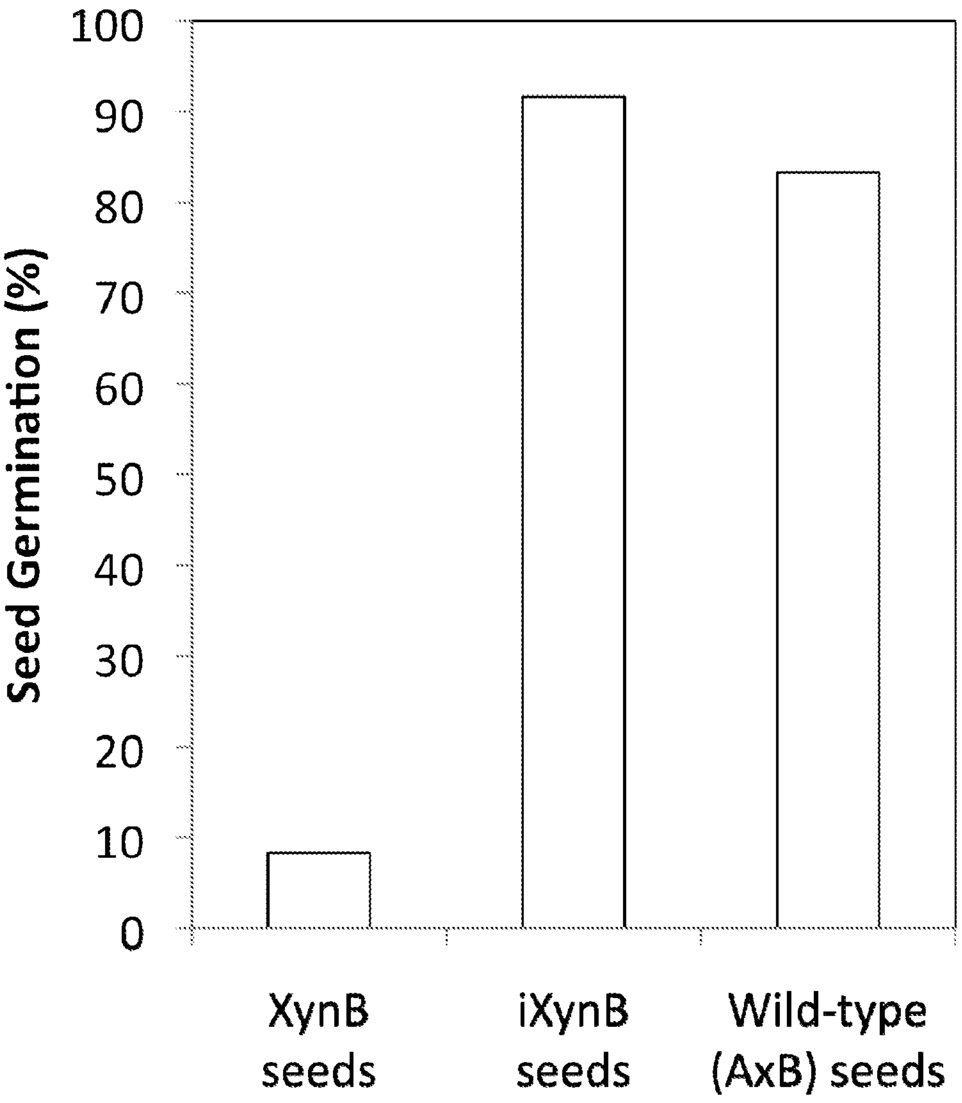
Figure 4E:
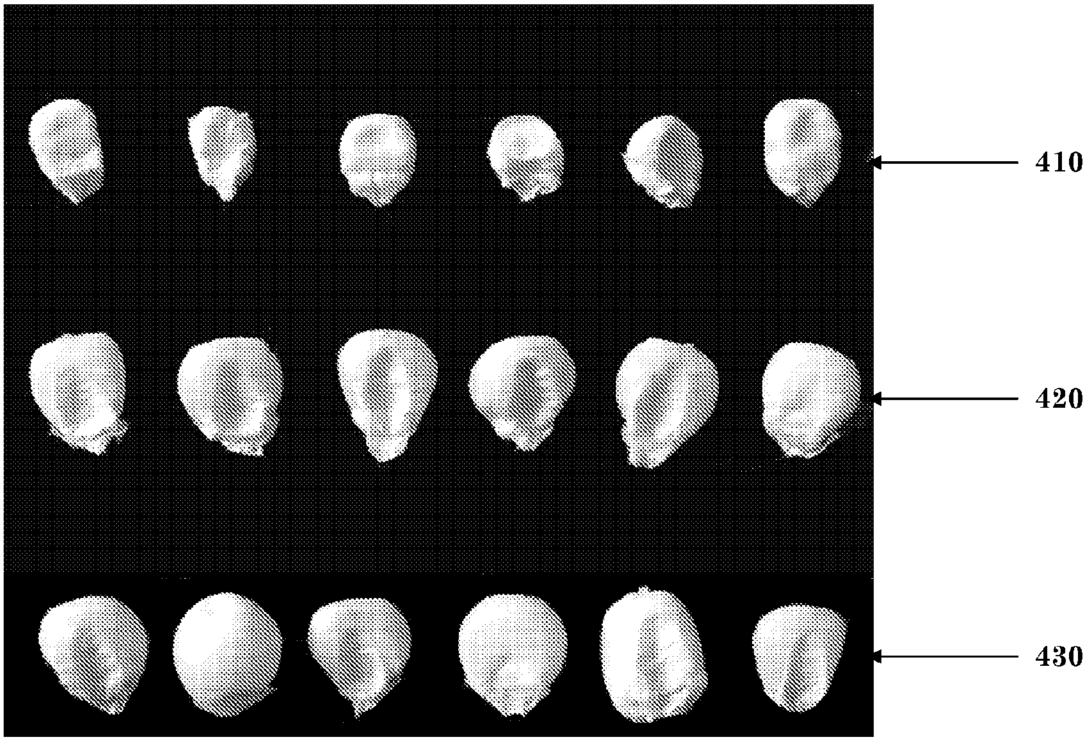

Referring to FIG. 4C, seed biomass was assessed. Seeds expressing native XynB (shriveled), iXynB (normal), wild-type (A×B, normal) were scored for presence or absence of the transgene and weighed. Average mass per seed was plotted. In contrast to the plants expressing native XynB, described above, plants expressing the iXynB yielded normal cobs with normal kernels (88.3% of grain, 174±49 mg per grain), similar to the A×B control plants (96% of grain, 170±69 mg per grain). Referring to FIG. 4*d*, seed germination was assessed. Seeds (n=12) from plant expressing native XynB, Tth iXynB and from wild type (A×B) plants were germinated on wet papers and germinated seeds were scored. Transgenic seeds encoding native XynB germinated poorly (8.3%) compared with transgenic seeds encoding iXynB (91.7%), or non-transgenic, wild-type (A×B) seeds (83.5%). Referring to FIG. 4E, seed morphology was assessed. Seeds 410 from transgenic plants expressing native XynB and seeds 420 form transgenic plants expressing iXynB were compared to seeds 430 from control plants (A×B). All seeds were photographed at the same magnification. As shown, seeds expressing XynB were shriveled, while seeds expressing iXynB were normal.

Referring to FIG. 4B, seeds were scored for presence or absence of the transgene and three seeds for each class were assayed for xylanase activity. Average xylanase activity is plotted. Xylanase activity was detectable in protein extracts from shriveled kernels possessing the xynB gene, whereas wild-type kernels from the same cob did not have activity. Kernels carrying the iXynB gene appeared normal, but following a 60° C. heat treatment displayed xylanase activity (13,638±794 μg RBB/mg protein/180 minutes; see supplemental online methods) at levels comparable to that of shriveled kernels from native XynB expressing plants (8,793±489 μg RBB/mg protein/180 minutes).

Figure 5A:
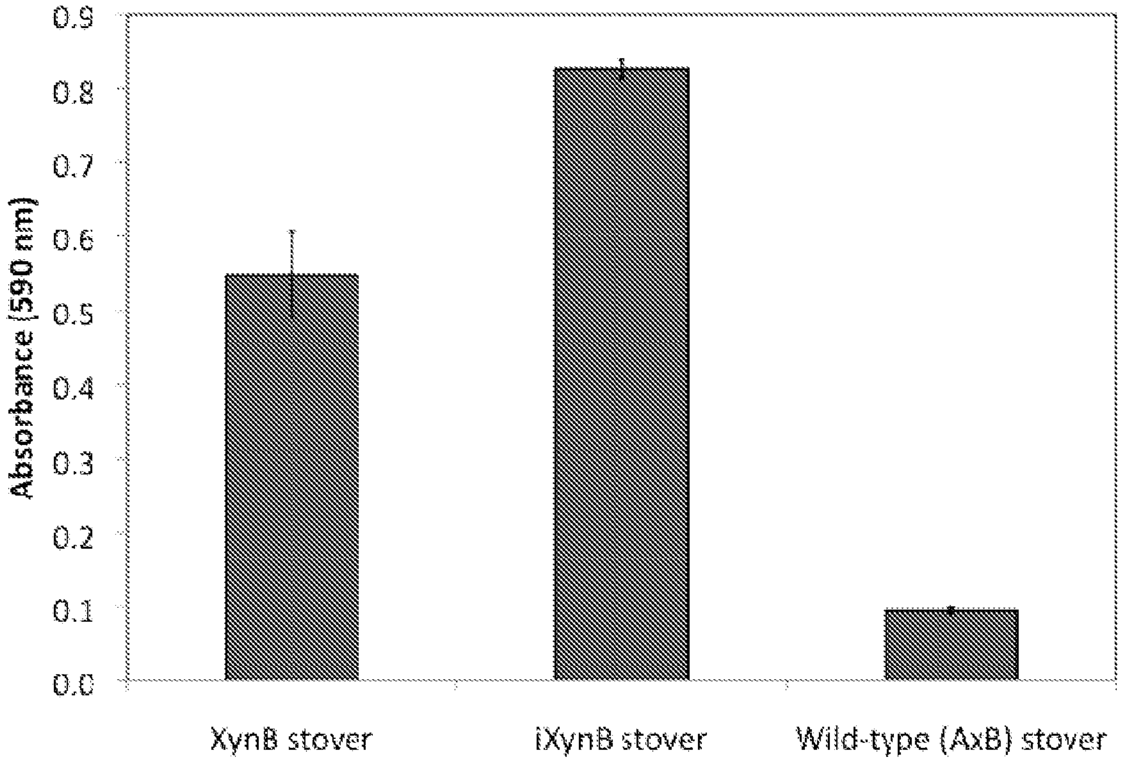
FIGS. 5A-B illustrate xylanase activity and glucose release from corn stover expressing native and intein-modified iXynB.

Referring to FIG. 5A, xylanase activity in corn stover was assessed. Stover samples (15 mg) from transgenic plants expressing XynB and iXynB, and wild-type (A×B) plants, was suspended in 500 uL protein extraction buffer, then incubated at 60° C. for 4 hours with one xylazyme tablet (Megazyme). Triplicate reactions were stopped by adding 1 mL of 2% Tris base, then absorbance at 590 nm was read for 10 mL of each reaction in 90 uL water. The average of the three highest expressing plants was plotted. The iXynB was tested as the basis for a cellulosic processing trait in hydrolysis of dried, transgenic maize stover. Stover samples from multiple transgenic events were assayed for xylanase activity and those showing representative xylanase activity were selected.

Figure 5B:
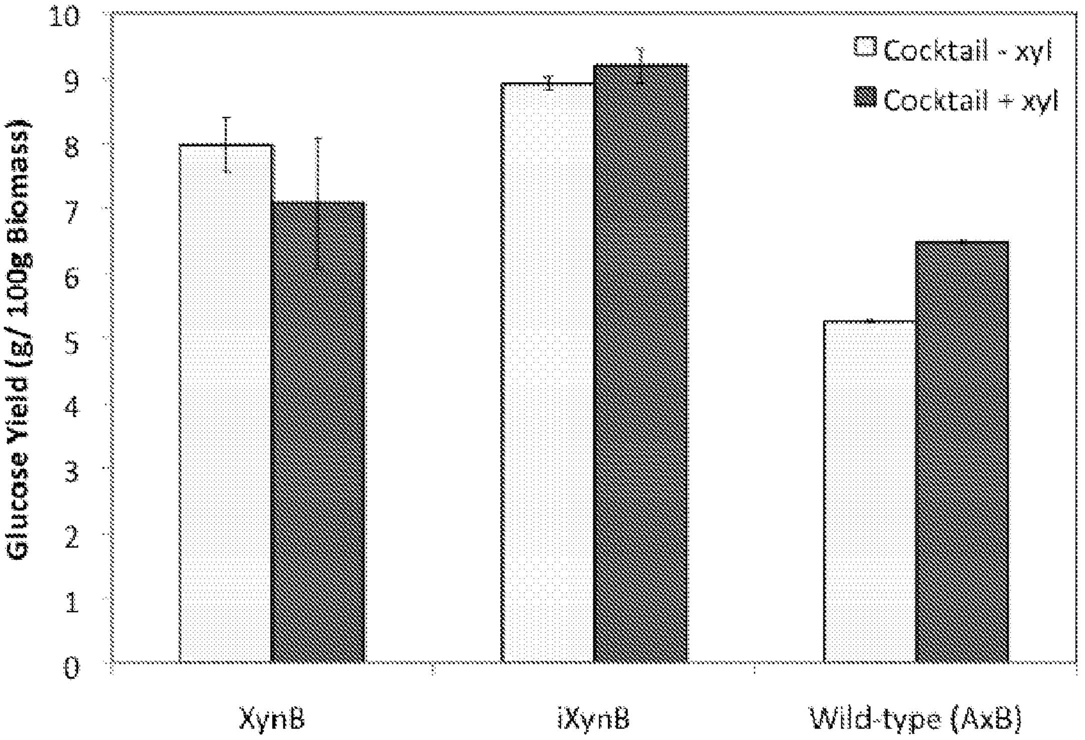

Referring to FIG. 5*b*, glucose release from corn stover was analyzed. After a simple water pretreatment of the corn stover samples, the solids were hydrolyzed using enzyme cocktails, with or without a xylanase (50° C. for 48 hours), after which the glucose yield was determined. In particular, corn stover (20 mg) from plants expressing XynB and iXynB, and wild-type (A×B) plants were heat treated and glucose release (g/100 g corn stover) was measured after incubation with enzyme cocktails with (cocktail with external xylanase) and without (cocktail without xylanase) externally added xylanase. Stover samples expressing the native XynB or the Tth iXynB showed improved hydrolysis compared with control stover from the wild type (A×B) plants. Whereas external xylanase (0.3 μM) enhanced glucose yield by 23.0% from wild type (A×B) plants, stover from iXynB plants had improved glucose release relative to wild type (A×B) plants by over 41%, with or without the use of external xylanase (0.3 μM). Increases in glucose production during hydrolysis therefore correlated with xylanase activity present in the stover samples used. The intein-modified enzyme rescued and protected the seed phenotype, thus preventing grain loss, and retained xylanase activity in seed and stover. The xylanse activity could be recovered after heat treatment. These results show that a iXynB may be provided as a cellulosic processing trait and a novel method to control CWD enzyme activity.

Example 2

The xynB xylanase, without its native signal peptide, and Tth-HB27 DnaE1 intein coding regions were codon optimized for expression in maize (Codon Devices, Cambridge, Mass.). The intein was inserted to the target gene by overlapping PCR of the N-extein, intein, and C-extein fragments. For mutagenesis, 5 μg of plasmid DNA encoding the target sequences was amplified in 10 PCR cycles using the GeneMorph II Random Mutagenesis Kit (Stratagene). PCR products were digested and ligated into the precut lambda ZAP II vector. Packaging and phage handling were conducted according to the manufacturer's protocols (Stratagene). Phage-infected XL1-Blue MRF' cells were grown on NZY plates containing IPTG (2.5 mM) and 0.2% AZCL-xylan oat (Megazyme) substrate.

Example 3

Xylanase activity assays were performed with phagemid rescued clones in SOLR *E. coli* cells (Agilent Technologies). Overnight cultures were grown in 96-well plates in AIM (Novagen) and lysed in 1× FastBreak lysis buffer (Promega). Lysate was split, heat treated, and then cooled on ice. After incubation with AZCL-xylan (37° C.), xylanase activity was measured at 590 nm on a Paradigm plate reader. Data are reported as the mean and s.d. Western blotting followed standard procedures.

Example 4

Structural models of the Tth iXynB were generated by inserting the homology model of the Tth intein into an X-ray crystal structure of the XynB catalytic domain (pdbID 1f5j) using the domain insertion module of Rosetta++v2.3 (Berrondo, M., et. al., 2008; Rohl et. al., 2005; Rohl et. al, 2004; Kuhlman, et. al., 2003, which is incorporated herein by reference as if fully set forth).

Example 5

Plant expression vectors were based on the "super-binary" system (Hiei et. al., 1994; Ishida et. al., 1996; Hiei et. al., 2006; Komari et. al., 1996, which is incorporated herein by reference as if fully set forth) and transformed in maize as described (Negrotto, D., Jolley M., Beer s., Wenck A. R., Hansen G. The use of phosphomannose-isomerase as a selectable marker to recover transgenic maize plants (*Zea mays* L.) via *Agrobacterium* transformation. Plant Cell Reports (2000)19:798-803, which is incorporated herein by reference as if fully set forth). Seed germination was done on wet paper. Stover hydrolysis was conducted using a three-step procedure including a 16 hour pretreatment in water at 55° C., a 24 hour autolysis at 55° C., and a 48 hour incubation in enzyme cocktails with or without xylanase addition at 50° C. Glucose release was quantified as described (NREL Laboratory Analytical Procedure (LAP) technical report (NREL/TP-510-42623): A. Sluiter, B. Hames, R. Ruiz, C. Scarlata, J. Sluiter, and D. Templeton, "Determination of Sugars, Byproducts, and Degradation Products in Liquid Fraction Process Samples," which is incorporated herein by reference as if fully set forth).

Example 6

Xylanase cloning and expression. *Dictyoglomus thermophilum* XynB xylanase (accession number P77853) was maize-codon optimized, synthesized (Codon Devices) and polymerase chain reaction (PCR) amplified. The sequence of the maize-codon optimized P77853 is set forth below. The xynB gene encoding the native XynB protein, without the nucleotides encoding amino acids 2-24 of N-terminal signal peptide, was cloned into the EcoRI and XhoI sites of the lambda ZAP®II vector following manufacturer's protocol (Stratagene). Phage-infected XL1-Blue MRF' *E. coli* cells were plated out on NZY agar plates containing 2.5 mM IPTG (Research Products International, Corp.) and 0.2% AZCL-xylan oat substrate (Megazyme). After overnight incubation at 37° C., plates were visually inspected for the development of blue color in and around phage plaques, indicative of xylanase activity.

```
XynB (P77853) maize codon-optimized sequence.
                                                        (SEQ ID NO: 31)
ATGCAAACAAGCATTACTCTGACATCCAACGCATCCGGTACGTTTGACGGTTACTATTACGAA

CTCTGGAAGGATACTGGCAATACAACAATGACGGTCTACACTCAAGGTCGCTTTTCCTGCCAG

TGGTCGAACATCAATAACGCGTTGTTTAGGACCGGGAAGAAATACAACCAGAATTGGCAGTCT

CTTGGCACAATCCGGATCACGTACTCTGCGACTTACAACCCAAACGGGAACTCCTACTTGTGT

ATCTATGGCTGGTCTACCAACCCATTGGTCGAGTTCTACATCGTTGAGTCCTGGGGGAACTGG

AGACCGCCTGGTGCCACGTCCCTGGGCCAAGTGACAATCGATGGCGGGACCTACGACATCTAT

AGGACGACACGCGTCAACCAGCCTTCCATTGTGGGGACAGCCACGTTCGATCAGTACTGGAGC

GTGCGCACCTCTAAGCGGACTTCAGGAACAGTGACCGTGACCGATCACTTCCGCGCCTGGGCG

AACCGGGGCCTGAACCTCGGCACAATAGACCAAATTACATTGTGCGTGGAGGGTTACCAAAGC

TCTGGATCAGCCAACATCACCCAGAACACCTTCTCTCAGGGCTCTTCTTCCGGCAGTTCGGGT

GGCTCATCCGGCTCCACAACGACTACTCGCATCGAGTGTGAGAACATGTCCTTGTCCGGACCC

TACGTTAGCAGGATCACCAATCCCTTTAATGGTATTGCGCTGTACGCCAACGGAGACACAGCC

CGCGCTACCGTTAACTTCCCCGCAAGTCGCAACTACAATTTCCGCCTGCGGGGTTGCGGCAAC

AACAATAATCTTGCCCGTGTGGACCTGAGGATCGACGGACGGACCGTCGGGACCTTTTATTAC

CAGGGCACATACCCCTGGGAGGCCCCAATTGACAATGTTTATGTCAGTGCGGGGAGTCATACA

GTCGAAATCACTGTTACTGCGGATAACGGCACATGGGACGTGTATGCCGACTACCTGGTGATA

CAGTGA
```

Phage lysates were produced using XL1-Blue MRF' *E. coli* cells following standard protocol (Stratagene). Xylanase activity from each lysate was measured either by using Enzchek® kit (Invitrogen™) or by adding AZCL-xylan substrate to 0.2%, incubating at 37° C. for up to 4 hr, and measuring the absorbance at 590 nm.

Example 7

Insertion of Tth intein into xynB. The Tth intein from *T. thermophilus* was optimized for maize codon usage (SEQ ID NO: 32, below), synthesized (Codon Devices), and inserted into xynB at 5'-side of selected cysteine, serine, or threonine codons using overlapping PCR. Briefly, three pieces of DNA representing the N-extein (N) and C-extein (C) of xynB, and the Tth intein (I), were PCR amplified using primers that overlapped the adjacent DNA fragment. These individual pieces of DNA were then assembled in a single PCR reaction using an N-extein sense primer and a C-extein antisense primer to generate intein-modified xynB gene constructs (referred to herein as a NIC). The 5'-end of the XynB N-extein primer included an EcoRI restriction site and the XynB C-extein reverse primer included the XhoI restriction site. NICs were gel purified using a QIAquick Gel Extraction kit (Qiagen), digested with EcoRI and XhoI restriction enzymes (New England Biolabs), the resulting DNA fragment was gel purified using a QIAquick Gel Extraction kit (Qiagen). Purified NIC was ligated into the EcoRI and XhoI sites of precut lambda ZAP®II vector and packaged into phage with a package extract following the manufacturer's procedure (Stratagene).

```
Tth intein sequence (SEQ ID NO: 32):
TGCCTGGCCGAGGGCTCGCTCGTCTTGGACGCGGCTACCGGGCAGAGGGTCCCTATCGAAAAG

GTGCGTCCGGGGATGGAAGTTTTCTCCTTGGGACCTGATTACAGACTGTATCGGGTGCCCGTT

TTGGAGGTCCTTGAGAGCGGGGTTAGGGAAGTTGTGCGCCTCAGAACTCGGTCAGGGAGAACG

CTGGTGTTGACACCAGATCACCCGCTTTTGACCCCCGAAGGTTGGAAACCTCTTTGTGACCTC

CCGCTTGGAACTCCAATTGCAGTCCCCGCAGAACTGCCTGTGGCGGGCCACTTGGCCCCACCT

GAAGAACGTGTTACGCTCCTGGCTCTTCTGTTGGGGGATGGGAACACAAAGCTGTCGGGTCGG

AGAGGTACACGTCCTAATGCCTTCTTCTACAGCAAAGACCCCGAATTGCTCGCGGCTTATCGC

CGGTGTGCAGAAGCCTTGGGTGCAAAGGTGAAAGCATACGTCCACCCGACTACGGGGGTGGTT

ACACTCGCAACCCTCGCTCCACGTCCTGGAGCTCAAGATCCTGTCAAACGCCTCGTTGTCGAG

GCGGGAATGGTTGCTAAAGCCGAAGAGAAGAGGGTCCCGGAGGAGGTGTTTCGTTACCGGCGT

GAGGCGTTGGCCCTTTTCTTGGGCCGTTTGTTCTCGACAGACGGCTCTGTTGAAAAGAAGAGG

ATCTCTTATTCAAGTGCCAGTTTGGGACTGGCCCAGGATGTCGCACATCTCTTGCTGCGCCTT

GGAATTACATCTCAACTCCGTTCGAGAGGGCCACGGGCTCACGAGGTTCTTATATCGGGCCGC

GAGGATATTTTGCGGTTTGCTGAACTTATCGGACCCTACCTCTTGGGGGCCAAGAGGGAGAGA

CTTGCAGCGCTGGAAGCTGAGGCCCGCAGGCGTTTGCCTGGACAGGGATGGCACTTGCGGCTT

GTTCTTCCTGCCGTGGCGTACAGAGTGAGCGAGGCTAAAAGGCGCTCGGGATTTTCGTGGAGT

GAAGCCGGTCGGCGCGTCGCAGTTGCGGGATCGTGTTTGTCATCTGGACTCAACCTCAAATTG

CCCAGACGCTACCTTTCTCGGCACCGGTTGTCGCTGCTCGGTGAGGCTTTTGCCGACCCTGGG

CTGGAAGCGCTCGCGGAAGGCCAAGTGCTCTGGGACCCTATTGTTGCTGTCGAACCGGCCGGT

AAGGCGAGAACATTCGACTTGCGCGTTCCACCCTTTGCAAACTTCGTGAGCGAGGACCTGGTG

GTGCATAAC
```

Example 8

Diagnostic plate screening for xylanase activity. Phage-infected XL1-Blue MRF' cells were plated (2~4×$10^3$ pfu/150 mm plate) on NZY agar plates containing 0.2% AZCL-xylan substrate and 2.5 mM IPTG. After overnight incubation at 37° C., plaques were scored for xylanase activity (manifested as blue color development in and around the plaques), then plates were incubated at 70° C. for up to six hours to identify plaques expressing thermoregulated intein-modified xylanase (see FIG. 1*a*). Based on the blue color development, each plaque was categorized as follows: permissive (blue at 37° C.), non-permissive (no color) and switching (blue only after exposure at 70° C.). Accordingly, the respective intein insertion in the xylanase was categorized as: permissive (intein insertion does not interfere with protein function, or intein is spliced during the overnight incubation at 37° C.), non-permissive (intein insertion interferes with protein function at all conditions tested), or switching (activity is not observed following the overnight incubation at 37° C., but xylanase activity is observed after an additional heat treatment at 70° C.).

Candidate plaques that showed heat inducible blue color development (referred to herein as a "switching phenotype") were isolated and purified. Purified candidate plaques with a repeatable phenotype were individually phagemid rescued into SOLR *E. coli* cells following the manufacture's procedures (STRATAGENE). Candidates are specified by intein insertion site, such as T134 and S158, followed by a number to designate the specific mutant. Lead candidates were analyzed using the xylanase switching activity assay (described below), western blot, and DNA sequence analysis.

Example 9

Xylanase switching activity assay. Cultures expressing native XynB or the iXynB in SOLR cells were inoculated from a single colony and grown in 5 mL of AIM (Novagen) supplemented with Carbenicillin (100 mg/L) and Kanamycin (50 mg/L) at 37° C. for 10 hours and then at 30° C. for 6 h hours in a shaking incubator, at 250 RPM. Cells were harvested at 3000 RPM for 15 min, pellets were resuspended in 250 μl lysis buffer containing 200 mM sodium phosphate pH=6.5, 1× FastBreak Lysis Buffer™ (Promega), and 0.2 μl DNase/mL Benzonase nuclease (Novagen). The lysate was diluted 10-fold in 200 mM sodium phosphate buffer pH=6.5. From the dilutions, 100 μl aliquots were heat pretreated at 25° C.-65° C. for up to 16 hrs and put on ice. Heat pretreated samples were mixed with 0.2 μg fine ground solid substrate of AZCL-xylan oat (Megazyme) and incubated at 37° C. for up to four hours. Samples were vortexed, centrifuged at 4,000 rpm for seven minutes and 50 μl of the supernatants were measured for absorbance at 590 nm on a Thermo Scientific Spectrophotometer. In the validation assays, cultures were grown in 96-well plates, the enzyme assays were performed in 384-well plates and absorbance was read on a BioTek Synergy™ Multi-mode microplate reader. Relative activity to native XynB and standard deviations were calculated from assays of eight independently inoculated replicate cultures.

Example 10

Western blot analysis. Cells were grown, collected and lysed as described above. Total cell lysate was mixed thoroughly and a 1:50 dilution was made using 1×PBS (137 mM NaCl, 2.7 mM KCl, 4.3 mM of $Na_2HPO_4$, and 1.47 mM of $KH_2PO_4$ adjusted to pH 7.4). 50 µl of each dilution was transferred to a sterile centrifuge or PCR tube and heat treated at temperatures and hours as specified.

Example 11

DNA sequencing. All DNA sequencing was performed by Agencourt.

Example 12

Structural Models. The X-ray crystal structure of the XynB catalytic domain was extracted from the PDB (pdbID 1f5j). The intein Tth homology model was generated using Swiss-Model (Arnold et. al., 2006; Kiefer et. al., 2009; Schwede et. al., 2003; Guex & Peitsch, 1997; Peitsch, 1995, which is incorporated herein by reference as if fully set forth) and the Tth intein sequence from GenPept (gi: 46200108, residues 768-1190). Briefly, this sequence was aligned against sequences from the Protein Databank NCBI sequence database using NCBI Blast blastp with defaults parameters. This resulted in hits from the start and end of the sequence. The below sequences are presented in alignments without sequence identifiers (SEQ ID NOs) to preserve positioning of one sequence relative to another. The sequence identifiers for all sequences requiring one in this paragraph and the following paragraph are set forth in the paragraph below the following paragraph.

```
>pdb|2IMZ|A Related structures Chain A, Crystal Structure of Mtu Reca Intein
Splicing Domain
pdb|2IMZ|B Related structures Chain B, Crystal Structure Of Mtu Reca Intein
Splicing Domain
Length = 168
Score = 64.7 bite (156), Expect = 5e-11, Method: Compositional matrix adjust.
Identities = 44/120 (36%), Positives = 57/120 (47%), Gaps = 3/120 (2%)
Query 2     LAEGSLVLDAATGQRVPIEKVRPG---MEVFSLGPDYRLYRVPVLEVLESGVREVVRLRT       58
            LAEG+ + D  TG    IE V  G   + V +   D  L+  PV+    + G R+V+ LR
Sbjct 2     LAEGTRIFDPVTGTTHRIEDVVDGRKPIHVVAAAKDGTLHARPVVSWFDQGTRDVIGLRI       61

Query 59    RSGRTLVLTPDHPLLTPEGWKPLCDLPLGTPIAVPAELPVAGHLAPPEERVTLLALLLGD      118
               G  L  TPDH +LT  GW+    +L  G  +A P      G  AP   RV  LA  L D
Sbjct 62    AGGAILWATPDHKVLTEYGWRAAGELRKGDRVAQPRRFDGFGDSAPIPARVQALADALDD      121

Score = 38.1 bits (87), Expect = 0.006, Method: Compositional matrix adjust.
Identities = 32/117 (27%), Positives = 49/117 (41%), Gaps = 15/117 (12%)
Query 313   LRLVLPAVAYRVSEAKRRSGFSWSEAGRRVAVAGSCLSSGLNLKLPRRYLSR-------H      365
            LR+   A+ +    + K  +   + W  AG         L G  +  PRR+
Sbjct 59    LRIAGGAILWATPDHKVLTEYGWRAAGE--------LRKGDRVAQPRRFDGFGDSAPIPA      110

Query 366   RLSLLGEAFADPGLEALAEGQVLWDPIVAVEPAGKARTFDLRVPPFANFVSEDLVVH        422
            R+   L +A D L  +   ++ +  I   V P  +ARTFDL V      V+E +VVH
Sbjct 111   RVQALADALDDKFLHDMLAEELRYSVIREVLPTRRARTFDLEVEELHTLVAEGVVVH        167
```

Due to the fact that there was not a good hit to the endonuclease domain, the sequence was trimmed to approximate the removal of the endonuclease domain (amino acids 1-102, 379-423), and aligned against the PDB sequence database. This resulted in high scoring alignments of the N- and C-terminal domains of the RecA mini-intein with the Tth intein sequence.

```
>pdb|2IMZ|A related structures Chain A, Crystal Structure of Mtu Reca Intein
Splicing Domain
Length = 168
Score = 74.7 bits (182), Expect = 1e-14, Method: Compositional matrix adjust.
Identities = 54/166 (32%), Positives = 75/166 (45%), Gaps = 17/166 (10%)
Query 2     LAEGSLVLDAATGQRVPIEKVRPG---MEVFSLGPDYRLYRVPVLEVLESGVREVVRLRT       58
            LAEG+ + D  TG    IE V  G   + V +   D  L+  PV+    + G R+V+ LR
Sbjct 2     LAEGTRIFDPVTGTTHRIEDVVDGRKPIHVVAAAKDGTLHARPVVSWFDQGTRDVIGLRI       61

Query 59    RSGRTLVLTPDHPLLTPEGWKPLCDLPLGTPIAVPAEL--------------PVAGHLAD      104
               G  L  TPDH +LT  GW+    +L  G  +A P                +A   L D
Sbjct 62    AGGAILWATPDHKVLTEYGWRAAGELRKGDRVAQPRRFDGFGDSAPIPARVQALADALDD      121
```

-continued

```
Query 105  PGLEALAEGQVLWDPIVAVEPAGKARTFDLRVPPFANFVSEDLVVH           150
           L +   ++ +  I V P  +ARTFDL V      V+E +VVH

Sbjct 122  KFLHDMLAEELRYSVIREVLPTRRARTFDLEVEELHTLVAEGVVVH           167
```

Using this sequence alignment a homology model of Tth (without the endonuclease domain) was constructed using Swiss Model. Sequences in the above comparison are assigned sequence identification numbers as follows:

(SEQ ID NO: 42)
LAEGSLVLDAATGQRVPIEKVRPG---MEVFSLGPDYRLYRVPVLEVLESGVREVVRLRT;

(SEQ ID NO: 43)
LAEG;

(SEQ ID NO: 44)
LAEGTRIFDPVTGTTHRIEDVVDGRKPIHVVAAAKDGTLHARPVVSWFDQGTRDVIGLRI;

(SEQ ID NO: 45)
RSGRTLVLTPDHPLLTPEGWKPLCDLPLGTPIAVPAELPVAGHLAPPEERVTLLALLLGD;

(SEQ ID NO: 46)
TPDH;

(SEQ ID NO: 47)
AGGAILWATPDHKVLTEYGWRAAGELRKGDRVAQPRRFDGFGDSAPIPARVQALADALDD;

(SEQ ID NO: 48)
LRLVLPAVAYRVSEAKRRSGFSWSEAGRRVAVAGSCLSSGLNLKLPRRYLSR-------H;

(SEQ ID NO: 49)
LRIAGGAILWATPDHKVLTEYGWRAAGE--------LRKGDRVAQPRRFDGFGDSAPIPA;

(SEQ ID NO: 50)
RLSLLGEAFADPGLEALAEGQVLWDPIVAVEPAGKARTFDLRVPPFANFVSEDLVVH;

(SEQ ID NO: 51)
ARTFDL;

(SEQ ID NO: 52)
RVQALADALDDKFLHDMLAEELRYSVIREVLPTRRARTFDLEVEELHTLVAEGVVVH;

(SEQ ID NO: 53)
RSGRTLVLTPDHPLLTPEGWKPLCDLPLGTPIAVPAEL--------------PVAGHLAD;

(SEQ ID NO: 54)
PGLEALAEGQVLWDPIVAVEPAGKARTFDLRVPPFANFVSEDLVVH;

(SEQ ID NO: 55)
KFLHDMLAEELRYSVIREVLPTRRARTFDLEVEELHTLVAEGVVVH (SEQ ID NO: 75)
LAEGSLVLDAATGQRVPIEKVRPG;

(SEQ ID NO: 76)
MEVFSLGPDYRLYRVPVLEVLESGVREVRLRT;

(SEQ ID NO: 77)
LRLVLPAVAYRVSEAKRRSGFSWSEAGRRVAVAGSCLSSGLNLKLPRRYLSR;

(SEQ ID NO: 78)
LRIAGGAILWATPDHKVLTEYGWRAAGE;

(SEQ ID NO: 79)
LRKGDRVAQPRRFDGFGDSAPIPA;

(SEQ ID NO: 80)
RSGRTLVLTPDHPLLTPEGWKPLCDLPLGTPIAVPAEL;
and (SEQ ID NO: 81)
PVAGHLAD.

Example 13

Figure 6:
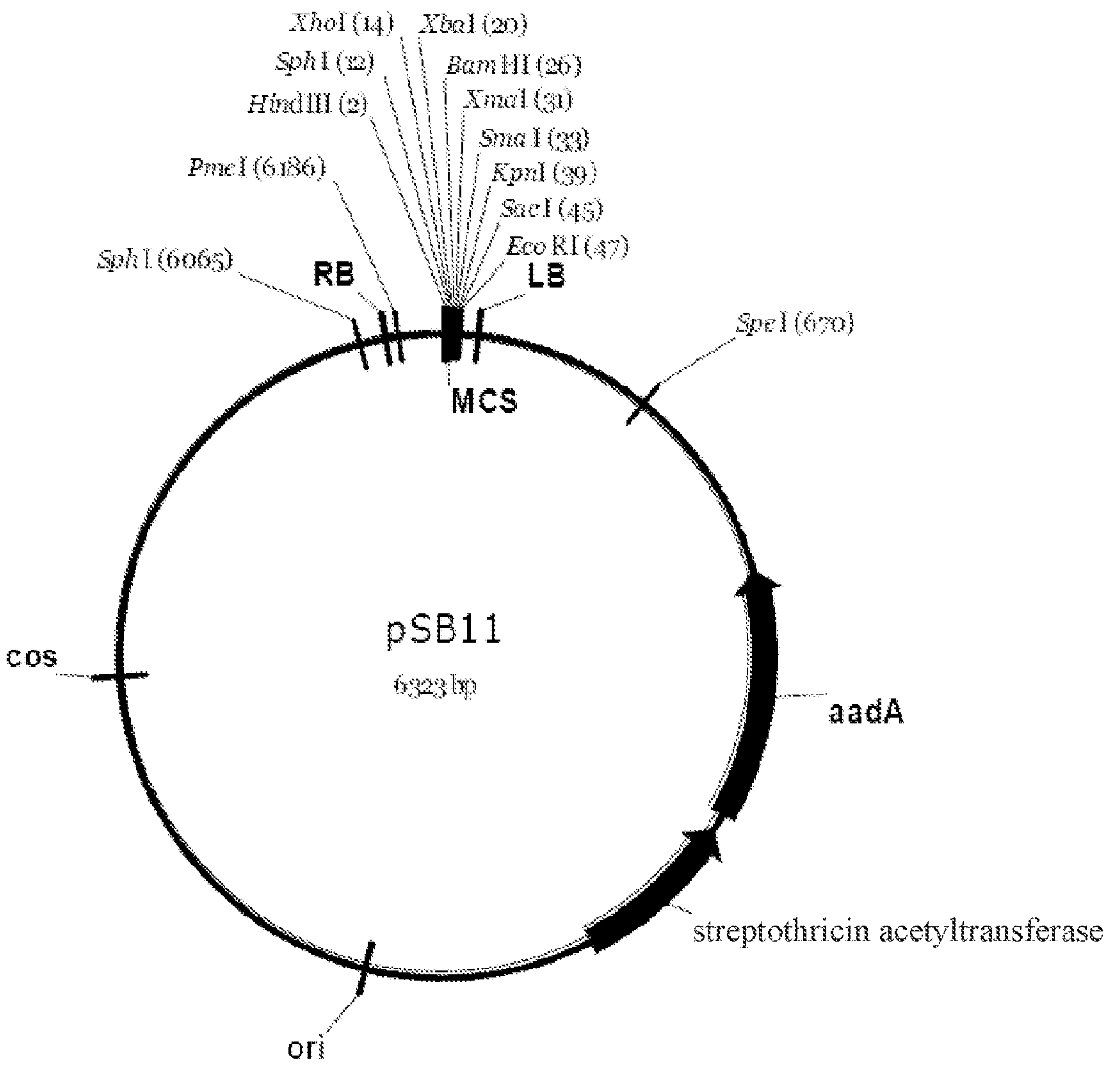
FIG. 6 illustrates the pSB11 plasmid.

Construction of vectors for maize transformation. The cell wall targeting signal sequence of barley alpha amylase (BAASS) was attached to the 5' end of the xynB nucleotide sequence encoding mature XynB protein, using fusion PCR. Native XynB or Tth iXynB were cloned into the intermediate vector pBluescript between the rice Ubi3 promoter (Sivamani & Qu, 2006) and nos terminator sequences. The expression cassette then was cloned into the KpnI-EcoRI sites of pAG2004 to generate a second intermediate vector capable of recombining with the pSB1 vector in triparental mating in *Agrobacterium tumefaciens* strain LBA4404 using procedures reported previously (Hiei et. al., 1994; Ishida et. al., 1996; Hiei et. al., 2006; Komari et. al., 1996).

pAG2004 (SEQ ID NO: 56) is a derivative of pSB11, which is itself a derivative of pBR322 and is available from Japan Tobacco. The pSB11 plasmid, shown in FIG. 6, is suitable for cloning and can be easily maintained in *E. coli*. The pSB11 conjugates with the pSB1 "super-binary" acceptor vector (a disarmed Ti plasmid), which can be maintained in the LB4404 strain of *Agrobacterium tumefaciens*, through homologous recombination using cos and on sites present in both vectors. The integration product represents a hybrid vector that can be subsequently used for plant transformation. The pSB1 contains virulence genes such as virB, virC and virG required for T-DNA processing and delivering to the plant cell. The pSB11 has a multiple cloning site containing unique restriction enzyme recognition sites for cloning expression cassettes with the target gene sequences. pAG2004 has some restriction sites removed in comparison to pSB11, one connection of rice Ubi3 promoter and PMI in HindIII-SpeI, and an altered multiple cloning site. Vector pAG2014 (SEQ ID NO: 57) includes the sequence encoding barley alpha amylase signal peptide (BAASS, SEQ ID NO: 33) fused to P77853 (SEQ ID NO: 19) cloned in pAG2004, and pAG2029 (SEQ ID NO: 58) includes BAASS fused to the sequence encoding P77853T134-195 (SEQ ID NO: 21).

Example 14

Seed phenotype and xylanase activity. Xylanase activity was measured in maize seeds. Individual seeds were weighed, grinded to a fine powder (100-150 mg) and dispensed into individual wells of a 96-well grinding block (Costar) loaded with 5.0 mm steel balls (Abbot). After adding 500 μl of Fast Break solution (Promega), the block was sealed with a mat (Costar), shaken at maximum speed in a Klecko shaker for 45 seconds and spun at 3200×g for 10 min at 4° C. Aliquots of 100 μl and 2 μl of supernatant were then withdrawn from each well for pretreatment and protein assays, respectively. Samples were pretreated at 60° C. in the absence of substrate. Subsequently, xylanase activity was determined in a 96-well assay block (Costar) using azurine-crosslinked arabinoxylan (Megazyme, 40 mg tablet/well) as a substrate in a medium (400 μl) containing 100 mM sodium phosphate pH 6.5, at 55° C. for 3 hours. The reaction was terminated by the addition of 2% Tris base (500 μl) followed by centrifugation at 3200×g for 5 minutes. Aliquots (100 μl) from each well were transferred to a 96-well plate and the absorbance at 596 nm was determined using a Tecan M 1000 reader. A serial dilution (100 μg to 1 μg in 100 μl) of Remazol Brilliant Blue R (RBB, Sigma) was used to generate a standard curve for the conversion of the absorbance values obtained from the xylanase assay into micrograms of RBB. Specific enzymatic activity was expressed as μg RBB/mg protein/180 min. Protein concentration was determined by the Bradford Quick Start method (Biorad) using bovine serum albumin (Pierce) as protein standard.

Example 15

Hydrolysis of Corn stover. Corn stover was dried in an air-circulating oven at 37° C. for two weeks, cut manually (1.0-1.5 inch) and milled using UDY mill (Model 014, UDY Corporation, Fort Collins, Co). Stover (20 mg) was mixed with 195 μl $H_2O$ and pretreated by incubation in a shaking incubator at 55° C., 300 rpm for 16 hrs. Pretreated stover was suspended in 640 μl polybuffer (50 mM sodium citrate, 20 mM potassium phosphate dibasic, 17 mM arginine, 40 mM glycine, 25 mM EPPS, 20 mM HEPES, 0.02% sodium azide) at pH 6.5 and placed in a shaking incubator at 55° C., 300 rpm for 48 hrs (first hydrolysis). Then, the pH was adjusted to 5.0 using concentrated HCl and incubated at 50° C., 250 rpm for 48 hrs (second hydrolysis) with an enzyme cocktail (0.5 μM Endoglucanase (C8546; Sigma, St. Louis, Mo.), 0.1 μM Cellobiohydrolase (E-CBHI; Megazyme, Wicklow, Ireland), 0.01 μM β-glycosidase (49291; Sigma)), or the enzyme cocktail plus 0.3 μM xylanase (X2753; Sigma).

Example 16

After hydrolysis, samples were heated at 95° C. for 20 min, spun at 9,000 g for 3 min, and clarified with 0.20 μm PVDF filters (Fisher Scientific, Pittsburgh, Pa.). Glucose was quantified by HPLC with Aminex HPX-87P column (Bio-Rad Laboratories, Hercules, Calif.) and RI detector (RID LOAD), operating at 0.6 ml/min and 85° C. with degassed water as the mobile phase.

Example 17

P77853-T134-100-101 (P77T134-100-101). The following sequences were used in this example. Sequence of Tth intein-modified xylanase P77T134-100-101:

```
P77T134-100-101 Nucleotide sequence
                                                (SEQ ID NO: 59)
atgcaaacaagcattactctgacatccaacgcatccggtacgtttgacggttactattac

gaactctggaaggatactggcaatacaacaatgacggtctacactcaaggtcgcttttcc

tgccagtggtcgaacatcaataacgcgttgtttaggaccgggaagaaatacaaccagaat

tggcagtctcttggcacaatccggatcacgtactctgcgacttacaacccaaacgggaac

tcctacttgtgtatctatggctggtctaccaacccattggtcgagttctacatcgttgag

tcctgggggaactggagaccgcctggtgcctgcctggccgagggctcgctcgtcttggac

gcggctaccgggcagagggtccctatcgaaaaggtgcgtccggggatggaagttttctcc
```

-continued ttgggacctgattacagactgtatcgggtgcccgttttggaggtccttgagagcggggtt agggaagttgtgcgcctcagaactcggtcagggagaacgctggtgttgacaccagatcac ccgcttttgacccccgaaggttggaaacctctttgtgacctcccgcttggaactccaatt gcagtccccgcagaactgcctgtggcgggccacttggccccacctgaagaacgtgttacg ctcctggctcttctgttgggggatgggaacacaaagctgtcgggtcggagaggtacacgt cctaatgccttcttctacagcaaaaaccccgaattgctcgcggcttatcgccggtgtgca gaagccttgggtgcaaaggtgaaagcatacgtccacccgactacgggggtggttacactc gcaaccctcgctccacgtcctggagctcaagatcctgtcaaacgcctcgttgtcgaggcg ggaatggttgctaaagccgaagagaagagggtcccggaggaggtgtttcgttaccggcgt gaggcgttggccctttttcttgggccgtttgttctcgacagacggctctgttgaaaagaag aggatctcttattcaagtgccagtttgggactggcccaggatgtcgcacatctcttgctg cgccttggaattacatctcaactccgttcgagagggccacgggctcacgaggttcttata tcgggccgcgaggatattttgcggtttgctgaacttatcggaccctacctcttgggggcc aagagggagagacttgcagcgctggaagctgaggcccgcaggcgtttgcctggacaggga tggcacttgcggcttgttcttcctgccgtggcgtacagagtgggcgaggcggaaaggcgc tcgggattttcgtggagtgaagccggtcggcgcgtcgcagttgcgggatcgtgtttgtca tctggactcaacctcaaattgcccagacgctacctttctcggcaccggttgtcgctgctc ggtgaggcttttgccgaccctgggctggaagcgctcgcggaaggccaagtgctctgggac cctattgttgctgtcgaaccggccggtaaggcgagaacattcgacttgcgcgttccaccc tttgcaaacttcgtgagcgaggacctggtggtgcataacaccgtcccccctgggccaagtg acaatcgatggcgggacctacgacatctataggacgacacgcgtcaaccagccttccatt gtggggacagccacgttcgatcagtactggagcgtgcgcacctctaagcggacttcagga acagtgaccgtgaccgatcacttccgcgcctgggcgaaccgggggcctgaacctcggcaca atagaccaaattacattgtgcgtggagggttaccaaagctctggatcagccaacatcacc cagaacaccttctctcagggctcttcttccggcagttcgggtggctcatccggctccaca acgactactcgcatcgagtgtgagaacatgtccttgtccggaccctacgttagcaggatc accaatccctttaatggtattgcgctgtacgccaacggagacacagcccgcgctaccgtt aacttccccgcaagtcgcaactacaatttccgcctgcggggttgcggcaacaacaataat cttgcccgtgtggacctgaggatcgacggacggaccgtcgggaccttttattaccagggc acataccccctgggaggccccaattgacaatgtttatgtcagtgcggggagtcatacagtc gaaatcactgttactgcggataacggcacatgggacgtgtatgccgactacctggtgata cagtga P77T134-100-101 Amino acid sequence (SEQ ID NO: 60)

MQTSITLTSNASGTFDGYYYELWKDTGNTTMTVYTQGRFSCQWSNINNALFRTGKKYNQN

WQSLGTIRITYSATYNPNGNSYLCIYGWSTNPLVEFYIVESWGNWRPPGACLAEGSLVLD

AATGQRVPIEKVRPGMEVFSLGPDYRLYRVPVLEVLESGVREVVRLRTRSGRTLVLTPDH

PLLTPEGWKPLCDLPLGTPIAVPAELPVAGHLAPPEERVTLLALLLGDGNTKLSGRRGTR

PNAFFYSKNPELLAAYRRCAEALGAKVKAYVHPTTGVVTLATLAPRPGAQDPVKRLVVEA

GMVAKAEEKRVPEEVFRYRREALALFLGRLFSTDGSVEKKRISYSSASLGLAQDVAHLLL

RLGITSQLRSRGPRAHEVLISGREDILRFAELIGPYLLGAKRERLAALEAEARRRLPGQG

-continued

WHLRLVLPAVAYRVGEAERRSGFSWSEAGRRVAVAGSCLSSGLNLKLPRRYLSRHRLSLL

GEAFADPGLEALAEGQVLWDPIVAVEPAGKARTFDLRVPPFANFVSEDLVVHNTVPLGQV

TIDGGTYDIYRTTRVNQPSIVGTATFDQYWSVRTSKRTSGTVTVTDHFRAWANRGLNLGT

IDQITLCVEGYQSSGSANITQNTFSQGSSSGSSGGSSGSTTTTRIECENMSLSGPYVSRI

TNPFNGIALYANGDTARATVNFPASRNYNFRLRGCGNNNNLARVDLRIDGRTVGTFYYQG

TYPWEAPIDNVYVSAGSHTVEITVTADNGTWDVYADYLVIQ

Coding sequence for cell wall targeting of Tth intein-modified xylanase P77T134-100-101:

BAASS:P77T134-100-101 Nucleotide sequence (SEQ ID NO: 61)

atggcgaacaaacatttgtccctctccctcttcctcgtcctccttggcctgtcggccagc ttggcctccgggcaacaaacaagcattactctgacatccaacgcatccggtacgtttgac ggttactattacgaactctggaaggatactggcaatacaacaatgacggtctacactcaa ggtcgcttttcctgccagtggtcgaacatcaataacgcgttgtttaggaccgggaagaaa tacaaccagaattggcagtctcttggcacaatccggatcacgtactctgcgacttacaac ccaaacgggaactcctacttgtgtatctatggctggtctaccaacccattggtcgagttc tacatcgttgagtcctggggggaactggagaccgcctggtgcctgcctggccgagggctcg ctcgtcttggacgcggctaccgggcagagggtccctatcgaaaaggtgcgtccggggatg gaagttttctccttgggacctgattacagactgtatcgggtgcccgttttggaggtcctt gagagcggggttagggaagttgtgcgcctcagaactcggtcagggagaacgctggtgttg acaccagatcacccgcttttgacccccgaaggttggaaacctctttgtgacctcccgctt ggaactccaattgcagtccccgcagaactgcctgtggcgggccacttggccccacctgaa gaacgtgttacgctcctggctcttctgttgggggatgggaacacaaagctgtcgggtcgg agaggtacacgtcctaatgccttcttctacagcaaaaaccccgaattgctcgcggcttat cgccggtgtgcagaagccttgggtgcaaaggtgaaagcatacgtccacccgactacgggg gtggttacactcgcaaccctcgctccacgtcctggagctcaagatcctgtcaaacgcctc gttgtcgaggcgggaatggttgctaaagccgaagagaagagggtcccggaggaggtgttt cgttaccggcgtgaggcgttggcccttttcttgggccgtttgttctcgacagacggctct gttgaaaagaagaggatctcttattcaagtgccagtttgggactggcccaggatgtcgca catctcttgctgcgccttggaattacatctcaactccgttcgagagggccacgggctcac gaggttcttatatcgggccgcgaggatattttgcggtttgctgaacttatcggaccctac ctcttggggggccaagagggagagacttgcagcgctggaagctgaggcccgcaggcgtttg cctggacagggatggcacttgcggcttgttcttcctgccgtggcgtacagagtgggcgag gcggaaaggcgctcgggattttcgtggagtgaagccggtcggcgcgtcgcagttgcggga tcgtgtttgtcatctggactcaacctcaaattgcccagacgctacctttctcggcaccgg ttgtcgctgctcggtgaggcttttgccgaccctgggctggaagcgctcgcggaaggccaa gtgctctgggaccctattgttgctgtcgaaccggccggtaaggcgagaacattcgacttg cgcgttccacccctttgcaaacttcgtgagcgaggacctggtggtgcataacaccgtcccc ctgggccaagtgacaatcgatggcgggacctacgacatctataggacgacacgcgtcaac cagccttccattgtggggacagccacgttcgatcagtactggagcgtgcgcacctctaag cggacttcaggaacagtgaccgtgaccgatcacttccgcgcctgggcgaaccggggcctg -continued aacctcggcacaatagaccaaattacattgtgcgtggagggttaccaaagctctggatca gccaacatcacccagaacaccttctctcagggctcttcttccggcagttcgggtggctca tccggctccacaacgactactcgcatcgagtgtgagaacatgtccttgtccggaccctac gttagcaggatcaccaatccctttaatggtattgcgctgtacgccaacggagacacagcc cgcgctaccgttaacttccccgcaagtcgcaactacaatttccgcctgcggggttgcggc aacaacaataatcttgcccgtgtggacctgaggatcgacggacggaccgtcgggaccttt tattaccagggcacatacccctgggaggccccaattgacaatgtttatgtcagtgcgggg agtcatacagtcgaaatcactgttactgcggataacggcacatgggacgtgtatgccgac tacctggtgatacagtga BAASS:P77T134-100-101 Amino acid sequence (SEQ ID NO: 62)

MANKHLSLSLFLVLLGLSASLASGQQTSITLTSNASGTFDGYYYELWKDTGNTTMTVYTQGRFSCQ

WSNINNALFRTGKKYNQNWQSLGTIRITYSATYNPNGNSYLCIYGWSTNPLVEFYIVESWGNWRP

PGACLAEGSLVLDAATGQRVPIEKVRPGMEVFSLGPDYRLYRVPVLEVLESGVREVVRLRT

RSGRTLVITPDHPLLTPEGWKPLCDLPLGTPIAVPAELPVAGHLAPPEERVTLLAILLGDGNTKLS

GRRGTRPNAFFYSKNPELLAAYRRCAEALGAKVKAYVHPTTGVVTLATLAPRPGAQDPVKRLVVEA

GMVAKAEEKRVPEEVFRYRREALALFLGRLFSTDGSVEKKRISYSSASLGLAQDVAHLLLRLGITS

QLRSRGPRAHEVLISGREDILRFAELIGPYLLGAKRERLAALEAEARRRLPGQGWHLRLVLPAVAY

RVGEAERRSGFSWSEAGRRVAVAGSCLSSGLNLKLPRRYLSRHRLSLLGEAFADPGLEALAEGQVL

WDPIVAVEPAGKARTFDLRVPPFANFVSEDLVVHNTVPLGQVTIDGGTYDIYRTTRVNQPSIVGTA

TFDQYWSVRTSKRTSGTVTVTDHFRAWANRGLNLGTIDQITLCVEGYQSSGSANITQNTFSQGSSS

GSSGGSSGSTTTTRIECENMSLSGPYVSRITNPFNGIALYANGDTARATVNFPASRNYNFRLRGCG

NNNNLARVDLRIDGRTVGTFYYQGTYPWEAPIDNVYVSAGSHTVEITVTADNGTWDVYADYLVIQ

Coding sequence for ER-retention of Tth intein-modified xylanase P77T134-100-101:

BAASS:P77T134-100-101:SEKDEL Nucleotide sequence (SEQ ID NO: 63)

atggcgaacaaacatttgtccctctccctcttcctcgtcctccttggcctgtcggccagc ttggcctccgggcaacaaacaagcattactctgacatccaacgcatccggtacgtttgac ggttactattacgaactctggaaggatactggcaatacaacaatgacggtctacactcaa ggtcgcttttcctgccagtggtcgaacatcaataacgcgttgtttaggaccgggaagaaa tacaaccagaattggcagtctcttggcacaatccggatcacgtactctgcgacttacaac ccaaacgggaactcctacttgtgtatctatggctggtctaccaacccattggtcgagttc tacatcgttgagtcctggggggaactggagaccgcctggtgcctgcctggccgagggctcg ctcgtcttggacgcggctaccgggcagagggtccctatcgaaaaggtgcgtccggggatg gaagttttctccttgggacctgattacagactgtatcgggtgcccgttttggaggtcctt gagagcggggttagggaagttgtgcgcctcagaactcggtcagggagaacgctggtgttg acaccagatcacccgcttttgacccccgaaggttggaaacctctttgtgacctcccgctt ggaactccaattgcagtccccgcagaactgcctgtggcgggccacttggccccacctgaa gaacgtgttacgctcctggctcttctgttgggggatgggaacacaaagctgtcgggtcgg agaggtacacgtcctaatgccttcttctacagcaaaaaccccgaattgctcgcggcttat -continued cgccggtgtgcagaagccttgggtgcaaaggtgaaagcatacgtccacccgactacgggg gtggttacactcgcaaccctcgctccacgtcctggagctcaagatcctgtcaaacgcctc gttgtcgaggcgggaatggttgctaaagccgaagagaagagggtcccggaggaggtgttt cgttaccggcgtgaggcgttggccctttttcttgggccgtttgttctcgacagacggctct gttgaaaagaagaggatctcttattcaagtgccagtttgggactggcccaggatgtcgca catctcttgctgcgccttggaattacatctcaactccgttcgagagggccacgggctcac gaggttcttatatcgggccgcgaggatattttgcggtttgctgaacttatcggaccctac ctcttgggggccaagagggagagacttgcagcgctggaagctgaggcccgcaggcgtttg cctggacagggatggcacttgcggcttgttcttcctgccgtggcgtacagagtgggcgag gcggaaaggcgctcgggattttcgtggagtgaagccggtcggcgcgtcgcagttgcggga tcgtgtttgtcatctggactcaacctcaaattgcccagacgctacctttctcggcaccgg ttgtcgctgctcggtgaggcttttgccgaccctgggctggaagcgctcgcggaaggccaa gtgctctgggaccctattgttgctgtcgaaccggccggtaaggcgagaacattcgacttg cgcgttccacccctttgcaaacttcgtgagcgaggacctggtggtgcataacaccgtcccc ctgggccaagtgacaatcgatggcgggacctacgacatctataggacgacacgcgtcaac cagccttccattgtggggacagccacgttcgatcagtactggagcgtgcgcacctctaag cggacttcaggaacagtgaccgtgaccgatcacttccgcgcctgggcgaaccggggcctg aacctcggcacaatagaccaaattacattgtgcgtggagggttaccaaagctctggatca gccaacatcacccagaacaccttctctcagggctcttcttccggcagttcgggtggctca tccggctccacaacgactactcgcatcgagtgtgagaacatgtccttgtccggaccctac gttagcaggatcaccaatccctttaatggtattgcgctgtacgccaacggagacacagcc cgcgctaccgttaacttccccgcaagtcgcaactacaatttccgcctgcggggttgcggc aacaacaataatcttgcccgtgtggacctgaggatcgacggacggaccgtcgggaccttt tattaccagggcacataccccctgggaggccccaattgacaatgtttatgtcagtgcgggg agtcatacagtcgaaatcactgttactgcggataacggcacatgggacgtgtatgccgac tacctggtgatacagagcgagaaggacgagctg tga BAASS:P77T134-100-101:SEKDEL Amino acid sequence (SEQ ID NO: 64)

MANKHLSLSLFLVLLGLSASLASGQQTSITLTSNASGTFDGYYYELWKDTGNTTMTVYTQ

GRFSCQWSNINNALFRTGKKYNQNWQSLGTIRITYSATYNPNGNSYLCIYGWSTNPLVEF

YIVESWGNWRPPGACLAEGSLVLDAATGQRVPIEKVRPGMEVFSLGPDYRLYRVPVLEVL

ESGVREVVRLRTRSGRTLVLTPDHPLLTPEGWKPLCDLPLGTPIAVPAELPVAGHLAPPE

ERVTLLALLLGDGNTKLSGRRGTRPNAFFYSKNPELLAAYRRCAEALGAKVKAYVHPTTG

VVTLATLAPRPGAQDPVKRLVVEAGMVAKAEEKRVPEEVFRYRREALALFLGRLFSTDGS

VEKKRISYSSASLGLAQDVAHLLLRLGITSQLRSRGPRAHEVLISGREDILRFAELIGPY

LLGAKRERLAALEAEARRRLPGQGWHLRLVLPAVAYRVGEAERRSGFSWSEAGRRVAVAG

SCLSSGLNLKLPRRYLSRHRLSLLGEAFADPGLEALAEGQVLWDPIVAVEPAGKARTFDL

RVPPFANFVSEDLVVHNTVPLGQVTIDGGTYDIYRTTRVNQPSIVGTATFDQYWSVRTSK

RTSGTVTVTDHFRAWANRGLNLGTIDQITLCVEGYQSSGSANITQNTFSQGSSSGSSGGS

-continued

SGSTTTTRIECENMSLSGPYVSRITNPFNGIALYANGDTARATVNFPASRNYNFRLRGCG

NNNNLARVDLRIDGRTVGTFYYQGTYPWEAPIDNVYVSAGSHTVEITVTADNGTWDVYAD

YLVIQSEKDEL

The coding sequences of SEQ ID NOS: 59, 61 and 63 were inserted between rice Ubi3 promoter and NOS terminator to generate constructs designated pAG2227, pAG2228 and pAG2229, respectively.

The expression cassette in pAG2227 (SEQ ID NO: 72) is OsUbi3P:P77853-T134-100-101, and has the sequence of SEQ ID NO: 65:

GGTACCGTCGACTCTAGTAACGGCCGCCAGTGTGCTGGAATTAATTCGGCTTGTCGACCA

CCCAACCCCATATCGACAGAGGATGTGAAGAACAGGTAAATCACGCAGAAGAACCCATCT

CTGATAGCAGCTATCGATTAGAACAACGAATCCATATTGGGTCCGTGGGAAATACTTACT

GCACAGGAAGGGGGCGATCTGACGAGGCCCCGCCACCGGCCTCGACCCGAGGCCGAGGCC

GACGAAGCGCCGGCGAGTACGGCGCCGCGGCGGCCTCTGCCCGTGCCCTCTGCGCGTGGG

AGGGAGAGGCCGCGGTGGTGGGGGCGCGCGCGCGCGCGCGCGCAGCTGGTGCGGCGGCGC

GGGGGTCAGCCGCCGAGCCGGCGGCGACGGAGGAGCAGGGCGGCGTGGACGCGAACTTCC

GATCGGTTGGTCAGAGTGCGCGAGTTGGGCTTAGCCAATTAGGTCTCAACAATCTATTGG

GCCGTAAAATTCATGGGCCCTGGTTTGTCTAGGCCCAATATCCCGTTCATTTCAGCCCAC

AAATATTTCCCCAGAGGATTATTAAGGCCCACACGCAGCTTATAGCAGATCAAGTACGAT

GTTTCCTGATCGTTGGATCGGAAACGTACGGTCTTGATCAGGCATGCCGACTTCGTCAAA

GAGAGGCGGCATGACCTGACGCGGAGTTGGTTCCGGGCACCGTCTGGATGGTCGTACCGG

GACCGGACACGTGTCGCGCCTCCAACTACATGGACACGTGTGGTGCTGCCATTGGGCCGT

ACGCGTGGCGGTGACCGCACCGGATGCTGCCTCGCACCGCCTTGCCCACGCTTTATATAG

AGAGGTTTTCTCTCCATTAATCGCATAGCGAGTCGAATCGACCGAAGGGGAGGGGGAGCG

AAGCTTTGCGTTCTCTAATCGCCTCGTCAAGGTAACTAATCAATCACCTCGTCCTAATCC

TCGAATCTCTCGTGGTGCCCGTCTAATCTCGCGATTTTGATGCTCGTGGTGGAAAGCGTA

GGAGGATCCCGTGCGAGTTAGTCTCAATCTCTCAGGGTTTCGTGCGATTTTAGGGTGATC

CACCTCTTAATCGAGTTACGGTTTCGTGCGATTTTAGGGTAATCCTCTTAATCTCTCATT

GATTTAGGGTTTCGTGAGAATCGAGGTAGGGATCTGTGTTATTTATATCGATCTAATAGA

TGGATTGGTTTTGAGATTGTTCTGTCAGATGGGGATTGTTTCGATATATTACCCTAATGA

TGTGTCAGATGGGGATTGTTTCGATATATTACCCTAATGATGTGTCAGATGGGGATTGTT

TCGATATATTACCCTAATGATGGATAATAAGAGTAGTTCACAGTTATGTTTTGATCCTGC

CACATAGTTTGAGTTTTGTGATCAGATTTAGTTTTACTTATTTGTGCTTAGTTCGGATGG

GATTGTTCTGATATTGTTCCAATAGATGAATAGCTCGTTAGGTTAAAATCTTTAGGTTGA

GTTAGGCGACACATAGTTTATTTCCTCTGGATTTGGATTGGAATTGTGTTCTTAGTTTTT

TTCCCCTGGATTTGGATTGGAATTGTGTGGAGCTGGGTTAGAGAATTACATCTGTATCGT

GTACACCTACTTGAACTGTAGAGCTTGGGTTCTAAGGTCAATTTAATCTGTATTGTATCT

GGCTCTTTGCCTAGTTGAACTGTAGTGCTGATGTTGTACTGTGTTTTTTTACCCGTTTTA

TTTGCTTTACTCGTGCAAATCAAATCTGTCAGATGCTAGAACTAGGTGGCTTTATTCTGT

GTTCTTACATAGATCTGTTGTCCTGTAGTTACTTATGTCAGTTTTGTTATTATCTGAAGA

TATTTTTGGTTGTTGCTTGTTGATGTGGTGTGAGCTGTGAGCAGCGCTCTTATGATTAAT

GATGCTGTCCAATTGTAGTGTAGTATGATGTGATTGATATGTTCATCTATTTTGAGCTGA

CAGTACCGATATCGTAGGATCTGGTGCCAACTTATTCTCCAGCTGCTTTTTTTTACCTAT

-continued

GTTAATTCCAATCCTTTCTTGCCTCTTCCAGATCCAGATAATGCAAACAAGCATTACTCT

GACATCCAACGCATCCGGTACGTTTGACGGTTACTATTACGAACTCTGGAAGGATACTGG

CAATACAACAATGACGGTCTACACTCAAGGTCGCTTTTCCTGCCAGTGGTCGAACATCAA

TAACGCGTTGTTTAGGACCGGGAAGAAATACAACCAGAATTGGCAGTCTCTTGGCACAAT

CCGGATCACGTACTCTGCGACTTACAACCCAAACGGGAACTCCTACTTGTGTATCTATGG

CTGGTCTACCAACCCATTGGTCGAGTTCTACATCGTTGAGTCCTGGGGGAACTGGAGACC

GCCTGGTGCCTGCCTGGCCGAGGGCTCGCTCGTCTTGGACGCGGCTACCGGGCAGAGGGT

CCCTATCGAAAAGGTGCGTCCGGGGATGGAAGTTTTCTCCTTGGGACCTGATTACAGACT

GTATCGGGTGCCCGTTTTGGAGGTCCTTGAGAGCGGGGTTAGGGAAGTTGTGCGCCTCAG

AACTCGGTCAGGGAGAACGCTGGTGTTGACACCAGATCACCCGCTTTTGACCCCCGAAGG

TTGGAAACCTCTTTGTGACCTCCCGCTTGGAACTCCAATTGCAGTCCCCGCAGAACTGCC

TGTGGCGGGCCACTTGGCCCCACCTGAAGAACGTGTTACGCTCCTGGCTCTTCTGTTGGG

GGATGGGAACACAAAGCTGTCGGGTCGGAGAGGTACACGTCCTAATGCCTTCTTCTACAG

CAAAAACCCCGAATTGCTCGCGGCTTATCGCCGGTGTGCAGAAGCCTTGGGTGCAAAGGT

GAAAGCATACGTCCACCCGACTACGGGGGTGGTTACACTCGCAACCCTCGCTCCACGTCC

TGGAGCTCAAGATCCTGTCAAACGCCTCGTTGTCGAGGCGGGAATGGTTGCTAAAGCCGA

AGAGAAGAGGGTCCCGGAGGAGGTGTTTCGTTACCGGCGTGAGGCGTTGGCCCTTTTCTT

GGGCCGTTTGTTCTCGACAGACGGCTCTGTTGAAAAGAAGAGGATCTCTTATTCAAGTGC

CAGTTTGGGACTGGCCCAGGATGTCGCACATCTCTTGCTGCGCCTTGGAATTACATCTCA

ACTCCGTTCGAGAGGGCCACGGGCTCACGAGGTTCTTATATCGGGCCGCGAGGATATTTT

GCGGTTTGCTGAACTTATCGGACCCTACCTCTTGGGGGCCAAGAGGGAGAGACTTGCAGC

GCTGGAAGCTGAGGCCCGCAGGCGTTTGCCTGGACAGGGATGGCACTTGCGGCTTGTTCT

TCCTGCCGTGGCGTACAGAGTGGGCGAGGCGGAAAGGCGCTCGGGATTTTCGTGGAGTGA

AGCCGGTCGGCGCGTCGCAGTTGCGGGATCGTGTTTGTCATCTGGACTCAACCTCAAATT

GCCCAGACGCTACCTTTCTCGGCACCGGTTGTCGCTGCTCGGTGAGGCTTTTGCCGACCC

TGGGCTGGAAGCGCTCGCGGAAGGCCAAGTGCTCTGGGACCCTATTGTTGCTGTCGAACC

GGCCGGTAAGGCGAGAACATTCGACTTGCGCGTTCCACCCTTTGCAAACTTCGTGAGCGA

GGACCTGGTGGTGCATAACACCGTCCCCCTGGGCCAAGTGACAATCGATGGCGGGACCTA

CGACATCTATAGGACGACACGCGTCAACCAGCCTTCCATTGTGGGGACAGCCACGTTCGA

TCAGTACTGGAGCGTGCGCACCTCTAAGCGGACTTCAGGAACAGTGACCGTGACCGATCA

CTTCCGCGCCTGGGCGAACCGGGGCCTGAACCTCGGCACAATAGACCAAATTACATTGTG

CGTGGAGGGTTACCAAAGCTCTGGATCAGCCAACATCACCCAGAACACCTTCTCTCAGGG

CTCTTCTTCCGGCAGTTCGGGTGGCTCATCCGGCTCCACAACGACTACTCGCATCGAGTG

TGAGAACATGTCCTTGTCCGGACCCTACGTTAGCAGGATCACCAATCCCTTTAATGGTAT

TGCGCTGTACGCCAACGGAGACACAGCCCGCGCTACCGTTAACTTCCCCGCAAGTCGCAA

CTACAATTTCCGCCTGCGGGGTTGCGGCAACAACAATAATCTTGCCCGTGTGGACCTGAG

GATCGACGGACGGACCGTCGGGACCTTTTATTACCAGGGCACATACCCCTGGGAGGCCCC

AATTGACAATGTTTATGTCAGTGCGGGGAGTCATACAGTCGAAATCACTGTTACTGCGGA

TAACGGCACATGGGACGTGTATGCCGACTACCTGGTGATACAGTGACCTAGGTCCCCGAA

TTTCCCCGATCGTTCAAACATTTGGCAATAAAGTTTCTTAAGATTGAATCCTGTTGCCGG

-continued

TCTTGCGATGATTATCATATAATTTCTGTTGAATTACGTTAAGCATGTAATAATTAACAT

GTAATGCATGACGTTATTTATGAGATGGGTTTTTATGATTAGAGTCCCGCAATTATACAT

TTAATACGCGATAGAAAACAAAATATAGCGCGCAAACTAGGATAAATTATCGCGCGCGGT

GTCATCTATGTTACTAGATCGGGAATTGGAATTC

The expression cassette in pAG2228 (SEQ ID NO: 73) is OsUbi3P:BAASS:P77853-T134-100-101:NosT, and has the sequence of SEQ ID NO: 66:

GGTACCGTCGACTCTAGTAACGGCCGCCAGTGTGCTGGAATTAATTCGGCTTGTCGACCA

CCCAACCCCATATCGACAGAGGATGTGAAGAACAGGTAAATCACGCAGAAGAACCCATCT

CTGATAGCAGCTATCGATTAGAACAACGAATCCATATTGGGTCCGTGGGAAATACTTACT

GCACAGGAAGGGGGCGATCTGACGAGGCCCCGCCACCGGCCTCGACCCGAGGCCGAGGCC

GACGAAGCGCCGGCGAGTACGGCGCCGCGGCGGCCTCTGCCCGTGCCCTCTGCGCGTGGG

AGGGAGAGGCCGCGGTGGTGGGGGCGCGCGCGCGCGCGCGCGCAGCTGGTGCGGCGGCGC

GGGGGTCAGCCGCCGAGCCGGCGGCGACGGAGGAGCAGGGCGGCGTGGACGCGAACTTCC

GATCGGTTGGTCAGAGTGCGCGAGTTGGGCTTAGCCAATTAGGTCTCAACAATCTATTGG

GCCGTAAAATTCATGGGCCCTGGTTTGTCTAGGCCCAATATCCCGTTCATTTCAGCCCAC

AAATATTTCCCCAGAGGATTATTAAGGCCCACACGCAGCTTATAGCAGATCAAGTACGAT

GTTTCCTGATCGTTGGATCGGAAACGTACGGTCTTGATCAGGCATGCCGACTTCGTCAAA

GAGAGGCGGCATGACCTGACGCGGAGTTGGTTCCGGGCACCGTCTGGATGGTCGTACCGG

GACCGGACACGTGTCGCGCCTCCAACTACATGGACACGTGTGGTGCTGCCATTGGGCCGT

ACGCGTGGCGGTGACCGCACCGGATGCTGCCTCGCACCGCCTTGCCCACGCTTTATATAG

AGAGGTTTTCTCTCCATTAATCGCATAGCGAGTCGAATCGACCGAAGGGGAGGGGGAGCG

AAGCTTTGCGTTCTCTAATCGCCTCGTCAAGGTAACTAATCAATCACCTCGTCCTAATCC

TCGAATCTCTCGTGGTGCCCGTCTAATCTCGCGATTTTGATGCTCGTGGTGGAAAGCGTA

GGAGGATCCCGTGCGAGTTAGTCTCAATCTCTCAGGGTTTCGTGCGATTTTAGGGTGATC

CACCTCTTAATCGAGTTACGGTTTCGTGCGATTTTAGGGTAATCCTCTTAATCTCTCATT

GATTTAGGGTTTCGTGAGAATCGAGGTAGGGATCTGTGTTATTTATATCGATCTAATAGA

TGGATTGGTTTTGAGATTGTTCTGTCAGATGGGGATTGTTTCGATATATTACCCTAATGA

TGTGTCAGATGGGGATTGTTTCGATATATTACCCTAATGATGTGTCAGATGGGGATTGTT

TCGATATATTACCCTAATGATGGATAATAAGAGTAGTTCACAGTTATGTTTTGATCCTGC

CACATAGTTTGAGTTTTGTGATCAGATTTAGTTTTACTTATTTGTGCTTAGTTCGGATGG

GATTGTTCTGATATTGTTCCAATAGATGAATAGCTCGTTAGGTTAAAATCTTTAGGTTGA

GTTAGGCGACACATAGTTTATTTCCTCTGGATTTGGATTGGAATTGTGTTCTTAGTTTTT

TTCCCCTGGATTTGGATTGGAATTGTGTGGAGCTGGGTTAGAGAATTACATCTGTATCGT

GTACACCTACTTGAACTGTAGAGCTTGGGTTCTAAGGTCAATTTAATCTGTATTGTATCT

GGCTCTTTGCCTAGTTGAACTGTAGTGCTGATGTTGTACTGTGTTTTTTTACCCGTTTTA

TTTGCTTTACTCGTGCAAATCAAATCTGTCAGATGCTAGAACTAGGTGGCTTTATTCTGT

GTTCTTACATAGATCTGTTGTCCTGTAGTTACTTATGTCAGTTTTGTTATTATCTGAAGA

TATTTTTGGTTGTTGCTTGTTGATGTGGTGTGAGCTGTGAGCAGCGCTCTTATGATTAAT

GATGCTGTCCAATTGTAGTGTAGTATGATGTGATTGATATGTTCATCTATTTTGAGCTGA

-continued

CAGTACCGATATCGTAGGATCTGGTGCCAACTTATTCTCCAGCTGCTTTTTTTTACCTAT

GTTAATTCCAATCCTTTCTTGCCTCTTCCAGATCCAGATAATGGCGAACAAACATTTGTC

CCTCTCCCTCTTCCTCGTCCTCCTTGGCCTGTCGGCCAGCTTGGCCTCCGGGCAACAAAC

AAGCATTACTCTGACATCCAACGCATCCGGTACGTTTGACGGTTACTATTACGAACTCTG

GAAGGATACTGGCAATACAACAATGACGGTCTACACTCAAGGTCGCTTTTCCTGCCAGTG

GTCGAACATCAATAACGCGTTGTTTAGGACCGGGAAGAAATACAACCAGAATTGGCAGTC

TCTTGGCACAATCCGGATCACGTACTCTGCGACTTACAACCCAAACGGGAACTCCTACTT

GTGTATCTATGGCTGGTCTACCAACCCATTGGTCGAGTTCTACATCGTTGAGTCCTGGGG

GAACTGGAGACCGCCTGGTGCCTGCCTGGCCGAGGGCTCGCTCGTCTTGGACGCGGCTAC

CGGGCAGAGGGTCCCTATCGAAAAGGTGCGTCCGGGGATGGAAGTTTTCTCCTTGGGACC

TGATTACAGACTGTATCGGGTGCCCGTTTTGGAGGTCCTTGAGAGCGGGGTTAGGGAAGT

TGTGCGCCTCAGAACTCGGTCAGGGAGAACGCTGGTGTTGACACCAGATCACCCGCTTTT

GACCCCCGAAGGTTGGAAACCTCTTTGTGACCTCCCGCTTGGAACTCCAATTGCAGTCCC

CGCAGAACTGCCTGTGGCGGGCCACTTGGCCCCACCTGAAGAACGTGTTACGCTCCTGGC

TCTTCTGTTGGGGGATGGGAACACAAAGCTGTCGGGTCGGAGAGGTACACGTCCTAATGC

CTTCTTCTACAGCAAAAACCCCGAATTGCTCGCGGCTTATCGCCGGTGTGCAGAAGCCTT

GGGTGCAAAGGTGAAAGCATACGTCCACCCGACTACGGGGGTGGTTACACTCGCAACCCT

CGCTCCACGTCCTGGAGCTCAAGATCCTGTCAAACGCCTCGTTGTCGAGGCGGGAATGGT

TGCTAAAGCCGAAGAGAAGAGGGTCCCGGAGGAGGTGTTTCGTTACCGGCGTGAGGCGTT

GGCCCTTTTCTTGGGCCGTTTGTTCTCGACAGACGGCTCTGTTGAAAAGAAGAGGATCTC

TTATTCAAGTGCCAGTTTGGGACTGGCCCAGGATGTCGCACATCTCTTGCTGCGCCTTGG

AATTACATCTCAACTCCGTTCGAGAGGGCCACGGGCTCACGAGGTTCTTATATCGGGCCG

CGAGGATATTTTGCGGTTTGCTGAACTTATCGGACCCTACCTCTTGGGGGCCAAGAGGGA

GAGACTTGCAGCGCTGGAAGCTGAGGCCCGCAGGCGTTTGCCTGGACAGGGATGGCACTT

GCGGCTTGTTCTTCCTGCCGTGGCGTACAGAGTGGGCGAGGCGGAAAGGCGCTCGGGATT

TTCGTGGAGTGAAGCCGGTCGGCGCGTCGCAGTTGCGGGATCGTGTTTGTCATCTGGACT

CAACCTCAAATTGCCCAGACGCTACCTTTCTCGGCACCGGTTGTCGCTGCTCGGTGAGGC

TTTTGCCGACCCTGGGCTGGAAGCGCTCGCGGAAGGCCAAGTGCTCTGGGACCCTATTGT

TGCTGTCGAACCGGCCGGTAAGGCGAGAACATTCGACTTGCGCGTTCCACCCTTTGCAAA

CTTCGTGAGCGAGGACCTGGTGGTGCATAACACCGTCCCCCTGGGCCAAGTGACAATCGA

TGGCGGGACCTACGACATCTATAGGACGACACGCGTCAACCAGCCTTCCATTGTGGGGAC

AGCCACGTTCGATCAGTACTGGAGCGTGCGCACCTCTAAGCGGACTTCAGGAACAGTGAC

CGTGACCGATCACTTCCGCGCCTGGGCGAACCGGGGCCTGAACCTCGGCACAATAGACCA

AATTACATTGTGCGTGGAGGGTTACCAAAGCTCTGGATCAGCCAACATCACCCAGAACAC

CTTCTCTCAGGGCTCTTCTTCCGGCAGTTCGGGTGGCTCATCCGGCTCCACAACGACTAC

TCGCATCGAGTGTGAGAACATGTCCTTGTCCGGACCCTACGTTAGCAGGATCACCAATCC

CTTTAATGGTATTGCGCTGTACGCCAACGGAGACACAGCCCGCGCTACCGTTAACTTCCC

CGCAAGTCGCAACTACAATTTCCGCCTGCGGGGTTGCGGCAACAACAATAATCTTGCCCG

TGTGGACCTGAGGATCGACGGACGGACCGTCGGGACCTTTTATTACCAGGGCACATACCC

CTGGGAGGCCCCAATTGACAATGTTTATGTCAGTGCGGGGAGTCATACAGTCGAAATCAC

TGTTACTGCGGATAACGGCACATGGGACGTGTATGCCGACTACCTGGTGATACAGTGACC

-continued

TAGGTCCCCGAATTTCCCCGATCGTTCAAACATTTGGCAATAAAGTTTCTTAAGATTGAA

TCCTGTTGCCGGTCTTGCGATGATTATCATATAATTTCTGTTGAATTACGTTAAGCATGT

AATAATTAACATGTAATGCATGACGTTATTTATGAGATGGGTTTTTATGATTAGAGTCCC

GCAATTATACATTTAATACGCGATAGAAAACAAAATATAGCGCGCAAACTAGGATAAATT

ATCGCGCGCGGTGTCATCTATGTTACTAGATCGGGAATTGGAATTC

The expression cassette in pAG2229 (SEQ ID NO: 74) is OsUbi3P:BAASS:P77853-T134-100-101:SEKDEL:NosT, and has the sequence of SEQ ID NO: 67:

GGTACCGTCGACTCTAGTAACGGCCGCCAGTGTGCTGGAATTAATTCGGCTTGTCGACCA

CCCAACCCCATATCGACAGAGGATGTGAAGAACAGGTAAATCACGCAGAAGAACCCATCT

CTGATAGCAGCTATCGATTAGAACAACGAATCCATATTGGGTCCGTGGGAAATACTTACT

GCACAGGAAGGGGGCGATCTGACGAGGCCCCGCCACCGGCCTCGACCCGAGGCCGAGGCC

GACGAAGCGCCGGCGAGTACGGCGCCGCGGCGGCCTCTGCCCGTGCCCTCTGCGCGTGGG

AGGGAGAGGCCGCGGTGGTGGGGGCGCGCGCGCGCGCGCGCGCAGCTGGTGCGGCGGCGC

GGGGGTCAGCCGCCGAGCCGGCGGCGACGGAGGAGCAGGGCGGCGTGGACGCGAACTTCC

GATCGGTTGGTCAGAGTGCGCGAGTTGGGCTTAGCCAATTAGGTCTCAACAATCTATTGG

GCCGTAAAATTCATGGGCCCTGGTTTGTCTAGGCCCAATATCCCGTTCATTTCAGCCCAC

AAATATTTCCCCAGAGGATTATTAAGGCCCACACGCAGCTTATAGCAGATCAAGTACGAT

GTTTCCTGATCGTTGGATCGGAAACGTACGGTCTTGATCAGGCATGCCGACTTCGTCAAA

GAGAGGCGGCATGACCTGACGCGGAGTTGGTTCCGGGCACCGTCTGGATGGTCGTACCGG

GACCGGACACGTGTCGCGCCTCCAACTACATGGACACGTGTGGTGCTGCCATTGGGCCGT

ACGCGTGGCGGTGACCGCACCGGATGCTGCCTCGCACCGCCTTGCCCACGCTTTATATAG

AGAGGTTTTCTCTCCATTAATCGCATAGCGAGTCGAATCGACCGAAGGGGAGGGGGAGCG

AAGCTTTGCGTTCTCTAATCGCCTCGTCAAGGTAACTAATCAATCACCTCGTCCTAATCC

TCGAATCTCTCGTGGTGCCCGTCTAATCTCGCGATTTTGATGCTCGTGGTGGAAAGCGTA

GGAGGATCCCGTGCGAGTTAGTCTCAATCTCTCAGGGTTTCGTGCGATTTTAGGGTGATC

CACCTCTTAATCGAGTTACGGTTTCGTGCGATTTTAGGGTAATCCTCTTAATCTCTCATT

GATTTAGGGTTTCGTGAGAATCGAGGTAGGGATCTGTGTTATTTATATCGATCTAATAGA

TGGATTGGTTTTGAGATTGTTCTGTCAGATGGGGATTGTTTCGATATATTACCCTAATGA

TGTGTCAGATGGGGATTGTTTCGATATATTACCCTAATGATGTGTCAGATGGGGATTGTT

TCGATATATTACCCTAATGATGGATAATAAGAGTAGTTCACAGTTATGTTTTGATCCTGC

CACATAGTTTGAGTTTTGTGATCAGATTTAGTTTTACTTATTTGTGCTTAGTTCGGATGG

GATTGTTCTGATATTGTTCCAATAGATGAATAGCTCGTTAGGTTAAAATCTTTAGGTTGA

GTTAGGCGACACATAGTTTATTTCCTCTGGATTTGGATTGGAATTGTGTTCTTAGTTTTT

TTCCCCTGGATTTGGATTGGAATTGTGTGGAGCTGGGTTAGAGAATTACATCTGTATCGT

GTACACCTACTTGAACTGTAGAGCTTGGGTTCTAAGGTCAATTTAATCTGTATTGTATCT

GGCTCTTTGCCTAGTTGAACTGTAGTGCTGATGTTGTACTGTGTTTTTTTACCCGTTTTA

TTTGCTTTACTCGTGCAAATCAAATCTGTCAGATGCTAGAACTAGGTGGCTTTATTCTGT

GTTCTTACATAGATCTGTTGTCCTGTAGTTACTTATGTCAGTTTTGTTATTATCTGAAGA

TATTTTTGGTTGTTGCTTGTTGATGTGGTGTGAGCTGTGAGCAGCGCTCTTATGATTAAT

-continued

GATGCTGTCCAATTGTAGTGTAGTATGATGTGATTGATATGTTCATCTATTTTGAGCTGA

CAGTACCGATATCGTAGGATCTGGTGCCAACTTATTCTCCAGCTGCTTTTTTTTACCTAT

GTTAATTCCAATCCTTTCTTGCCTCTTCCAGATCCAGATAATGGCGAACAAACATTTGTC

CCTCTCCCTCTTCCTCGTCCTCCTTGGCCTGTCGGCCAGCTTGGCCTCCGGGCAACAAAC

AAGCATTACTCTGACATCCAACGCATCCGGTACGTTTGACGGTTACTATTACGAACTCTG

GAAGGATACTGGCAATACAACAATGACGGTCTACACTCAAGGTCGCTTTTCCTGCCAGTG

GTCGAACATCAATAACGCGTTGTTTAGGACCGGGAAGAAATACAACCAGAATTGGCAGTC

TCTTGGCACAATCCGGATCACGTACTCTGCGACTTACAACCCAAACGGGAACTCCTACTT

GTGTATCTATGGCTGGTCTACCAACCCATTGGTCGAGTTCTACATCGTTGAGTCCTGGGG

GAACTGGAGACCGCCTGGTGCCTGCCTGGCCGAGGGCTCGCTCGTCTTGGACGCGGCTAC

CGGGCAGAGGGTCCCTATCGAAAAGGTGCGTCCGGGGATGGAAGTTTTCTCCTTGGGACC

TGATTACAGACTGTATCGGGTGCCCGTTTTGGAGGTCCTTGAGAGCGGGGTTAGGGAAGT

TGTGCGCCTCAGAACTCGGTCAGGGAGAACGCTGGTGTTGACACCAGATCACCCGCTTTT

GACCCCCGAAGGTTGGAAACCTCTTTGTGACCTCCCGCTTGGAACTCCAATTGCAGTCCC

CGCAGAACTGCCTGTGGCGGGCCACTTGGCCCCACCTGAAGAACGTGTTACGCTCCTGGC

TCTTCTGTTGGGGGATGGGAACACAAAGCTGTCGGGTCGGAGAGGTACACGTCCTAATGC

CTTCTTCTACAGCAAAAACCCCGAATTGCTCGCGGCTTATCGCCGGTGTGCAGAAGCCTT

GGGTGCAAAGGTGAAAGCATACGTCCACCCGACTACGGGGGTGGTTACACTCGCAACCCT

CGCTCCACGTCCTGGAGCTCAAGATCCTGTCAAACGCCTCGTTGTCGAGGCGGGAATGGT

TGCTAAAGCCGAAGAGAAGAGGGTCCCGGAGGAGGTGTTTCGTTACCGGCGTGAGGCGTT

GGCCCTTTTCTTGGGCCGTTTGTTCTCGACAGACGGCTCTGTTGAAAAGAAGAGGATCTC

TTATTCAAGTGCCAGTTTGGGACTGGCCCAGGATGTCGCACATCTCTTGCTGCGCCTTGG

AATTACATCTCAACTCCGTTCGAGAGGGCCACGGGCTCACGAGGTTCTTATATCGGGCCG

CGAGGATATTTTGCGGTTTGCTGAACTTATCGGACCCTACCTCTTGGGGGCCAAGAGGGA

GAGACTTGCAGCGCTGGAAGCTGAGGCCCGCAGGCGTTTGCCTGGACAGGGATGGCACTT

GCGGCTTGTTCTTCCTGCCGTGGCGTACAGAGTGGGCGAGGCGGAAAGGCGCTCGGGATT

TTCGTGGAGTGAAGCCGGTCGGCGCGTCGCAGTTGCGGGATCGTGTTTGTCATCTGGACT

CAACCTCAAATTGCCCAGACGCTACCTTTCTCGGCACCGGTTGTCGCTGCTCGGTGAGGC

TTTTGCCGACCCTGGGCTGGAAGCGCTCGCGGAAGGCCAAGTGCTCTGGGACCCTATTGT

TGCTGTCGAACCGGCCGGTAAGGCGAGAACATTCGACTTGCGCGTTCCACCCTTTGCAAA

CTTCGTGAGCGAGGACCTGGTGGTGCATAACACCGTCCCCCTGGGCCAAGTGACAATCGA

TGGCGGGACCTACGACATCTATAGGACGACACGCGTCAACCAGCCTTCCATTGTGGGGAC

AGCCACGTTCGATCAGTACTGGAGCGTGCGCACCTCTAAGCGGACTTCAGGAACAGTGAC

CGTGACCGATCACTTCCGCGCCTGGGCGAACCGGGGCCTGAACCTCGGCACAATAGACCA

AATTACATTGTGCGTGGAGGGTTACCAAAGCTCTGGATCAGCCAACATCACCCAGAACAC

CTTCTCTCAGGGCTCTTCTTCCGGCAGTTCGGGTGGCTCATCCGGCTCCACAACGACTAC

TCGCATCGAGTGTGAGAACATGTCCTTGTCCGGACCCTACGTTAGCAGGATCACCAATCC

CTTTAATGGTATTGCGCTGTACGCCAACGGAGACACAGCCCGCGCTACCGTTAACTTCCC

CGCAAGTCGCAACTACAATTTCCGCCTGCGGGGTTGCGGCAACAACAATAATCTTGCCCG

TGTGGACCTGAGGATCGACGGACGGACCGTCGGGACCTTTTATTACCAGGGCACATACCC

-continued

CTGGGAGGCCCCAATTGACAATGTTTATGTCAGTGCGGGGAGTCATACAGTCGAAATCAC

TGTTACTGCGGATAACGGCACATGGGACGTGTATGCCGACTACCTGGTGATACAGAGCGA

GAAGGACGAGCTGTGACCTAGGTCCCCGAATTTCCCCGATCGTTCAAACATTTGGCAATA

AAGTTTCTTAAGATTGAATCCTGTTGCCGGTCTTGCGATGATTATCATATAATTTCTGTT

GAATTACGTTAAGCATGTAATAATTAACATGTAATGCATGACGTTATTTATGAGATGGGT

TTTTATGATTAGAGTCCCGCAATTATACATTTAATACGCGATAGAAAACAAAATATAGCG

CGCAAACTAGGATAAATTATCGCGCGCGGTGTCATCTATGTTACTAGATCGGGAATTGGA

ATTC

The expression cassettes in pAG2361 (SEQ ID NO: 70) and pAG4004 (SEQ ID NO: 71) are ZmUbilP:mmUBQ: ZmKozak:BAASS:P77853-T134-100-101:SEKDEL:NosT, with a sequence of SEQ ID NO: 68:

GGTACCCTGCAGTGCAGCGTGACCCGGTCGTGCCCCTCTCTAGAGATAATGAGCATTGCA

TGTCTAAGTTATAAAAAATTACCACATATTTTTTTTGTCACACTTGTTTGAAGTGCAGTT

TATCTATCTTTATACATATATTTAAACTTTACTCTACGAATAATATAATCTATAGTACTA

CAATAATATCAGTGTTTTAGAGAATCATATAAATGAACAGTTAGACATGGTCTAAAGGAC

AATTGAGTATTTTGACAACAGGACTCTACAGTTTTATCTTTTTAGTGTGCATGTGTTCTC

CTTTTTTTTTGCAAATAGCTTCACCTATATAATACTTCATCCATTTTATTAGTACATCCA

TTTAGGGTTTAGGGTTAATGGTTTTTATAGACTAATTTTTTTAGTACATCTATTTTATTC

TATTTTAGCCTCTAAATTAAGAAAACTAAAACTCTATTTTAGTTTTTTTATTTAATAATT

TAGATATAAAATAGAATAAAATAAAGTGACTAAAAATTAAACAAATACCCTTTAAGAAAT

TAAAAAAACTAAGGAAACATTTTTCTTGTTTCGAGTAGATAATGCCAGCCTGTTAAACGC

CGTCGACGAGTCTAACGGACACCAACCAGCGAACCAGCAGCGTCGCGTCGGGCCAAGCGA

AGCAGACGGCACGGCATCTCTGTCGCTGCCTCTGGACCCCTCTCGAGAGTTCCGCTCCAC

CGTTGGACTTGCTCCGCTGTCGGCATCCAGAAATTGCGTGGCGGAGCGGCAGACGTGAGC

CGGCACGGCAGGCGGCCTCCTCCTCCTCTCACGGCACGGCAGCTACGGGGGATTCCTTTC

CCACCGCTCCTTCGCTTTCCCTTCCTCGCCCGCCGTAATAAATAGACACCCCCTCCACAC

CCTCTTTCCCCAACCTCGTGTTGTTCGGAGCGCACACACACACAACCAGATCTCCCCCAA

ATCCACCCGTCGGCACCTCCGCTTCAAGGTACGCCGCTCGTCCTCCCCCCCCCCCCCTCT

CTACCTTCTCTAGATCGGCGTTCCGGTCCATGGTTAGGGCCCGGTAGTTCTACTTCTGTT

CATGTTTGTGTTAGATCCGTGTTTGTGTTAGATCCGTGCTGCTAGCGTTCGTACACGGAT

GCGACCTGTACGTCAGACACGTTCTGATTGCTAACTTGCCAGTGTTTCTCTTTGGGGAAT

CCTGGGATGGCTCTAGCCGTTCCGCAGACGGGATCGATTTCATGATTTTTTTTGTTTCGT

TGCATAGGGTTTGGTTTGCCCTTTTCCTTTATTTCAATATATGCCGTGCACTTGTTTGTC

GGGTCATCTTTTCATGCTTTTTTTTGTCTTGGTTGTGATGATGTGGTCTGGTTGGGCGGT

CGTTCTAGATCGGAGTAGAATTCTGTTTCAAACTACCTGGTGGATTTATTAATTTTGGAT

CTGTATGTGTGTGCCATACATATTCATAGTTACGAATTGAAGATGATGGATGGAAATATC

GATCTAGGATAGGTATACATGTTGATGCGGGTTTTACTGATGCATATACAGAGATGCTTT

TTGTTCGCTTGGTTGTGATGATGTGGTGTGGTTGGGCGGTCGTTCATTCGTTCTAGATCG

GAGTAGAATACTGTTTCAAACTACCTGGTGTATTTATTAATTTTGGAACTGTATGTGTGT

GTCATACATCTTCATAGTTACGAGTTTAAGATGGATGGAAATATCGATCTAGGATAGGTA

TACATGTTGATGTGGGTTTTACTGATGCATATACATGATGGCATATGCAGCATCTATTCA

-continued

TATGCTCTAACCTTGAGTACCTATCTATTATAATAAACAAGTATGTTTTATAATTATTTT

GATCTTGATATACTTGGATGATGGCATATGCAGCAGCTATATGTGGATTTTTTTAGCCCT

GCCTTCATACGCTATTTATTTGCTTGGTACTGTTTCTTTTGTCGATGCTCACCCTGTTGT

TTGGTGTTACTTCTGCAGATCCAGATCGGATCCTAAACCATGGCGAACAAACATTTGTCC

CTCTCCCTCTTCCTCGTCCTCCTTGGCCTGTCGGCCAGCTTGGCCTCCGGGCAACAAACA

AGCATTACTCTGACATCCAACGCATCCGGTACGTTTGACGGTTACTATTACGAACTCTGG

AAGGATACTGGCAATACAACAATGACGGTCTACACTCAAGGTCGCTTTTCCTGCCAGTGG

TCGAACATCAATAACGCGTTGTTTAGGACCGGGAAGAAATACAACCAGAATTGGCAGTCT

CTTGGCACAATCCGGATCACGTACTCTGCGACTTACAACCCAAACGGGAACTCCTACTTG

TGTATCTATGGCTGGTCTACCAACCCATTGGTCGAGTTCTACATCGTTGAGTCCTGGGGG

AACTGGAGACCGCCTGGTGCCTGCCTGGCCGAGGGCTCGCTCGTCTTGGACGCGGCTACC

GGGCAGAGGGTCCCTATCGAAAAGGTGCGTCCGGGGATGGAAGTTTTCTCCTTGGGACCT

GATTACAGACTGTATCGGGTGCCCGTTTTGGAGGTCCTTGAGAGCGGGGTTAGGGAAGTT

GTGCGCCTCAGAACTCGGTCAGGGAGAACGCTGGTGTTGACACCAGATCACCCGCTTTTG

ACCCCCGAAGGTTGGAAACCTCTTTGTGACCTCCCGCTTGGAACTCCAATTGCAGTCCCC

GCAGAACTGCCTGTGGCGGGCCACTTGGCCCCACCTGAAGAACGTGTTACGCTCCTGGCT

CTTCTGTTGGGGGATGGGAACACAAAGCTGTCGGGTCGGAGAGGTACACGTCCTAATGCC

TTCTTCTACAGCAAAAACCCCGAATTGCTCGCGGCTTATCGCCGGTGTGCAGAAGCCTTG

GGTGCAAAGGTGAAAGCATACGTCCACCCGACTACGGGGGTGGTTACACTCGCAACCCTC

GCTCCACGTCCTGGAGCTCAAGATCCTGTCAAACGCCTCGTTGTCGAGGCGGGAATGGTT

GCTAAAGCCGAAGAGAAGAGGGTCCCGGAGGAGGTGTTTCGTTACCGGCGTGAGGCGTTG

GCCCTTTTCTTGGGCCGTTTGTTCTCGACAGACGGCTCTGTTGAAAAGAAGAGGATCTCT

TATTCAAGTGCCAGTTTGGGACTGGCCCAGGATGTCGCACATCTCTTGCTGCGCCTTGGA

ATTACATCTCAACTCCGTTCGAGAGGGCCACGGGCTCACGAGGTTCTTATATCGGGCCGC

GAGGATATTTTGCGGTTTGCTGAACTTATCGGACCCTACCTCTTGGGGGCCAAGAGGGAG

AGACTTGCAGCGCTGGAAGCTGAGGCCCGCAGGCGTTTGCCTGGACAGGGATGGCACTTG

CGGCTTGTTCTTCCTGCCGTGGCGTACAGAGTGGGCGAGGCTGAAAGGCGCTCGGGATTT

TCGTGGAGTGAAGCCGGTCGGCGCGTCGCAGTTGCGGGATCGTGTTTGTCATCTGGACTC

AACCTCAAATTGCCCAGACGCTACCTTTCTCGGCACCGGTTGTCGCTGCTCGGTGAGGCT

TTTGCCGACCCTGGGCTGGAAGCGCTCGCGGAAGGCCAAGTGCTCTGGGACCCTATTGTT

GCTGTCGAACCGGCCGGTAAGGCGAGAACATTCGACTTGCGCGTTCCACCCTTTGCAAAC

TTCGTGAGCGAGGACCTGGTGGTGCATAACACCGTCCCCCTGGGCCAAGTGACAATCGAT

GGCGGGACCTACGACATCTATAGGACGACACGCGTCAACCAGCCTTCCATTGTGGGGACA

GCCACGTTCGATCAGTACTGGAGCGTGCGCACCTCTAAGCGGACTTCAGGAACAGTGACC

GTGACCGATCACTTCCGCGCCTGGGCGAACCGGGGCCTGAACCTCGGCACAATAGACCAA

ATTACATTGTGCGTGGAGGGTTACCAAAGCTCTGGATCAGCCAACATCACCCAGAACACC

-continued

```
TTCTCTCAGGGCTCTTCTTCCGGCAGTTCGGGTGGCTCATCCGGCTCCACAACGACTACT

CGCATCGAGTGTGAGAACATGTCCTTGTCCGGACCCTACGTTAGCAGGATCACCAATCCC

TTTAATGGTATTGCGCTGTACGCCAACGGAGACACAGCCCGCGCTACCGTTAACTTCCCC

GCAAGTCGCAACTACAATTTCCGCCTGCGGGGTTGCGGCAACAACAATAATCTTGCCCGT

GTGGACCTGAGGATCGACGGACGGACCGTCGGGACCTTTTATTACCAGGGCACATACCCC

TGGGAGGCCCCAATTGACAATGTTTATGTCAGTGCGGGGAGTCATACAGTCGAAATCACT

GTTACTGCGGATAACGGCACATGGGACGTGTATGCCGACTACCTGGTGATACAGAGCGAG

AAGGACGAGCTGTGACCTAGGTCCCCGAATTTCCCCGATCGTTCAAACATTTGGCAATAA

AGTTTCTTAAGATTGAATCCTGTTGCCGGTCTTGCGATGATTATCATATAATTTCTGTTG

AATTACGTTAAGCATGTAATAATTAACATGTAATGCATGACGTTATTTATGAGATGGGTT

TTTATGATTAGAGTCCCGCAATTATACATTTAATACGCGATAGAAAACAAAATATAGCGC

GCAAACTAGGATAAATTATCGCGCGCGGTGTCATCTATGTTACTAGATCGGGAATTGGAA

TTC
```

Figure 7A:
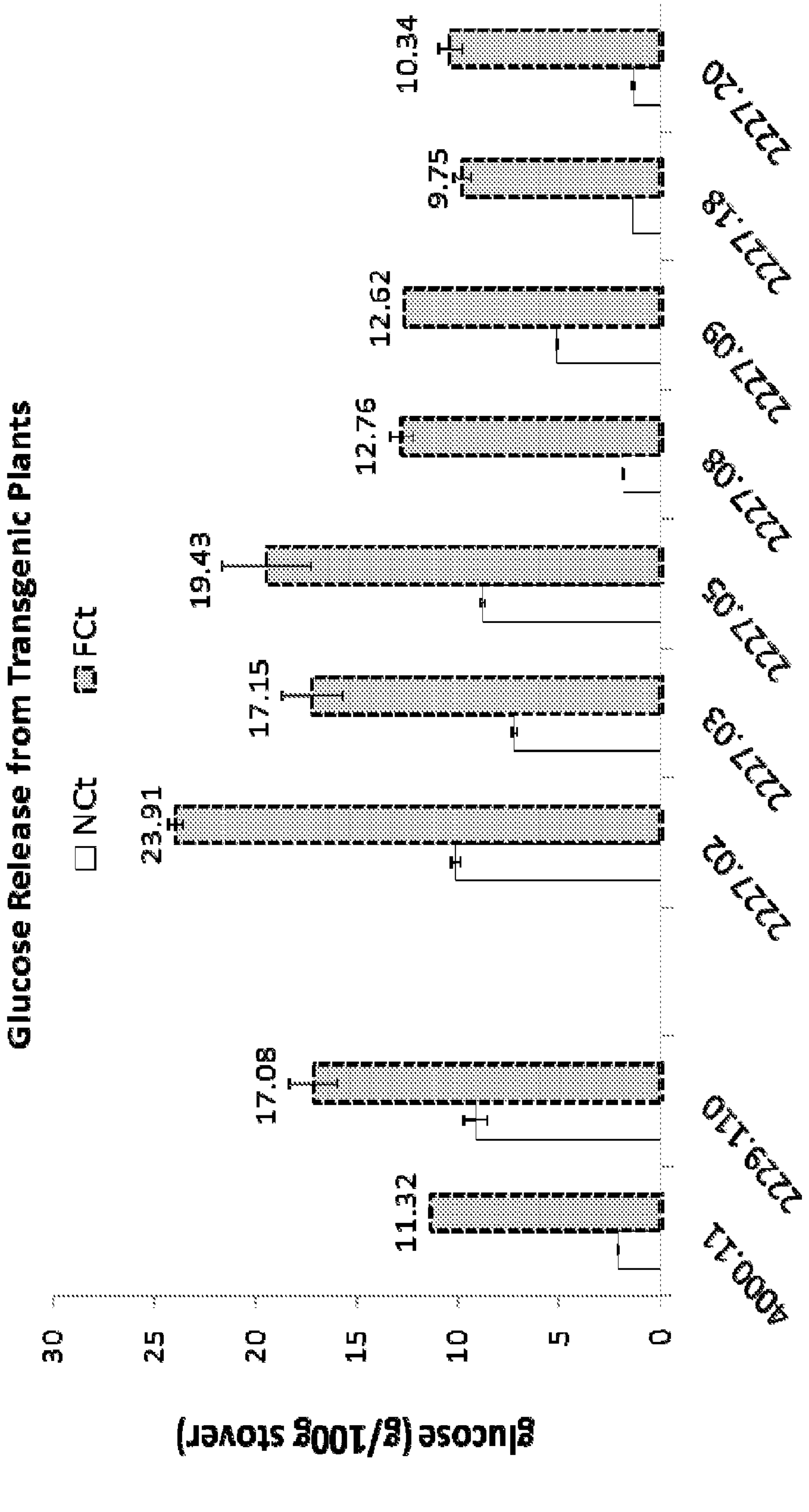
FIGS. 7A, 7B and 7C illustrate processing results with transgenic plants containing P77853-T134-100-101, where P77853 is XynB, the Tth intein is inserted at position T134, and the Tth intein has the mutation designations 100 and 101. The different plants were made using vectors pAG4000 (transgenic control plant), pAG2014, pAG2227, pAG2228, and pAG2229. In these figures NCt is data for plants that were processed, but no external enzymes were added during hydrolysis; Ct-Xyl is data for plants that were processed using external enzymes but no xylanase enzyme during hydrolysis; and FCt is data for plants that were processed using a full cocktail of external enzymes, including xylanase.
Figure 7B:
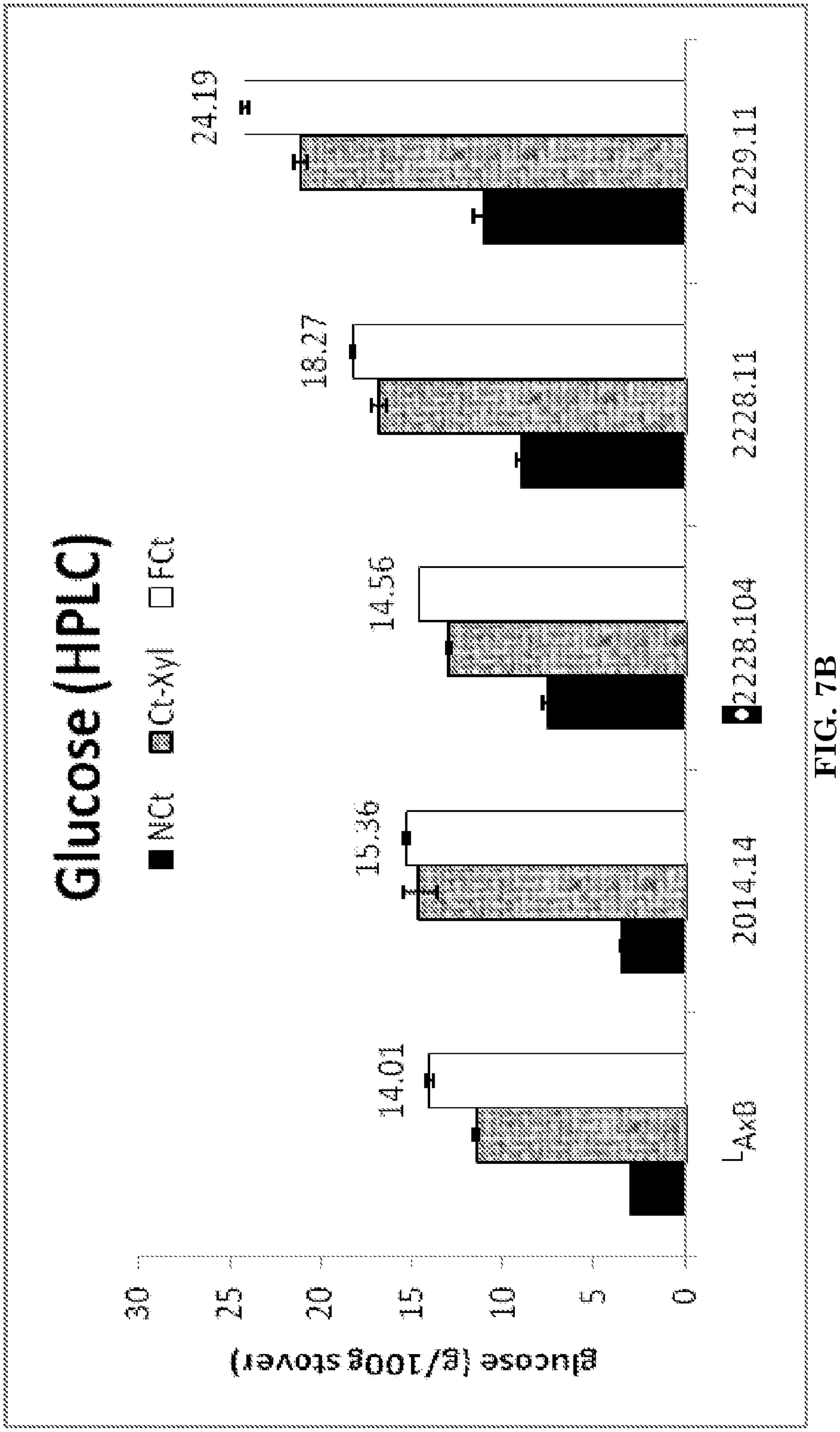
Figure 7C:
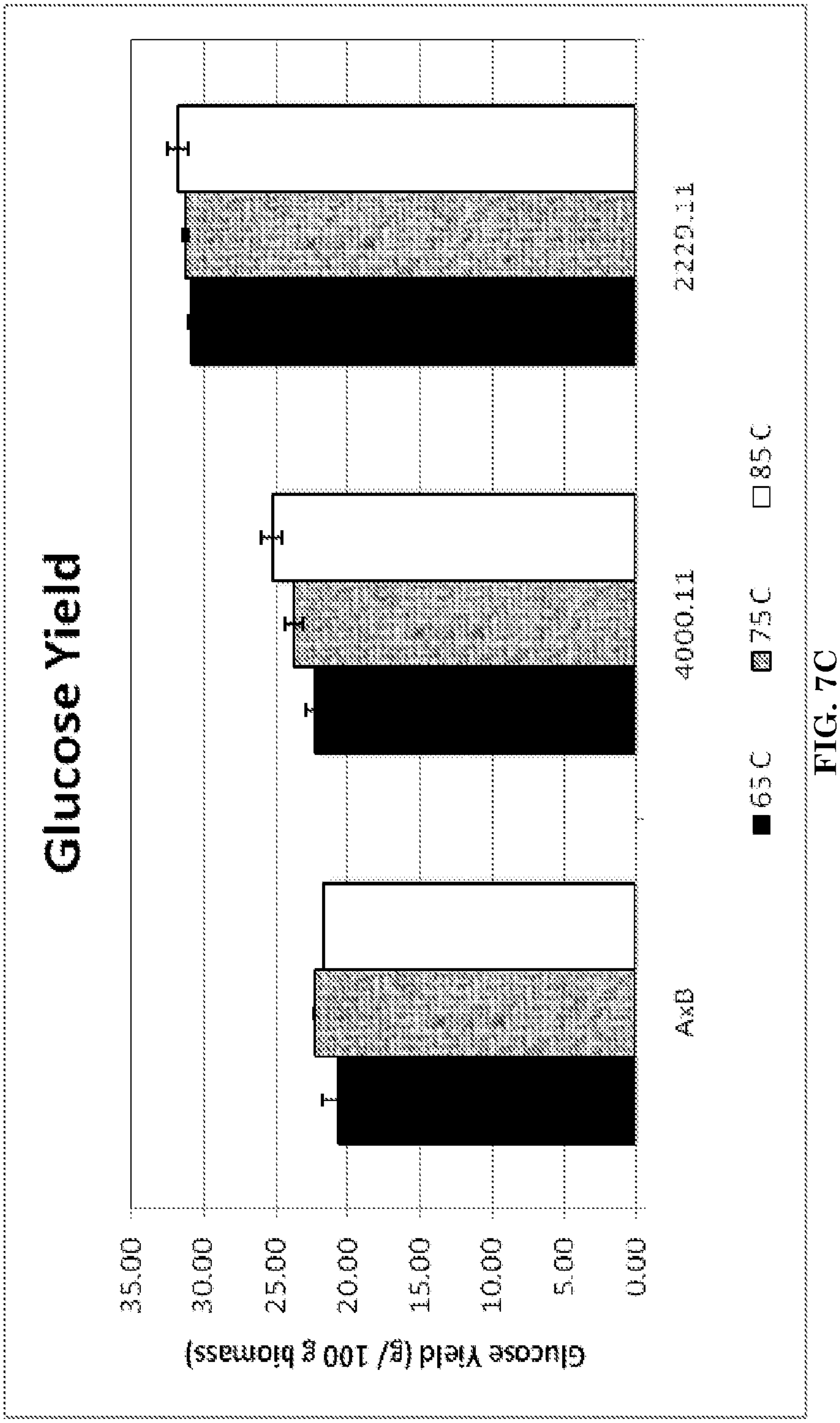

Introduction of the above constructs by transformation created the following transgenic maize events: 2227.02, 2227.03, 2227.05, 2227.08, 2227.09, 2228.104, 2228.11 and 2229.11. The first four numbers in each of these events indicates the pAG plasmid number for the plasmid used to create the plant. For example, pAG2227 was used to create the transgenic maize event 2227.02. The numbers after the decimal indicate the specific number for the event. For example, 2227.02, 2227.03, 2227.05, 2227.08, and 2227.09 are independent transgenic events made with pAG2227; 2228.104 and 2228.11 are independent transgenic events made with pAG2228; and 2229.11 is an independent transgenic event made with pAG2229. In FIGS. 7A-7C, "4000.11" refers to a control transgenic event containing the selection cassette that is present in pAG4000.

Processing Conditions

Transgenic corn stover was milled and processed with a modified pretreatment and hydrolysis procedure. 20.0 mg milled stover was added to 2-mL eppendorf tubes with pretreatment chemical solution (195 uL 0.175 M $(NH_4)HSO_3$, 0.175 M $(NH_4)_2CO_3$) at a liquor-to-solid (L/S) ratio of 10 or less. The pretreatment was conducted in a shaker with 350 rpm at either 55° C. (default condition that was used unless otherwise indicated), 65° C., 75° C., or 85° C. for 16 hours.

The pretreated stover was subject to enzymatic hydrolysis in Britton-Robinson polybuffer with sodium azide. The enzymatic hydrolysis was conducted at 2% (w:v) solids content, pH 4.9, 50° C. in a New Brunswick shaker at 250 rpm for varying amounts of time, up to 72 hours). A full in-house enzyme cocktail (FCt) comprising major individual enzyme component was used for plant stover evaluation with a loading of ~10 FPU. In conjunction, two types of hydrolysis were run in parallel: full enzyme cocktail (FCt), and cocktail minus enzyme (NCt). Accellerase™ 1500 was loaded at 10 FPU/g dry mass and Accellerase™ XY at 0.1 mL/g dry mass. Glucose yield was measured by YSI.

Processing results are presented in Table 1, below and in FIGS. 7A, 7B and 7C.

TABLE 1

| Construct | | No Cocktail (NC) Glucose (Glu) % Yield | NC Glu Std Dev | NC Xylose (Xylo) % Yield | NC Xylo Std Dev | Full Cocktail (FC) Glu % Yield | FC Glu Std Dev | FC Xylo % Yield | FC Xylo Std Dev |
|---|---|---|---|---|---|---|---|---|---|
| P77853:T134-100-101 | 2227.02 | 10.0695 | 0.2205 | 0.6566 | 0.0245 | 23.912 | 0.392 | 4.65745 | 0.10045 |
| P77853:T134-100-101 | 2227.03 | 7.203 | 0.147 | 0.343 | 0.098 | 17.15 | 1.519 | 3.95185 | 0.45815 |
| P77853:T134-100-101 | 2227.05 | 8.722 | 0.098 | 0.47775 | 0.03675 | 19.4285 | 2.2295 | 3.42755 | 0.33565 |
| P77853:T134-100-101 | 2229.11 | 9.0895 | 0.6125 | 1.37445 | 0.15925 | 17.0765 | 1.2005 | 4.7432 | 0.3038 |
| negative ck | 4000.11 | 2.058 | 0.0245 | 0.33565 | 0.08085 | 11.319 | 0.098 | 4.08415 | 0.07595 |

FIG. 7A shows processing results for transgenic plants made using pAG4000, pAG2229, and pAG2227. Hydrolysis using either a full enzyme cocktail (FCt) or no external enzyme cocktail (NCt) are shown. In FIG. 7A, the transgenic plant labeled 4000.11 represents the negative control, which does not express an intein-modified enzyme. In FIG. 7A, all of the transgenic plants expressing an intein-modified enzyme out perform 4000.11 because they yield more glucose under both FCt and NCt hydrolysis conditions. FIG. 7B shows similar processing results for transgenic plants made using pAG2014, pAG2228, and pAG2229, and a non-transgenic plant labeled "A×B". In FIG. 7B, all of the selected transgenic plants outperform the non-transgenic plant, A×B, in terms of glucose production. FIG. 7C shows processing results at different temperatures for a non-transgenic plant (A×B), a transgenic plant made with pAG4000 (4000.11), and a transgenic plant expressing an intein-modified enzyme made with pAG2229 (2229.11). In FIG. 7C the pretreatment was conducted at either 65 C, 75 C, or 85 C.

Example 18

Additional sequences. Sequences referred to herein include but are not limited to the following:

>S158-39

(SEQ ID NO: 1)

CAAACAAGCATTACTCTGACATCCAACGCATCCGGTACGTTTGACGGTTACTATTACGAA

CTCTGGAAGGATACTGGCAATACAACAATGACGGTCTACACTCAAGGTCGCTTTTCCTGC

CAGTGGTCGAACATCAATAACGCGTTGTTTAGGACCGGGAAGAAATACAACCAGAATTGG

CAGTCTCTTGGCACAATCCGGATCACGTACTCTGCGACTTACAACCCAAACGGGAACTCC

TACTTGTGTATCTATGGCTGGTCTACCAACCCATTGGTCGAGTTCTACATCGTTGAGTCC

TGGGGGAACTGGAGACCGCCTGGTGCCACGTCCCTGGGCCAAGTGACAATCGATGGCGGG

ACCTACGACATCTATAGGACGACACGCGTCAACCAGCCT*TGCCTGGCCGAGGGCTCGCTC*

*GTCTTGGACGCGGCTACCGGGCAGAGGGTCCCTATCGAAAAGGTGCGTCCGGGGATGGAA*

*GTTTTCTCCTTGGGACCTGATTACAGACTGTATCGGGTGCCCGTTTTGGAGGTCCTTGAG*

*AGCGGGGTTGGGGAAGTTGTGCGCCTCAGAACTCGGTCAGGGAGAACGCTGGTGTTGACA*

*CCAGATCACCCGCTTTTGACCCCCGAAGGTTGGAAACCTCTTTGTGACCTCCCGCTTGGA*

*ACTCCAATTGCAGTCCCCGCAGAACTGCCTGTGGCGGGCCACTTGGCCCCACCTGAAGAA*

*CGTGTTACGCTCCTGGCTCTTCTGTTGGGGGATGGGAACACAAAGCTGTCGGGTCGGAGA*

*GGTACACGTCCTAATGCCTTCTTCTACAGCAAAGACCCCGAATTGCTCGCGGCTTATCGC*

*CGGTGTGCAGAAGCCTTGGGTGCAAAGGTGAAAGCATACGTCCACCCGACTACGGGGGTG*

*GTTACACTCGCAACCCTCGCTCCACGTCCTGGAGCTCAAGATCCTGTCAAACGCCTCGTT*

*GTCGAGGCGGGAATGGTTGCTAAAGCCGAAGAGAAGAGGGTCCCGGAGGAGGTGTTTCGT*

*TACCGGCGTGAGGCGTTGGCCCTTTTCTTGGGCCGTTTGTCCTCGACAGACGGCTCTGTT*

*GAAAGGAAGAGGATCTCTTATTCAAGTGCCAGTTTGGGACTGGCCCAGGATGTCGCACAT*

*CTCTTGCTGCGCCTTGGAATTACATCTCAACTCCGTTCGAGAGGGCCACGGGCTCACGAG*

*GTTCTTATATCGGGCCGCGAGGATATTTTGCGGTTTGCTGAACTTATCGGACCCTACCTC*

*TTGGGGGCCAAGAGGGAGAGACTTGCAGCGCTGGAAGCTGAGGCCCGCAGGCGTTTGCCT*

*GGACAGGGATGGCACTTGCGGCTTGTTCTTCCTGCCGTGGCGTACAGAGTGAGCGAGGCT*

*AAAAGGCGCTCGGGATTTTCGTGGAGTGAAGCCGGTCAGCGCGTCGCAGTTGCGGGATCG*

*TGTTTGTCATCTGGACTCAACCTCAAATTGCCCAGACGCTACCTTTCTCGGCACCGGTTG*

*TCGCTGCTCGGTGAGGCTTTTGCCGACCCTGGGCTGGAAGCGCTCGCGGAAGGCCAAGTG*

*CTCTGGGACCCTATTGTTGCTGTCGAACCGGCCGGTAAGGCGAGAACATTCGACTTGCGC*

*GTTCCACCCTTTGCAAACTTCGTGAGCGAGGACCTGGTGGTGCATAAC*TCCATTGTGGGG

ACAGCCACGTTCGATCAGTACTGGAGCGTGCGCACCTCTAAGCGGACTTCAGGAACAGTG

ACCGTGACCGATCACTTCCGCGCCTGGGCGAACCGGGGCCTGAACCTCGGCACAATAGAC

CAAATTACATTGTGCGTGGAGGGTTACCAAAGCTCTGGATCAGCCAACATCACCCAGAAC

ACCTTCTCTCAGGGCTCTTCTTCCGGCAGTTCGGGTGGCTCATCCGGCTCCACAACGACT

ACTCGCATCGAGTGTGAGAACATGTCCTTGTCCGGACCCTACGTTAGCAGGATCACCAAT

CCCTTTAATGGTATTGCGCTGTACGCCAACGGAGACACAGCCCGCGCTACCGTTAACTTC

CCCGCAAGTCGCAACTACAATTTCCGCCTGCGGGGTTGCGGCAACAACAATAATCTTGCC

CGTGTGGACCTGAGGATCGACGGACGGACCGTCGGGACCTTTTATTACCAGGGCACATAC

CCCTGGGAGGCCCCAATTGACAATGTTTATGTCAGTGCGGGGAGTCATACAGTCGAAATC

-continued

ACTGTTACTGCGGATAACGGCACATGGGACGTGTATGCCGACTACCTGGTGATACAG

>S158-39

(SEQ ID NO: 2)

QTSITLTSNASGTFDGYYYELWKDTGNTTMTVYTQGRFSCQWSNINNALFRTGKKYNQNW

QSLGTIRITYSATYNPNGNSYLCIYGWSTNPLVEFYIVESWGNWRPPGATSLGQVTIDGG

TYDIYRTTRVNQPCLAEGSLVLDAATGQRVPIEKVRPGMEVFSLGPDYRLYRVPVLEVLE

SGVGEVVRLRTRSGRTLVLTPDHPLLTPEGWKPLCDLPLGTPIAVPAELPVAGHLAPPEE

RVTLLALLLGDGNTKLSGRRGTRPNAFFYSKDPELLAAYRRCAEALGAKVKAYVHPTTGV

VTLATLAPRPGAQDPVKRLVVEAGMVAKAEEKRVPEEVFRYRREALALFLGRLSSTDGSV

ERKRISYSSASLGLAQDVAHLLLRLGITSQLRSRGPRAHEVLISGREDILRFAELIGPYL

LGAKRERLAALEAEARRRLPGQGWHLRLVLPAVAYRVSEAKRRSGFSWSEAGQRVAVAGS

CLSSGLNLKLPRRYLSRHRLSLLGEAFADPGLEALAEGQVLWDPIVAVEPAGKARTFDLR

VPPFANFVSEDLVVHNSIVGTATFDQYWSVRTSKRTSGTVTVTDHFRAWANRGLNLGTID

QITLCVEGYQSSGSANITQNTFSQGSSSGSSGGSSGSTTTTRIECENMSLSGPYVSRITN

PFNGIALYANGDTARATVNFPASRNYNFRLRGCGNNNNLARVDLRIDGRTVGTFYYQGTY

PWEAPIDNVYVSAGSHTVEITVTADNGTWDVYADYLVIQ (SEQ ID NO: 3)

>S158-21

(SEQ ID NO: 4)

>S158-21

(SEQ ID NO: 5)

>T134-180

(SEQ ID NO: 6)

>T134-180

(SEQ ID NO: 7)

>T134-100-165 (also called T134-1065)

>T134-100-165 (also called T134-1065)

(SEQ ID NO: 8)

QTSITLTSNASGTFDGYYYELWKDTGNTTMTVYTQGRFSCQWSNINNALFRTGKKYNQNW

QSLGTIRITYSATYNPNGNSYLCIYGWSTNPLVEFYIVESWGNWRPPGACLAEGSLVLDA

ATGQRVPIEKVRPGMEVFSLGPDYRLYRVPVLEVLESGVREVVRLRTRSGRTLVLTPDHP

LLTPEGWKPLCDLPLGTPIAVPAELPVAGHLAPPEERVTLLALLLGDGNTKLSGRRGTRP

NAFFYSKNPELLAAYRRCAEALGAKVKAYVHPTTGVVTLATLAPRPGAQDPVKRLVVEAG

MVAKAEEKRVPEEVFRYRREALALFLGRLFSTDGSVEKKRISYSSASLGLAQDVAHLLLR

LGITSQLRSRGPRAHEVLISGREDILRFAELIGPYLLGAKRERLAALEAEARRRLPGQGW

HLRLVLPAVAYRVSEAKRRSGFSWSEAGRRVAVAGSCLSSGLNLKLPRRYLSRHRLSLLG

EAFADPGLEALAEGQVLWDPIVAVEPAGKARTFDLRVPPFANFVSEDLVVHNTVPLGQVT

IDGGTYDIYRTTRVNQPSIVGTATFDQYWSVRTSKRTSGTVTVTDHFRAWANRGLNLGTI

DQITLCVEGYQSSGSANITQNTFSQGSSSGSSGGSSGSTTTTRIECENMSLSGPYVSRIT

NPFNGIALYANGDTARATVNFPASRNYNFRLRGCGNNNNLARVDLRIDGRTVGTFYYQGT

YPWEAPIDNVYVSAGSHTVEITVSADNGTWDVYADYLVIQ

-continued (SEQ ID NO: 9)
>T134-10068 (also called T134-100-68)

>T134-10068 (also called T134-100-68)
(SEQ ID NO: 10)
QTSITLTSNASGTFDGYYYELWKDTGNTTMTVYTQGRFSCQWSNINNALFRTGKKYNQNW

QSLGTIRITYSATYNPNGNSYLCIYGWSTNPLVEFYIVESWGNWRPPGACLAEGSLVLDA

ATGQRVPIEKVRPGMEVFSLGPDYRLYRVPVLEVLESGVREVVRLRTRSERTLVLTPDHP

LLTPEGWKPLCDLPLGTPIAVPAELPVAGHLAPPEERVTLLALLLGDGNTKLSGRRGTRP

NAFFHSKDPELLAAYRRCAEALGAKVKAYVHPTTGVVTLATLAPRPGAQDPVKRLVVEAG

MVAKAEEKRVPEEVFRYRREALALFLGRLFSTDGSVEKKRISYSSASLGLAQDVAHLLLR

LGITSQLRSRGPRAHEVLISGREDILRFAELIGPYLLGAKRERLAALEAEARRRLPVQGW

HSRLVLPAVAYRVSEAKRRSGFSWSEAGRRVAVAGSCLSSGLNLKLPRRYLSRHRLSLLG

EAFADPGLEALAEGQVLWDPIVAVEPAGKARTFDLRVPPFANFVSEDLVVHNTVPLGQVT

IDGGTYDIYRTTRVNQPSIVGTATFDQYWSVRTSKRTSGTVTVTDHFRAWANRGLNLGTI

DQITLCVEGYQSSGSANITQNTFSQGSSSGSSGGSSGSTTTTRIECENMSLSGPYVSRIT

NPFNGIALYANGDTARATVNFPASRNYNFRLRGCGNNNNLARVDLRIDGRTVGTFYYQGT

YPWEAPIDNVYVSAGSHTVEITVTADNGTWDVYADYLVIQ (SEQ ID NO: 11)
>T134-10039 (also called T134-100-39)

>T134-10039 (also called T134-100-39)
(SEQ ID NO: 12)
QTSITLTSNASGTFDGYYYELWKDTGNTTMTVYTQGRFSCQWSNINNALFRTGKKYNQNW

QSLGTIRITYSATYNPNGNSYLCIYGWSTNPLVEFYIVESWGNWRPPGACLAEGSLVLDA

ATGQRVPIEKVRPGMEVFSLGPDYRLYRVPVLEVLESGVREVVRLRTRSGRTLVLTPDHP

LLTPEGWKPLCDLPLGTPIAVPAELPVAGHLAPPEERVTLLALLLGDGNTKLSGRRGTRP

NAFFYSKDPELLAAYRRCAEALGAKVKAYVHPTTGVVTLATLAPRPGAQDPVKRLVVEAG

MVAKAEEKRVPEEVFRYRREALALFLGRLFSTDGSVEKKRISYSSASLGLAQDVAHLLLR

LGITSQLRSRGPRAHEVLISGREDILRFAELIGPYLLGAKRERLAALEAEARRRLPGQGW

HLRLVLPAVAYRVSEAKRRSGFSWSEAGRRVAVAGSCLSSGLNLKLPRRYLSRHRLSLLG

EAFADPGLEALAEGLVLWDPIVAVEPAGKARTFDLRVPPFANFVSEDLVVHNTVPLGQVT

IDGGTYDIYRTTRVNQPSIVGTATFDQYWSVRTSKRTSGTVTVTDHFRAWANRGLNLGTI

DQITLCVEGYQSSGSANITQNTFSQGSSSGSSGGSSGSTTTTRIECENMSLSGPYVSRIT

NPFNGIALYANGDTARATVNFPASRNYNFRLRGCGNNNNLARVDLRIDGRTVGTFYYQGT

YPWEAPIDNVYVSAGSHTVEITVTADNGTWDVYADYLVIQ

>T134-100
(SEQ ID NO: 13)
CAAACAAGCATTACTCTGACATCCAACGCATCCGGTACGTTTGACGGTTACTATTACGAA

CTCTGGAAGGATACTGGCAATACAACAATGACGGTCTACACTCAAGGTCGCTTTTCCTGC

CAGTGGTCGAACATCAATAACGCGTTGTTTAGGACCGGGAAGAAATACAACCAGAATTGG

CAGTCTCTTGGCACAATCCGGATCACGTACTCTGCGACTTACAACCCAAACGGGAACTCC

TACTTGTGTATCTATGGCTGGTCTACCAACCCATTGGTCGAGTTCTACATCGTTGAGTCC

TGGGGGAACTGGAGACCGCCTGGTGCCTGCCTGGCCGAGGGCTCGCTCGTCTTGGACGCG

GCTACCGGGCAGAGGGTCCCTATCGAAAAGGTGCGTCCGGGGATGGAAGTTTTCTCCTTG

GGACCTGATTACAGACTGTATCGGGTGCCCGTTTTGGAGGTCCTTGAGAGCGGGGTTAGG

GAAGTTGTGCGCCTCAGAACTCGGTCAGGGAGAACGCTGGTGTTGACACCAGATCACCCG

-continued

CTTTTGACCCCCGAAGGTTGGAAACCTCTTTGTGACCTCCCGCTTGGAACTCCAATTGCA

GTCCCCGCAGAACTGCCTGTGGCGGGCCACTTGGCCCCACCTGAAGAACGTGTTACGCTC

CTGGCTCTTCTGTTGGGGGATGGGAACACAAAGCTGTCGGGTCGGAGAGGTACACGTCCT

AATGCCTTCTTCTACAGCAAAGACCCCGAATTGCTCGCGGCTTATCGCCGGTGTGCAGAA

GCCTTGGGTGCAAAGGTGAAAGCATACGTCCACCCGACTACGGGGGTGGTTACACTCGCA

ACCCTCGCTCCACGTCCTGGAGCTCAAGATCCTGTCAAACGCCTCGTTGTCGAGGCGGGA

ATGGTTGCTAAAGCCGAAGAGAAGAGGGTCCCGGAGGAGGTGTTTCGTTACCGGCGTGAG

GCGTTGGCCCTTTTCTTGGGCCGTTTGTTCTCGACAGACGGCTCTGTTGAAAAGAAGAGG

ATCTCTTATTCAAGTGCCAGTTTGGGACTGGCCCAGGATGTCGCACATCTCTTGCTGCGC

CTTGGAATTACATCTCAACTCCGTTCGAGAGGGCCACGGGCTCACGAGGTTCTTATATCG

GGCCGCGAGGATATTTTGCGGTTTGCTGAACTTATCGGACCCTACCTCTTGGGGGCCAAG

AGGGAGAGACTTGCAGCGCTGGAAGCTGAGGCCCGCAGGCGTTTGCCTGGACAGGGATGG

CACTTGCGGCTTGTTCTTCCTGCCGTGGCGTACAGAGTGAGCGAGGCTAAAAGGCGCTCG

GGATTTTCGTGGAGTGAAGCCGGTCGGCGCGTCGCAGTTGCGGGATCGTGTTTGTCATCT

GGACTCAACCTCAAATTGCCCAGACGCTACCTTTCTCGGCACCGGTTGTCGCTGCTCGGT

GAGGCTTTTGCCGACCCTGGGCTGGAAGCGCTCGCGGAAGGCCAAGTGCTCTGGGACCCT

ATTGTTGCTGTCGAACCGGCCGGTAAGGCGAGAACATTCGACTTGCGCGTTCCACCCTTT

GCAAACTTCGTGAGCGAGGACCTGGTGGTGCATAACACCGTCCCCC TGGGCCAAGTGAC

AATCGATGGCGGGACCTACGACATCTATAGGACGACACGCGTCAACCAGCCTTCCATTGT

GGGGACAGCCACGTTCGATCAGTACTGGAGCGTGCGCACCTCTAAGCGGACTTCAGGAAC

AGTGACCGTGACCGATCACTTCCGCGCCTGGGCGAACCGGGGCCTGAACCTCGGCACAAT

AGACCAAATTACATTGTGCGTGGAGGGTTACCAAAGCTCTGGATCAGCCAACATCACCCA

GAACACCTTCTCTCAGGGCTCTTCTTCCGGCAGTTCGGGTGGCTCATCCGGCTCCACAAC

GACTACTCGCATCGAGTGTGAGAACATGTCCTTGTCCGGACCCTACGTTAGCAGGATCAC

CAATCCCTTTAATGGTATTGCGCTGTACGCCAACGGAGACACAGCCCGCGCTACCGTTAA

CTTCCCCGCAAGTCGCAACTACAATTTCCGCCTGCGGGGTTGCGGCAACAACAATAATCT

TGCCCGTGTGGACCTGAGGATCGACGGACGGACCGTCGGGACCTTTTATTACCAGGGCAC

ATACCCCTGGGAGGCCCCAATTGACAATGTTTATGTCAGTGCGGGGAGTCATACAGTCGA

AATCACTGTTACTGCGGATAACGGCACATGGGACGTGTATGCCGACTACCTGGTGATACA

G

>T134-100

(SEQ ID NO: 14)

QTSITLTSNASGTFDGYYYELWKDTGNTTMTVYTQGRFSCQWSNINNALFRTGKKYNQNW

QSLGTIRITYSATYNPNGNSYLCIYGWSTNPLVEFYIVESWGNWRPPGACLAEGSLVLDA

ATGQRVPIEKVRPGMEVFSLGPDYRLYRVPVLEVLESGVREVVRLRTRSGRTLVLTPDHP

LLTPEGWKPLCDLPLGTPIAVPAELPVAGHLAPPEERVTLLALLLGDGNTKLSGRRGTRP

NAFFYSKDPELLAAYRRCAEALGAKVKAYVHPTTGVVTLATLAPRPGAQDPVKRLVVEAG

MVAKAEEKRVPEEVFRYRREALALFLGRLFSTDGSVEKKRISYSSASLGLAQDVAHLLLR

LGITSQLRSRGPRAHEVLISGREDILRFAELIGPYLLGAKRERLAALEAEARRRLPGQGW

HLRLVLPAVAYRVSEAKRRSGFSWSEAGRRVAVAGSCLSSGLNLKLPRRYLSRHRLSLLG

EAFADPGLEALAEGQVLWDPIVAVEPAGKARTFDLRVPPFANFVSEDLVVHNTVPLGQVT

-continued

IDGGTYDIYRTTRVNQPSIVGTATFDQYWSVRTSKRTSGTVTVTDHFRAWANRGLNLGTI

DQITLCVEGYQSSGSANITQNTFSQGSSSGSSGGSSGSTTTTRIECENMSLSGPYVSRIT

NPFNGIALYANGDTARATVNFPASRNYNFRLRGCGNNNNLARVDLRIDGRTVGTFYYQGT

YPWEAPIDNVYVSAGSHTVEITVTADNGTWDVYADYLVIQ

Sequences of S158-30-m79-110

(SEQ ID NO: 15)

>S158-30-m79-110 (intein is italicized, nt changes are shown as the underlined text)

CAAACAAGCATTACTCTGACATCCAACGCATCCGGTACGTTTGACGGTTACAATTACGAA

CTCTGGAAGGATACTGGCAATACAACAATGACGGTCTACACTCAAGGTCGCTTTTCCTGC

CAGTGGTCGAACATCAATAACGCGTTGTTTAGGACCGGGAAGAAATACAACCAGAATTGG

CAGTCTCTTGGCACAATCCGGATCACGTACTCTGCGACTTACAACCCAAACGGGAACTCC

TACTTGTGTATCTATGGCTGGTCTACCAACCCATTGGTCGAGTTCTACATCGTTGAGTCC

TGGGGGAACTGGAGACCGCCTGGTGCCACGTCCCTGGGCCAAGTGACAATCGATGGCGGG

ACCTACGACATCTATAGGACGACACGCGTCAACCAGCCT*TGCCTGGCCGAGGGCTCGCTC*

*GTCTTGGACGCGGCTACCGGGCAGAGGGTCCCTATCGAAAAGGTGCGTCCGGGGATGGAA*

*GTTTTCTCCTTGGGACCTGATTACAGACTGTATCAGGTGCCCGTTTTGGAGGTCCTTGAG*

*AGCGGGGTTGGGGAAGTTGTGCGCCTCAGAACTCGGTCAGGGAGAACGCTGGTGTTGACA*

*CCAGATCACCCGCTTTTGACCCCCGAAGGTTGGAAACCTCTTTGTGACCTCCCGCTTGGA*

*ACTCCAATTGCAGTCCCCGCAGAACTGCCTGTGGCGGGCCACTTGGCCCCACCTGAAGAA*

*CGTGTTACGCCCCTGGCTCTTCTGTTGGGGGATGGGAACACAAAGCTGTCGGGTCGGAGA*

*GGTACACGTCCTAATGCCTTCTTCTACTGCAAAGACCCCGAATTGCTCGCGGCTTATCGC*

*CGGTGTGCAGAAGCCTTGGGTGCAAAGGTGAAAGCATACGTCCACCCGACTACGGGGGTG*

*GTTACACTCGCAACCCTCGCTCCACGTCCTGGAGCTCAAGATCCTGTCAAACGCCTCGTT*

*GTCGAGGCGGGAATGGTTGCTAAAGCCGAAGAGAAGAGGGTCCCGGAGGAGGTGTTCCGT*

*TACCGGCGTGAGGCGTTGGCCCTTTTCTTGGGCCGTTTGTTCTCGACAGACGGCTCTGTT*

*GAAAAGAAGAGGATCTCTTATTCAAGTGCCAGTTTGGGACTGGCCCAGGATGTCGCACAT*

*CTCTTGCTGCGCCTTGGAATTACATCTCAACTCCGTTCGAGAGGGCCACGGGCTCACGAG*

*GTTCTTATATCGGGCCGCGAGGATATTTTGCGGTTTGCTGAACTTATCGGACCCTACCTC*

*TTGGGGGCCAAGAGGGAGAGACTTGCAGCGCTGGAAGCTGAGGCCCGCAGGCGTTTGCCT*

*GGACAGGGATGGCACTTGCGGCTTGTTCTTCCTGCCGTGGCGTACAGAGTGAGCGAGGCT*

*AAAAGGCGCTCGGGATTTTCGTGGAGTGAAGCCGGTCGGCGCGTCGCAGTTGCGGGATCG*

*TGTTTGTCATCTGGACTCAACCTCAAATTGCCCAGACGCTACCTTTCTCGGCACCGGTTG*

*TCGATGCTCGGTGAGGCTTTTGCCGACCCTGGGCTGGAAGCGCTCGCGGAAGGCCAAGTG*

*CTCTGGGACCCTATTGTTGCTGTCGAACCGGCCGGTAAGGCGAGAACATTCGACTTGCGC*

*GTTCCACCCTTTGCAAACTTCGCGAGCGAGGACCTGGTGGTGCATAAC*TCCATTGTGGGG

ACAGCCACGTTCGATCAGTACTGGAGCGTGCGCACCTCTAAGCGGACTTCAGGAACAGTG

ACCGTGACCGATCACTTCCGCGCCTGGGCGAACCGGGGCCTGAACCTCGGCACAATAGAC

CAAATTACATTGTGCGTGGAGGGTTACCAAAGCTCTGGATCAGCCAACATCACCCAGAAC

ACCTTCTCTCAGGGCTCTTCTTCCGGCAGTTCGGGTGGCTCATCCGGCTCCACAACGACT

ACTCGCATCGAGTGTGAGAACATGTCCTTGTCCGGACCCTACGTTAGCAGGATCACCAAT

CCCTTTAATGGTATTGCGCTGTACGCCAACGGAGACACAGCCCGCGCTACCGTTAACTTC

CCCGCAAGTCGCAACTACAATTTCCGCCTGCGGGGTTGCGGCAACAACAATAATCTTGCC

-continued

CGTGTGGACCTGAGGATCGACGGACGGACCGTCGGGACCTTTTATTACCAGGGCACATAC

CCCTGGGAGGCCCCAATTGACAATGTTTATGTCAGTGCGGGGAGTCATACAGTCGAAATC

ACTGTTACTGCGGATAACGGCACATGGGACGTGTATGCCGACTACCTGGTGATACAGTGA

>S158-30-m79-110

(SEQ ID NO: 16)

QTSITLTSNASGTFDGYNYELWKDTGNTTMTVYTQGRFSCQWSNINNALFRTGKKYNQNW

QSLGTIRITYSATYNPNGNSYLCIYGWSTNPLVEFYIVESWGNWRPPGATSLGQVTIDGG

TYDIYRTTRVNQPCLAEGSLVLDAATGQRVPIEKVRPGMEVFSLGPDYRLYQVPVLEVLE

SGVGEVVRLRTRSGRTLVLTPDHPLLTPEGWKPLCDLPLGTPIAVPAELPVAGHLAPPEE

RVTPLALLLGDGNTKLSGRRGTRPNAFFYCKDPELLAAYRRCAEALGAKVKAYVHPTTGV

VTLATLAPRPGAQDPVKRLVVEAGMVAKAEEKRVPEEVFRYRREALALFLGRLFSTDGSV

EKKRISYSSASLGLAQDVAHLLLRLGITSQLRSRGPRAHEVLISGREDILRFAELIGPYL

LGAKRERLAALEAEARRRLPGQGWHLRLVLPAVAYRVSEAKRRSGFSWSEAGRRVAVAGS

CLSSGLNLKLPRRYLSRHRLSMLGEAFADPGLEALAEGQVLWDPIVAVEPAGKARTFDLR

VPPFANFASEDLVVHNSIVGTATFDQYWSVRTSKRTSGTVTVTDHFRAWANRGLNLGTID

QITLCVEGYQSSGSANITQNTFSQGSSSGSSGGSSGSTTTTRIECENMSLSGPYVSRITN

PFNGIALYANGDTARATVNFPASRNYNFRLRGCGNNNNLARVDLRIDGRTVGTFYYQGTY

PWEAPIDNVYVSAGSHTVEITVTADNGTWDVYADYLVIQ (SEQ ID NO: 17)

1 QTSITLTSNASGTFDGYNYELWKDTGNTTMTVYTQGRFSCQWSNINNALFRTGKKYNQNW

61 QSLGTIRITYSATYNPNGNSYLCIYGWSTNPLVEFYIVESWGNWRPPGATSLGQVTIDGG

121 TYDIYRTTRVNQPCLAEGSLVLDAATGQRVPIEKVRPGMEVFSLGPDYRLYQVPVLEVLE

181 SGVGEVVRLRTRSGRTLVLTPDHPLLTPEGWKPLCDLPLGTPIAVPAELPVAGHLAPPEE

241 RVTPLALLLGDGNTKLSGRRGTRPNAFFYCKDPELLAAYRRCAEALGAKVKAYVHPTTGV

301 VTLATLAPRPGAQDPVKRLVVEAGMVAKAEEKRVPEEVFRYRREALALFLGRLFSTDGSV

361 EKKRISYSSASLGLAQDVAHLLLRLGITSQLRSRGPRAHEVLISGREDILRFAELIGPYL

421 LGAKRERLAALEAEARRRLPGQGWHLRLVLPAVAYRVSEAKRRSGFSWSEAGRRVAVAGS

481 CLSSGLNLKLPRRYLSRHRLSMLGEAFADPGLEALAEGQVLWDPIVAVEPAGKARTFDLR

541 VPPFANFASEDLVVHNSIVGTATFDQYWSVRTSKRTSGTVTVTDHFRAWANRGLNLGTID

601 QITLCVEGYQSSGSANITQNTFSQGSSSGSSGGSSGSTTTTRIECENMSLSGPYVSRITN

661 PFNGIALYANGDTARATVNFPASRNYNFRLRGCGNNNNLARVDLRIDGRTVGTFYYQGTY

721 PWEAPIDNVYVSAGSHTVEITVTADNGTWDVYADYLVIQ- (SEQ ID NO: 17

(amino acid sequence
and

SEQ ID NO: 18

(nucleic acid sequence)

1 CAAACAAGCATTACTCTGACATCCAACGCATCCGGTACGTTTGACGGTTACAATTACGAA

61 CTCTGGAAGGATACTGGCAATACAACAATGACGGTCTACACTCAAGGTCGCTTTTCCTGC

121 CAGTGGTCGAACATCAATAACGCGTTGTTTAGGACCGGGAAGAAATACAACCAGAATTGG

181 CAGTCTCTTGGCACAATCCGGATCACGTACTCTGCGACTTACAACCCAAACGGGAACTCC

241 TACTTGTGTATCTATGGCTGGTCTACCAACCCATTGGTCGAGTTCTACATCGTTGAGTCC

301 TGGGGGAACTGGAGACCGCCTGGTGCCACGTCCCTGGGCCAAGTGACAATCGATGGCGGG

361 ACCTACGACATCTATAGGACGACACGCGTCAACCAGCCTTGCCTGGCCGAGGGCTCGCTC

-continued

421 GTCTTGGACGCGGCTACCGGGCAGAGGGTCCCTATCGAAAAGGTGCGTCCGGGGATGGAA

481 GTTTTCTCCTTGGGACCTGATTACAGACTGTATCAGGTGCCCGTTTTGGAGGTCCTTGAG

541 AGCGGGGTTGGGGAAGTTGTGCGCCTCAGAACTCGGTCAGGGAGAACGCTGGTGTTGACA

601 CCAGATCACCCGCTTTTGACCCCCGAAGGTTGGAAACCTCTTTGTGACCTCCCGCTTGGA

661 ACTCCAATTGCAGTCCCCGCAGAACTGCCTGTGGCGGGCCACTTGGCCCCACCTGAAGAA

721 CGTGTTACGCCCCTGGCTCTTCTGTTGGGGGATGGGAACACAAAGCTGTCGGGTCGGAGA

781 GGTACACGTCCTAATGCCTTCTTCTACTGCAAAGACCCCGAATTGCTCGCGGCTTATCGC

841 CGGTGTGCAGAAGCCTTGGGTGCAAAGGTGAAAGCATACGTCCACCCGACTACGGGGGTG

901 GTTACACTCGCAACCCTCGCTCCACGTCCTGGAGCTCAAGATCCTGTCAAACGCCTCGTT

961 GTCGAGGCGGGAATGGTTGCTAAAGCCGAAGAGAAGAGGGTCCCGGAGGAGGTGTTCCGT

1021 TACCGGCGTGAGGCGTTGGCCCTTTTCTTGGGCCGTTTGTTCTCGACAGACGGCTCTGTT

1081 GAAAAGAAGAGGATCTCTTATTCAAGTGCCAGTTTGGGACTGGCCCAGGATGTCGCACAT

1141 CTCTTGCTGCGCCTTGGAATTACATCTCAACTCCGTTCGAGAGGGCCACGGGCTCACGAG

1201 GTTCTTATATCGGGCCGCGAGGATATTTTGCGGTTTGCTGAACTTATCGGACCCTACCTC

1261 TTGGGGGCCAAGAGGGAGAGACTTGCAGCGCTGGAAGCTGAGGCCCGCAGGCGTTTGCCT

1321 GGACAGGGATGGCACTTGCGGCTTGTTCTTCCTGCCGTGGCGTACAGAGTGAGCGAGGCT

1381 AAAAGGCGCTCGGGATTTTCGTGGAGTGAAGCCGGTCGGCGCGTCGCAGTTGCGGGATCG

1441 TGTTTGTCATCTGGACTCAACCTCAAATTGCCCAGACGCTACCTTTCTCGGCACCGGTTG

1501 TCGATGCTCGGTGAGGCTTTTGCCGACCCTGGGCTGGAAGCGCTCGCGGAAGGCCAAGTG

1561 CTCTGGGACCCTATTGTTGCTGTCGAACCGGCCGGTAAGGCGAGAACATTCGACTTGCGC

1621 GTTCCACCCTTTGCAAACTTCGCGAGCGAGGACCTGGTGGTGCATAACTCCATTGTGGGG

1681 ACAGCCACGTTCGATCAGTACTGGAGCGTGCGCACCTCTAAGCGGACTTCAGGAACAGTG

1741 ACCGTGACCGATCACTTCCGCGCCTGGGCGAACCGGGGCCTGAACCTCGGCACAATAGAC

1801 CAAATTACATTGTGCGTGGAGGGTTACCAAAGCTCTGGATCAGCCAACATCACCCAGAAC

1861 ACCTTCTCTCAGGGCTCTTCTTCCGGCAGTTCGGGTGGCTCATCCGGCTCCACAACGACT

1921 ACTCGCATCGAGTGTGAGAACATGTCCTTGTCCGGACCCTACGTTAGCAGGATCACCAAT

1981 CCCTTTAATGGTATTGCGCTGTACGCCAACGGAGACACAGCCCGCGCTACCGTTAACTTC

2041 CCCGCAAGTCGCAACTACAATTTCCGCCTGCGGGGTTGCGGCAACAACAATAATCTTGCC

2101 CGTGTGGACCTGAGGATCGACGGACGGACCGTCGGGACCTTTTATTACCAGGGCACATAC

2161 CCCTGGGAGGCCCCAATTGACAATGTTTATGTCAGTGCGGGGAGTCATACAGTCGAAATC

2221 ACTGTTACTGCGGATAACGGCACATGGGACGTGTATGCCGACTACCTGGTGATACAGTGA

SEQ ID NO: 19

(XynB, P77853 protein sequence)

QTSITLTSNASGTFDGYYYELWKDTGNTTMTVYTQGRFSCQWSNINNALFRTGKKYNQNW

QSLGTIRITYSATYNPNGNSYLCIYGWSTNPLVEFYIVESWGNWRPPGATSLGQVTIDGG

TYDIYRTTRVNQPSIVGTATFDQYWSVRTSKRTSGTVTVTDHFRAWANRGLNLGTIDQIT

-continued

LCVEGYQSSGSANITQNTFSQGSSSGSSGGSSGSTTTTRIECENMSLSGPYVSRITNPFN

GIALYANGDTARATVNFPASRNYNFRLRGCGNNNNLARVDLRIDGRTVGTFYYQGTYPWE

APIDNVYVSAGSHTVEITVTADNGTWDVYADYLVIQ

In the sequence above, S158 is underlined. The position numbering refers to position 158 in the native protein sequence, which includes a native signal peptide (MFLKKLSKLL LVVLLVAVYT QVNA (SEQ ID NO: 39)) that is not present in the above sequence.

SEQ ID NO: 20

(XynB, P77853 DNA sequence)

ATGCAAACAAGCATTACTCTGACATCCAACGCATCCGGTACGTTTGACGGTTACTATTACGAA

CTCTGGAAGGATACTGGCAATACAACAATGACGGTCTACACTCAAGGTCGCTTTTCCTGCCAG

TGGTCGAACATCAATAACGCGTTGTTTAGGACCGGGAAGAAATACAACCAGAATTGGCAGTCT

CTTGGCACAATCCGGATCACGTACTCTGCGACTTACAACCCAAACGGGAACTCCTACTTGTGT

ATCTATGGCTGGTCTACCAACCCATTGGTCGAGTTCTACATCGTTGAGTCCTGGGGGAACTGG

AGACCGCCTGGTGCCACGTCCCTGGGCCAAGTGACAATCGATGGCGGGACCTACGACATCTAT

AGGACGACACGCGTCAACCAGCCTTCCATTGTGGGGACAGCCACGTTCGATCAGTACTGGAGC

GTGCGCACCTCTAAGCGGACTTCAGGAACAGTGACCGTGACCGATCACTTCCGCGCCTGGGCG

AACCGGGGCCTGAACCTCGGCACAATAGACCAAATTACATTGTGCGTGGAGGGTTACCAAAGC

TCTGGATCAGCCAACATCACCCAGAACACCTTCTCTCAGGGCTCTTCTTCCGGCAGTTCGGGT

GGCTCATCCGGCTCCACAACGACTACTCGCATCGAGTGTGAGAACATGTCCTTGTCCGGACCC

TACGTTAGCAGGATCACCAATCCCTTTAATGGTATTGCGCTGTACGCCAACGGAGACACAGCC

CGCGCTACCGTTAACTTCCCCGCAAGTCGCAACTACAATTTCCGCCTGCGGGGTTGCGGCAAC

AACAATAATCTTGCCCGTGTGGACCTGAGGATCGACGGACGGACCGTCGGGACCTTTTATTAC

CAGGGCACATACCCCTGGGAGGCCCCAATTGACAATGTTTATGTCAGTGCGGGGAGTCATACA

GTCGAAATCACTGTTACTGCGGATAACGGCACATGGGACGTGTATGCCGACTACCTGGTGATA

CAGTGA

T134-195

(SEQ ID NO: 21)

QTSITLTSNASGTFDGYYYELWKDTGNTTMTVYTQGRFSCQWSNINNALFRTGKKYNQNW

QSLGTIRITYSATYNPNGNSYLCIYGWSTNPLVEFYIVESWGNWRPPGACLAEGSLVLDA

ATGQRVPIEKVRPGMEVFSLGPDYRLYRVPVLEVLESGVREVVRLRTRSGRTLVLTPDHP

LLTPEGWKPLCDLPLGTPIAVPAELPVAGHLAPPEERVTLLALLLGDGNTKLSGRRGTRP

NASFYSKDPELLAAYRRCAEALGAKVKAYVHPTTGVVTLATLAPRPGAQDPVKRLVVEAG

MVAKAEEKRVPEEVFRYRREALALFLGRLFSTDGSVEKKRISYSSASLGLAQDVAHLLLR

LGIRSQLRSRGPRAHEVLISGREDILRFAELIGPYLLGAKRERLAALEAEARRRLPGQGW

HLRLVLPAVAYRVSEAKRRSGFSWSEAGRRVAVAGSCLSSGLNLKLPRRYLSRHRLSLLG

EAFADPGLEALAEGQVLWDPIVAVEPAGKARTFDLRVPPFANFVSEDLVVHNTSLGQVTI

DGGTYDIYRTTRVNQPSIVGTATFDQYWSVRTSKRTSGTVTVTDHFRAWANRGLNLGTID

QITLCVEGYQSSGSANITQNTFSQGSSSGSSGGSSGSTTTTRIECENMSLSGPYVSRITN

PFNGIALYANGDTARATVNFPASRNYNFRLRGCGNNNNLARVDLRIDGRTVGTFYYQGTY

PWEAPIDNVYVSAGSHTVEITVTADNGTWDVYADYLVIQ

-continued

Tth-S158-39 Intein Sequence (SEQ ID NO: 22)

CLAEGSLVLDAATGQRVPIEKVRPGMEVFSLGPDYRLYRVPVLEVLESGVGEVVRLRTRS
GRTLVLTPDHPLLTPEGWKPLCDLPLGTPIAVPAELPVAGHLAPPEERVTLLALLLGDGN
TKLSGRRGTRPNAFFYSKDPELLAAYRRCAEALGAKVKAYVHPTTGVVTLATLAPRPGAQ
DPVKRLVVEAGMVAKAEEKRVPEEVFRYRREALALFLGRLSSTDGSVERKRISYSSASLG
LAQDVAHLLLRLGITSQLRSRGPRAHEVLISGREDILRFAELIGPYLLGAKRERLAALEA
EARRRLPGQGWHLRLVLPAVAYRVSEAKRRSGFSWSEAGQRVAVAGSCLSSGLNLKLPRR
YLSRHRLSLLGEAFADPGLEALAEGQVLWDPIVAVEPAGKARTFDLRVPPFANFVSEDLV
VHN (SEQ ID NO: 23)

Tth-T134-195 Intein Sequence (SEQ ID NO: 24)

Tth-S158-21 Intein Sequence (SEQ ID NO: 25)

Tth T134-180 Intein Sequence

Tth T134-100-65 intein sequence, also called Tth T134-1065 intein sequence (SEQ ID NO: 26)

CLAEGSLVLDAATGQRVPIEKVRPGMEVFSLGPDYRLYRVPVLEVLESGVREVVRLRTRS
GRTLVLTPDHPLLTPEGWKPLCDLPLGTPIAVPAELPVAGHLAPPEERVTLLALLLGDGN
TKLSGRRGTRPNAFFYSKNPELLAAYRRCAEALGAKVKAYVHPTTGVVTLATLAPRPGAQ
DPVKRLVVEAGMVAKAEEKRVPEEVFRYRREALALFLGRLFSTDGSVEKKRISYSSASLG
LAQDVAHLLLRLGITSQLRSRGPRAHEVLISGREDILRFAELIGPYLLGAKRERLAALEA
EARRRLPGQGWHLRLVLPAVAYRVSEAKRRSGFSWSEAGRRVAVAGSCLSSGLNLKLPRR
YLSRHRLSLLGEAFADPGLEALAEGQVLWDPIVAVEPAGKARTFDLRVPPFANFVSEDLV
VHN

Tth T134-100-68 intein sequence, also called Tth T134-10068 intein sequence (SEQ ID NO: 27)

CLAEGSLVLDAATGQRVPIEKVRPGMEVFSLGPDYRLYRVPVLEVLESGVREVVRLRTRS
ERTLVLTPDHPLLTPEGWKPLCDLPLGTPIAVPAELPVAGHLAPPEERVTLLALLLGDGN
TKLSGRRGTRPNAFFHSKDPELLAAYRRCAEALGAKVKAYVHPTTGVVTLATLAPRPGAQ
DPVKRLVVEAGMVAKAEEKRVPEEVFRYRREALALFLGRLFSTDGSVEKKRISYSSASLG
LAQDVAHLLLRLGITSQLRSRGPRAHEVLISGREDILRFAELIGPYLLGAKRERLAALEA
EARRRLPVQGWHSRLVLPAVAYRVSEAKRRSGFSWSEAGRRVAVAGSCLSSGLNLKLPRR
YLSRHRLSLLGEAFADPGLEALAEGQVLWDPIVAVEPAGKARTFDLRVPPFANFVSEDLV
VHN

Tth T134-100-39 intein sequence, also called Tth T134-10039 intein sequence (SEQ ID NO: 28)

CLAEGSLVLDAATGQRVPIEKVRPGMEVFSLGPDYRLYRVPVLEVLESGVREVVRLRTRS
GRTLVLTPDHPLLTPEGWKPLCDLPLGTPIAVPAELPVAGHLAPPEERVTLLALLLGDGN
TKLSGRRGTRPNAFFYSKDPELLAAYRRCAEALGAKVKAYVHPTTGVVTLATLAPRPGAQ
DPVKRLVVEAGMVAKAEEKRVPEEVFRYRREALALFLGRLFSTDGSVEKKRISYSSASLG

-continued

LAQDVAHLLLRLGITSQLRSRGPRAHEVLISGREDILRFAELIGPYLLGAKRERLAALEA

EARRRLPGQGWHLRLVLPAVAYRVSEAKRRSGFSWSEAGRRVAVAGSCLSSGLNLKLPRR

YLSRHRLSLLGEAFADPGLEALAEGLVLWDPIVAVEPAGKARTFDLRVPPFANFVSEDLV

VHN

Tth T134-100

(SEQ ID NO: 29)

CLAEGSLVLDAATGQRVPIEKVRPGMEVFSLGPDYRLYRVPVLEVLESGVREVVRLRTRS

GRTLVLTPDHPLLTPEGWKPLCDLPLGTPIAVPAELPVAGHLAPPEERVTLLALLLGDGN

TKLSGRRGTRPNAFFYSKDPELLAAYRRCAEALGAKVKAYVHPTTGVVTLATLAPRPGAQ

DPVKRLVVEAGMVAKAEEKRVPEEVFRYRREALALFLGRLFSTDGSVEKKRISYSSASLG

LAQDVAHLLLRLGITSQLRSRGPRAHEVLISGREDILRFAELIGPYLLGAKRERLAALEA

EARRRLPGQGWHLRLVLPAVAYRVSEAKRRSGFSWSEAGRRVAVAGSCLSSGLNLKLPRR

YLSRHRLSLLGEAFADPGLEALAEGQVLWDPIVAVEPAGKARTFDLRVPPFANFVSEDLV

VHN

Tth 5158-30-m79-110

(SEQ ID NO: 30)

CLAEGSLVLDAATGQRVPIEKVRPGMEVFSLGPDYRLYQVPVLEVLESGVGEVVRLRTRS

GRTLVLTPDHPLLTPEGWKPLCDLPLGTPIAVPAELPVAGHLAPPEERVTPLALLLGDGN

TKLSGRRGTRPNAFFYCKDPELLAAYRRCAEALGAKVKAYVHPTTGVVTLATLAPRPGAQ

DPVKRLVVEAGMVAKAEEKRVPEEVFRYRREALALFLGRLFSTDGSVEKKRISYSSASLG

LAQDVAHLLLRLGITSQLRSRGPRAHEVLISGREDILRFAELIGPYLLGAKRERLAALEA

EARRRLPGQGWHLRLVLPAVAYRVSEAKRRSGFSWSEAGRRVAVAGSCLSSGLNLKLPRR

YLSRHRLSMLGEAFADPGLEALAEGQVLWDPIVAVEPAGKARTFDLRVPPFANFASEDLV

VHN

Tth (SEQ ID NO: 34)

CLAEGSLVLDAATGQRVPIEKVRPGMEVFSLGPDYRLYRVPVLEVLESGVREVVRLRTRS

GRTLVLTPDHPLLTPEGWKPLCDLPLGTPIAVPAELPVAGHLAPPEERVTLLALLLGDGN

TKLSGRRGTRPNAFFYSKDPELLAAYRRCAEALGAKVKAYVHPTTGVVTLATLAPRPGAQ

DPVKRLVVEAGMVAKAEEKRVPEEVFRYRREALALFLGRLFSTDGSVEKKRISYSSASLG

LAQDVAHLLLRLGITSQLRSRGPRAHEVLISGREDILRFAELIGPYLLGAKRERLAALEA

EARRRLPGQGWHLRLVLPAVAYRVSEAKRRSGFSWSEAGRRVAVAGSCLSSGLNLKLPRR

YLSRHRLSLLGEAFADPGLEALAEGQVLWDPIVAVEPAGKARTFDLRVPPFANFVSEDLV

VHN

S158 19

(SEQ ID NO: 35)

atgttcctta agaaactgtc taagttgctg ctcgtcgtgc tccttgttgc cgtttacaca 60
caggtcaacg cgcaaacaag cattactctg acatccaacg catccggtac gtttgacggt 120
tactattacg aactctggaa ggatactggc aatacaacaa tgacggtcta cactcaaggt 180
cgcttttcct gccagtggtc gaacatcaat aacgcgttgt ttaggaccgg gaagaaatac 240
aaccagaatt ggcagtctct tggcacaatc cggatcacgt actctgcgac ttacaaccca 300
aacgggaact cctacttgtg tatctatggc tggtctacca acccattggt cgagttctac 360
atcgttgagt cctgggggaa ctggagaccg cctggtgcca cgtccctggg ccaagtgaca 420
atcgatggcg ggacctacga catctatagg acgacacgcg tcaaccagcc ttgcctggcc 480
gagggctcgc tcgtcttgga cgcggctacc gggcagaggg tccctatcga aaaggtgcgt 540

-continued

```
ccggggatgg aagttttctc cttgggacct gattacagac tgtatcgggt gcccgttttg       600
gaggtccttg agagcggggt tggggaagtt gtgcgcctca gaactcggtc agggagaacg       660
ctggtgttga caccagatca cccgcttttg acccccgaag gttggaaacc tctttgtgac       720
ctcccgcttg gaactccaat tgcagtcccc gcagaactgc ctgtggcggg ccacttggcc       780
ccacctgaag aacgtgttac gctcctggct cttctgttgg gggatgggaa cacaaagctg       840
tcgggtcgga gaggtacacg tcctattgcc ttcttctaca gcaaagaccc cgaattgctc       900
gcggcttatc gccggtgtgc agaagccttg ggtgcaaagg tgaaagcata cgtccacccg       960
actacggggg tggttacact cgcaaccctc gctccacgtc ctggagctca agatcctgtc      1020
aaacgcctcg ttgtcgaggc gggaatggtt gctaaagccg aagagaagag ggtcccggag      1080
gaggtgtttc gttaccggcg tgaggcgttg gcccttttct tgggccgttt gttctcgaca      1140
gacggctctg ttgaaaagaa gaggatctct tattcaagtg ccagtttggg actggcccag      1200
gatgtcgcac atctcttgct gcgccttgga attacatctc aactccgttc gagagggcca      1260
cgggctcacg aggttcttat atcgggccgc gaggatattt tgcggtttgc tgaacttatc      1320
ggaccctacc tcttgggggc caagagggag agacttgcag cgctggaagc tgaggcccgc      1380
aggcgtttgc ctggacaggg atggcacttg cggcttgttc ttcctgccgt ggcgtacaga      1440
gtgagcgagg ctaaaaggcg ctcgggattt tcgtggagtg aagccggtcg gcgcgtcgca      1500
gttgcgggat cgtgtttgtc atctggactc aacctcaaat tgcccagacg ctacctttct      1560
cggcaccggt tgtcgctgct cggtgaggct tttgccgacc ctgggctgga agcgctcgcg      1620
gaaggccaag tgctctggga ccctattgtt gctgtcgaac cggccggtaa ggcgagaaca      1680
ttcgacttgc gcgttccacc ctttgcaaac ttcgtgagcg aggacctggt ggtgcataac      1740
tccattgtgg ggacagccac gttcgatcag tactggagcg tgcgcacctc taagcggact      1800
tcaggaacag tgaccgtgac cgatcacttc cgcgcctggg cgaaccgggg cctgaacctc      1860
ggcacaatag accaaattac attgtgcgtg gagggttacc aaagctctgg atcagccaac      1920
atcacccaga acaccttctc tcagggctct tcttccggca gttcgggtgg ctcatccggc      1980
tccacaacga ctactcgcat cgagtgtgag aacatgtcct tgtccggacc ctacgttagc      2040
aggatcacca atccctttaa tggtattgcg ctgtacgcca acggagacac agcccgcgct      2100
accgttaact tccccgcaag tcgcaactac aatttccgcc tgcggggttg cggcaacaac      2160
aataatcttg cccgtgtgga cctgaggatc gacggacgga ccgtcgggac cttttattac      2220
cagggcacat acccctggga ggccccaatt gacaatgttt atgtcagtgc ggggagtcat      2280
acagtcgaaa tcactgttac tgcggataac ggcacatggg acgtgtatgc cgactacctg      2340
gtgatacag
```

(SEQ ID NO: 36)
S158-3103

(SEQ ID NO: 37)
S158-3108

S158-30

(SEQ ID NO: 38)

```
atgttcctta agaaactgtc taagttgctg ctcgtcgtgc tccttgttgc cgtttacaca        60
caggtcaacg cgcaaacaag cattactctg acatccaacg catccggtac gtttgacggt       120
tactattacg aactctggaa ggatactggc aatacaacaa tgacggtcta cactcaaggt       180
cgcttttcct gccagtggtc gaacatcaat aacgcgttgt ttaggaccgg gaagaaatac       240
aaccagaatt ggcagtctct tggcacaatc cggatcacgt actctgcgac ttacaaccca       300
```

-continued

```
aacgggaact cctacttgtg tatctatggc tggtctacca acccattggt cgagttctac     360
atcgttgagt cctgggggaa ctggagaccg cctggtgcca cgtccctggg ccaagtgaca     420
atcgatggcg ggacctacga catctatagg acgacacgcg tcaaccagcc ttgcctggcc     480
gagggctcgc tcgtcttgga cgcggctacc gggcagaggg tccctatcga aaaggtgcgt     540
ccggggatgg aagttttctc cttgggacct gattacagac tgtatcgggt gcccgttttg     600
gaggtccttg agagcggggt tagggaagtt gtgcgcctca gaactcggtc agggagaacg     660
ctggtgttga caccagatca cccgcttttg acccccgaag gttggaaacc tctttgtgac     720
ctcccgcttg gaactccaat tgcagtcccc gcagaactgc ctgtggcggg ccacttggcc     780
ccacctgaag aacgtgttac gctcctggct cttctgttgg gggatgggaa cacaaagctg     840
tcgggtcgga gaggtacacg tcctaatgcc ttcttctaca gcaaagaccc cgaattgctc     900
gcggcttatc gccggtgtgc agaagccttg ggtgcaaagg tgaaagcata cgtccacccg     960
actacggggg tggttacact cgcaaccctc gctccacgtc ctggagctca agatcctgtc    1020
aaacgcctcg ttgtcgaggc gggaatggtt gctaaagccg aagagaagag ggtcccggag    1080
gaggtgtttc gttaccggcg tgaggcgttg gccctttttct tgggccgttt gttctcgaca    1140
gacggctctg ttgaaaagaa gaggatctct tattcaagtg ccagtttggg actggcccag    1200
gatgtcgcac atctcttgct gcgccttgga attacatctc aactccgttc gagagggcca    1260
cgggctcacg aggttcttat atcgggccgc gaggatattt tgcggtttgc tgaacttatc    1320
ggaccctacc tcttgggggc caagagggag agacttgcag cgctggaagc tgaggcccgc    1380
aggcgtttgc ctggacaggg atggcacttg cggcttgttc ttcctgccgt ggcgtacaga    1440
gtgagcgagg ctaaaaggcg ctcgggattt tcgtggagtg aagccggtcg gcgcgtcgca    1500
gttgcgggat cgtgtttgtc atctggactc aacctcaaat tgcccagacg ctacctttct    1560
cggcaccggt tgtcgatgct cggtgaggct tttgccgacc ctgggctgga agcgctcgcg    1620
gaaggccaag tgctctggga ccctattgtt gctgtcgaac cggccggtaa ggcgagaaca    1680
ttcgacttgc gcgttccacc ctttgcaaac ttcgtgagcg aggacctggt ggtgcataac    1740
tccattgtgg ggacagccac gttcgatcag tactggagcg tgcgcacctc taagcggact    1800
tcaggaacag tgaccgtgac cgatcacttc cgcgcctggg cgaaccgggg cctgaacctc    1860
ggcacaatag accaaattac attgtgcgtg gagggttacc aaagctctgg atcagccaac    1920
atcacccaga acaccttctc tcagggctct tcttccggca gttcgggtgg ctcatccggc    1980
tccacaacga ctactcgcat cgagtgtgag aacatgtcct tgtccggacc ctacgttagc    2040
aggatcacca atccctttaa tggtattgcg ctgtacgcca acggagacac agcccgcgct    2100
accgttaact tccccgcaag tcgcaactac aatttccgcc tgcggggttg cggcaacaac    2160
aataatcttg cccgtgtgga cctgaggatc gacggacgga ccgtcgggac cttttattac    2220
cagggcacat acccctggga ggccccaatt gacaatgttt atgtcagtgc ggggagtcat    2280
acagtcgaaa tcactgttac tgcggataac ggcacatggg acgtgtatgc cgactacctg    2340
gtgatacag
```

REFERENCES

1. <bibcit> Nelson, E., Tilman, D., Polasky, S, Tiffany D. Environmental, economic, and energetic costs and benefits of biodiesel and ethanol biofuels. Proc Natl Acad Sci USA. 103:11206-11210 (2006).
2. Klass, D L. Biomass for renewable energy and fuels. In Encyclopedia of Energy, ed. CJ Cleveland, 1, 193-212 (2004). London: Elsevier.
3. Lynd, L. R, Laser, M. S., Bransby, D., Dale, B. E., Davison, B., Hamilton, R., Himmel, M., Keller, M., McMillan, J. D., Sheehan, J., Wyman, C. E. How biotech can transform biofuels. Nature Biotechnology, 26:169-172 (2008).
4. Himmel, M. E., Ding, S. Y., Johnson, D. K., Adney, W. S., Nimlos, M. R., Brady, J. W., Foust, T. D. Biomass Recalcitrance: Engineering Plants and Enzymes for Biofuels Production. Science, 315:804-807, 2007.
5. Hood, E. E., Love, R., Lane, J., Bray, J., Clough, R., Pappu, K., Drees, C., Hood, K. R., Yoon, S., Ahmad, A., Howard, J. A. Subcellular targeting is a key condition for high-level accumulation of cellulase protein in transgenic maize seed. Plant Biotechnology Journal, 5:1-11, 2007.
6. Lynd L R, van Zyl W H, McBride J E, Laser M. Consolidated bioprocessing of cellulosic biomass: an update. Curr Opin Biotechnol. 2005. 16(5):577-83.
7. Sairam, R. V., Al-Abed, D., Johnson, J., Muszynski, M. G., Raab, M., Reddy, T. V., Goldman, S. 2008. Maize. In Compendium of Transgenic Crop Plants: Transgenic Cereals and Forage Grasses, ed. C. Kole and T. C. Hall, 2:49-81. Blackwell Publishing, Ltd.
8. Sainz, M. B. Commercial cellulosic ethanol: The role of plant expressed enzymes. In Vitro Cell. Dev. Biol.—Plant, 45:314-329, 2009.
9. Harholt, J., Bach I C, Lind-Bouquin S, Nunan K J, Madrid S M, Brinch-Pedersen H, Holm P B, Scheller H V. Generation of transgenic wheat (*Triticum aestivum* L.) accumulating heterologous endo-xylanase or ferulic acid esterase in the endosperm. Plant Biotechnol J. 8:351-362 (2010).
10. Hood E E, Bailey M R, Beifuss K, Magallanes-Lundback M, Horn M E, Callaway E, Delaney D E, Clough R, Howard J A. Criteria for high-level expression of a fungal laccase gene in transgenic maize. Plant Biotechnol J. 2003 March; 1(2):129-40.
11. Taylor, L. E., Dai, Z., Decker, S. R., Brunecky, R., Adney, W. S., Ding, S. Y., Himmel, M. E. Heterologous expression of glycosyl hydrolases in planta: a new departure for biofuels. TIBTEC., 26(8):413-424, 2008.
12. Perler, F. B., Davis, E. O., Dean, G. E., Gimble, F. S., Jack, W. E., Neff, N., Noren, C. J., Thorner, J., Belfort, M. Protein splicing elements: inteins and exteins—a definition of terms and recommended nomenclature. Nucleic Acids Research, 22(7):1125-1127, 1994.
13. Saleh L, Perler F B. Protein splicing in cis and trans. Chem Rec. 2006; 6(4):183-93. Review.
14. Xu, M. Q., Southworth, M. W., Mersha, F. B., Hornstra, L. J., Perler, F. P. In vitro protein splicing of purified precursor and the identification of a branched intermediate. Cell, 75:1371-1377, 1993.
15. Xu M Q, Perler F B. The mechanism of protein splicing and its modulation by mutation. EMBO J. 1996 Oct. 1; 15(19):5146-53.
16. Tan C, Bellaiche Y, Cherry S, Häder S, Gayko U, Perrimon N. Temperature-sensitive control of protein activity by conditionally splicing inteins. Nat Biotechnol. 2004 July; 22(7):871-6. Epub 2004 Jun. 6.
17. Mootz H D, Blum E S, Tyszkiewicz A B, Muir T W. Conditional protein splicing: a new tool to control protein structure and function in vitro and in vivo. J Am Chem Soc. 2003 Sep. 3; 125(35):10561-9
18. Evanko D. Controlling proteins the intein way. Nat Methods. 2007 February; 4(2):112-3.
19. Selig, M. J., Knoshaug, E. P., Adney, W. S., Himmel, M. E., Decker, S. R., Synergistic enhancement of cellobiohydrolase performance on pretreated corn stover by addition of xylanase and esterase activities. Bioresource Technology, 99:4997-5005, 2008.
20. Selig, M. J., Adney, W. S., Himmel, M. E., Decker, S. R. The impact of cell wall acetylation on corn stover hydrolysis by cellulolytic and xylanolytic enzymes. Cellulose, 16:711-722, 2009.
21. Dylan, D, and Cann, I., Enzymatic deconstruction of xylan for biofuel production. Glob Change Biol Bioenergy. 2009 February; 1(1):2-17.
22. Amitai G, Callahan B P, Stanger M J, Belfort G, Belfort M. Modulation of intein activity by its neighboring extein substrates. Proc Natl Acad Sci USA. 2009 Jul. 7; 106(27): 11005-10. Epub 2009 Jun. 17.
23. Rogers, J. C. Two barley alpha-amylase gene families are regulated differently in aleurone cells. J. Biol. Chem., 260: 3731-3738, 1985.
24. Lebler, J. Economics improve for first commercial cellulosic ethanol plants. New York Times, Feb. 16, 2010.
25. Mosier, N., Wyman, C., Dale, B., Elander, R., Lee, Y. Y., Holtzapple, M., Ladisch, M. Features of promising technologies for pretreatment of lignocellulosic biomass. Bioresource Tech. 96:673-686, 2005.
26. Berrondo M, Ostermeier M, Gray J J. Structure prediction of domain insertion proteins from structures of individual domains. Structure. 2008; 16(4):513-27.
27. C. A. Rohl, C. E. Strauss, K. M. S. Misura, D. Baker. Protein structure prediction using Rosetta. Methods in Enzymology, 383:66-93 (2004).
28. C. A. Rohl. Protein structure estimation from minimal restraints using Rosetta. Methods in Enzymology, 394: 244-260 (2005).
29. B. Kuhlman, G. Dantas, G. C. Ireton, G. Varani, B. L. Stoddard, D. Baker, Design of a novel globular protein fold with atomic-level accuracy. Science, 302:1364-1368 (2003).
30. Hiei Y., Ohta S., Komari T., and Kumashiro T. Efficient transformation of rice (*Oryza sativa* L.) mediated by *Agrobacterium* and sequence analysis of the boundaries of the T-DNA. Plant J. 6: 271-282 (1994)
31. Ishida Y., Saito H., Ohta S., Hiei Y., Komari T., and Kumashiro T. High efficiency transformation of maize (*Zea mays* L.) mediated by *Agrobacterium tumefaciens*. Nature Biotech. 14: 745 (1996)
32. Hiei, Y., and Komari, T. Improved protocols for transformation of indica rice mediated by *Agrobacterium tumefaciens*. Plant Cell, Tissue and Organ Culture 85, 271-283 (2006)
33. Komari T., Hiei Y., Saito Y., Mural N., and Kumashiro T. Vectors carrying two separate T-DNAs for cotransformation of higher plants mediated by *Agrobacterium tumefaciens* and segregation of transformants free from selection markers. Plant J. 10:165-174 (1996)
34. Negrotto D., Jolley M., Beer s., Wenck A. R., Hansen G. The use of phosphomannose-isomerase as a selectable marker to recover transgenic maize plants (*Zea mays* L.) via *Agrobacterium* transformation. Plant Cell Reports (2000)19:798-803.
35. NREL Laboratory Analytical Procedure (LAP) technical report (NREL/TP-510-42623): A. Sluiter, B. Hames, R. Ruiz, C. Scarlata, J. Sluiter, and D. Templeton, Determination of Sugars, Byproducts, and Degradation Products in Liquid Fraction Process Samples. 14 Pp.
36. Sivamani, E., and Qu, R. Expression enhancement of a rice polyubiquitin gene promoter. Plant Molecular Biology, 60:225-239, 2006.
37. Arnold K., Bordoli L., Kopp J., and Schwede T. (2006). The SWISS-MODEL Workspace: A web-based environment for protein structure homology modelling. Bioinformatics, 22, 195-201.
38. Kiefer F, Arnold K, Kiinzli M, Bordoli L, Schwede T (2009). The SWISS-MODEL Repository and associated resources. Nucleic Acids Research. 37, D387-D392.
39. Schwede T, Kopp J, Guex N, and Peitsch M C (2003) SWISS-MODEL: an automated protein homology-modeling server. Nucleic Acids Research 31: 3381-3385.
40. Guex, N. and Peitsch, M. C. (1997) SWISS-MODEL and the Swiss-PdbViewer: An environment for comparative protein modelling. Electrophoresis 18: 2714-2723.
41. Peitsch, M. C. Protein modelling by E-mail. Bio/Technology, 1995 13: 658-660.

The references cited throughout this application, are incorporated for all purposes apparent herein and in the references themselves as if each reference was fully set forth. For the sake of presentation, specific ones of these references are cited at particular locations herein. A citation of a reference at a particular location indicates a manner(s) in which the teachings of the reference are incorporated. However, a citation of a reference at a particular location does not limit the manner in which all of the teachings of the cited reference are incorporated for all purposes.

It is understood, therefore, that this invention is not limited to the particular embodiments disclosed, but is intended to cover all modifications which are within the spirit and scope of the invention as defined by the appended claims; the above description; and/or shown in the attached drawings.

What is claimed is:

1. A transgenic plant having an autohydrolytic trait, the transgenic plant comprising an expression vector having a sequence that encodes an intein-modified xylanase having an intein internally fused within a xylanase, wherein the intein-modified xylanase comprises an amino acid sequence selected from SEQ ID NOS: 60, 62, 64, 8, 10, 12, 16, 17, or 21 and has decreased activity relative to the xylanase.

2. The transgenic plant of claim 1, wherein the transgenic plant is a maize plant, a switchgrass plant, or a sorghum plant, and the part thereof comprises the expression vector.

3. A method of producing a transgenic plant having an autohydrolytic trait comprising: providing an expression vector having a sequence that encodes an intein-modified xylanase having an intein internally fused within a xylanase and transforming a plant or part thereof with the expression construct, wherein the intein-modified xylanase comprises an amino acid sequence selected from SEQ ID NOS: 60, 62, 64, 8, 10, 12, 16, 17, or 21 and has decreased activity relative to the xylanase.

4. The method of claim 3, wherein the plant or part thereof is a maize plant or part thereof, a switchgrass plant or part thereof, or a sorghum plant or part thereof.

5. A seed from a transgenic plant of claim 1, wherein the seed comprises the expression vector.

6. A transgenic plant having an autohydrolytic trait, the transgenic plant comprising an expression vector having a sequence that encodes an intein-modified xylanase having an intein internally fused within a xylanase, wherein the intein-modified xylanase comprises the amino acid sequence of SEQ ID NO: 64 and has decreased activity relative to the xylanase.

7. The transgenic plant of claim 3, wherein the transgenic plant is a maize plant, a switchgrass plant, or a sorghum plant.

* * * * *

SEQUENCE LISTING

```
<160> NUMBER OF SEQ ID NOS: 81

<210> SEQ ID NO 1
<211> LENGTH: 2277
<212> TYPE: DNA
<213> ORGANISM: Artificial Sequence
<220> FEATURE:
<223> OTHER INFORMATION: Synthetic construct, S158-39 DNA sequence

<400> SEQUENCE: 1

caaacaagca ttactctgac atccaacgca tccggtacgt ttgacggtta ctattacgaa     60

ctctggaagg atactggcaa tacaacaatg acggtctaca ctcaaggtcg cttttcctgc    120

cagtggtcga acatcaataa cgcgttgttt aggaccggga agaaatacaa ccagaattgg    180

cagtctcttg gcacaatccg gatcacgtac tctgcgactt acaacccaaa cgggaactcc    240

tacttgtgta tctatggctg gtctaccaac ccattggtcg agttctacat cgttgagtcc    300

tgggggaact ggagaccgcc tggtgccacg tccctgggcc aagtgacaat cgatggcggg    360

acctacgaca tctataggac gacacgcgtc aaccagcctt gcctggccga gggctcgctc    420

gtcttggacg cggctaccgg gcagagggtc cctatcgaaa aggtgcgtcc ggggatggaa    480

gttttctcct tgggacctga ttacagactg tatcgggtgc ccgttttgga ggtccttgag    540

agcggggttg gggaagttgt gcgcctcaga actcggtcag ggagaacgct ggtgttgaca    600

ccagatcacc cgcttttgac ccccgaaggt tggaaacctc tttgtgacct cccgcttgga    660

actccaattg cagtccccgc agaactgcct gtggcgggcc acttggcccc acctgaagaa    720

cgtgttacgc tcctggctct tctgttgggg gatgggaaca caaagctgtc gggtcggaga    780

ggtacacgtc ctaatgcctt cttctacagc aaagaccccg aattgctcgc ggcttatcgc    840

cggtgtgcag aagccttggg tgcaaaggtg aaagcatacg tccacccgac tacgggggtg    900

gttacactcg caaccctcgc tccacgtcct ggagctcaag atcctgtcaa acgcctcgtt    960

gtcgaggcgg gaatggttgc taaagccgaa gagaagaggg tcccggagga ggtgtttcgt   1020

taccggcgtg aggcgttggc ccttttcttg ggccgtttgt cctcgacaga cggctctgtt   1080

gaaaggaaga ggatctctta ttcaagtgcc agtttgggac tggcccagga tgtcgcacat   1140

ctcttgctgc gccttggaat tacatctcaa ctccgttcga gagggccacg ggctcacgag   1200

gttcttatat cgggccgcga ggatattttg cggtttgctg aacttatcgg accctacctc   1260

ttgggggcca agagggagag acttgcagcg ctggaagctg aggcccgcag gcgtttgcct   1320
```

```
ggacagggat ggcacttgcg gcttgttctt cctgccgtgg cgtacagagt gagcgaggct   1380

aaaaggcgct cgggattttc gtggagtgaa gccggtcagc gcgtcgcagt tgcgggatcg   1440

tgtttgtcat ctggactcaa cctcaaattg cccagacgct acctttctcg gcaccggttg   1500

tcgctgctcg gtgaggcttt tgccgaccct gggctggaag cgctcgcgga aggccaagtg   1560

ctctgggacc ctattgttgc tgtcgaaccg gccggtaagg cgagaacatt cgacttgcgc   1620

gttccaccct ttgcaaactt cgtgagcgag gacctggtgg tgcataactc cattgtgggg   1680

acagccacgt tcgatcagta ctggagcgtg cgcacctcta agcggacttc aggaacagtg   1740

accgtgaccg atcacttccg cgcctgggcg aaccggggcc tgaacctcgg cacaatagac   1800

caaattacat tgtgcgtgga gggttaccaa agctctggat cagccaacat cacccagaac   1860

accttctctc agggctcttc ttccggcagt tcgggtggct catccggctc cacaacgact   1920

actcgcatcg agtgtgagaa catgtccttg tccggaccct acgttagcag gatcaccaat   1980

ccctttaatg gtattgcgct gtacgccaac ggagacacag cccgcgctac cgttaacttc   2040

cccgcaagtc gcaactacaa tttccgcctg cggggttgcg gcaacaacaa taatcttgcc   2100

cgtgtggacc tgaggatcga cggacggacc gtcgggacct tttattacca gggcacatac   2160

ccctgggagg ccccaattga caatgtttat gtcagtgcgg ggagtcatac agtcgaaatc   2220

actgttactg cggataacgg cacatgggac gtgtatgccg actacctggt gatacag      2277


<210> SEQ ID NO 2
<211> LENGTH: 759
<212> TYPE: PRT
<213> ORGANISM: Artificial Sequence
<220> FEATURE:
<223> OTHER INFORMATION: Synthetic construct, S158-39 protein

<400> SEQUENCE: 2

Gln Thr Ser Ile Thr Leu Thr Ser Asn Ala Ser Gly Thr Phe Asp Gly
1               5                   10                  15

Tyr Tyr Tyr Glu Leu Trp Lys Asp Thr Gly Asn Thr Thr Met Thr Val
            20                  25                  30

Tyr Thr Gln Gly Arg Phe Ser Cys Gln Trp Ser Asn Ile Asn Asn Ala
        35                  40                  45

Leu Phe Arg Thr Gly Lys Lys Tyr Asn Gln Asn Trp Gln Ser Leu Gly
    50                  55                  60

Thr Ile Arg Ile Thr Tyr Ser Ala Thr Tyr Asn Pro Asn Gly Asn Ser
65                  70                  75                  80

Tyr Leu Cys Ile Tyr Gly Trp Ser Thr Asn Pro Leu Val Glu Phe Tyr
                85                  90                  95

Ile Val Glu Ser Trp Gly Asn Trp Arg Pro Pro Gly Ala Thr Ser Leu
            100                 105                 110

Gly Gln Val Thr Ile Asp Gly Gly Thr Tyr Asp Ile Tyr Arg Thr Thr
        115                 120                 125

Arg Val Asn Gln Pro Cys Leu Ala Glu Gly Ser Leu Val Leu Asp Ala
    130                 135                 140

Ala Thr Gly Gln Arg Val Pro Ile Glu Lys Val Arg Pro Gly Met Glu
145                 150                 155                 160

Val Phe Ser Leu Gly Pro Asp Tyr Arg Leu Tyr Arg Val Pro Val Leu
                165                 170                 175

Glu Val Leu Glu Ser Gly Val Gly Glu Val Val Arg Leu Arg Thr Arg
            180                 185                 190

Ser Gly Arg Thr Leu Val Leu Thr Pro Asp His Pro Leu Leu Thr Pro
```

-continued

```
        195                 200                 205

Glu Gly Trp Lys Pro Leu Cys Asp Leu Pro Leu Gly Thr Pro Ile Ala
    210                 215                 220

Val Pro Ala Glu Leu Pro Val Ala Gly His Leu Ala Pro Pro Glu Glu
225                 230                 235                 240

Arg Val Thr Leu Leu Ala Leu Leu Leu Gly Asp Gly Asn Thr Lys Leu
                245                 250                 255

Ser Gly Arg Arg Gly Thr Arg Pro Asn Ala Phe Phe Tyr Ser Lys Asp
            260                 265                 270

Pro Glu Leu Leu Ala Ala Tyr Arg Arg Cys Ala Glu Ala Leu Gly Ala
        275                 280                 285

Lys Val Lys Ala Tyr Val His Pro Thr Thr Gly Val Val Thr Leu Ala
    290                 295                 300

Thr Leu Ala Pro Arg Pro Gly Ala Gln Asp Pro Val Lys Arg Leu Val
305                 310                 315                 320

Val Glu Ala Gly Met Val Ala Lys Ala Glu Glu Lys Arg Val Pro Glu
                325                 330                 335

Glu Val Phe Arg Tyr Arg Arg Glu Ala Leu Ala Leu Phe Leu Gly Arg
            340                 345                 350

Leu Ser Ser Thr Asp Gly Ser Val Glu Arg Lys Arg Ile Ser Tyr Ser
        355                 360                 365

Ser Ala Ser Leu Gly Leu Ala Gln Asp Val Ala His Leu Leu Leu Arg
    370                 375                 380

Leu Gly Ile Thr Ser Gln Leu Arg Ser Arg Gly Pro Arg Ala His Glu
385                 390                 395                 400

Val Leu Ile Ser Gly Arg Glu Asp Ile Leu Arg Phe Ala Glu Leu Ile
                405                 410                 415

Gly Pro Tyr Leu Leu Gly Ala Lys Arg Glu Arg Leu Ala Ala Leu Glu
            420                 425                 430

Ala Glu Ala Arg Arg Arg Leu Pro Gly Gln Gly Trp His Leu Arg Leu
        435                 440                 445

Val Leu Pro Ala Val Ala Tyr Arg Val Ser Glu Ala Lys Arg Arg Ser
    450                 455                 460

Gly Phe Ser Trp Ser Glu Ala Gly Gln Arg Val Ala Val Ala Gly Ser
465                 470                 475                 480

Cys Leu Ser Ser Gly Leu Asn Leu Lys Leu Pro Arg Arg Tyr Leu Ser
                485                 490                 495

Arg His Arg Leu Ser Leu Leu Gly Glu Ala Phe Ala Asp Pro Gly Leu
            500                 505                 510

Glu Ala Leu Ala Glu Gly Gln Val Leu Trp Asp Pro Ile Val Ala Val
        515                 520                 525

Glu Pro Ala Gly Lys Ala Arg Thr Phe Asp Leu Arg Val Pro Pro Phe
    530                 535                 540

Ala Asn Phe Val Ser Glu Asp Leu Val Val His Asn Ser Ile Val Gly
545                 550                 555                 560

Thr Ala Thr Phe Asp Gln Tyr Trp Ser Val Arg Thr Ser Lys Arg Thr
                565                 570                 575

Ser Gly Thr Val Thr Val Thr Asp His Phe Arg Ala Trp Ala Asn Arg
            580                 585                 590

Gly Leu Asn Leu Gly Thr Ile Asp Gln Ile Thr Leu Cys Val Glu Gly
        595                 600                 605

Tyr Gln Ser Ser Gly Ser Ala Asn Ile Thr Gln Asn Thr Phe Ser Gln
    610                 615                 620
```

```
Gly Ser Ser Ser Gly Ser Ser Gly Gly Ser Ser Gly Ser Thr Thr Thr
625                 630                 635                 640

Thr Arg Ile Glu Cys Glu Asn Met Ser Leu Ser Gly Pro Tyr Val Ser
                645                 650                 655

Arg Ile Thr Asn Pro Phe Asn Gly Ile Ala Leu Tyr Ala Asn Gly Asp
            660                 665                 670

Thr Ala Arg Ala Thr Val Asn Phe Pro Ala Ser Arg Asn Tyr Asn Phe
        675                 680                 685

Arg Leu Arg Gly Cys Gly Asn Asn Asn Asn Leu Ala Arg Val Asp Leu
    690                 695                 700

Arg Ile Asp Gly Arg Thr Val Gly Thr Phe Tyr Tyr Gln Gly Thr Tyr
705                 710                 715                 720

Pro Trp Glu Ala Pro Ile Asp Asn Val Tyr Val Ser Ala Gly Ser His
                725                 730                 735

Thr Val Glu Ile Thr Val Thr Ala Asp Asn Gly Thr Trp Asp Val Tyr
            740                 745                 750

Ala Asp Tyr Leu Val Ile Gln
        755
```

<210> SEQ ID NO 3
<211> LENGTH: 2277
<212> TYPE: DNA
<213> ORGANISM: Artificial Sequence
<220> FEATURE:
<223> OTHER INFORMATION: Synthetic construct, S158-21 DNA sequence

<400> SEQUENCE: 3

```
caaacaagca ttactctgac atccaacgca tccggtacgt ttgacggtta ctattacgaa     60

ctctggaagg atactggcaa tacaacaatg acggtctaca ctcaaggtcg cttttcctgc    120

cagtggtcga acatcaataa cgcgttgttt aggaccggga agaaatacaa ccagaattgg    180

cagtctcttg gcacaatccg gatcacgtac tctgcgactt acaacccaaa cgggaactcc    240

tacttgtgta tctatggctg gtctaccaac ccattggtcg agttctacat cgttgagtcc    300

tgggggaact ggagaccgcc tggtgccacg tccctgggcc aagtgacaat cgatggcggg    360

acctacgaca tctataggac gacacgcgtc aaccagcctt gcctggccga gggctcgctc    420

gtcttggacg cggctaccgg gcagagggtc cctatcgaaa aggtgcgtcc ggggatggaa    480

gttttctcct tgggacctga ttacagactg tatcgggtgc ccgttttgga ggtccttgag    540

agcggggtta gggaagttgt gcgcctcaga actcggtcag ggagaacgct ggtgttgaca    600

ccagatcacc cgcttttgac cccgaaggt tggaaacctc tttgtgacct cccgcttgga    660

actccaattg cagtccccgc agaactgcct gtggcgggcc acttggcccc acctgaagaa    720

cgtgttacgc tcctggctct tctgttgggg gatgggaaca caaagctgtc gggtcggaga    780

ggtacacgtc ctaatgcctt cttctacagc aaagaccccg aattgctcgc ggcttatcgc    840

cggtgtggag aagccttggg tgcaaaggtg aaagcatacg tccacccgac tacgggggtg    900

gttacactcg caaccctcgc tccacgtcct ggagctcaag atcctgtcaa acgcctcgtt    960

gtcgaggcgg gaatggttgc taaagccgaa gagaagaggg tcccggagga ggtgtttcgt   1020

taccggcgtg aggcgttggc ccttttcttg ggccgtttgt tctcgacaga cggctctgtt   1080

gaaaagaaga ggatctctta ttcaagtgcc agtttgggac tggcccagga tgtcgcacat   1140

ctcttgctgc gccttggaat tacatctcaa ctccgttcga gagggccacg ggctcacgag   1200

gttcttatat cgggccgcga ggatattttg cggtttgctg aacttatcgg accctacctc   1260
```

-continued

```
ttgggggcca agagggagag acttgcagcg ctggaagctg aggcccgcag gcgtttgcct   1320

ggacagggat ggcacttgcg gcttgttctt cctgccgtgg cgtacagagt gagcgaggct   1380

aaaaggcgct cgggattttc gtggagtgaa gccggtcggc gcgtcgcagt tgcgggatcg   1440

tgtttgtcat ctggactcaa cctcaaattg cccagacgct acctttctca gcaccggttg   1500

tcgctgctcg gtgaggcttt tgccgaccct gggctggaag cgctcgcgga aggccaagtg   1560

ctctgggacc ctattgttgc tgtcgaaccg gccggtaagg cgagaacatt cgacttgcgc   1620

gttccaccct ttgcaaactt cgtgagcgag gacctggtgg tgcataactc cattgtgggg   1680

acagccacgt tcgatcagta ctggagcgtg cgcacctcta agcggacttc aggaacagtg   1740

accgtgaccg atcacttccg cgcctgggcg aaccggggcc tgaacctcgg cacaatagac   1800

caaattacat tgtgcgtgga gggttaccaa agctctggat cagccaacat cacccagaac   1860

accttctctc agggctcttc ttccggcagt tcgggtggct catccggctc cacaacgact   1920

actcgcatcg agtgtgagaa catgtccttg tccggaccct acgttagcag gatcaccaat   1980

ccctttaatg gtattgcgct gtacgccaac ggagacacag cccgcgctac cgttaacttc   2040

cccgcaagtc gcaactacaa tttccgcctg cggggttgcg gcaacaacaa taatcttgcc   2100

cgtgtggacc tgaggatcga cggacggacc gtcgggacct tttattacca gggcacatac   2160

ccctgggagg ccccaattga caatgtttat gtcagtgcgg ggagtcatac agtcgaaatc   2220

actgttactg cggataacgg cacatgggac gtgtatgccg actacctggt gatacag      2277


<210> SEQ ID NO 4
<211> LENGTH: 759
<212> TYPE: PRT
<213> ORGANISM: Artificial Sequence
<220> FEATURE:
<223> OTHER INFORMATION: Synthetic construct, S158-21 protein

<400> SEQUENCE: 4

Gln Thr Ser Ile Thr Leu Thr Ser Asn Ala Ser Gly Thr Phe Asp Gly
1               5                   10                  15

Tyr Tyr Tyr Glu Leu Trp Lys Asp Thr Gly Asn Thr Thr Met Thr Val
            20                  25                  30

Tyr Thr Gln Gly Arg Phe Ser Cys Gln Trp Ser Asn Ile Asn Asn Ala
        35                  40                  45

Leu Phe Arg Thr Gly Lys Lys Tyr Asn Gln Asn Trp Gln Ser Leu Gly
    50                  55                  60

Thr Ile Arg Ile Thr Tyr Ser Ala Thr Tyr Asn Pro Asn Gly Asn Ser
65                  70                  75                  80

Tyr Leu Cys Ile Tyr Gly Trp Ser Thr Asn Pro Leu Val Glu Phe Tyr
                85                  90                  95

Ile Val Glu Ser Trp Gly Asn Trp Arg Pro Pro Gly Ala Thr Ser Leu
            100                 105                 110

Gly Gln Val Thr Ile Asp Gly Gly Thr Tyr Asp Ile Tyr Arg Thr Thr
        115                 120                 125

Arg Val Asn Gln Pro Cys Leu Ala Glu Gly Ser Leu Val Leu Asp Ala
    130                 135                 140

Ala Thr Gly Gln Arg Val Pro Ile Glu Lys Val Arg Pro Gly Met Glu
145                 150                 155                 160

Val Phe Ser Leu Gly Pro Asp Tyr Arg Leu Tyr Arg Val Pro Val Leu
                165                 170                 175

Glu Val Leu Glu Ser Gly Val Arg Glu Val Val Arg Leu Arg Thr Arg
```

```
        180                 185                 190

Ser Gly Arg Thr Leu Val Leu Thr Pro Asp His Pro Leu Leu Thr Pro
    195                 200                 205

Glu Gly Trp Lys Pro Leu Cys Asp Leu Pro Leu Gly Thr Pro Ile Ala
    210                 215                 220

Val Pro Ala Glu Leu Pro Val Ala Gly His Leu Ala Pro Pro Glu Glu
225                 230                 235                 240

Arg Val Thr Leu Leu Ala Leu Leu Leu Gly Asp Gly Asn Thr Lys Leu
                245                 250                 255

Ser Gly Arg Arg Gly Thr Arg Pro Asn Ala Phe Phe Tyr Ser Lys Asp
            260                 265                 270

Pro Glu Leu Leu Ala Ala Tyr Arg Arg Cys Gly Glu Ala Leu Gly Ala
        275                 280                 285

Lys Val Lys Ala Tyr Val His Pro Thr Thr Gly Val Val Thr Leu Ala
    290                 295                 300

Thr Leu Ala Pro Arg Pro Gly Ala Gln Asp Pro Val Lys Arg Leu Val
305                 310                 315                 320

Val Glu Ala Gly Met Val Ala Lys Ala Glu Glu Lys Arg Val Pro Glu
                325                 330                 335

Glu Val Phe Arg Tyr Arg Arg Glu Ala Leu Ala Leu Phe Leu Gly Arg
            340                 345                 350

Leu Phe Ser Thr Asp Gly Ser Val Glu Lys Lys Arg Ile Ser Tyr Ser
        355                 360                 365

Ser Ala Ser Leu Gly Leu Ala Gln Asp Val Ala His Leu Leu Leu Arg
    370                 375                 380

Leu Gly Ile Thr Ser Gln Leu Arg Ser Arg Gly Pro Arg Ala His Glu
385                 390                 395                 400

Val Leu Ile Ser Gly Arg Glu Asp Ile Leu Arg Phe Ala Glu Leu Ile
                405                 410                 415

Gly Pro Tyr Leu Leu Gly Ala Lys Arg Glu Arg Leu Ala Ala Leu Glu
            420                 425                 430

Ala Glu Ala Arg Arg Arg Leu Pro Gly Gln Gly Trp His Leu Arg Leu
        435                 440                 445

Val Leu Pro Ala Val Ala Tyr Arg Val Ser Glu Ala Lys Arg Arg Ser
    450                 455                 460

Gly Phe Ser Trp Ser Glu Ala Gly Arg Arg Val Ala Val Ala Gly Ser
465                 470                 475                 480

Cys Leu Ser Ser Gly Leu Asn Leu Lys Leu Pro Arg Arg Tyr Leu Ser
                485                 490                 495

Gln His Arg Leu Ser Leu Leu Gly Glu Ala Phe Ala Asp Pro Gly Leu
            500                 505                 510

Glu Ala Leu Ala Glu Gly Gln Val Leu Trp Asp Pro Ile Val Ala Val
        515                 520                 525

Glu Pro Ala Gly Lys Ala Arg Thr Phe Asp Leu Arg Val Pro Pro Phe
    530                 535                 540

Ala Asn Phe Val Ser Glu Asp Leu Val Val His Asn Ser Ile Val Gly
545                 550                 555                 560

Thr Ala Thr Phe Asp Gln Tyr Trp Ser Val Arg Thr Ser Lys Arg Thr
                565                 570                 575

Ser Gly Thr Val Thr Val Thr Asp His Phe Arg Ala Trp Ala Asn Arg
            580                 585                 590

Gly Leu Asn Leu Gly Thr Ile Asp Gln Ile Thr Leu Cys Val Glu Gly
        595                 600                 605
```

-continued

```
Tyr Gln Ser Ser Gly Ser Ala Asn Ile Thr Gln Asn Thr Phe Ser Gln
    610                 615                 620

Gly Ser Ser Ser Gly Ser Ser Gly Gly Ser Ser Gly Ser Thr Thr Thr
625                 630                 635                 640

Thr Arg Ile Glu Cys Glu Asn Met Ser Leu Ser Gly Pro Tyr Val Ser
                645                 650                 655

Arg Ile Thr Asn Pro Phe Asn Gly Ile Ala Leu Tyr Ala Asn Gly Asp
            660                 665                 670

Thr Ala Arg Ala Thr Val Asn Phe Pro Ala Ser Arg Asn Tyr Asn Phe
        675                 680                 685

Arg Leu Arg Gly Cys Gly Asn Asn Asn Asn Leu Ala Arg Val Asp Leu
    690                 695                 700

Arg Ile Asp Gly Arg Thr Val Gly Thr Phe Tyr Tyr Gln Gly Thr Tyr
705                 710                 715                 720

Pro Trp Glu Ala Pro Ile Asp Asn Val Tyr Val Ser Ala Gly Ser His
                725                 730                 735

Thr Val Glu Ile Thr Val Thr Ala Asp Asn Gly Thr Trp Asp Val Tyr
            740                 745                 750

Ala Asp Tyr Leu Val Ile Gln
        755


<210> SEQ ID NO 5
<211> LENGTH: 2280
<212> TYPE: DNA
<213> ORGANISM: Artificial Sequence
<220> FEATURE:
<223> OTHER INFORMATION: Synthetic construct, T134-180 DNA sequence

<400> SEQUENCE: 5

caaacaagca ttactctgac atccaacgca tccggtacgt ttgacggtta ctattacgaa     60

ctctggaagg atactggcaa tacaacaatg acggtctaca ctcaaggtcg cttttcctgc    120

cagtggtcga acatcaataa cgcgttgttt aggaccggga agaaatacaa ccagaattgg    180

cagtctcttg gcacaatccg gatcacgtac tctgcgactt acaacccaaa cgggaactcc    240

tacttgtgta tctatggctg gtctaccaac ccattggtcg agttctacat cgttgagtcc    300

tgggggaact ggagaccgcc tggtgcctgc ctggccgagg gctcgctcgt cttggacgcg    360

gctaccgggc agagggtccc tatcgaaaag gtgcgtccgg ggatggaagt tttctccttg    420

ggacctgatt acagactgta tcgggtgccc gttttggagg tccttgagag cggggttagg    480

gaagttgtgc gcctcagaac tcggtcaggg agaacgctgg tgttgacacc agatcacccg    540

cttttgaccc ccgaaggttg gaaacctctt tgtgacctcc cgcttggaac tccaattgca    600

gtccccgcag aactgcctgt ggcgggccac ttggccccac ctgaagaacg tgttacgctc    660

ctggctcttc tgttggggga tgggaacaca aagctgtcgg gtcggagagg tacacgtcct    720

aatgccttct tctacagcaa agaccccgaa ttgctcgcgg cttatcgccg gtgtgcagaa    780

gccttgggtg caaaggtgaa agcatacgtc cacccgacta cgggggtggt tacactcgca    840

accctcgctc cacgtcctgg agctcaagat cctgtcaaac gcctcgttgt cgaggcggga    900

atggttgcta aagccgaaga gaagagggtc ccggaggagg tgtttcgtta ccggcgtgag    960

gcgttggccc ttttcttggg ccgtttgttc tcgacagacg gctctgttga aaagaagagg   1020

atctcttatt caagtgccag tttgggactg gcccaggatg tcgcacatct cttgctgcgc   1080

cttggaatta catctcaact ccgttcgaga gggccacggg ctcacgaggt tcttatatcg   1140
```

```
ggccgcgagg atattttgcg gtttgctgaa cttatcggac cctacctctt gggggccaag   1200

agggagagac ttgcagcgct ggaagctgag gcccgcaggc gtttgcctgg acagggatgg   1260

cacttgcggc ttgttcttcc tgccgtggcg tacagagtga gcgaggctaa aaggcgctcg   1320

ggattttcgt ggagtgaagc cggtcggcgc gtcgcagttg cgggatcgtg tttgtcatct   1380

ggactcaacc tcaaattgcc cagacgctac ctttctcggc accggttgtc gctgctcggt   1440

gaggcttttg ccgaccctgg gctggaagcg ctcgcggaag gccaagtgct ctgggaccct   1500

attgttgctg tcgaaccggc cggtaaggcg agaacattcg acttgcgcgt tccacccttt   1560

gcaaacttcg tgagcgagga cctggtggtg cataacacgt cccccatggg ccaagtgaca   1620

atcgatggcg ggacctacga catctatagg acgacacgcg tcaaccagcc ttccattgtg   1680

gggacagcca cgttcgatca gtactggagc gtgcgcacct ctaagcggac ttcaggaaca   1740

gtgaccgtga ccgatcactt ccgcgcctgg gcgaaccggg gcctgaacct cggcacaata   1800

gaccaaatta cattgtgcgt ggagggttac caaagctctg gatcagccaa catcacccag   1860

aacaccttct ctcagggctc ttcttccggc agttcgggtg gctcatccgg ctccacaacg   1920

actactcgca tcgagtgtga gaacatgtcc ttgtccggac cctacgttag caggatcacc   1980

aatcccttta atggtattgc gctgtacgcc aacggagaca cagcccgcgc taccgttaac   2040

ttccccgcaa gtcgcaacta caatttccgc ctgcggggtt gcggcaacaa caataatctt   2100

gcccgtgtgg acctgaggat cgacggacgg accgtcggga ccttttatta ccagggcaca   2160

taccccctggg aggccccaat tgacaatgtt tatgtcagtg cggggagtca tacagtcgaa   2220

atcactgtta ctgcggataa cggcacatgg gacgtgtatg ccgactacct ggtgatacag   2280
```

<210> SEQ ID NO 6
<211> LENGTH: 760
<212> TYPE: PRT
<213> ORGANISM: Artificial Sequence
<220> FEATURE:
<223> OTHER INFORMATION: Synthetic construct, T134-180 protein

<400> SEQUENCE: 6

```
Gln Thr Ser Ile Thr Leu Thr Ser Asn Ala Ser Gly Thr Phe Asp Gly
1               5                   10                  15

Tyr Tyr Tyr Glu Leu Trp Lys Asp Thr Gly Asn Thr Thr Met Thr Val
            20                  25                  30

Tyr Thr Gln Gly Arg Phe Ser Cys Gln Trp Ser Asn Ile Asn Asn Ala
        35                  40                  45

Leu Phe Arg Thr Gly Lys Lys Tyr Asn Gln Asn Trp Gln Ser Leu Gly
    50                  55                  60

Thr Ile Arg Ile Thr Tyr Ser Ala Thr Tyr Asn Pro Asn Gly Asn Ser
65                  70                  75                  80

Tyr Leu Cys Ile Tyr Gly Trp Ser Thr Asn Pro Leu Val Glu Phe Tyr
                85                  90                  95

Ile Val Glu Ser Trp Gly Asn Trp Arg Pro Pro Gly Ala Cys Leu Ala
            100                 105                 110

Glu Gly Ser Leu Val Leu Asp Ala Ala Thr Gly Gln Arg Val Pro Ile
        115                 120                 125

Glu Lys Val Arg Pro Gly Met Glu Val Phe Ser Leu Gly Pro Asp Tyr
    130                 135                 140

Arg Leu Tyr Arg Val Pro Val Leu Glu Val Leu Glu Ser Gly Val Arg
145                 150                 155                 160

Glu Val Val Arg Leu Arg Thr Arg Ser Gly Arg Thr Leu Val Leu Thr
```

```
                165                 170                 175

Pro Asp His Pro Leu Leu Thr Pro Glu Gly Trp Lys Pro Leu Cys Asp
            180                 185                 190

Leu Pro Leu Gly Thr Pro Ile Ala Val Pro Ala Glu Leu Pro Val Ala
        195                 200                 205

Gly His Leu Ala Pro Pro Glu Glu Arg Val Thr Leu Leu Ala Leu Leu
    210                 215                 220

Leu Gly Asp Gly Asn Thr Lys Leu Ser Gly Arg Arg Gly Thr Arg Pro
225                 230                 235                 240

Asn Ala Phe Phe Tyr Ser Lys Asp Pro Glu Leu Leu Ala Ala Tyr Arg
                245                 250                 255

Arg Cys Ala Glu Ala Leu Gly Ala Lys Val Lys Ala Tyr Val His Pro
            260                 265                 270

Thr Thr Gly Val Val Thr Leu Ala Thr Leu Ala Pro Arg Pro Gly Ala
        275                 280                 285

Gln Asp Pro Val Lys Arg Leu Val Val Glu Ala Gly Met Val Ala Lys
    290                 295                 300

Ala Glu Glu Lys Arg Val Pro Glu Glu Val Phe Arg Tyr Arg Arg Glu
305                 310                 315                 320

Ala Leu Ala Leu Phe Leu Gly Arg Leu Phe Ser Thr Asp Gly Ser Val
                325                 330                 335

Glu Lys Lys Arg Ile Ser Tyr Ser Ser Ala Ser Leu Gly Leu Ala Gln
            340                 345                 350

Asp Val Ala His Leu Leu Leu Arg Leu Gly Ile Thr Ser Gln Leu Arg
        355                 360                 365

Ser Arg Gly Pro Arg Ala His Glu Val Leu Ile Ser Gly Arg Glu Asp
    370                 375                 380

Ile Leu Arg Phe Ala Glu Leu Ile Gly Pro Tyr Leu Leu Gly Ala Lys
385                 390                 395                 400

Arg Glu Arg Leu Ala Ala Leu Glu Ala Glu Ala Arg Arg Arg Leu Pro
                405                 410                 415

Gly Gln Gly Trp His Leu Arg Leu Val Leu Pro Ala Val Ala Tyr Arg
            420                 425                 430

Val Ser Glu Ala Lys Arg Arg Ser Gly Phe Ser Trp Ser Glu Ala Gly
        435                 440                 445

Arg Arg Val Ala Val Ala Gly Ser Cys Leu Ser Ser Gly Leu Asn Leu
    450                 455                 460

Lys Leu Pro Arg Arg Tyr Leu Ser Arg His Arg Leu Ser Leu Leu Gly
465                 470                 475                 480

Glu Ala Phe Ala Asp Pro Gly Leu Glu Ala Leu Ala Glu Gly Gln Val
                485                 490                 495

Leu Trp Asp Pro Ile Val Ala Val Glu Pro Ala Gly Lys Ala Arg Thr
            500                 505                 510

Phe Asp Leu Arg Val Pro Pro Phe Ala Asn Phe Val Ser Glu Asp Leu
        515                 520                 525

Val Val His Asn Thr Ser Pro Met Gly Gln Val Thr Ile Asp Gly Gly
    530                 535                 540

Thr Tyr Asp Ile Tyr Arg Thr Thr Arg Val Asn Gln Pro Ser Ile Val
545                 550                 555                 560

Gly Thr Ala Thr Phe Asp Gln Tyr Trp Ser Val Arg Thr Ser Lys Arg
                565                 570                 575

Thr Ser Gly Thr Val Thr Val Thr Asp His Phe Arg Ala Trp Ala Asn
            580                 585                 590
```

-continued

```
Arg Gly Leu Asn Leu Gly Thr Ile Asp Gln Ile Thr Leu Cys Val Glu
        595                 600                 605

Gly Tyr Gln Ser Ser Gly Ser Ala Asn Ile Thr Gln Asn Thr Phe Ser
    610                 615                 620

Gln Gly Ser Ser Ser Gly Ser Ser Gly Gly Ser Ser Gly Ser Thr Thr
625                 630                 635                 640

Thr Thr Arg Ile Glu Cys Glu Asn Met Ser Leu Ser Gly Pro Tyr Val
                645                 650                 655

Ser Arg Ile Thr Asn Pro Phe Asn Gly Ile Ala Leu Tyr Ala Asn Gly
            660                 665                 670

Asp Thr Ala Arg Ala Thr Val Asn Phe Pro Ala Ser Arg Asn Tyr Asn
        675                 680                 685

Phe Arg Leu Arg Gly Cys Gly Asn Asn Asn Asn Leu Ala Arg Val Asp
    690                 695                 700

Leu Arg Ile Asp Gly Arg Thr Val Gly Thr Phe Tyr Tyr Gln Gly Thr
705                 710                 715                 720

Tyr Pro Trp Glu Ala Pro Ile Asp Asn Val Tyr Val Ser Ala Gly Ser
                725                 730                 735

His Thr Val Glu Ile Thr Val Thr Ala Asp Asn Gly Thr Trp Asp Val
            740                 745                 750

Tyr Ala Asp Tyr Leu Val Ile Gln
        755                 760


<210> SEQ ID NO 7
<211> LENGTH: 2280
<212> TYPE: DNA
<213> ORGANISM: Artificial Sequence
<220> FEATURE:
<223> OTHER INFORMATION: Synthetic construct, T134-100-165 DNA sequence

<400> SEQUENCE: 7

caaacaagca ttactctgac atccaacgca tccggtacgt ttgacggtta ctattacgaa     60

ctctggaagg atactggcaa tacaacaatg acggtctaca ctcaaggtcg cttttcctgc    120

cagtggtcga acatcaataa cgcgttgttt aggaccggga agaaatacaa ccagaattgg    180

cagtctcttg gcacaatccg gatcacgtac tctgcgactt acaacccaaa cgggaactcc    240

tacttgtgta tctatggctg gtctaccaac ccattggtcg agttctacat cgttgagtcc    300

tgggggaact ggagaccgcc tggtgcctgc ctggccgagg gctcgctcgt cttggacgcg    360

gctaccgggc agagggtccc tatcgaaaag gtgcgtccgg ggatggaagt tttctccttg    420

ggacctgatt acagactgta tcgggtgccc gttttggagg tccttgagag cggggttagg    480

gaagttgtgc gcctcagaac tcggtcaggg agaacgctgg tgttgacacc agatcacccg    540

cttttgaccc ccgaaggttg gaaacctctt tgtgacctcc cgcttggaac tccaattgca    600

gtccccgcag aactgcctgt ggcgggccac ttggccccac ctgaagaacg tgttacgctc    660

ctggctcttc tgttgggggga tgggaacaca aagctgtcgg gtcggagagg tacacgtcct    720

aatgccttct tctacagcaa aaaccccgaa ttgctcgcgg cttatcgccg gtgtgcagaa    780

gccttgggtg caaaggtgaa agcatacgtc cacccgacta cgggggtggt tacactcgca    840

accctcgctc cacgtcctgg agctcaagat cctgtcaaac gcctcgttgt cgaggcggga    900

atggttgcta aagccgaaga gaagagggtc ccggaggagg tgtttcgtta ccggcgtgag    960

gcgttggccc ttttcttggg ccgtttgttc tcgacagacg gctctgttga aaagaagagg   1020

atctcttatt caagtgccag tttgggactg gcccaggatg tcgcacatct cttgctgcgc   1080
```

cttggaatta catctcaact ccgttcgaga gggccacggg ctcacgaggt tcttatatcg 1140
ggccgcgagg atattttgcg gtttgctgaa cttatcggac cctacctctt gggggccaag 1200
agggagagac ttgcagcgct ggaagctgag gcccgcaggc gtttgcctgg acagggatgg 1260
cacttgcggc ttgttcttcc tgccgtggcg tacagagtga gcgaggctaa aaggcgctcg 1320
ggattttcgt ggagtgaagc cggtcggcgc gtcgcagttg cgggatcgtg tttgtcatct 1380
ggactcaacc tcaaattgcc cagacgctac ctttctcggc accggttgtc gctgctcggt 1440
gaggcttttg ccgaccctgg gctggaagcg ctcgcggaag gccaagtgct ctgggaccct 1500
attgttgctg tcgaaccggc cggtaaggcg agaacattcg acttgcgcgt tccacccttt 1560
gcaaacttcg tgagcgagga cctggtggtg cataacaccg tccccctggg ccaagtgaca 1620
atcgatggcg ggacctacga catctatagg acgacacgcg tcaaccagcc ttccattgtg 1680
gggacagcca cgttcgatca gtactggagc gtgcgcacct ctaagcggac ttcaggaaca 1740
gtgaccgtga ccgatcactt ccgcgcctgg gcgaaccggg gcctgaacct cggcacaata 1800
gaccaaatta cattgtgcgt ggagggttac caaagctctg gatcagccaa catcacccag 1860
aacaccttct ctcagggctc ttcttccggc agttcgggtg gctcatccgg ctccacaacg 1920
actactcgca tcgagtgtga gaacatgtcc ttgtccggac cctacgttag caggatcacc 1980
aatcccttta atggtattgc gctgtacgcc aacggagaca cagcccgcgc taccgttaac 2040
ttccccgcaa gtcgcaacta caatttccgc ctgcggggtt gcggcaacaa caataatctt 2100
gcccgtgtgg acctgaggat cgacggacgg accgtcggga ccttttatta ccagggcaca 2160
tacccctggg aggccccaat tgacaatgtt tatgtcagtg cggggagtca tacagtcgaa 2220
atcactgtta gtgcggataa cggcacatgg gacgtgtatg ccgactacct ggtgatacag 2280

<210> SEQ ID NO 8
<211> LENGTH: 760
<212> TYPE: PRT
<213> ORGANISM: Artificial Sequence
<220> FEATURE:
<223> OTHER INFORMATION: Synthetic construct, T134-100-165 protein

<400> SEQUENCE: 8

Gln Thr Ser Ile Thr Leu Thr Ser Asn Ala Ser Gly Thr Phe Asp Gly
1 5 10 15

Tyr Tyr Tyr Glu Leu Trp Lys Asp Thr Gly Asn Thr Thr Met Thr Val
20 25 30

Tyr Thr Gln Gly Arg Phe Ser Cys Gln Trp Ser Asn Ile Asn Asn Ala
35 40 45

Leu Phe Arg Thr Gly Lys Lys Tyr Asn Gln Asn Trp Gln Ser Leu Gly
50 55 60

Thr Ile Arg Ile Thr Tyr Ser Ala Thr Tyr Asn Pro Asn Gly Asn Ser
65 70 75 80

Tyr Leu Cys Ile Tyr Gly Trp Ser Thr Asn Pro Leu Val Glu Phe Tyr
85 90 95

Ile Val Glu Ser Trp Gly Asn Trp Arg Pro Pro Gly Ala Cys Leu Ala
100 105 110

Glu Gly Ser Leu Val Leu Asp Ala Ala Thr Gly Gln Arg Val Pro Ile
115 120 125

Glu Lys Val Arg Pro Gly Met Glu Val Phe Ser Leu Gly Pro Asp Tyr
130 135 140

Arg Leu Tyr Arg Val Pro Val Leu Glu Val Leu Glu Ser Gly Val Arg

-continued

```
145                 150                 155                 160

Glu Val Val Arg Leu Arg Thr Arg Ser Gly Arg Thr Leu Val Leu Thr
                165                 170                 175

Pro Asp His Pro Leu Leu Thr Pro Glu Gly Trp Lys Pro Leu Cys Asp
            180                 185                 190

Leu Pro Leu Gly Thr Pro Ile Ala Val Pro Ala Glu Leu Pro Val Ala
        195                 200                 205

Gly His Leu Ala Pro Pro Glu Glu Arg Val Thr Leu Leu Ala Leu Leu
    210                 215                 220

Leu Gly Asp Gly Asn Thr Lys Leu Ser Gly Arg Arg Gly Thr Arg Pro
225                 230                 235                 240

Asn Ala Phe Phe Tyr Ser Lys Asn Pro Glu Leu Leu Ala Ala Tyr Arg
                245                 250                 255

Arg Cys Ala Glu Ala Leu Gly Ala Lys Val Lys Ala Tyr Val His Pro
            260                 265                 270

Thr Thr Gly Val Val Thr Leu Ala Thr Leu Ala Pro Arg Pro Gly Ala
        275                 280                 285

Gln Asp Pro Val Lys Arg Leu Val Val Glu Ala Gly Met Val Ala Lys
    290                 295                 300

Ala Glu Glu Lys Arg Val Pro Glu Glu Val Phe Arg Tyr Arg Arg Glu
305                 310                 315                 320

Ala Leu Ala Leu Phe Leu Gly Arg Leu Phe Ser Thr Asp Gly Ser Val
                325                 330                 335

Glu Lys Lys Arg Ile Ser Tyr Ser Ser Ala Ser Leu Gly Leu Ala Gln
            340                 345                 350

Asp Val Ala His Leu Leu Leu Arg Leu Gly Ile Thr Ser Gln Leu Arg
        355                 360                 365

Ser Arg Gly Pro Arg Ala His Glu Val Leu Ile Ser Gly Arg Glu Asp
    370                 375                 380

Ile Leu Arg Phe Ala Glu Leu Ile Gly Pro Tyr Leu Leu Gly Ala Lys
385                 390                 395                 400

Arg Glu Arg Leu Ala Ala Leu Glu Ala Glu Ala Arg Arg Arg Leu Pro
                405                 410                 415

Gly Gln Gly Trp His Leu Arg Leu Val Leu Pro Ala Val Ala Tyr Arg
            420                 425                 430

Val Ser Glu Ala Lys Arg Arg Ser Gly Phe Ser Trp Ser Glu Ala Gly
        435                 440                 445

Arg Arg Val Ala Val Ala Gly Ser Cys Leu Ser Ser Gly Leu Asn Leu
    450                 455                 460

Lys Leu Pro Arg Arg Tyr Leu Ser Arg His Arg Leu Ser Leu Leu Gly
465                 470                 475                 480

Glu Ala Phe Ala Asp Pro Gly Leu Glu Ala Leu Ala Glu Gly Gln Val
                485                 490                 495

Leu Trp Asp Pro Ile Val Ala Val Glu Pro Ala Gly Lys Ala Arg Thr
            500                 505                 510

Phe Asp Leu Arg Val Pro Pro Phe Ala Asn Phe Val Ser Glu Asp Leu
        515                 520                 525

Val Val His Asn Thr Val Pro Leu Gly Gln Val Thr Ile Asp Gly Gly
    530                 535                 540

Thr Tyr Asp Ile Tyr Arg Thr Thr Arg Val Asn Gln Pro Ser Ile Val
545                 550                 555                 560

Gly Thr Ala Thr Phe Asp Gln Tyr Trp Ser Val Arg Thr Ser Lys Arg
                565                 570                 575
```

```
Thr Ser Gly Thr Val Thr Val Thr Asp His Phe Arg Ala Trp Ala Asn
            580                 585                 590

Arg Gly Leu Asn Leu Gly Thr Ile Asp Gln Ile Thr Leu Cys Val Glu
        595                 600                 605

Gly Tyr Gln Ser Ser Gly Ser Ala Asn Ile Thr Gln Asn Thr Phe Ser
    610                 615                 620

Gln Gly Ser Ser Ser Gly Ser Ser Gly Gly Ser Ser Gly Ser Thr Thr
625                 630                 635                 640

Thr Thr Arg Ile Glu Cys Glu Asn Met Ser Leu Ser Gly Pro Tyr Val
                645                 650                 655

Ser Arg Ile Thr Asn Pro Phe Asn Gly Ile Ala Leu Tyr Ala Asn Gly
            660                 665                 670

Asp Thr Ala Arg Ala Thr Val Asn Phe Pro Ala Ser Arg Asn Tyr Asn
        675                 680                 685

Phe Arg Leu Arg Gly Cys Gly Asn Asn Asn Asn Leu Ala Arg Val Asp
    690                 695                 700

Leu Arg Ile Asp Gly Arg Thr Val Gly Thr Phe Tyr Tyr Gln Gly Thr
705                 710                 715                 720

Tyr Pro Trp Glu Ala Pro Ile Asp Asn Val Tyr Val Ser Ala Gly Ser
                725                 730                 735

His Thr Val Glu Ile Thr Val Ser Ala Asp Asn Gly Thr Trp Asp Val
            740                 745                 750

Tyr Ala Asp Tyr Leu Val Ile Gln
        755                 760
```

```
<210> SEQ ID NO 9
<211> LENGTH: 2280
<212> TYPE: DNA
<213> ORGANISM: Artificial Sequence
<220> FEATURE:
<223> OTHER INFORMATION: Synthetic construct, T134-10068 DNA sequence

<400> SEQUENCE: 9

caaacaagca ttactctgac atccaacgca tccggtacgt ttgacggtta ctattacgaa     60

ctctggaagg atactggcaa tacaacaatg acggtctaca ctcaaggtcg cttttcctgc    120

cagtggtcga acatcaataa cgcgttgttt aggaccggga agaaatacaa ccagaattgg    180

cagtctcttg gcacaatccg gatcacgtac tctgcgactt acaacccaaa cgggaactcc    240

tacttgtgta tctatggctg gtctaccaac ccattggtcg agttctacat cgttgagtcc    300

tgggggaact ggagaccgcc tggtgcctgc ctggccgagg gctcgctcgt cttggacgcg    360

gctaccgggc agagggtccc tatcgaaaag gtgcgtccgg ggatggaagt tttctccctg    420

ggacctgatt acagactgta tcgggtgccc gttttggagg tccttgagag cggggttagg    480

gaagttgtgc gcctcagaac tcggtcagag agaacgctgg tgttgacacc agatcacccg    540

cttttgaccc ccgaaggttg gaaacctctt tgtgacctcc cgcttggaac tccaattgca    600

gtccccgcag aactgcctgt ggcgggccac ttggccccac ctgaagaacg tgttacgctc    660

ctggctcttc tgttggggga tgggaacaca aagctgtcgg gtcggagagg tacacgtcct    720

aatgccttct tccacagcaa agaccccgaa ttgctcgcgg cttatcgccg gtgtgcagaa    780

gccttgggtg caaaggtgaa agcatacgtc cacccgacta cgggggtggt tacactcgca    840

accctcgccc cacgtcctgg agctcaagat cctgtcaaac gcctcgttgt cgaggcggga    900

atggttgcta aagccgaaga gaagagggtc ccggaggagg tgtttcgtta ccggcgtgag    960
```

-continued

```
gcgttggccc ttttcttggg ccgtttgttc tcgacagacg gctctgttga aaagaagagg   1020

atctcttatt caagtgccag tttggggctg gcccaggatg tcgcacatct cttgctgcgc   1080

cttggaatta catctcaact ccgttcgaga gggccacggg ctcacgaggt tcttatatcg   1140

ggccgcgagg atattttgcg gtttgctgaa cttatcggac cctacctctt gggggccaag   1200

agggagagac ttgcagcgct ggaagctgag gcccgcaggc gtttgcctgt acagggatgg   1260

cactcgcggc ttgttcttcc tgccgtggcg tacagagtga gcgaggctaa aaggcgctcg   1320

ggattttcgt ggagtgaagc cggtcggcgc gtcgcagttg cgggatcgtg tttgtcatct   1380

ggactcaacc tcaaattgcc cagacgctac ctttctcggc accggttgtc gctgctcggt   1440

gaggcttttg ccgaccctgg gctggaagcg ctcgcggaag gccaagtgct ctgggaccct   1500

attgttgctg tcgaaccggc cggtaaggcg agaacattcg acttgcgcgt tccacccttt   1560

gcaaacttcg tgagcgagga cctggtggtg cataacaccg tcccccctggg ccaagtgaca   1620

atcgatggcg ggacctacga catctatagg acgacacgcg tcaaccagcc ttccattgtg   1680

gggacagcca cgttcgatca gtactggagc gtgcgcacct ctaagcggac ttcaggaaca   1740

gtgaccgtga ccgatcactt ccgcgcctgg gcgaaccggg gcctgaacct cggcacaata   1800

gaccaaatta cattgtgcgt ggagggttac caaagctctg gatcagccaa catcacccag   1860

aacaccttct ctcagggctc ttcttccggc agttcgggtg gctcatccgg ctccacaacg   1920

actactcgca tcgagtgtga gaacatgtcc ttgtccggac cctacgttag caggatcacc   1980

aatcccttta atggtattgc gctgtacgcc aacggagaca cagcccgcgc taccgttaac   2040

ttccccgcaa gtcgcaacta caatttccgc ctgcggggtt gcggcaacaa caataatctt   2100

gcccgtgtgg acctgaggat cgacggacgg accgtcggga ccttttatta ccagggcaca   2160

taccccctggg aggccccaat tgacaatgtt tatgtcagtg cggggagtca tacagtcgaa   2220

atcactgtta ctgcggataa cggcacatgg gacgtgtatg ccgactacct ggtgatacag   2280
```

```
<210> SEQ ID NO 10
<211> LENGTH: 760
<212> TYPE: PRT
<213> ORGANISM: Artificial Sequence
<220> FEATURE:
<223> OTHER INFORMATION: Synthetic construct, T134-10068 protein

<400> SEQUENCE: 10

Gln Thr Ser Ile Thr Leu Thr Ser Asn Ala Ser Gly Thr Phe Asp Gly
1               5                   10                  15

Tyr Tyr Tyr Glu Leu Trp Lys Asp Thr Gly Asn Thr Thr Met Thr Val
            20                  25                  30

Tyr Thr Gln Gly Arg Phe Ser Cys Gln Trp Ser Asn Ile Asn Asn Ala
        35                  40                  45

Leu Phe Arg Thr Gly Lys Lys Tyr Asn Gln Asn Trp Gln Ser Leu Gly
    50                  55                  60

Thr Ile Arg Ile Thr Tyr Ser Ala Thr Tyr Asn Pro Asn Gly Asn Ser
65                  70                  75                  80

Tyr Leu Cys Ile Tyr Gly Trp Ser Thr Asn Pro Leu Val Glu Phe Tyr
                85                  90                  95

Ile Val Glu Ser Trp Gly Asn Trp Arg Pro Pro Gly Ala Cys Leu Ala
            100                 105                 110

Glu Gly Ser Leu Val Leu Asp Ala Ala Thr Gly Gln Arg Val Pro Ile
        115                 120                 125

Glu Lys Val Arg Pro Gly Met Glu Val Phe Ser Leu Gly Pro Asp Tyr
```

-continued

```
    130                 135                 140

Arg Leu Tyr Arg Val Pro Val Leu Glu Val Leu Glu Ser Gly Val Arg
145                 150                 155                 160

Glu Val Val Arg Leu Arg Thr Arg Ser Glu Arg Thr Leu Val Leu Thr
                165                 170                 175

Pro Asp His Pro Leu Leu Thr Pro Glu Gly Trp Lys Pro Leu Cys Asp
            180                 185                 190

Leu Pro Leu Gly Thr Pro Ile Ala Val Pro Ala Glu Leu Pro Val Ala
        195                 200                 205

Gly His Leu Ala Pro Pro Glu Glu Arg Val Thr Leu Leu Ala Leu Leu
    210                 215                 220

Leu Gly Asp Gly Asn Thr Lys Leu Ser Gly Arg Arg Gly Thr Arg Pro
225                 230                 235                 240

Asn Ala Phe Phe His Ser Lys Asp Pro Glu Leu Leu Ala Ala Tyr Arg
                245                 250                 255

Arg Cys Ala Glu Ala Leu Gly Ala Lys Val Lys Ala Tyr Val His Pro
            260                 265                 270

Thr Thr Gly Val Val Thr Leu Ala Thr Leu Ala Pro Arg Pro Gly Ala
        275                 280                 285

Gln Asp Pro Val Lys Arg Leu Val Val Glu Ala Gly Met Val Ala Lys
    290                 295                 300

Ala Glu Glu Lys Arg Val Pro Glu Glu Val Phe Arg Tyr Arg Arg Glu
305                 310                 315                 320

Ala Leu Ala Leu Phe Leu Gly Arg Leu Phe Ser Thr Asp Gly Ser Val
                325                 330                 335

Glu Lys Lys Arg Ile Ser Tyr Ser Ser Ala Ser Leu Gly Leu Ala Gln
            340                 345                 350

Asp Val Ala His Leu Leu Leu Arg Leu Gly Ile Thr Ser Gln Leu Arg
        355                 360                 365

Ser Arg Gly Pro Arg Ala His Glu Val Leu Ile Ser Gly Arg Glu Asp
    370                 375                 380

Ile Leu Arg Phe Ala Glu Leu Ile Gly Pro Tyr Leu Leu Gly Ala Lys
385                 390                 395                 400

Arg Glu Arg Leu Ala Ala Leu Glu Ala Glu Ala Arg Arg Arg Leu Pro
                405                 410                 415

Val Gln Gly Trp His Ser Arg Leu Val Leu Pro Ala Val Ala Tyr Arg
            420                 425                 430

Val Ser Glu Ala Lys Arg Arg Ser Gly Phe Ser Trp Ser Glu Ala Gly
        435                 440                 445

Arg Arg Val Ala Val Ala Gly Ser Cys Leu Ser Ser Gly Leu Asn Leu
    450                 455                 460

Lys Leu Pro Arg Arg Tyr Leu Ser Arg His Arg Leu Ser Leu Leu Gly
465                 470                 475                 480

Glu Ala Phe Ala Asp Pro Gly Leu Glu Ala Leu Ala Glu Gly Gln Val
                485                 490                 495

Leu Trp Asp Pro Ile Val Ala Val Glu Pro Ala Gly Lys Ala Arg Thr
            500                 505                 510

Phe Asp Leu Arg Val Pro Pro Phe Ala Asn Phe Val Ser Glu Asp Leu
        515                 520                 525

Val Val His Asn Thr Val Pro Leu Gly Gln Val Thr Ile Asp Gly Gly
    530                 535                 540

Thr Tyr Asp Ile Tyr Arg Thr Thr Arg Val Asn Gln Pro Ser Ile Val
545                 550                 555                 560
```

```
Gly Thr Ala Thr Phe Asp Gln Tyr Trp Ser Val Arg Thr Ser Lys Arg
                565                 570                 575

Thr Ser Gly Thr Val Thr Val Thr Asp His Phe Arg Ala Trp Ala Asn
            580                 585                 590

Arg Gly Leu Asn Leu Gly Thr Ile Asp Gln Ile Thr Leu Cys Val Glu
        595                 600                 605

Gly Tyr Gln Ser Ser Gly Ser Ala Asn Ile Thr Gln Asn Thr Phe Ser
    610                 615                 620

Gln Gly Ser Ser Ser Gly Ser Ser Gly Gly Ser Ser Gly Ser Thr Thr
625                 630                 635                 640

Thr Thr Arg Ile Glu Cys Glu Asn Met Ser Leu Ser Gly Pro Tyr Val
                645                 650                 655

Ser Arg Ile Thr Asn Pro Phe Asn Gly Ile Ala Leu Tyr Ala Asn Gly
            660                 665                 670

Asp Thr Ala Arg Ala Thr Val Asn Phe Pro Ala Ser Arg Asn Tyr Asn
        675                 680                 685

Phe Arg Leu Arg Gly Cys Gly Asn Asn Asn Asn Leu Ala Arg Val Asp
    690                 695                 700

Leu Arg Ile Asp Gly Arg Thr Val Gly Thr Phe Tyr Tyr Gln Gly Thr
705                 710                 715                 720

Tyr Pro Trp Glu Ala Pro Ile Asp Asn Val Tyr Val Ser Ala Gly Ser
                725                 730                 735

His Thr Val Glu Ile Thr Val Thr Ala Asp Asn Gly Thr Trp Asp Val
            740                 745                 750

Tyr Ala Asp Tyr Leu Val Ile Gln
        755                 760
```

<210> SEQ ID NO 11
<211> LENGTH: 2280
<212> TYPE: DNA
<213> ORGANISM: Artificial Sequence
<220> FEATURE:
<223> OTHER INFORMATION: Synthetic construct, T134-10039 DNA sequence

<400> SEQUENCE: 11

```
caaacaagca ttactctgac atccaacgca tccggtacgt ttgacggtta ctattacgaa     60

ctctggaagg atactggcaa tacaacaatg acggtctaca ctcaaggtcg cttttcctgc    120

cagtggtcga acatcaataa cgcgttgttt aggaccggga agaaatacaa ccagaattgg    180

cagtctcttg gcacaatccg gatcacgtac tctgcgactt acaacccaaa cgggaactcc    240

tacttgtgta tctatggctg gtctaccaac ccattggtcg agttctacat cgttgagtcc    300

tgggggaact ggagaccgcc tggtgcctgc ctggccgagg gctcgctcgt cttggacgcg    360

gctaccgggc agagggtccc tatcgaaaag gtgcgtccgg ggatggaagt tttctccttg    420

ggacctgatt acagactgta tcgggtgccc gttttggagg tccttgagag cggggttagg    480

gaagttgtgc gcctcagaac tcggtcaggg agaacgctgg tgttgacacc agatcacccg    540

cttttgaccc ccgaaggttg gaaacctctt tgtgacctcc cgcttggaac tccaattgca    600

gtccccgcag aactgcctgt ggcgggccac ttggccccac ctgaagaacg tgttacgctc    660

ctggctcttc tgttgggggga tgggaacaca aagctgtcgg gtcggagagg tacacgtcct    720

aatgccttct tctacagcaa agaccccgaa ttgctcgcgg cttatcgccg gtgtgcagaa    780

gccttgggtg caaaggtgaa agcatacgtc cacccgacta cgggggtggt tacactcgca    840

accctcgctc cacgtcctgg agctcaagat cctgtcaaac gcctcgttgt cgaggcggga    900
```

```
atggttgcta aagccgaaga gaagagggtc ccggaggagg tgtttcgtta ccggcgtgag    960

gcgttggccc ttttcttggg ccgtttgttc tcgacagacg gctctgttga aaagaagagg   1020

atctcttatt caagtgccag tttgggactg gcccaggatg tcgcacatct cttgctgcgc   1080

cttggaatta catctcaact ccgttcgaga gggccacggg ctcacgaggt tcttatatcg   1140

ggccgcgagg atattttgcg gtttgctgaa cttatcggac cctacctctt gggggccaag   1200

agggagagac ttgcagcgct ggaagctgag gcccgcaggc gtttgcctgg acagggatgg   1260

cacttgcggc ttgttcttcc tgccgtggcg tacagagtga gcgaggctaa aaggcgctcg   1320

ggattttcgt ggagtgaagc cggtcggcgc gtcgcagttg cgggatcgtg tttgtcatct   1380

ggactcaacc tcaaattgcc cagacgctac ctttctcggc accggttgtc gctgctcggt   1440

gaggcttttg ccgaccctgg gctggaagcg ctcgcggaag gcctagtgct ctgggaccct   1500

attgttgctg tcgaaccggc cggtaaggcg agaacattcg acttgcgcgt tccacccttt   1560

gcaaacttcg tgagcgagga cctggtggtg cataacaccg tcccccctggg ccaagtgaca   1620

atcgatggcg ggacctacga catctatagg acgacacgcg tcaaccagcc ttccattgtg   1680

gggacagcca cgttcgatca gtactggagc gtgcgcacct ctaagcggac ttcaggaaca   1740

gtgaccgtga ccgatcactt ccgcgcctgg gcgaaccggg gcctgaacct cggcacaata   1800

gaccaaatta cattgtgcgt ggagggttac caaagctctg gatcagccaa catcacccag   1860

aacaccttct ctcagggctc ttcttccggc agttcgggtg gctcatccgg ctccacaacg   1920

actactcgca tcgagtgtga gaacatgtcc ttgtccggac cctacgttag caggatcacc   1980

aatcccttta atggtattgc gctgtacgcc aacggagaca cagcccgcgc taccgttaac   2040

ttccccgcaa gtcgcaacta caatttccgc ctgcggggtt gcggcaacaa caataatctt   2100

gcccgtgtgg acctgaggat cgacggacgg accgtcggga ccttttatta ccagggcaca   2160

tacccctggg aggccccaat tgacaatgtt tatgtcagtg cggggagtca tacagtcgaa   2220

atcactgtta ctgcggataa cggcacatgg gacgtgtatg ccgactacct ggtgatacag   2280
```

```
<210> SEQ ID NO 12
<211> LENGTH: 760
<212> TYPE: PRT
<213> ORGANISM: Artificial Sequence
<220> FEATURE:
<223> OTHER INFORMATION: Synthetic construct, T134-10039 protein

<400> SEQUENCE: 12

Gln Thr Ser Ile Thr Leu Thr Ser Asn Ala Ser Gly Thr Phe Asp Gly
1               5                   10                  15

Tyr Tyr Tyr Glu Leu Trp Lys Asp Thr Gly Asn Thr Thr Met Thr Val
            20                  25                  30

Tyr Thr Gln Gly Arg Phe Ser Cys Gln Trp Ser Asn Ile Asn Asn Ala
        35                  40                  45

Leu Phe Arg Thr Gly Lys Lys Tyr Asn Gln Asn Trp Gln Ser Leu Gly
    50                  55                  60

Thr Ile Arg Ile Thr Tyr Ser Ala Thr Tyr Asn Pro Asn Gly Asn Ser
65                  70                  75                  80

Tyr Leu Cys Ile Tyr Gly Trp Ser Thr Asn Pro Leu Val Glu Phe Tyr
                85                  90                  95

Ile Val Glu Ser Trp Gly Asn Trp Arg Pro Pro Gly Ala Cys Leu Ala
            100                 105                 110

Glu Gly Ser Leu Val Leu Asp Ala Ala Thr Gly Gln Arg Val Pro Ile
```

```
        115                 120                 125

Glu Lys Val Arg Pro Gly Met Glu Val Phe Ser Leu Gly Pro Asp Tyr
    130                 135                 140

Arg Leu Tyr Arg Val Pro Val Leu Glu Val Leu Glu Ser Gly Val Arg
145                 150                 155                 160

Glu Val Val Arg Leu Arg Thr Arg Ser Gly Arg Thr Leu Val Leu Thr
                165                 170                 175

Pro Asp His Pro Leu Leu Thr Pro Glu Gly Trp Lys Pro Leu Cys Asp
            180                 185                 190

Leu Pro Leu Gly Thr Pro Ile Ala Val Pro Ala Glu Leu Pro Val Ala
        195                 200                 205

Gly His Leu Ala Pro Pro Glu Glu Arg Val Thr Leu Leu Ala Leu Leu
    210                 215                 220

Leu Gly Asp Gly Asn Thr Lys Leu Ser Gly Arg Arg Gly Thr Arg Pro
225                 230                 235                 240

Asn Ala Phe Phe Tyr Ser Lys Asp Pro Glu Leu Leu Ala Ala Tyr Arg
                245                 250                 255

Arg Cys Ala Glu Ala Leu Gly Ala Lys Val Lys Ala Tyr Val His Pro
            260                 265                 270

Thr Thr Gly Val Val Thr Leu Ala Thr Leu Ala Pro Arg Pro Gly Ala
        275                 280                 285

Gln Asp Pro Val Lys Arg Leu Val Val Glu Ala Gly Met Val Ala Lys
    290                 295                 300

Ala Glu Glu Lys Arg Val Pro Glu Glu Val Phe Arg Tyr Arg Arg Glu
305                 310                 315                 320

Ala Leu Ala Leu Phe Leu Gly Arg Leu Phe Ser Thr Asp Gly Ser Val
                325                 330                 335

Glu Lys Lys Arg Ile Ser Tyr Ser Ser Ala Ser Leu Gly Leu Ala Gln
            340                 345                 350

Asp Val Ala His Leu Leu Leu Arg Leu Gly Ile Thr Ser Gln Leu Arg
        355                 360                 365

Ser Arg Gly Pro Arg Ala His Glu Val Leu Ile Ser Gly Arg Glu Asp
    370                 375                 380

Ile Leu Arg Phe Ala Glu Leu Ile Gly Pro Tyr Leu Leu Gly Ala Lys
385                 390                 395                 400

Arg Glu Arg Leu Ala Ala Leu Glu Ala Glu Ala Arg Arg Arg Leu Pro
                405                 410                 415

Gly Gln Gly Trp His Leu Arg Leu Val Leu Pro Ala Val Ala Tyr Arg
            420                 425                 430

Val Ser Glu Ala Lys Arg Arg Ser Gly Phe Ser Trp Ser Glu Ala Gly
        435                 440                 445

Arg Arg Val Ala Val Ala Gly Ser Cys Leu Ser Ser Gly Leu Asn Leu
    450                 455                 460

Lys Leu Pro Arg Arg Tyr Leu Ser Arg His Arg Leu Ser Leu Leu Gly
465                 470                 475                 480

Glu Ala Phe Ala Asp Pro Gly Leu Glu Ala Leu Ala Glu Gly Leu Val
                485                 490                 495

Leu Trp Asp Pro Ile Val Ala Val Glu Pro Ala Gly Lys Ala Arg Thr
            500                 505                 510

Phe Asp Leu Arg Val Pro Pro Phe Ala Asn Phe Val Ser Glu Asp Leu
        515                 520                 525

Val Val His Asn Thr Val Pro Leu Gly Gln Val Thr Ile Asp Gly Gly
    530                 535                 540
```

```
Thr Tyr Asp Ile Tyr Arg Thr Thr Arg Val Asn Gln Pro Ser Ile Val
545                 550                 555                 560

Gly Thr Ala Thr Phe Asp Gln Tyr Trp Ser Val Arg Thr Ser Lys Arg
                565                 570                 575

Thr Ser Gly Thr Val Thr Val Thr Asp His Phe Arg Ala Trp Ala Asn
            580                 585                 590

Arg Gly Leu Asn Leu Gly Thr Ile Asp Gln Ile Thr Leu Cys Val Glu
        595                 600                 605

Gly Tyr Gln Ser Ser Gly Ser Ala Asn Ile Thr Gln Asn Thr Phe Ser
    610                 615                 620

Gln Gly Ser Ser Ser Gly Ser Ser Gly Gly Ser Ser Gly Ser Thr Thr
625                 630                 635                 640

Thr Thr Arg Ile Glu Cys Glu Asn Met Ser Leu Ser Gly Pro Tyr Val
                645                 650                 655

Ser Arg Ile Thr Asn Pro Phe Asn Gly Ile Ala Leu Tyr Ala Asn Gly
            660                 665                 670

Asp Thr Ala Arg Ala Thr Val Asn Phe Pro Ala Ser Arg Asn Tyr Asn
        675                 680                 685

Phe Arg Leu Arg Gly Cys Gly Asn Asn Asn Asn Leu Ala Arg Val Asp
    690                 695                 700

Leu Arg Ile Asp Gly Arg Thr Val Gly Thr Phe Tyr Tyr Gln Gly Thr
705                 710                 715                 720

Tyr Pro Trp Glu Ala Pro Ile Asp Asn Val Tyr Val Ser Ala Gly Ser
                725                 730                 735

His Thr Val Glu Ile Thr Val Thr Ala Asp Asn Gly Thr Trp Asp Val
            740                 745                 750

Tyr Ala Asp Tyr Leu Val Ile Gln
        755                 760
```

<210> SEQ ID NO 13
<211> LENGTH: 2280
<212> TYPE: DNA
<213> ORGANISM: Artificial Sequence
<220> FEATURE:
<223> OTHER INFORMATION: Synthetic construct, T134-100 DNA sequence

<400> SEQUENCE: 13

```
caaacaagca ttactctgac atccaacgca tccggtacgt ttgacggtta ctattacgaa     60

ctctggaagg atactggcaa tacaacaatg acggtctaca ctcaaggtcg cttttcctgc    120

cagtggtcga acatcaataa cgcgttgttt aggaccggga agaaatacaa ccagaattgg    180

cagtctcttg gcacaatccg gatcacgtac tctgcgactt acaacccaaa cgggaactcc    240

tacttgtgta tctatggctg gtctaccaac ccattggtcg agttctacat cgttgagtcc    300

tgggggaact ggagaccgcc tggtgcctgc ctggccgagg gctcgctcgt cttggacgcg    360

gctaccgggc agagggtccc tatcgaaaag gtgcgtccgg ggatggaagt tttctccttg    420

ggacctgatt acagactgta tcgggtgccc gttttggagg tccttgagag cggggttagg    480

gaagttgtgc gcctcagaac tcggtcaggg agaacgctgg tgttgacacc agatcacccg    540

cttttgaccc ccgaaggttg gaaacctctt tgtgacctcc cgcttggaac tccaattgca    600

gtccccgcag aactgcctgt ggcgggccac ttggccccac ctgaagaacg tgttacgctc    660

ctggctcttc tgttggggga tgggaacaca aagctgtcgg gtcggagagg tacacgtcct    720

aatgccttct tctacagcaa agaccccgaa ttgctcgcgg cttatcgccg gtgtgcagaa    780
```

-continued

```
gccttgggtg caaaggtgaa agcatacgtc cacccgacta cgggggtggt tacactcgca    840

accctcgctc cacgtcctgg agctcaagat cctgtcaaac gcctcgttgt cgaggcggga    900

atggttgcta aagccgaaga gaagagggtc ccggaggagg tgtttcgtta ccggcgtgag    960

gcgttggccc ttttcttggg ccgtttgttc tcgacagacg gctctgttga aaagaagagg   1020

atctcttatt caagtgccag tttgggactg gcccaggatg tcgcacatct cttgctgcgc   1080

cttggaatta catctcaact ccgttcgaga gggccacggg ctcacgaggt tcttatatcg   1140

ggccgcgagg atattttgcg gtttgctgaa cttatcggac cctacctctt gggggccaag   1200

agggagagac ttgcagcgct ggaagctgag gcccgcaggc gtttgcctgg acagggatgg   1260

cacttgcggc ttgttcttcc tgccgtggcg tacagagtga gcgaggctaa aaggcgctcg   1320

ggattttcgt ggagtgaagc cggtcggcgc gtcgcagttg cgggatcgtg tttgtcatct   1380

ggactcaacc tcaaattgcc cagacgctac ctttctcggc accggttgtc gctgctcggt   1440

gaggcttttg ccgaccctgg gctggaagcg ctcgcggaag gccaagtgct ctgggaccct   1500

attgttgctg tcgaaccggc cggtaaggcg agaacattcg acttgcgcgt tccacccttt   1560

gcaaacttcg tgagcgagga cctggtggtg cataacaccg tccccctggg ccaagtgaca   1620

atcgatggcg ggacctacga catctatagg acgacacgcg tcaaccagcc ttccattgtg   1680

gggacagcca cgttcgatca gtactggagc gtgcgcacct ctaagcggac ttcaggaaca   1740

gtgaccgtga ccgatcactt ccgcgcctgg gcgaaccggg gcctgaacct cggcacaata   1800

gaccaaatta cattgtgcgt ggagggttac caaagctctg gatcagccaa catcacccag   1860

aacaccttct ctcagggctc ttcttccggc agttcgggtg gctcatccgg ctccacaacg   1920

actactcgca tcgagtgtga gaacatgtcc ttgtccggac cctacgttag caggatcacc   1980

aatcccttta atggtattgc gctgtacgcc aacggagaca cagcccgcgc taccgttaac   2040

ttccccgcaa gtcgcaacta caatttccgc ctgcggggtt gcggcaacaa caataatctt   2100

gcccgtgtgg acctgaggat cgacggacgg accgtcggga ccttttatta ccagggcaca   2160

tacccctggg aggccccaat tgacaatgtt tatgtcagtg cggggagtca tacagtcgaa   2220

atcactgtta ctgcggataa cggcacatgg gacgtgtatg ccgactacct ggtgatacag   2280
```

```
<210> SEQ ID NO 14
<211> LENGTH: 760
<212> TYPE: PRT
<213> ORGANISM: Artificial Sequence
<220> FEATURE:
<223> OTHER INFORMATION: Synthetic construct, T134-100 protein

<400> SEQUENCE: 14

Gln Thr Ser Ile Thr Leu Thr Ser Asn Ala Ser Gly Thr Phe Asp Gly
1               5                   10                  15

Tyr Tyr Tyr Glu Leu Trp Lys Asp Thr Gly Asn Thr Thr Met Thr Val
            20                  25                  30

Tyr Thr Gln Gly Arg Phe Ser Cys Gln Trp Ser Asn Ile Asn Asn Ala
        35                  40                  45

Leu Phe Arg Thr Gly Lys Lys Tyr Asn Gln Asn Trp Gln Ser Leu Gly
    50                  55                  60

Thr Ile Arg Ile Thr Tyr Ser Ala Thr Tyr Asn Pro Asn Gly Asn Ser
65                  70                  75                  80

Tyr Leu Cys Ile Tyr Gly Trp Ser Thr Asn Pro Leu Val Glu Phe Tyr
                85                  90                  95

Ile Val Glu Ser Trp Gly Asn Trp Arg Pro Pro Gly Ala Cys Leu Ala
```

-continued

```
            100                 105                 110

Glu Gly Ser Leu Val Leu Asp Ala Ala Thr Gly Gln Arg Val Pro Ile
        115                 120                 125

Glu Lys Val Arg Pro Gly Met Glu Val Phe Ser Leu Gly Pro Asp Tyr
    130                 135                 140

Arg Leu Tyr Arg Val Pro Val Leu Glu Val Leu Glu Ser Gly Val Arg
145                 150                 155                 160

Glu Val Val Arg Leu Arg Thr Arg Ser Gly Arg Thr Leu Val Leu Thr
            165                 170                 175

Pro Asp His Pro Leu Leu Thr Pro Glu Gly Trp Lys Pro Leu Cys Asp
            180                 185                 190

Leu Pro Leu Gly Thr Pro Ile Ala Val Pro Ala Glu Leu Pro Val Ala
        195                 200                 205

Gly His Leu Ala Pro Pro Glu Glu Arg Val Thr Leu Leu Ala Leu Leu
    210                 215                 220

Leu Gly Asp Gly Asn Thr Lys Leu Ser Gly Arg Arg Gly Thr Arg Pro
225                 230                 235                 240

Asn Ala Phe Phe Tyr Ser Lys Asp Pro Glu Leu Leu Ala Ala Tyr Arg
            245                 250                 255

Arg Cys Ala Glu Ala Leu Gly Ala Lys Val Lys Ala Tyr Val His Pro
            260                 265                 270

Thr Thr Gly Val Val Thr Leu Ala Thr Leu Ala Pro Arg Pro Gly Ala
        275                 280                 285

Gln Asp Pro Val Lys Arg Leu Val Val Glu Ala Gly Met Val Ala Lys
    290                 295                 300

Ala Glu Glu Lys Arg Val Pro Glu Glu Val Phe Arg Tyr Arg Arg Glu
305                 310                 315                 320

Ala Leu Ala Leu Phe Leu Gly Arg Leu Phe Ser Thr Asp Gly Ser Val
            325                 330                 335

Glu Lys Lys Arg Ile Ser Tyr Ser Ser Ala Ser Leu Gly Leu Ala Gln
            340                 345                 350

Asp Val Ala His Leu Leu Leu Arg Leu Gly Ile Thr Ser Gln Leu Arg
        355                 360                 365

Ser Arg Gly Pro Arg Ala His Glu Val Leu Ile Ser Gly Arg Glu Asp
    370                 375                 380

Ile Leu Arg Phe Ala Glu Leu Ile Gly Pro Tyr Leu Leu Gly Ala Lys
385                 390                 395                 400

Arg Glu Arg Leu Ala Ala Leu Glu Ala Glu Ala Arg Arg Arg Leu Pro
            405                 410                 415

Gly Gln Gly Trp His Leu Arg Leu Val Leu Pro Ala Val Ala Tyr Arg
            420                 425                 430

Val Ser Glu Ala Lys Arg Arg Ser Gly Phe Ser Trp Ser Glu Ala Gly
        435                 440                 445

Arg Arg Val Ala Val Ala Gly Ser Cys Leu Ser Ser Gly Leu Asn Leu
    450                 455                 460

Lys Leu Pro Arg Arg Tyr Leu Ser Arg His Arg Leu Ser Leu Leu Gly
465                 470                 475                 480

Glu Ala Phe Ala Asp Pro Gly Leu Glu Ala Leu Ala Glu Gly Gln Val
            485                 490                 495

Leu Trp Asp Pro Ile Val Ala Val Glu Pro Ala Gly Lys Ala Arg Thr
            500                 505                 510

Phe Asp Leu Arg Val Pro Pro Phe Ala Asn Phe Val Ser Glu Asp Leu
        515                 520                 525
```

```
Val Val His Asn Thr Val Pro Leu Gly Gln Val Thr Ile Asp Gly Gly
    530                 535                 540

Thr Tyr Asp Ile Tyr Arg Thr Thr Arg Val Asn Gln Pro Ser Ile Val
545                 550                 555                 560

Gly Thr Ala Thr Phe Asp Gln Tyr Trp Ser Val Arg Thr Ser Lys Arg
                565                 570                 575

Thr Ser Gly Thr Val Thr Val Thr Asp His Phe Arg Ala Trp Ala Asn
            580                 585                 590

Arg Gly Leu Asn Leu Gly Thr Ile Asp Gln Ile Thr Leu Cys Val Glu
        595                 600                 605

Gly Tyr Gln Ser Ser Gly Ser Ala Asn Ile Thr Gln Asn Thr Phe Ser
    610                 615                 620

Gln Gly Ser Ser Ser Gly Ser Ser Gly Gly Ser Ser Gly Ser Thr Thr
625                 630                 635                 640

Thr Thr Arg Ile Glu Cys Glu Asn Met Ser Leu Ser Gly Pro Tyr Val
                645                 650                 655

Ser Arg Ile Thr Asn Pro Phe Asn Gly Ile Ala Leu Tyr Ala Asn Gly
            660                 665                 670

Asp Thr Ala Arg Ala Thr Val Asn Phe Pro Ala Ser Arg Asn Tyr Asn
        675                 680                 685

Phe Arg Leu Arg Gly Cys Gly Asn Asn Asn Asn Leu Ala Arg Val Asp
    690                 695                 700

Leu Arg Ile Asp Gly Arg Thr Val Gly Thr Phe Tyr Tyr Gln Gly Thr
705                 710                 715                 720

Tyr Pro Trp Glu Ala Pro Ile Asp Asn Val Tyr Val Ser Ala Gly Ser
                725                 730                 735

His Thr Val Glu Ile Thr Val Thr Ala Asp Asn Gly Thr Trp Asp Val
            740                 745                 750

Tyr Ala Asp Tyr Leu Val Ile Gln
        755                 760


<210> SEQ ID NO 15
<211> LENGTH: 2280
<212> TYPE: DNA
<213> ORGANISM: Artificial Sequence
<220> FEATURE:
<223> OTHER INFORMATION: Synthetic construct, S158-30-m79-110 DNA
      sequence

<400> SEQUENCE: 15

caaacaagca ttactctgac atccaacgca tccggtacgt ttgacggtta caattacgaa      60

ctctggaagg atactggcaa tacaacaatg acggtctaca ctcaaggtcg cttttcctgc     120

cagtggtcga acatcaataa cgcgttgttt aggaccggga agaaatacaa ccagaattgg     180

cagtctcttg gcacaatccg gatcacgtac tctgcgactt acaacccaaa cgggaactcc     240

tacttgtgta tctatggctg gtctaccaac ccattggtcg agttctacat cgttgagtcc     300

tgggggaact ggagaccgcc tggtgccacg tccctgggcc aagtgacaat cgatggcggg     360

acctacgaca tctataggac gacacgcgtc aaccagcctt gcctggccga gggctcgctc     420

gtcttggacg cggctaccgg gcagagggtc cctatcgaaa aggtgcgtcc ggggatggaa     480

gttttctcct tgggacctga ttacagactg tatcaggtgc ccgttttgga ggtccttgag     540

agcggggttg gggaagttgt gcgcctcaga actcggtcag ggagaacgct ggtgttgaca     600

ccagatcacc cgcttttgac ccccgaaggt tggaaacctc tttgtgacct cccgcttgga     660
```

```
actccaattg cagtccccgc agaactgcct gtggcgggcc acttggcccc acctgaagaa    720

cgtgttacgc ccctggctct tctgttgggg gatgggaaca caaagctgtc gggtcggaga    780

ggtacacgtc ctaatgcctt cttctactgc aaagaccccg aattgctcgc ggcttatcgc    840

cggtgtgcag aagccttggg tgcaaaggtg aaagcatacg tccacccgac tacgggggtg    900

gttacactcg caaccctcgc tccacgtcct ggagctcaag atcctgtcaa acgcctcgtt    960

gtcgaggcgg gaatggttgc taaagccgaa gagaagaggg tcccggagga ggtgttccgt   1020

taccggcgtg aggcgttggc ccttttcttg ggccgtttgt tctcgacaga cggctctgtt   1080

gaaaagaaga ggatctctta ttcaagtgcc agtttgggac tggcccagga tgtcgcacat   1140

ctcttgctgc gccttggaat tacatctcaa ctccgttcga gagggccacg ggctcacgag   1200

gttcttatat cgggccgcga ggatattttg cggtttgctg aacttatcgg accctacctc   1260

ttgggggcca agagggagag acttgcagcg ctggaagctg aggcccgcag gcgtttgcct   1320

ggacagggat ggcacttgcg gcttgttctt cctgccgtgg cgtacagagt gagcgaggct   1380

aaaaggcgct cgggattttc gtggagtgaa gccggtcggc gcgtcgcagt tgcgggatcg   1440

tgtttgtcat ctggactcaa cctcaaattg cccagacgct acctttctcg gcaccggttg   1500

tcgatgctcg gtgaggcttt tgccgaccct gggctggaag cgctcgcgga aggccaagtg   1560

ctctgggacc ctattgttgc tgtcgaaccg gccggtaagg cgagaacatt cgacttgcgc   1620

gttccaccct ttgcaaactt cgcgagcgag gacctggtgg tgcataactc cattgtgggg   1680

acagccacgt tcgatcagta ctggagcgtg cgcacctcta agcggacttc aggaacagtg   1740

accgtgaccg atcacttccg cgcctgggcg aaccggggcc tgaacctcgg cacaatagac   1800

caaattacat tgtgcgtgga gggttaccaa agctctggat cagccaacat cacccagaac   1860

accttctctc agggctcttc ttccggcagt tcgggtggct catccggctc cacaacgact   1920

actcgcatcg agtgtgagaa catgtccttg tccggaccct acgttagcag gatcaccaat   1980

ccctttaatg gtattgcgct gtacgccaac ggagacacag cccgcgctac cgttaacttc   2040

cccgcaagtc gcaactacaa tttccgcctg cggggttgcg gcaacaacaa taatcttgcc   2100

cgtgtggacc tgaggatcga cggacggacc gtcgggacct tttattacca gggcacatac   2160

ccctgggagg ccccaattga caatgtttat gtcagtgcgg ggagtcatac agtcgaaatc   2220

actgttactg cggataacgg cacatgggac gtgtatgccg actacctggt gatacagtga   2280
```

<210> SEQ ID NO 16
<211> LENGTH: 759
<212> TYPE: PRT
<213> ORGANISM: Artificial Sequence
<220> FEATURE:
<223> OTHER INFORMATION: Synthetic construct, S158-30-m79-110 protein

<400> SEQUENCE: 16

```
Gln Thr Ser Ile Thr Leu Thr Ser Asn Ala Ser Gly Thr Phe Asp Gly
1               5                   10                  15

Tyr Asn Tyr Glu Leu Trp Lys Asp Thr Gly Asn Thr Thr Met Thr Val
            20                  25                  30

Tyr Thr Gln Gly Arg Phe Ser Cys Gln Trp Ser Asn Ile Asn Asn Ala
        35                  40                  45

Leu Phe Arg Thr Gly Lys Lys Tyr Asn Gln Asn Trp Gln Ser Leu Gly
    50                  55                  60

Thr Ile Arg Ile Thr Tyr Ser Ala Thr Tyr Asn Pro Asn Gly Asn Ser
65                  70                  75                  80
```

-continued

```
Tyr Leu Cys Ile Tyr Gly Trp Ser Thr Asn Pro Leu Val Glu Phe Tyr
                85                  90                  95

Ile Val Glu Ser Trp Gly Asn Trp Arg Pro Pro Gly Ala Thr Ser Leu
            100                 105                 110

Gly Gln Val Thr Ile Asp Gly Gly Thr Tyr Asp Ile Tyr Arg Thr Thr
        115                 120                 125

Arg Val Asn Gln Pro Cys Leu Ala Glu Gly Ser Leu Val Leu Asp Ala
    130                 135                 140

Ala Thr Gly Gln Arg Val Pro Ile Glu Lys Val Arg Pro Gly Met Glu
145                 150                 155                 160

Val Phe Ser Leu Gly Pro Asp Tyr Arg Leu Tyr Gln Val Pro Val Leu
                165                 170                 175

Glu Val Leu Glu Ser Gly Val Gly Glu Val Val Arg Leu Arg Thr Arg
            180                 185                 190

Ser Gly Arg Thr Leu Val Leu Thr Pro Asp His Pro Leu Leu Thr Pro
        195                 200                 205

Glu Gly Trp Lys Pro Leu Cys Asp Leu Pro Leu Gly Thr Pro Ile Ala
    210                 215                 220

Val Pro Ala Glu Leu Pro Val Ala Gly His Leu Ala Pro Pro Glu Glu
225                 230                 235                 240

Arg Val Thr Pro Leu Ala Leu Leu Leu Gly Asp Gly Asn Thr Lys Leu
                245                 250                 255

Ser Gly Arg Arg Gly Thr Arg Pro Asn Ala Phe Phe Tyr Cys Lys Asp
            260                 265                 270

Pro Glu Leu Leu Ala Ala Tyr Arg Arg Cys Ala Glu Ala Leu Gly Ala
        275                 280                 285

Lys Val Lys Ala Tyr Val His Pro Thr Thr Gly Val Val Thr Leu Ala
    290                 295                 300

Thr Leu Ala Pro Arg Pro Gly Ala Gln Asp Pro Val Lys Arg Leu Val
305                 310                 315                 320

Val Glu Ala Gly Met Val Ala Lys Ala Glu Glu Lys Arg Val Pro Glu
                325                 330                 335

Glu Val Phe Arg Tyr Arg Arg Glu Ala Leu Ala Leu Phe Leu Gly Arg
            340                 345                 350

Leu Phe Ser Thr Asp Gly Ser Val Glu Lys Lys Arg Ile Ser Tyr Ser
        355                 360                 365

Ser Ala Ser Leu Gly Leu Ala Gln Asp Val Ala His Leu Leu Leu Arg
    370                 375                 380

Leu Gly Ile Thr Ser Gln Leu Arg Ser Arg Gly Pro Arg Ala His Glu
385                 390                 395                 400

Val Leu Ile Ser Gly Arg Glu Asp Ile Leu Arg Phe Ala Glu Leu Ile
                405                 410                 415

Gly Pro Tyr Leu Leu Gly Ala Lys Arg Glu Arg Leu Ala Ala Leu Glu
            420                 425                 430

Ala Glu Ala Arg Arg Arg Leu Pro Gly Gln Gly Trp His Leu Arg Leu
        435                 440                 445

Val Leu Pro Ala Val Ala Tyr Arg Val Ser Glu Ala Lys Arg Arg Ser
    450                 455                 460

Gly Phe Ser Trp Ser Glu Ala Gly Arg Arg Val Ala Val Ala Gly Ser
465                 470                 475                 480

Cys Leu Ser Ser Gly Leu Asn Leu Lys Leu Pro Arg Arg Tyr Leu Ser
                485                 490                 495

Arg His Arg Leu Ser Met Leu Gly Glu Ala Phe Ala Asp Pro Gly Leu
```

```
            500                 505                 510

Glu Ala Leu Ala Glu Gly Gln Val Leu Trp Asp Pro Ile Val Ala Val
        515                 520                 525

Glu Pro Ala Gly Lys Ala Arg Thr Phe Asp Leu Arg Val Pro Pro Phe
    530                 535                 540

Ala Asn Phe Ala Ser Glu Asp Leu Val Val His Asn Ser Ile Val Gly
545                 550                 555                 560

Thr Ala Thr Phe Asp Gln Tyr Trp Ser Val Arg Thr Ser Lys Arg Thr
                565                 570                 575

Ser Gly Thr Val Thr Val Thr Asp His Phe Arg Ala Trp Ala Asn Arg
            580                 585                 590

Gly Leu Asn Leu Gly Thr Ile Asp Gln Ile Thr Leu Cys Val Glu Gly
        595                 600                 605

Tyr Gln Ser Ser Gly Ser Ala Asn Ile Thr Gln Asn Thr Phe Ser Gln
    610                 615                 620

Gly Ser Ser Ser Gly Ser Ser Gly Gly Ser Ser Gly Ser Thr Thr Thr
625                 630                 635                 640

Thr Arg Ile Glu Cys Glu Asn Met Ser Leu Ser Gly Pro Tyr Val Ser
                645                 650                 655

Arg Ile Thr Asn Pro Phe Asn Gly Ile Ala Leu Tyr Ala Asn Gly Asp
            660                 665                 670

Thr Ala Arg Ala Thr Val Asn Phe Pro Ala Ser Arg Asn Tyr Asn Phe
        675                 680                 685

Arg Leu Arg Gly Cys Gly Asn Asn Asn Asn Leu Ala Arg Val Asp Leu
    690                 695                 700

Arg Ile Asp Gly Arg Thr Val Gly Thr Phe Tyr Tyr Gln Gly Thr Tyr
705                 710                 715                 720

Pro Trp Glu Ala Pro Ile Asp Asn Val Tyr Val Ser Ala Gly Ser His
                725                 730                 735

Thr Val Glu Ile Thr Val Thr Ala Asp Asn Gly Thr Trp Asp Val Tyr
            740                 745                 750

Ala Asp Tyr Leu Val Ile Gln
        755


<210> SEQ ID NO 17
<211> LENGTH: 759
<212> TYPE: PRT
<213> ORGANISM: Artificial Sequence
<220> FEATURE:
<223> OTHER INFORMATION: Synthetic construct, Modified Protein

<400> SEQUENCE: 17

Gln Thr Ser Ile Thr Leu Thr Ser Asn Ala Ser Gly Thr Phe Asp Gly
1               5                   10                  15

Tyr Asn Tyr Glu Leu Trp Lys Asp Thr Gly Asn Thr Thr Met Thr Val
            20                  25                  30

Tyr Thr Gln Gly Arg Phe Ser Cys Gln Trp Ser Asn Ile Asn Asn Ala
        35                  40                  45

Leu Phe Arg Thr Gly Lys Lys Tyr Asn Gln Asn Trp Gln Ser Leu Gly
    50                  55                  60

Thr Ile Arg Ile Thr Tyr Ser Ala Thr Tyr Asn Pro Asn Gly Asn Ser
65                  70                  75                  80

Tyr Leu Cys Ile Tyr Gly Trp Ser Thr Asn Pro Leu Val Glu Phe Tyr
                85                  90                  95

Ile Val Glu Ser Trp Gly Asn Trp Arg Pro Pro Gly Ala Thr Ser Leu
```

-continued

```
            100                 105                 110

Gly Gln Val Thr Ile Asp Gly Gly Thr Tyr Asp Ile Tyr Arg Thr Thr
        115                 120                 125

Arg Val Asn Gln Pro Cys Leu Ala Glu Gly Ser Leu Val Leu Asp Ala
    130                 135                 140

Ala Thr Gly Gln Arg Val Pro Ile Glu Lys Val Arg Pro Gly Met Glu
145                 150                 155                 160

Val Phe Ser Leu Gly Pro Asp Tyr Arg Leu Tyr Gln Val Pro Val Leu
                165                 170                 175

Glu Val Leu Glu Ser Gly Val Gly Glu Val Val Arg Leu Arg Thr Arg
            180                 185                 190

Ser Gly Arg Thr Leu Val Leu Thr Pro Asp His Pro Leu Leu Thr Pro
        195                 200                 205

Glu Gly Trp Lys Pro Leu Cys Asp Leu Pro Leu Gly Thr Pro Ile Ala
    210                 215                 220

Val Pro Ala Glu Leu Pro Val Ala Gly His Leu Ala Pro Pro Glu Glu
225                 230                 235                 240

Arg Val Thr Pro Leu Ala Leu Leu Leu Gly Asp Gly Asn Thr Lys Leu
                245                 250                 255

Ser Gly Arg Arg Gly Thr Arg Pro Asn Ala Phe Phe Tyr Cys Lys Asp
            260                 265                 270

Pro Glu Leu Leu Ala Ala Tyr Arg Arg Cys Ala Glu Ala Leu Gly Ala
        275                 280                 285

Lys Val Lys Ala Tyr Val His Pro Thr Thr Gly Val Val Thr Leu Ala
    290                 295                 300

Thr Leu Ala Pro Arg Pro Gly Ala Gln Asp Pro Val Lys Arg Leu Val
305                 310                 315                 320

Val Glu Ala Gly Met Val Ala Lys Ala Glu Glu Lys Arg Val Pro Glu
                325                 330                 335

Glu Val Phe Arg Tyr Arg Arg Glu Ala Leu Ala Leu Phe Leu Gly Arg
            340                 345                 350

Leu Phe Ser Thr Asp Gly Ser Val Glu Lys Lys Arg Ile Ser Tyr Ser
        355                 360                 365

Ser Ala Ser Leu Gly Leu Ala Gln Asp Val Ala His Leu Leu Leu Arg
    370                 375                 380

Leu Gly Ile Thr Ser Gln Leu Arg Ser Arg Gly Pro Arg Ala His Glu
385                 390                 395                 400

Val Leu Ile Ser Gly Arg Glu Asp Ile Leu Arg Phe Ala Glu Leu Ile
                405                 410                 415

Gly Pro Tyr Leu Leu Gly Ala Lys Arg Glu Arg Leu Ala Ala Leu Glu
            420                 425                 430

Ala Glu Ala Arg Arg Arg Leu Pro Gly Gln Gly Trp His Leu Arg Leu
        435                 440                 445

Val Leu Pro Ala Val Ala Tyr Arg Val Ser Glu Ala Lys Arg Arg Ser
    450                 455                 460

Gly Phe Ser Trp Ser Glu Ala Gly Arg Arg Val Ala Val Ala Gly Ser
465                 470                 475                 480

Cys Leu Ser Ser Gly Leu Asn Leu Lys Leu Pro Arg Arg Tyr Leu Ser
                485                 490                 495

Arg His Arg Leu Ser Met Leu Gly Glu Ala Phe Ala Asp Pro Gly Leu
            500                 505                 510

Glu Ala Leu Ala Glu Gly Gln Val Leu Trp Asp Pro Ile Val Ala Val
        515                 520                 525
```

```
Glu Pro Ala Gly Lys Ala Arg Thr Phe Asp Leu Arg Val Pro Pro Phe
    530                 535                 540

Ala Asn Phe Ala Ser Glu Asp Leu Val Val His Asn Ser Ile Val Gly
545                 550                 555                 560

Thr Ala Thr Phe Asp Gln Tyr Trp Ser Val Arg Thr Ser Lys Arg Thr
                565                 570                 575

Ser Gly Thr Val Thr Val Thr Asp His Phe Arg Ala Trp Ala Asn Arg
            580                 585                 590

Gly Leu Asn Leu Gly Thr Ile Asp Gln Ile Thr Leu Cys Val Glu Gly
        595                 600                 605

Tyr Gln Ser Ser Gly Ser Ala Asn Ile Thr Gln Asn Thr Phe Ser Gln
    610                 615                 620

Gly Ser Ser Ser Gly Ser Ser Gly Gly Ser Ser Gly Ser Thr Thr Thr
625                 630                 635                 640

Thr Arg Ile Glu Cys Glu Asn Met Ser Leu Ser Gly Pro Tyr Val Ser
                645                 650                 655

Arg Ile Thr Asn Pro Phe Asn Gly Ile Ala Leu Tyr Ala Asn Gly Asp
            660                 665                 670

Thr Ala Arg Ala Thr Val Asn Phe Pro Ala Ser Arg Asn Tyr Asn Phe
        675                 680                 685

Arg Leu Arg Gly Cys Gly Asn Asn Asn Asn Leu Ala Arg Val Asp Leu
    690                 695                 700

Arg Ile Asp Gly Arg Thr Val Gly Thr Phe Tyr Tyr Gln Gly Thr Tyr
705                 710                 715                 720

Pro Trp Glu Ala Pro Ile Asp Asn Val Tyr Val Ser Ala Gly Ser His
                725                 730                 735

Thr Val Glu Ile Thr Val Thr Ala Asp Asn Gly Thr Trp Asp Val Tyr
            740                 745                 750

Ala Asp Tyr Leu Val Ile Gln
        755
```

<210> SEQ ID NO 18
<211> LENGTH: 2280
<212> TYPE: DNA
<213> ORGANISM: Artificial Sequence
<220> FEATURE:
<223> OTHER INFORMATION: Synthetic construct, Modifed Protein Coding Seq.

<400> SEQUENCE: 18

```
caaacaagca ttactctgac atccaacgca tccggtacgt ttgacggtta caattacgaa     60

ctctggaagg atactggcaa tacaacaatg acggtctaca ctcaaggtcg cttttcctgc    120

cagtggtcga acatcaataa cgcgttgttt aggaccggga agaaatacaa ccagaattgg    180

cagtctcttg gcacaatccg gatcacgtac tctgcgactt acaacccaaa cgggaactcc    240

tacttgtgta tctatggctg gtctaccaac ccattggtcg agttctacat cgttgagtcc    300

tgggggaact ggagaccgcc tggtgccacg tccctgggcc aagtgacaat cgatggcggg    360

acctacgaca tctataggac gacacgcgtc aaccagcctt gcctggccga gggctcgctc    420

gtcttggacg cggctaccgg gcagagggtc cctatcgaaa aggtgcgtcc ggggatggaa    480

gttttctcct tgggacctga ttacagactg tatcaggtgc ccgttttgga ggtccttgag    540

agcggggttg gggaagttgt gcgcctcaga actcggtcag ggagaacgct ggtgttgaca    600

ccagatcacc cgcttttgac cccgaaggt tggaaacctc tttgtgacct cccgcttgga    660
```

actccaattg cagtccccgc agaactgcct gtggcgggcc acttggcccc acctgaagaa 720
cgtgttacgc ccctggctct tctgttgggg gatgggaaca caaagctgtc gggtcggaga 780
ggtacacgtc ctaatgcctt cttctactgc aaagaccccg aattgctcgc ggcttatcgc 840
cggtgtgcag aagccttggg tgcaaaggtg aaagcatacg tccacccgac tacgggggtg 900
gttacactcg caaccctcgc tccacgtcct ggagctcaag atcctgtcaa acgcctcgtt 960
gtcgaggcgg gaatggttgc taaagccgaa gagaagaggg tcccggagga ggtgttccgt 1020
taccggcgtg aggcgttggc ccttttcttg ggccgtttgt tctcgacaga cggctctgtt 1080
gaaaagaaga ggatctctta ttcaagtgcc agtttgggac tggcccagga tgtcgcacat 1140
ctcttgctgc gccttggaat tacatctcaa ctccgttcga gagggccacg ggctcacgag 1200
gttcttatat cgggccgcga ggatattttg cggtttgctg aacttatcgg accctacctc 1260
ttgggggcca agagggagag acttgcagcg ctggaagctg aggcccgcag gcgtttgcct 1320
ggacagggat ggcacttgcg gcttgttctt cctgccgtgg cgtacagagt gagcgaggct 1380
aaaaggcgct cgggattttc gtggagtgaa gccggtcggc gcgtcgcagt tgcgggatcg 1440
tgtttgtcat ctggactcaa cctcaaattg cccagacgct acctttctcg gcaccggttg 1500
tcgatgctcg gtgaggcttt tgccgaccct gggctggaag cgctcgcgga aggccaagtg 1560
ctctgggacc ctattgttgc tgtcgaaccg gccggtaagg cgagaacatt cgacttgcgc 1620
gttccaccct ttgcaaactt cgcgagcgag gacctggtgg tgcataactc cattgtgggg 1680
acagccacgt tcgatcagta ctggagcgtg cgcacctcta agcggacttc aggaacagtg 1740
accgtgaccg atcacttccg cgcctgggcg aaccggggcc tgaacctcgg cacaatagac 1800
caaattacat tgtgcgtgga gggttaccaa agctctggat cagccaacat cacccagaac 1860
accttctctc agggctcttc ttccggcagt tcgggtggct catccggctc cacaacgact 1920
actcgcatcg agtgtgagaa catgtccttg tccggaccct acgttagcag gatcaccaat 1980
ccctttaatg gtattgcgct gtacgccaac ggagacacag cccgcgctac cgttaacttc 2040
cccgcaagtc gcaactacaa tttccgcctg cggggttgcg gcaacaacaa taatcttgcc 2100
cgtgtggacc tgaggatcga cggacggacc gtcgggacct tttattacca gggcacatac 2160
ccctgggagg ccccaattga caatgtttat gtcagtgcgg ggagtcatac agtcgaaatc 2220
actgttactg cggataacgg cacatgggac gtgtatgccg actacctggt gatacagtga 2280

<210> SEQ ID NO 19
<211> LENGTH: 325
<212> TYPE: PRT
<213> ORGANISM: Dictyoglomus thermophilum

<400> SEQUENCE: 19

Gln Thr Ser Ile Thr Leu Thr Ser Asn Ala Ser Gly Thr Phe Asp Gly
1               5                   10                  15

Tyr Tyr Tyr Glu Leu Trp Lys Asp Thr Gly Asn Thr Thr Met Thr Val
            20                  25                  30

Tyr Thr Gln Gly Arg Phe Ser Cys Gln Trp Ser Asn Ile Asn Asn Ala
        35                  40                  45

Leu Phe Arg Thr Gly Lys Lys Tyr Asn Gln Asn Trp Gln Ser Leu Gly
    50                  55                  60

Thr Ile Arg Ile Thr Tyr Ser Ala Thr Tyr Asn Pro Asn Gly Asn Ser
65                  70                  75                  80

Tyr Leu Cys Ile Tyr Gly Trp Ser Thr Asn Pro Leu Val Glu Phe Tyr
                85                  90                  95

```
Ile Val Glu Ser Trp Gly Asn Trp Arg Pro Pro Gly Ala Thr Ser Leu
            100                 105                 110

Gly Gln Val Thr Ile Asp Gly Gly Thr Tyr Ser Ile Val Gly Thr Ala
        115                 120                 125

Thr Phe Asp Gln Tyr Trp Ser Val Arg Thr Ser Lys Arg Thr Ser Gly
    130                 135                 140

Thr Val Thr Val Thr Asp His Phe Arg Ala Trp Ala Asn Arg Gly Leu
145                 150                 155                 160

Asn Leu Gly Thr Ile Asp Gln Ile Thr Leu Cys Val Glu Gly Tyr Gln
                165                 170                 175

Ser Ser Gly Ser Ala Asn Ile Thr Gln Asn Thr Phe Ser Gln Gly Ser
            180                 185                 190

Ser Ser Gly Ser Ser Gly Gly Ser Ser Gly Ser Thr Thr Thr Thr Arg
        195                 200                 205

Ile Glu Cys Glu Asn Met Ser Leu Ser Gly Pro Tyr Val Ser Arg Ile
    210                 215                 220

Thr Asn Pro Phe Asn Gly Ile Ala Leu Tyr Ala Asn Gly Asp Thr Ala
225                 230                 235                 240

Arg Ala Thr Val Asn Phe Pro Ala Ser Arg Asn Tyr Asn Phe Arg Leu
                245                 250                 255

Arg Gly Cys Gly Asn Asn Asn Asn Leu Ala Arg Val Asp Leu Arg Ile
            260                 265                 270

Asp Gly Arg Thr Val Gly Thr Phe Tyr Tyr Gln Gly Thr Tyr Pro Trp
        275                 280                 285

Glu Ala Pro Ile Asp Asn Val Tyr Val Ser Ala Gly Ser His Thr Val
    290                 295                 300

Glu Ile Thr Val Thr Ala Asp Asn Gly Thr Trp Asp Val Tyr Ala Asp
305                 310                 315                 320

Tyr Leu Val Ile Gln
                325


<210> SEQ ID NO 20
<211> LENGTH: 1014
<212> TYPE: DNA
<213> ORGANISM: Artificial Sequence
<220> FEATURE:
<223> OTHER INFORMATION: Synthetic construct, XynB, P77853 DNA sequence

<400> SEQUENCE: 20

atgcaaacaa gcattactct gacatccaac gcatccggta cgtttgacgg ttactattac      60

gaactctgga aggatactgg caatacaaca atgacggtct acactcaagg tcgcttttcc     120

tgccagtggt cgaacatcaa taacgcgttg tttaggaccg ggaagaaata caaccagaat     180

tggcagtctc ttggcacaat ccggatcacg tactctgcga cttacaaccc aaacgggaac     240

tcctacttgt gtatctatgg ctggtctacc aacccattgg tcgagttcta catcgttgag     300

tcctggggga actggagacc gcctggtgcc acgtccctgg gccaagtgac aatcgatggc     360

gggacctacg acatctatag gacgacacgc gtcaaccagc cttccattgt ggggacagcc     420

acgttcgatc agtactggag cgtgcgcacc tctaagcgga cttcaggaac agtgaccgtg     480

accgatcact tccgcgcctg ggcgaaccgg ggcctgaacc tcggcacaat agaccaaatt     540

acattgtgcg tggagggtta ccaaagctct ggatcagcca acatcaccca gaacaccttc     600

tctcagggct cttcttccgg cagttcgggt ggctcatccg gctccacaac gactactcgc     660

atcgagtgtg agaacatgtc cttgtccgga ccctacgtta gcaggatcac caatcccttt     720
```

```
aatggtattg cgctgtacgc caacggagac acagcccgcg ctaccgttaa cttccccgca    780

agtcgcaact acaatttccg cctgcggggt tgcggcaaca acaataatct tgcccgtgtg    840

gacctgagga tcgacggacg gaccgtcggg accttttatt accagggcac atacccctgg    900

gaggccccaa ttgacaatgt ttatgtcagt gcggggagtc atacagtcga aatcactgtt    960

actgcggata acggcacatg ggacgtgtat gccgactacc tggtgataca gtga         1014
```

<210> SEQ ID NO 21
<211> LENGTH: 759
<212> TYPE: PRT
<213> ORGANISM: Artificial Sequence
<220> FEATURE:
<223> OTHER INFORMATION: Synthetic construct, T134-195 protein

<400> SEQUENCE: 21

```
Gln Thr Ser Ile Thr Leu Thr Ser Asn Ala Ser Gly Thr Phe Asp Gly
1               5                   10                  15

Tyr Tyr Tyr Glu Leu Trp Lys Asp Thr Gly Asn Thr Thr Met Thr Val
            20                  25                  30

Tyr Thr Gln Gly Arg Phe Ser Cys Gln Trp Ser Asn Ile Asn Asn Ala
        35                  40                  45

Leu Phe Arg Thr Gly Lys Lys Tyr Asn Gln Asn Trp Gln Ser Leu Gly
    50                  55                  60

Thr Ile Arg Ile Thr Tyr Ser Ala Thr Tyr Asn Pro Asn Gly Asn Ser
65                  70                  75                  80

Tyr Leu Cys Ile Tyr Gly Trp Ser Thr Asn Pro Leu Val Glu Phe Tyr
                85                  90                  95

Ile Val Glu Ser Trp Gly Asn Trp Arg Pro Pro Gly Ala Cys Leu Ala
            100                 105                 110

Glu Gly Ser Leu Val Leu Asp Ala Ala Thr Gly Gln Arg Val Pro Ile
        115                 120                 125

Glu Lys Val Arg Pro Gly Met Glu Val Phe Ser Leu Gly Pro Asp Tyr
    130                 135                 140

Arg Leu Tyr Arg Val Pro Val Leu Glu Val Leu Glu Ser Gly Val Arg
145                 150                 155                 160

Glu Val Val Arg Leu Arg Thr Arg Ser Gly Arg Thr Leu Val Leu Thr
                165                 170                 175

Pro Asp His Pro Leu Leu Thr Pro Glu Gly Trp Lys Pro Leu Cys Asp
            180                 185                 190

Leu Pro Leu Gly Thr Pro Ile Ala Val Pro Ala Glu Leu Pro Val Ala
        195                 200                 205

Gly His Leu Ala Pro Pro Glu Glu Arg Val Thr Leu Leu Ala Leu Leu
    210                 215                 220

Leu Gly Asp Gly Asn Thr Lys Leu Ser Gly Arg Arg Gly Thr Arg Pro
225                 230                 235                 240

Asn Ala Ser Phe Tyr Ser Lys Asp Pro Glu Leu Leu Ala Ala Tyr Arg
                245                 250                 255

Arg Cys Ala Glu Ala Leu Gly Ala Lys Val Lys Ala Tyr Val His Pro
            260                 265                 270

Thr Thr Gly Val Val Thr Leu Ala Thr Leu Ala Pro Arg Pro Gly Ala
        275                 280                 285

Gln Asp Pro Val Lys Arg Leu Val Val Glu Ala Gly Met Val Ala Lys
    290                 295                 300

Ala Glu Glu Lys Arg Val Pro Glu Glu Val Phe Arg Tyr Arg Arg Glu
```

305 310 315 320

Ala Leu Ala Leu Phe Leu Gly Arg Leu Phe Ser Thr Asp Gly Ser Val
325 330 335

Glu Lys Lys Arg Ile Ser Tyr Ser Ser Ala Ser Leu Gly Leu Ala Gln
340 345 350

Asp Val Ala His Leu Leu Leu Arg Leu Gly Ile Arg Ser Gln Leu Arg
355 360 365

Ser Arg Gly Pro Arg Ala His Glu Val Leu Ile Ser Gly Arg Glu Asp
370 375 380

Ile Leu Arg Phe Ala Glu Leu Ile Gly Pro Tyr Leu Leu Gly Ala Lys
385 390 395 400

Arg Glu Arg Leu Ala Ala Leu Glu Ala Glu Ala Arg Arg Arg Leu Pro
405 410 415

Gly Gln Gly Trp His Leu Arg Leu Val Leu Pro Ala Val Ala Tyr Arg
420 425 430

Val Ser Glu Ala Lys Arg Arg Ser Gly Phe Ser Trp Ser Glu Ala Gly
435 440 445

Arg Arg Val Ala Val Ala Gly Ser Cys Leu Ser Ser Gly Leu Asn Leu
450 455 460

Lys Leu Pro Arg Arg Tyr Leu Ser Arg His Arg Leu Ser Leu Leu Gly
465 470 475 480

Glu Ala Phe Ala Asp Pro Gly Leu Glu Ala Leu Ala Glu Gly Gln Val
485 490 495

Leu Trp Asp Pro Ile Val Ala Val Glu Pro Ala Gly Lys Ala Arg Thr
500 505 510

Phe Asp Leu Arg Val Pro Pro Phe Ala Asn Phe Val Ser Glu Asp Leu
515 520 525

Val Val His Asn Thr Ser Leu Gly Gln Val Thr Ile Asp Gly Gly Thr
530 535 540

Tyr Asp Ile Tyr Arg Thr Thr Arg Val Asn Gln Pro Ser Ile Val Gly
545 550 555 560

Thr Ala Thr Phe Asp Gln Tyr Trp Ser Val Arg Thr Ser Lys Arg Thr
565 570 575

Ser Gly Thr Val Thr Val Thr Asp His Phe Arg Ala Trp Ala Asn Arg
580 585 590

Gly Leu Asn Leu Gly Thr Ile Asp Gln Ile Thr Leu Cys Val Glu Gly
595 600 605

Tyr Gln Ser Ser Gly Ser Ala Asn Ile Thr Gln Asn Thr Phe Ser Gln
610 615 620

Gly Ser Ser Ser Gly Ser Ser Gly Gly Ser Ser Gly Ser Thr Thr Thr
625 630 635 640

Thr Arg Ile Glu Cys Glu Asn Met Ser Leu Ser Gly Pro Tyr Val Ser
645 650 655

Arg Ile Thr Asn Pro Phe Asn Gly Ile Ala Leu Tyr Ala Asn Gly Asp
660 665 670

Thr Ala Arg Ala Thr Val Asn Phe Pro Ala Ser Arg Asn Tyr Asn Phe
675 680 685

Arg Leu Arg Gly Cys Gly Asn Asn Asn Asn Leu Ala Arg Val Asp Leu
690 695 700

Arg Ile Asp Gly Arg Thr Val Gly Thr Phe Tyr Tyr Gln Gly Thr Tyr
705 710 715 720

Pro Trp Glu Ala Pro Ile Asp Asn Val Tyr Val Ser Ala Gly Ser His
725 730 735

```
Thr Val Glu Ile Thr Val Thr Ala Asp Asn Gly Thr Trp Asp Val Tyr
            740                 745                 750

Ala Asp Tyr Leu Val Ile Gln
        755
```

<210> SEQ ID NO 22
<211> LENGTH: 423
<212> TYPE: PRT
<213> ORGANISM: Artificial Sequence
<220> FEATURE:
<223> OTHER INFORMATION: Synthetic construct, Tth-S158-39 Intein Sequence

<400> SEQUENCE: 22

```
Cys Leu Ala Glu Gly Ser Leu Val Leu Asp Ala Ala Thr Gly Gln Arg
1               5                   10                  15

Val Pro Ile Glu Lys Val Arg Pro Gly Met Glu Val Phe Ser Leu Gly
            20                  25                  30

Pro Asp Tyr Arg Leu Tyr Arg Val Pro Val Leu Glu Val Leu Glu Ser
        35                  40                  45

Gly Val Gly Glu Val Val Arg Leu Arg Thr Arg Ser Gly Arg Thr Leu
    50                  55                  60

Val Leu Thr Pro Asp His Pro Leu Leu Thr Pro Glu Gly Trp Lys Pro
65                  70                  75                  80

Leu Cys Asp Leu Pro Leu Gly Thr Pro Ile Ala Val Pro Ala Glu Leu
                85                  90                  95

Pro Val Ala Gly His Leu Ala Pro Pro Glu Glu Arg Val Thr Leu Leu
            100                 105                 110

Ala Leu Leu Leu Gly Asp Gly Asn Thr Lys Leu Ser Gly Arg Arg Gly
        115                 120                 125

Thr Arg Pro Asn Ala Phe Phe Tyr Ser Lys Asp Pro Glu Leu Leu Ala
    130                 135                 140

Ala Tyr Arg Arg Cys Ala Glu Ala Leu Gly Ala Lys Val Lys Ala Tyr
145                 150                 155                 160

Val His Pro Thr Thr Gly Val Val Thr Leu Ala Thr Leu Ala Pro Arg
                165                 170                 175

Pro Gly Ala Gln Asp Pro Val Lys Arg Leu Val Val Glu Ala Gly Met
            180                 185                 190

Val Ala Lys Ala Glu Glu Lys Arg Val Pro Glu Glu Val Phe Arg Tyr
        195                 200                 205

Arg Arg Glu Ala Leu Ala Leu Phe Leu Gly Arg Leu Ser Ser Thr Asp
    210                 215                 220

Gly Ser Val Glu Arg Lys Arg Ile Ser Tyr Ser Ser Ala Ser Leu Gly
225                 230                 235                 240

Leu Ala Gln Asp Val Ala His Leu Leu Leu Arg Leu Gly Ile Thr Ser
                245                 250                 255

Gln Leu Arg Ser Arg Gly Pro Arg Ala His Glu Val Leu Ile Ser Gly
            260                 265                 270

Arg Glu Asp Ile Leu Arg Phe Ala Glu Leu Ile Gly Pro Tyr Leu Leu
        275                 280                 285

Gly Ala Lys Arg Glu Arg Leu Ala Ala Leu Glu Ala Glu Ala Arg Arg
    290                 295                 300

Arg Leu Pro Gly Gln Gly Trp His Leu Arg Leu Val Leu Pro Ala Val
305                 310                 315                 320

Ala Tyr Arg Val Ser Glu Ala Lys Arg Arg Ser Gly Phe Ser Trp Ser
```

```
                325                 330                 335

Glu Ala Gly Gln Arg Val Ala Val Ala Gly Ser Cys Leu Ser Ser Gly
            340                 345                 350

Leu Asn Leu Lys Leu Pro Arg Arg Tyr Leu Ser Arg His Arg Leu Ser
        355                 360                 365

Leu Leu Gly Glu Ala Phe Ala Asp Pro Gly Leu Glu Ala Leu Ala Glu
    370                 375                 380

Gly Gln Val Leu Trp Asp Pro Ile Val Ala Val Glu Pro Ala Gly Lys
385                 390                 395                 400

Ala Arg Thr Phe Asp Leu Arg Val Pro Pro Phe Ala Asn Phe Val Ser
                405                 410                 415

Glu Asp Leu Val Val His Asn
            420


<210> SEQ ID NO 23
<211> LENGTH: 423
<212> TYPE: PRT
<213> ORGANISM: Artificial Sequence
<220> FEATURE:
<223> OTHER INFORMATION: Synthetic construct, Tth-T134-195 Intein
      Sequence

<400> SEQUENCE: 23

Cys Leu Ala Glu Gly Ser Leu Val Leu Asp Ala Ala Thr Gly Gln Arg
1               5                   10                  15

Val Pro Ile Glu Lys Val Arg Pro Gly Met Glu Val Phe Ser Leu Gly
            20                  25                  30

Pro Asp Tyr Arg Leu Tyr Arg Val Pro Val Leu Glu Val Leu Glu Ser
        35                  40                  45

Gly Val Arg Glu Val Val Arg Leu Arg Thr Arg Ser Gly Arg Thr Leu
    50                  55                  60

Val Leu Thr Pro Asp His Pro Leu Leu Thr Pro Glu Gly Trp Lys Pro
65                  70                  75                  80

Leu Cys Asp Leu Pro Leu Gly Thr Pro Ile Ala Val Pro Ala Glu Leu
                85                  90                  95

Pro Val Ala Gly His Leu Ala Pro Pro Glu Glu Arg Val Thr Leu Leu
            100                 105                 110

Ala Leu Leu Leu Gly Asp Gly Asn Thr Lys Leu Ser Gly Arg Arg Gly
        115                 120                 125

Thr Arg Pro Asn Ala Ser Phe Tyr Ser Lys Asp Pro Glu Leu Leu Ala
    130                 135                 140

Ala Tyr Arg Arg Cys Ala Glu Ala Leu Gly Ala Lys Val Lys Ala Tyr
145                 150                 155                 160

Val His Pro Thr Thr Gly Val Val Thr Leu Ala Thr Leu Ala Pro Arg
                165                 170                 175

Pro Gly Ala Gln Asp Pro Val Lys Arg Leu Val Val Glu Ala Gly Met
            180                 185                 190

Val Ala Lys Ala Glu Glu Lys Arg Val Pro Glu Glu Val Phe Arg Tyr
        195                 200                 205

Arg Arg Glu Ala Leu Ala Leu Phe Leu Gly Arg Leu Phe Ser Thr Asp
    210                 215                 220

Gly Ser Val Glu Lys Lys Arg Ile Ser Tyr Ser Ser Ala Ser Leu Gly
225                 230                 235                 240

Leu Ala Gln Asp Val Ala His Leu Leu Leu Arg Leu Gly Ile Arg Ser
                245                 250                 255
```

Gln Leu Arg Ser Arg Gly Pro Arg Ala His Glu Val Leu Ile Ser Gly
260 265 270

Arg Glu Asp Ile Leu Arg Phe Ala Glu Leu Ile Gly Pro Tyr Leu Leu
275 280 285

Gly Ala Lys Arg Glu Arg Leu Ala Ala Leu Glu Ala Glu Ala Arg Arg
290 295 300

Arg Leu Pro Gly Gln Gly Trp His Leu Arg Leu Val Leu Pro Ala Val
305 310 315 320

Ala Tyr Arg Val Ser Glu Ala Lys Arg Arg Ser Gly Phe Ser Trp Ser
325 330 335

Glu Ala Gly Arg Arg Val Ala Val Ala Gly Ser Cys Leu Ser Ser Gly
340 345 350

Leu Asn Leu Lys Leu Pro Arg Arg Tyr Leu Ser Arg His Arg Leu Ser
355 360 365

Leu Leu Gly Glu Ala Phe Ala Asp Pro Gly Leu Glu Ala Leu Ala Glu
370 375 380

Gly Gln Val Leu Trp Asp Pro Ile Val Ala Val Glu Pro Ala Gly Lys
385 390 395 400

Ala Arg Thr Phe Asp Leu Arg Val Pro Pro Phe Ala Asn Phe Val Ser
405 410 415

Glu Asp Leu Val Val His Asn
420

<210> SEQ ID NO 24
<211> LENGTH: 423
<212> TYPE: PRT
<213> ORGANISM: Artificial Sequence
<220> FEATURE:
<223> OTHER INFORMATION: Synthetic construct, Tth-S158-21 Intein Sequence

<400> SEQUENCE: 24

Cys Leu Ala Glu Gly Ser Leu Val Leu Asp Ala Ala Thr Gly Gln Arg
1 5 10 15

Val Pro Ile Glu Lys Val Arg Pro Gly Met Glu Val Phe Ser Leu Gly
20 25 30

Pro Asp Tyr Arg Leu Tyr Arg Val Pro Val Leu Glu Val Leu Glu Ser
35 40 45

Gly Val Arg Glu Val Val Arg Leu Arg Thr Arg Ser Gly Arg Thr Leu
50 55 60

Val Leu Thr Pro Asp His Pro Leu Leu Thr Pro Glu Gly Trp Lys Pro
65 70 75 80

Leu Cys Asp Leu Pro Leu Gly Thr Pro Ile Ala Val Pro Ala Glu Leu
85 90 95

Pro Val Ala Gly His Leu Ala Pro Pro Glu Glu Arg Val Thr Leu Leu
100 105 110

Ala Leu Leu Leu Gly Asp Gly Asn Thr Lys Leu Ser Gly Arg Arg Gly
115 120 125

Thr Arg Pro Asn Ala Phe Phe Tyr Ser Lys Asp Pro Glu Leu Leu Ala
130 135 140

Ala Tyr Arg Arg Cys Gly Glu Ala Leu Gly Ala Lys Val Lys Ala Tyr
145 150 155 160

Val His Pro Thr Thr Gly Val Val Thr Leu Ala Thr Leu Ala Pro Arg
165 170 175

Pro Gly Ala Gln Asp Pro Val Lys Arg Leu Val Val Glu Ala Gly Met
180 185 190

Val Ala Lys Ala Glu Glu Lys Arg Val Pro Glu Glu Val Phe Arg Tyr
195 200 205

Arg Arg Glu Ala Leu Ala Leu Phe Leu Gly Arg Leu Phe Ser Thr Asp
210 215 220

Gly Ser Val Glu Lys Lys Arg Ile Ser Tyr Ser Ser Ala Ser Leu Gly
225 230 235 240

Leu Ala Gln Asp Val Ala His Leu Leu Leu Arg Leu Gly Ile Thr Ser
245 250 255

Gln Leu Arg Ser Arg Gly Pro Arg Ala His Glu Val Leu Ile Ser Gly
260 265 270

Arg Glu Asp Ile Leu Arg Phe Ala Glu Leu Ile Gly Pro Tyr Leu Leu
275 280 285

Gly Ala Lys Arg Glu Arg Leu Ala Ala Leu Glu Ala Glu Ala Arg Arg
290 295 300

Arg Leu Pro Gly Gln Gly Trp His Leu Arg Leu Val Leu Pro Ala Val
305 310 315 320

Ala Tyr Arg Val Ser Glu Ala Lys Arg Arg Ser Gly Phe Ser Trp Ser
325 330 335

Glu Ala Gly Arg Arg Val Ala Val Ala Gly Ser Cys Leu Ser Ser Gly
340 345 350

Leu Asn Leu Lys Leu Pro Arg Arg Tyr Leu Ser Gln His Arg Leu Ser
355 360 365

Leu Leu Gly Glu Ala Phe Ala Asp Pro Gly Leu Glu Ala Leu Ala Glu
370 375 380

Gly Gln Val Leu Trp Asp Pro Ile Val Ala Val Glu Pro Ala Gly Lys
385 390 395 400

Ala Arg Thr Phe Asp Leu Arg Val Pro Pro Phe Ala Asn Phe Val Ser
405 410 415

Glu Asp Leu Val Val His Asn
420

<210> SEQ ID NO 25
<211> LENGTH: 423
<212> TYPE: PRT
<213> ORGANISM: Artificial Sequence
<220> FEATURE:
<223> OTHER INFORMATION: Synthetic construct, Tth T134-180 Intein Sequence

<400> SEQUENCE: 25

Cys Leu Ala Glu Gly Ser Leu Val Leu Asp Ala Ala Thr Gly Gln Arg
1 5 10 15

Val Pro Ile Glu Lys Val Arg Pro Gly Met Glu Val Phe Ser Leu Gly
20 25 30

Pro Asp Tyr Arg Leu Tyr Arg Val Pro Val Leu Glu Val Leu Glu Ser
35 40 45

Gly Val Arg Glu Val Val Arg Leu Arg Thr Arg Ser Gly Arg Thr Leu
50 55 60

Val Leu Thr Pro Asp His Pro Leu Leu Thr Pro Glu Gly Trp Lys Pro
65 70 75 80

Leu Cys Asp Leu Pro Leu Gly Thr Pro Ile Ala Val Pro Ala Glu Leu
85 90 95

Pro Val Ala Gly His Leu Ala Pro Pro Glu Glu Arg Val Thr Leu Leu
100 105 110

Ala Leu Leu Leu Gly Asp Gly Asn Thr Lys Leu Ser Gly Arg Arg Gly

```
        115                 120                 125

Thr Arg Pro Asn Ala Phe Phe Tyr Ser Lys Asp Pro Glu Leu Leu Ala
    130                 135                 140

Ala Tyr Arg Arg Cys Ala Glu Ala Leu Gly Ala Lys Val Lys Ala Tyr
145                 150                 155                 160

Val His Pro Thr Thr Gly Val Val Thr Leu Ala Thr Leu Ala Pro Arg
                165                 170                 175

Pro Gly Ala Gln Asp Pro Val Lys Arg Leu Val Val Glu Ala Gly Met
            180                 185                 190

Val Ala Lys Ala Glu Glu Lys Arg Val Pro Glu Glu Val Phe Arg Tyr
        195                 200                 205

Arg Arg Glu Ala Leu Ala Leu Phe Leu Gly Arg Leu Phe Ser Thr Asp
    210                 215                 220

Gly Ser Val Glu Lys Lys Arg Ile Ser Tyr Ser Ser Ala Ser Leu Gly
225                 230                 235                 240

Leu Ala Gln Asp Val Ala His Leu Leu Leu Arg Leu Gly Ile Thr Ser
                245                 250                 255

Gln Leu Arg Ser Arg Gly Pro Arg Ala His Glu Val Leu Ile Ser Gly
            260                 265                 270

Arg Glu Asp Ile Leu Arg Phe Ala Glu Leu Ile Gly Pro Tyr Leu Leu
        275                 280                 285

Gly Ala Lys Arg Glu Arg Leu Ala Ala Leu Glu Ala Glu Ala Arg Arg
    290                 295                 300

Arg Leu Pro Gly Gln Gly Trp His Leu Arg Leu Val Leu Pro Ala Val
305                 310                 315                 320

Ala Tyr Arg Val Ser Glu Ala Lys Arg Arg Ser Gly Phe Ser Trp Ser
                325                 330                 335

Glu Ala Gly Arg Arg Val Ala Val Ala Gly Ser Cys Leu Ser Ser Gly
            340                 345                 350

Leu Asn Leu Lys Leu Pro Arg Arg Tyr Leu Ser Arg His Arg Leu Ser
        355                 360                 365

Leu Leu Gly Glu Ala Phe Ala Asp Pro Gly Leu Glu Ala Leu Ala Glu
    370                 375                 380

Gly Gln Val Leu Trp Asp Pro Ile Val Ala Val Glu Pro Ala Gly Lys
385                 390                 395                 400

Ala Arg Thr Phe Asp Leu Arg Val Pro Pro Phe Ala Asn Phe Val Ser
                405                 410                 415

Glu Asp Leu Val Val His Asn
            420


<210> SEQ ID NO 26
<211> LENGTH: 423
<212> TYPE: PRT
<213> ORGANISM: Artificial Sequence
<220> FEATURE:
<223> OTHER INFORMATION: Synthetic construct, Tth T134-100-65 protein

<400> SEQUENCE: 26

Cys Leu Ala Glu Gly Ser Leu Val Leu Asp Ala Ala Thr Gly Gln Arg
1               5                   10                  15

Val Pro Ile Glu Lys Val Arg Pro Gly Met Glu Val Phe Ser Leu Gly
            20                  25                  30

Pro Asp Tyr Arg Leu Tyr Arg Val Pro Val Leu Glu Val Leu Glu Ser
        35                  40                  45

Gly Val Arg Glu Val Val Arg Leu Arg Thr Arg Ser Gly Arg Thr Leu
```

```
    50                  55                  60

Val Leu Thr Pro Asp His Pro Leu Leu Thr Pro Glu Gly Trp Lys Pro
65                  70                  75                  80

Leu Cys Asp Leu Pro Leu Gly Thr Pro Ile Ala Val Pro Ala Glu Leu
                85                  90                  95

Pro Val Ala Gly His Leu Ala Pro Pro Glu Glu Arg Val Thr Leu Leu
            100                 105                 110

Ala Leu Leu Leu Gly Asp Gly Asn Thr Lys Leu Ser Gly Arg Arg Gly
        115                 120                 125

Thr Arg Pro Asn Ala Phe Phe Tyr Ser Lys Asn Pro Glu Leu Leu Ala
    130                 135                 140

Ala Tyr Arg Arg Cys Ala Glu Ala Leu Gly Ala Lys Val Lys Ala Tyr
145                 150                 155                 160

Val His Pro Thr Thr Gly Val Val Thr Leu Ala Thr Leu Ala Pro Arg
                165                 170                 175

Pro Gly Ala Gln Asp Pro Val Lys Arg Leu Val Val Glu Ala Gly Met
            180                 185                 190

Val Ala Lys Ala Glu Glu Lys Arg Val Pro Glu Glu Val Phe Arg Tyr
        195                 200                 205

Arg Arg Glu Ala Leu Ala Leu Phe Leu Gly Arg Leu Phe Ser Thr Asp
    210                 215                 220

Gly Ser Val Glu Lys Lys Arg Ile Ser Tyr Ser Ser Ala Ser Leu Gly
225                 230                 235                 240

Leu Ala Gln Asp Val Ala His Leu Leu Leu Arg Leu Gly Ile Thr Ser
                245                 250                 255

Gln Leu Arg Ser Arg Gly Pro Arg Ala His Glu Val Leu Ile Ser Gly
            260                 265                 270

Arg Glu Asp Ile Leu Arg Phe Ala Glu Leu Ile Gly Pro Tyr Leu Leu
        275                 280                 285

Gly Ala Lys Arg Glu Arg Leu Ala Ala Leu Glu Ala Glu Ala Arg Arg
    290                 295                 300

Arg Leu Pro Gly Gln Gly Trp His Leu Arg Leu Val Leu Pro Ala Val
305                 310                 315                 320

Ala Tyr Arg Val Ser Glu Ala Lys Arg Arg Ser Gly Phe Ser Trp Ser
                325                 330                 335

Glu Ala Gly Arg Arg Val Ala Val Ala Gly Ser Cys Leu Ser Ser Gly
            340                 345                 350

Leu Asn Leu Lys Leu Pro Arg Arg Tyr Leu Ser Arg His Arg Leu Ser
        355                 360                 365

Leu Leu Gly Glu Ala Phe Ala Asp Pro Gly Leu Glu Ala Leu Ala Glu
    370                 375                 380

Gly Gln Val Leu Trp Asp Pro Ile Val Ala Val Glu Pro Ala Gly Lys
385                 390                 395                 400

Ala Arg Thr Phe Asp Leu Arg Val Pro Pro Phe Ala Asn Phe Val Ser
                405                 410                 415

Glu Asp Leu Val Val His Asn
            420
```

<210> SEQ ID NO 27
<211> LENGTH: 423
<212> TYPE: PRT
<213> ORGANISM: Artificial Sequence
<220> FEATURE:
<223> OTHER INFORMATION: Synthetic construct, Tth T134-100-68 protein

<400> SEQUENCE: 27

```
Cys Leu Ala Glu Gly Ser Leu Val Leu Asp Ala Ala Thr Gly Gln Arg
1               5                   10                  15

Val Pro Ile Glu Lys Val Arg Pro Gly Met Glu Val Phe Ser Leu Gly
            20                  25                  30

Pro Asp Tyr Arg Leu Tyr Arg Val Pro Val Leu Glu Val Leu Glu Ser
        35                  40                  45

Gly Val Arg Glu Val Val Arg Leu Arg Thr Arg Ser Glu Arg Thr Leu
    50                  55                  60

Val Leu Thr Pro Asp His Pro Leu Leu Thr Pro Glu Gly Trp Lys Pro
65                  70                  75                  80

Leu Cys Asp Leu Pro Leu Gly Thr Pro Ile Ala Val Pro Ala Glu Leu
                85                  90                  95

Pro Val Ala Gly His Leu Ala Pro Pro Glu Glu Arg Val Thr Leu Leu
            100                 105                 110

Ala Leu Leu Leu Gly Asp Gly Asn Thr Lys Leu Ser Gly Arg Arg Gly
        115                 120                 125

Thr Arg Pro Asn Ala Phe Phe His Ser Lys Asp Pro Glu Leu Leu Ala
    130                 135                 140

Ala Tyr Arg Arg Cys Ala Glu Ala Leu Gly Ala Lys Val Lys Ala Tyr
145                 150                 155                 160

Val His Pro Thr Thr Gly Val Val Thr Leu Ala Thr Leu Ala Pro Arg
                165                 170                 175

Pro Gly Ala Gln Asp Pro Val Lys Arg Leu Val Val Glu Ala Gly Met
            180                 185                 190

Val Ala Lys Ala Glu Glu Lys Arg Val Pro Glu Glu Val Phe Arg Tyr
        195                 200                 205

Arg Arg Glu Ala Leu Ala Leu Phe Leu Gly Arg Leu Phe Ser Thr Asp
    210                 215                 220

Gly Ser Val Glu Lys Lys Arg Ile Ser Tyr Ser Ser Ala Ser Leu Gly
225                 230                 235                 240

Leu Ala Gln Asp Val Ala His Leu Leu Leu Arg Leu Gly Ile Thr Ser
                245                 250                 255

Gln Leu Arg Ser Arg Gly Pro Arg Ala His Glu Val Leu Ile Ser Gly
            260                 265                 270

Arg Glu Asp Ile Leu Arg Phe Ala Glu Leu Ile Gly Pro Tyr Leu Leu
        275                 280                 285

Gly Ala Lys Arg Glu Arg Leu Ala Ala Leu Glu Ala Glu Ala Arg Arg
    290                 295                 300

Arg Leu Pro Val Gln Gly Trp His Ser Arg Leu Val Leu Pro Ala Val
305                 310                 315                 320

Ala Tyr Arg Val Ser Glu Ala Lys Arg Arg Ser Gly Phe Ser Trp Ser
                325                 330                 335

Glu Ala Gly Arg Arg Val Ala Val Ala Gly Ser Cys Leu Ser Ser Gly
            340                 345                 350

Leu Asn Leu Lys Leu Pro Arg Arg Tyr Leu Ser Arg His Arg Leu Ser
        355                 360                 365

Leu Leu Gly Glu Ala Phe Ala Asp Pro Gly Leu Glu Ala Leu Ala Glu
    370                 375                 380

Gly Gln Val Leu Trp Asp Pro Ile Val Ala Val Glu Pro Ala Gly Lys
385                 390                 395                 400

Ala Arg Thr Phe Asp Leu Arg Val Pro Pro Phe Ala Asn Phe Val Ser
                405                 410                 415
```

Glu Asp Leu Val Val His Asn
420

<210> SEQ ID NO 28
<211> LENGTH: 423
<212> TYPE: PRT
<213> ORGANISM: Artificial Sequence
<220> FEATURE:
<223> OTHER INFORMATION: Synthetic construct, Tth T134-100-39 protein

<400> SEQUENCE: 28

Cys Leu Ala Glu Gly Ser Leu Val Leu Asp Ala Ala Thr Gly Gln Arg
1 5 10 15

Val Pro Ile Glu Lys Val Arg Pro Gly Met Glu Val Phe Ser Leu Gly
20 25 30

Pro Asp Tyr Arg Leu Tyr Arg Val Pro Val Leu Glu Val Leu Glu Ser
35 40 45

Gly Val Arg Glu Val Val Arg Leu Arg Thr Arg Ser Gly Arg Thr Leu
50 55 60

Val Leu Thr Pro Asp His Pro Leu Leu Thr Pro Glu Gly Trp Lys Pro
65 70 75 80

Leu Cys Asp Leu Pro Leu Gly Thr Pro Ile Ala Val Pro Ala Glu Leu
85 90 95

Pro Val Ala Gly His Leu Ala Pro Pro Glu Glu Arg Val Thr Leu Leu
100 105 110

Ala Leu Leu Leu Gly Asp Gly Asn Thr Lys Leu Ser Gly Arg Arg Gly
115 120 125

Thr Arg Pro Asn Ala Phe Phe Tyr Ser Lys Asp Pro Glu Leu Leu Ala
130 135 140

Ala Tyr Arg Arg Cys Ala Glu Ala Leu Gly Ala Lys Val Lys Ala Tyr
145 150 155 160

Val His Pro Thr Thr Gly Val Val Thr Leu Ala Thr Leu Ala Pro Arg
165 170 175

Pro Gly Ala Gln Asp Pro Val Lys Arg Leu Val Val Glu Ala Gly Met
180 185 190

Val Ala Lys Ala Glu Glu Lys Arg Val Pro Glu Glu Val Phe Arg Tyr
195 200 205

Arg Arg Glu Ala Leu Ala Leu Phe Leu Gly Arg Leu Phe Ser Thr Asp
210 215 220

Gly Ser Val Glu Lys Lys Arg Ile Ser Tyr Ser Ser Ala Ser Leu Gly
225 230 235 240

Leu Ala Gln Asp Val Ala His Leu Leu Leu Arg Leu Gly Ile Thr Ser
245 250 255

Gln Leu Arg Ser Arg Gly Pro Arg Ala His Glu Val Leu Ile Ser Gly
260 265 270

Arg Glu Asp Ile Leu Arg Phe Ala Glu Leu Ile Gly Pro Tyr Leu Leu
275 280 285

Gly Ala Lys Arg Glu Arg Leu Ala Ala Leu Glu Ala Glu Ala Arg Arg
290 295 300

Arg Leu Pro Gly Gln Gly Trp His Leu Arg Leu Val Leu Pro Ala Val
305 310 315 320

Ala Tyr Arg Val Ser Glu Ala Lys Arg Arg Ser Gly Phe Ser Trp Ser
325 330 335

Glu Ala Gly Arg Arg Val Ala Val Ala Gly Ser Cys Leu Ser Ser Gly
340 345 350

```
Leu Asn Leu Lys Leu Pro Arg Arg Tyr Leu Ser Arg His Arg Leu Ser
        355                 360                 365

Leu Leu Gly Glu Ala Phe Ala Asp Pro Gly Leu Glu Ala Leu Ala Glu
    370                 375                 380

Gly Leu Val Leu Trp Asp Pro Ile Val Ala Val Glu Pro Ala Gly Lys
385                 390                 395                 400

Ala Arg Thr Phe Asp Leu Arg Val Pro Pro Phe Ala Asn Phe Val Ser
                405                 410                 415

Glu Asp Leu Val Val His Asn
            420


<210> SEQ ID NO 29
<211> LENGTH: 423
<212> TYPE: PRT
<213> ORGANISM: Artificial Sequence
<220> FEATURE:
<223> OTHER INFORMATION: Synthetic construct, Tth T134-100 protein

<400> SEQUENCE: 29

Cys Leu Ala Glu Gly Ser Leu Val Leu Asp Ala Ala Thr Gly Gln Arg
1               5                   10                  15

Val Pro Ile Glu Lys Val Arg Pro Gly Met Glu Val Phe Ser Leu Gly
            20                  25                  30

Pro Asp Tyr Arg Leu Tyr Arg Val Pro Val Leu Glu Val Leu Glu Ser
        35                  40                  45

Gly Val Arg Glu Val Val Arg Leu Arg Thr Arg Ser Gly Arg Thr Leu
    50                  55                  60

Val Leu Thr Pro Asp His Pro Leu Leu Thr Pro Glu Gly Trp Lys Pro
65                  70                  75                  80

Leu Cys Asp Leu Pro Leu Gly Thr Pro Ile Ala Val Pro Ala Glu Leu
                85                  90                  95

Pro Val Ala Gly His Leu Ala Pro Pro Glu Glu Arg Val Thr Leu Leu
            100                 105                 110

Ala Leu Leu Leu Gly Asp Gly Asn Thr Lys Leu Ser Gly Arg Arg Gly
        115                 120                 125

Thr Arg Pro Asn Ala Phe Phe Tyr Ser Lys Asp Pro Glu Leu Leu Ala
    130                 135                 140

Ala Tyr Arg Arg Cys Ala Glu Ala Leu Gly Ala Lys Val Lys Ala Tyr
145                 150                 155                 160

Val His Pro Thr Thr Gly Val Val Thr Leu Ala Thr Leu Ala Pro Arg
                165                 170                 175

Pro Gly Ala Gln Asp Pro Val Lys Arg Leu Val Val Glu Ala Gly Met
            180                 185                 190

Val Ala Lys Ala Glu Glu Lys Arg Val Pro Glu Glu Val Phe Arg Tyr
        195                 200                 205

Arg Arg Glu Ala Leu Ala Leu Phe Leu Gly Arg Leu Phe Ser Thr Asp
    210                 215                 220

Gly Ser Val Glu Lys Lys Arg Ile Ser Tyr Ser Ser Ala Ser Leu Gly
225                 230                 235                 240

Leu Ala Gln Asp Val Ala His Leu Leu Leu Arg Leu Gly Ile Thr Ser
                245                 250                 255

Gln Leu Arg Ser Arg Gly Pro Arg Ala His Glu Val Leu Ile Ser Gly
            260                 265                 270

Arg Glu Asp Ile Leu Arg Phe Ala Glu Leu Ile Gly Pro Tyr Leu Leu
        275                 280                 285
```

```
Gly Ala Lys Arg Glu Arg Leu Ala Ala Leu Glu Ala Glu Ala Arg Arg
    290                 295                 300

Arg Leu Pro Gly Gln Gly Trp His Leu Arg Leu Val Leu Pro Ala Val
305                 310                 315                 320

Ala Tyr Arg Val Ser Glu Ala Lys Arg Arg Ser Gly Phe Ser Trp Ser
                325                 330                 335

Glu Ala Gly Arg Arg Val Ala Val Ala Gly Ser Cys Leu Ser Ser Gly
            340                 345                 350

Leu Asn Leu Lys Leu Pro Arg Arg Tyr Leu Ser Arg His Arg Leu Ser
        355                 360                 365

Leu Leu Gly Glu Ala Phe Ala Asp Pro Gly Leu Glu Ala Leu Ala Glu
    370                 375                 380

Gly Gln Val Leu Trp Asp Pro Ile Val Ala Val Glu Pro Ala Gly Lys
385                 390                 395                 400

Ala Arg Thr Phe Asp Leu Arg Val Pro Pro Phe Ala Asn Phe Val Ser
                405                 410                 415

Glu Asp Leu Val Val His Asn
            420


<210> SEQ ID NO 30
<211> LENGTH: 423
<212> TYPE: PRT
<213> ORGANISM: Artificial Sequence
<220> FEATURE:
<223> OTHER INFORMATION: Synthetic construct, Tth S158-30-m79-110
      protein

<400> SEQUENCE: 30

Cys Leu Ala Glu Gly Ser Leu Val Leu Asp Ala Ala Thr Gly Gln Arg
1               5                   10                  15

Val Pro Ile Glu Lys Val Arg Pro Gly Met Glu Val Phe Ser Leu Gly
            20                  25                  30

Pro Asp Tyr Arg Leu Tyr Gln Val Pro Val Leu Glu Val Leu Glu Ser
        35                  40                  45

Gly Val Gly Glu Val Val Arg Leu Arg Thr Arg Ser Gly Arg Thr Leu
    50                  55                  60

Val Leu Thr Pro Asp His Pro Leu Leu Thr Pro Glu Gly Trp Lys Pro
65                  70                  75                  80

Leu Cys Asp Leu Pro Leu Gly Thr Pro Ile Ala Val Pro Ala Glu Leu
                85                  90                  95

Pro Val Ala Gly His Leu Ala Pro Pro Glu Glu Arg Val Thr Pro Leu
            100                 105                 110

Ala Leu Leu Leu Gly Asp Gly Asn Thr Lys Leu Ser Gly Arg Arg Gly
        115                 120                 125

Thr Arg Pro Asn Ala Phe Phe Tyr Cys Lys Asp Pro Glu Leu Leu Ala
    130                 135                 140

Ala Tyr Arg Arg Cys Ala Glu Ala Leu Gly Ala Lys Val Lys Ala Tyr
145                 150                 155                 160

Val His Pro Thr Thr Gly Val Val Thr Leu Ala Thr Leu Ala Pro Arg
                165                 170                 175

Pro Gly Ala Gln Asp Pro Val Lys Arg Leu Val Val Glu Ala Gly Met
            180                 185                 190

Val Ala Lys Ala Glu Glu Lys Arg Val Pro Glu Glu Val Phe Arg Tyr
        195                 200                 205

Arg Arg Glu Ala Leu Ala Leu Phe Leu Gly Arg Leu Phe Ser Thr Asp
```

```
    210                 215                 220

Gly Ser Val Glu Lys Lys Arg Ile Ser Tyr Ser Ser Ala Ser Leu Gly
225                 230                 235                 240

Leu Ala Gln Asp Val Ala His Leu Leu Leu Arg Leu Gly Ile Thr Ser
                245                 250                 255

Gln Leu Arg Ser Arg Gly Pro Arg Ala His Glu Val Leu Ile Ser Gly
            260                 265                 270

Arg Glu Asp Ile Leu Arg Phe Ala Glu Leu Ile Gly Pro Tyr Leu Leu
        275                 280                 285

Gly Ala Lys Arg Glu Arg Leu Ala Ala Leu Glu Ala Glu Ala Arg Arg
    290                 295                 300

Arg Leu Pro Gly Gln Gly Trp His Leu Arg Leu Val Leu Pro Ala Val
305                 310                 315                 320

Ala Tyr Arg Val Ser Glu Ala Lys Arg Arg Ser Gly Phe Ser Trp Ser
                325                 330                 335

Glu Ala Gly Arg Arg Val Ala Val Ala Gly Ser Cys Leu Ser Ser Gly
            340                 345                 350

Leu Asn Leu Lys Leu Pro Arg Arg Tyr Leu Ser Arg His Arg Leu Ser
        355                 360                 365

Met Leu Gly Glu Ala Phe Ala Asp Pro Gly Leu Glu Ala Leu Ala Glu
    370                 375                 380

Gly Gln Val Leu Trp Asp Pro Ile Val Ala Val Glu Pro Ala Gly Lys
385                 390                 395                 400

Ala Arg Thr Phe Asp Leu Arg Val Pro Pro Phe Ala Asn Phe Ala Ser
                405                 410                 415

Glu Asp Leu Val Val His Asn
            420


<210> SEQ ID NO 31
<211> LENGTH: 1014
<212> TYPE: DNA
<213> ORGANISM: Artificial Sequence
<220> FEATURE:
<223> OTHER INFORMATION: Synthetic construct, XynB (P77853) maize
      codon-optimized DNA sequence

<400> SEQUENCE: 31

atgcaaacaa gcattactct gacatccaac gcatccggta cgtttgacgg ttactattac      60

gaactctgga aggatactgg caatacaaca atgacggtct acactcaagg tcgcttttcc     120

tgccagtggt cgaacatcaa taacgcgttg tttaggaccg ggaagaaata caaccagaat     180

tggcagtctc ttggcacaat ccggatcacg tactctgcga cttacaaccc aaacgggaac     240

tcctacttgt gtatctatgg ctggtctacc aacccattgg tcgagttcta catcgttgag     300

tcctggggga actggagacc gcctggtgcc acgtccctgg gccaagtgac aatcgatggc     360

gggacctacg acatctatag gacgacacgc gtcaaccagc cttccattgt ggggacagcc     420

acgttcgatc agtactggag cgtgcgcacc tctaagcgga cttcaggaac agtgaccgtg     480

accgatcact tccgcgcctg ggcgaaccgg ggcctgaacc tcggcacaat agaccaaatt     540

acattgtgcg tggagggtta ccaaagctct ggatcagcca acatcaccca gaacaccttc     600

tctcagggct cttcttccgg cagttcgggt ggctcatccg gctccacaac gactactcgc     660

atcgagtgtg agaacatgtc cttgtccgga ccctacgtta gcaggatcac caatcccttt     720

aatggtattg cgctgtacgc caacggagac acagcccgcg ctaccgttaa cttccccgca     780

agtcgcaact acaatttccg cctgcggggt tgcggcaaca acaataatct tgcccgtgtg     840
```

gacctgagga tcgacggacg gaccgtcggg accttttatt accagggcac atacccctgg 900
gaggccccaa ttgacaatgt ttatgtcagt gcggggagtc atacagtcga aatcactgtt 960
actgcggata acggcacatg ggacgtgtat gccgactacc tggtgataca gtga 1014

<210> SEQ ID NO 32
<211> LENGTH: 1269
<212> TYPE: DNA
<213> ORGANISM: Thermus thermophilus

<400> SEQUENCE: 32
tgcctggccg agggctcgct cgtcttggac gcggctaccg ggcagagggt ccctatcgaa 60
aaggtgcgtc cggggatgga agttttctcc ttgggacctg attacagact gtatcgggtg 120
cccgttttgg aggtccttga gagcggggtt agggaagttg tgcgcctcag aactcggtca 180
gggagaacgc tggtgttgac accagatcac ccgcttttga cccccgaagg ttggaaacct 240
ctttgtgacc tcccgcttgg aactccaatt gcagtccccg cagaactgcc tgtggcgggc 300
cacttggccc cacctgaaga acgtgttacg ctcctggctc ttctgttggg ggatgggaac 360
acaaagctgt cgggtcggag aggtacacgt cctaatgcct tcttctacag caaagacccc 420
gaattgctcg cggcttatcg ccggtgtgca gaagccttgg gtgcaaaggt gaaagcatac 480
gtccacccga ctacgggggt ggttacactc gcaaccctcg ctccacgtcc tggagctcaa 540
gatcctgtca aacgcctcgt tgtcgaggcg ggaatggttg ctaaagccga agagaagagg 600
gtcccggagg aggtgtttcg ttaccggcgt gaggcgttgg cccttttctt gggccgtttg 660
ttctcgacag acggctctgt tgaaaagaag aggatctctt attcaagtgc cagtttggga 720
ctggcccagg atgtcgcaca tctcttgctg cgccttggaa ttacatctca actccgttcg 780
agagggccac gggctcacga ggttcttata tcgggccgcg aggatatttt gcggtttgct 840
gaacttatcg gaccctacct cttgggggcc aagagggaga gacttgcagc gctggaagct 900
gaggcccgca ggcgtttgcc tggacaggga tggcacttgc ggcttgttct tcctgccgtg 960
gcgtacagag tgagcgaggc taaaaggcgc tcgggatttt cgtggagtga agccggtcgg 1020
cgcgtcgcag ttgcgggatc gtgtttgtca tctggactca acctcaaatt gcccagacgc 1080
tacctttctc ggcaccggtt gtcgctgctc ggtgaggctt ttgccgaccc tgggctggaa 1140
gcgctcgcgg aaggccaagt gctctgggac cctattgttg ctgtcgaacc ggccggtaag 1200
gcgagaacat tcgacttgcg cgttccaccc tttgcaaact tcgtgagcga ggacctggtg 1260
gtgcataac 1269

<210> SEQ ID NO 33
<211> LENGTH: 75
<212> TYPE: DNA
<213> ORGANISM: Hordeum vulgare

<400> SEQUENCE: 33
atggcgaaca aacatttgtc cctctccctc ttcctcgtcc tccttggcct gtcggccagc 60
ttggcctccg ggcaa 75

<210> SEQ ID NO 34
<211> LENGTH: 423
<212> TYPE: PRT
<213> ORGANISM: Thermus thermophilus

<400> SEQUENCE: 34

```
Cys Leu Ala Glu Gly Ser Leu Val Leu Asp Ala Ala Thr Gly Gln Arg
1               5                   10                  15

Val Pro Ile Glu Lys Val Arg Pro Gly Met Glu Val Phe Ser Leu Gly
            20                  25                  30

Pro Asp Tyr Arg Leu Tyr Arg Val Pro Val Leu Glu Val Leu Glu Ser
        35                  40                  45

Gly Val Arg Glu Val Val Arg Leu Arg Thr Arg Ser Gly Arg Thr Leu
    50                  55                  60

Val Leu Thr Pro Asp His Pro Leu Leu Thr Pro Glu Gly Trp Lys Pro
65                  70                  75                  80

Leu Cys Asp Leu Pro Leu Gly Thr Pro Ile Ala Val Pro Ala Glu Leu
                85                  90                  95

Pro Val Ala Gly His Leu Ala Pro Pro Glu Glu Arg Val Thr Leu Leu
            100                 105                 110

Ala Leu Leu Leu Gly Asp Gly Asn Thr Lys Leu Ser Gly Arg Arg Gly
        115                 120                 125

Thr Arg Pro Asn Ala Phe Phe Tyr Ser Lys Asp Pro Glu Leu Leu Ala
    130                 135                 140

Ala Tyr Arg Arg Cys Ala Glu Ala Leu Gly Ala Lys Val Lys Ala Tyr
145                 150                 155                 160

Val His Pro Thr Thr Gly Val Val Thr Leu Ala Thr Leu Ala Pro Arg
                165                 170                 175

Pro Gly Ala Gln Asp Pro Val Lys Arg Leu Val Val Glu Ala Gly Met
            180                 185                 190

Val Ala Lys Ala Glu Glu Lys Arg Val Pro Glu Glu Val Phe Arg Tyr
        195                 200                 205

Arg Arg Glu Ala Leu Ala Leu Phe Leu Gly Arg Leu Phe Ser Thr Asp
    210                 215                 220

Gly Ser Val Glu Lys Lys Arg Ile Ser Tyr Ser Ser Ala Ser Leu Gly
225                 230                 235                 240

Leu Ala Gln Asp Val Ala His Leu Leu Leu Arg Leu Gly Ile Thr Ser
                245                 250                 255

Gln Leu Arg Ser Arg Gly Pro Arg Ala His Glu Val Leu Ile Ser Gly
            260                 265                 270

Arg Glu Asp Ile Leu Arg Phe Ala Glu Leu Ile Gly Pro Tyr Leu Leu
        275                 280                 285

Gly Ala Lys Arg Glu Arg Leu Ala Ala Leu Glu Ala Glu Ala Arg Arg
    290                 295                 300

Arg Leu Pro Gly Gln Gly Trp His Leu Arg Leu Val Leu Pro Ala Val
305                 310                 315                 320

Ala Tyr Arg Val Ser Glu Ala Lys Arg Arg Ser Gly Phe Ser Trp Ser
                325                 330                 335

Glu Ala Gly Arg Arg Val Ala Val Ala Gly Ser Cys Leu Ser Ser Gly
            340                 345                 350

Leu Asn Leu Lys Leu Pro Arg Arg Tyr Leu Ser Arg His Arg Leu Ser
        355                 360                 365

Leu Leu Gly Glu Ala Phe Ala Asp Pro Gly Leu Glu Ala Leu Ala Glu
    370                 375                 380

Gly Gln Val Leu Trp Asp Pro Ile Val Ala Val Glu Pro Ala Gly Lys
385                 390                 395                 400

Ala Arg Thr Phe Asp Leu Arg Val Pro Pro Phe Ala Asn Phe Val Ser
                405                 410                 415

Glu Asp Leu Val Val His Asn
```

420

<210> SEQ ID NO 35
<211> LENGTH: 2349
<212> TYPE: DNA
<213> ORGANISM: Artificial Sequence
<220> FEATURE:
<223> OTHER INFORMATION: Synthetic construct, S158 19 DNA sequence

<400> SEQUENCE: 35
atgttcctta agaaactgtc taagttgctg ctcgtcgtgc tccttgttgc cgtttacaca 60
caggtcaacg cgcaaacaag cattactctg acatccaacg catccggtac gtttgacggt 120
tactattacg aactctggaa ggatactggc aatacaacaa tgacggtcta cactcaaggt 180
cgcttttcct gccagtggtc gaacatcaat aacgcgttgt ttaggaccgg gaagaaatac 240
aaccagaatt ggcagtctct tggcacaatc cggatcacgt actctgcgac ttacaaccca 300
aacgggaact cctacttgtg tatctatggc tggtctacca acccattggt cgagttctac 360
atcgttgagt cctgggggaa ctggagaccg cctggtgcca cgtccctggg ccaagtgaca 420
atcgatggcg ggacctacga catctatagg acgacacgcg tcaaccagcc ttgcctggcc 480
gagggctcgc tcgtcttgga cgcggctacc gggcagaggg tccctatcga aaaggtgcgt 540
ccggggatgg aagttttctc cttgggacct gattacagac tgtatcgggt gcccgttttg 600
gaggtccttg agagcggggt tggggaagtt gtgcgcctca gaactcggtc agggagaacg 660
ctggtgttga caccagatca cccgcttttg acccccgaag gttggaaacc tctttgtgac 720
ctcccgcttg gaactccaat tgcagtcccc gcagaactgc ctgtggcggg ccacttggcc 780
ccacctgaag aacgtgttac gctcctggct cttctgttgg gggatgggaa cacaaagctg 840
tcgggtcgga gaggtacacg tcctattgcc ttcttctaca gcaaagaccc cgaattgctc 900
gcggcttatc gccggtgtgc agaagccttg ggtgcaaagg tgaaagcata cgtccacccg 960
actacggggg tggttacact cgcaaccctc gctccacgtc ctggagctca agatcctgtc 1020
aaacgcctcg ttgtcgaggc gggaatggtt gctaaagccg aagagaagag ggtcccggag 1080
gaggtgtttc gttaccggcg tgaggcgttg gcccttttct tgggccgttt gttctcgaca 1140
gacggctctg ttgaaaagaa gaggatctct tattcaagtg ccagtttggg actggcccag 1200
gatgtcgcac atctcttgct gcgccttgga attacatctc aactccgttc gagagggcca 1260
cgggctcacg aggttcttat atcgggccgc gaggatattt tgcggtttgc tgaacttatc 1320
ggaccctacc tcttgggggc caagagggag agacttgcag cgctggaagc tgaggcccgc 1380
aggcgtttgc ctggacaggg atggcacttg cggcttgttc ttcctgccgt ggcgtacaga 1440
gtgagcgagg ctaaaaggcg ctcgggattt tcgtggagtg aagccggtcg gcgcgtcgca 1500
gttgcgggat cgtgtttgtc atctggactc aacctcaaat tgcccagacg ctacctttct 1560
cggcaccggt tgtcgctgct cggtgaggct tttgccgacc ctgggctgga agcgctcgcg 1620
gaaggccaag tgctctggga ccctattgtt gctgtcgaac cggccggtaa ggcgagaaca 1680
ttcgacttgc gcgttccacc ctttgcaaac ttcgtgagcg aggacctggt ggtgcataac 1740
tccattgtgg ggacagccac gttcgatcag tactggagcg tgcgcacctc taagcggact 1800
tcaggaacag tgaccgtgac cgatcacttc cgcgcctggg cgaaccgggg cctgaacctc 1860
ggcacaatag accaaattac attgtgcgtg gagggttacc aaagctctgg atcagccaac 1920
atcacccaga acaccttctc tcagggctct tcttccggca gttcgggtgg ctcatccggc 1980
tccacaacga ctactcgcat cgagtgtgag aacatgtcct tgtccggacc ctacgttagc 2040
aggatcacca atccctttaa tggtattgcg ctgtacgcca acggagacac agcccgcgct 2100
accgttaact tccccgcaag tcgcaactac aatttccgcc tgcggggttg cggcaacaac 2160
aataatcttg cccgtgtgga cctgaggatc gacggacgga ccgtcgggac cttttattac 2220
cagggcacat acccctggga ggccccaatt gacaatgttt atgtcagtgc ggggagtcat 2280
acagtcgaaa tcactgttac tgcggataac ggcacatggg acgtgtatgc cgactacctg 2340
gtgatacag 2349

<210> SEQ ID NO 36
<211> LENGTH: 2349
<212> TYPE: DNA
<213> ORGANISM: Artificial Sequence
<220> FEATURE:
<223> OTHER INFORMATION: Synthetic construct, S158-3103 DNA sequence

<400> SEQUENCE: 36
atgttcctta agaaactgtc taagttgctg ctcgtcgtgc tccttgttgc cgtttacaca 60
caggtcaacg cgcaaacaag cattactctg acatccaacg catccggtac gtttgacggt 120
tactattacg aactctggaa ggatactggc aatacaacaa tgacggtcta cactcaaggt 180
cgcttttcct gccagtggtc gaacatcaat aacgcgttgt ttaggaccgg gaagaaatac 240
aaccagaatt ggcagtctct tggcacaatc cggatcacgt actctgcgac ttacaaccca 300
aacgggaact cctacttgtg tatctatggc tggtctacca acccattggt cgagttctac 360
atcgttgagt cctgggggaa ctggagaccg cctggtgcca cgtccctggg ccaagtgaca 420
atcgatggcg ggacctacga catctatagg acgacacgcg tcaaccagcc ttgcctggcc 480
gagggctcgc tcgtcttgga cgcggctacc gggcagaggg tccctatcga aaaggtgcgt 540
ccggggatgg aagttttctc cttgggacct gattacagac tgtatcgggt gcccgttttg 600
gaggtccttg agagcggggt tggggaagtt gtgcgcctca gaactcggtc agggagaacg 660
ctggtgttga caccagatca cccgcttttg acccccgaag gttggaaacc tctttgtgac 720
ctcccgcttg gaactccaat tgcagtcccc gcagaactgc ctgtggcggg ccacttggcc 780
ccacctgaag aacgtgttac gctcctggct cttctgttgg gggatgggaa cacaaagctg 840
tcgggtcgga gaggtacacg tcctaatgcc ttcttctaca gcaaagaccc cgaattgctc 900
gcggcttatc gccggtgtgc agaagccttg ggtgcaaagg tgaaagcata cgtccacccg 960
actacggggg tggttacact cgcaaccctc gctccacgtc ctggagctca agatcctgtc 1020
aaacgcctcg ttgtcgaggc gggaatggtt gctaaagccg aagagaagag ggtcccggag 1080
gaggtgtttc gttaccggcg tgaggcgttg gccctttttct tgggccgttt gttctcgaca 1140
gacggctctg ttgaaaagaa gaggatctct tattcaagtg ccagtttggg actggcccag 1200
gatgtcgcac atctcttgct gcgccttgga attacatctc aactccgttc gagagggcca 1260
cgggctcacg aggttcttat atcgggccgc gaggatattt tgcggtttgc tgaacttatc 1320
ggaccctacc tcttgggggc caagagggag agacttgcag cgctggaagc tgaggcccgc 1380
aggcgtttgc ctggacaggg atggcacttg cggcttgttc ttcctgccgt ggcgtacaga 1440
gtgagcgagg ctaaaaggcg ctcgggattt tcgtggagtg aagccggtcg gcgcgtcgca 1500
gttgcgggat cgtgtttgtc atctggactc aacctcaaat tgcccagacg ctacctttct 1560
cggcaccggt tgtcgatgct cggtgaggct tttgccgacc ctgggctgga agcgctcgcg 1620
gaaggccaag tgctctggga ccctattgtt gctgtcgaac cggccggtaa ggcgagaaca 1680
ttcgacttgc gcgttccacc ctttgcaaac ttcgtgagcg aggacctggt ggtgcataac 1740
tccattgtgg ggacagccac gttcgatcag tactggagcg tgcgcacctc taagcggact 1800
tcaggaacag tgaccgtgac cgatcacttc cgcgcctggg cgaaccgggg cctgaacctc 1860
ggcacaatag accaaattac attgtgcgtg gagggttacc aaagctctgg atcagccaac 1920
atcacccaga acaccttctc tcagggctct tcttccggca gttcgggtgg ctcatccggc 1980
tccacaacga ctgctcgcat cgagtgtgag aacatgtcct tgtccggtcc ctacgttagc 2040
aggatcacca atccctttaa tggtattgcg ctgtacgcca acggagacac agcccgcgct 2100
accgttaact tccccgcaag tcgcaactac aatttccgcc tgcggggttg cggcaacaac 2160
aataatcttg cccgtgtgga cctgaggatc gacggacgga ccgtcgggac cttttattac 2220
cagggcacat acccctggga ggccccaatt gacaatgttt atgtcagtgc ggggagtcat 2280
acagtcgaaa tcactgttac tgcggataac ggcacatggg acgtgtatgc cgactacctg 2340
gtgatacag 2349

<210> SEQ ID NO 37
<211> LENGTH: 2349
<212> TYPE: DNA
<213> ORGANISM: Artificial Sequence
<220> FEATURE:
<223> OTHER INFORMATION: Synthetic construct, S158-3108 DNA sequence

<400> SEQUENCE: 37
atgttcctta agaaactgtc taagttgctg ctcgtcgtgc tccttgttgc cgtttacaca 60
caggtcaacg cgcaaacaag cattactctg acatccaacg catccggtac gtttgacggt 120
tactattacg aactctggaa ggatactggc aatacaacaa tgacggtcta cactcaaggt 180
cgcttttcct gccagtggtc gaacatcaat aacgcgttgt ttaggaccgg gaagaaatac 240
aaccagaatt ggcagtctct tggcacaatc cggatcacgt actctgcgac ttacaaccca 300
aacgggaact cctacttgtg tatctatggc tggtctacca acccattggt cgagttctac 360
atcgttgagt cctgggggaa ctggagaccg cctggtgcca cgtccctggg ccaagtgaca 420
atcgatggcg ggacctacga catctatagg acgacacgcg tcaaccagcc ttgcctggcc 480
gagggctcgc tcgtcttgga cgcggctacc gggcagaggg tccctatcga aaaggtgcgt 540
ccggggatgg aagttttctc cttgggacct gattacagac tgtatcgggt gcccgttttg 600
gaggtccttg agagcggggt tggggaagtt gtgcgcctca gaactcggtc agggagaacg 660
ctggtgttga caccagatca cccgcttttg acccccgaag gttggaaacc tctttgtgac 720
ctcccgcttg gaactccaat tgcagtcccc gcagaactgc ctgtggcggg ccacttggcc 780
ccacctgaag aacgtgttac gctcctggct cttctgttgg gggatgggaa cacaaagctg 840
tcgggtcgga gaggtacacg tcctaatgcc ttcttctaca gcaaagaccc cgaattgctc 900
gcggcttatc gccggtgtgc agaagccttg ggtgcaaagg tgaaagcata cgtccacccg 960
actacggggg tggttacact cgcaaccctc gctccacgtc ctggagctca agatcctgtc 1020
aaacgcctcg ttgtcgaggc gggaatggtt gctaaagccg aagagaagag ggtcccggag 1080
gaggtgtttc gttaccggcg tgaggcgttg gcccttttct tgggccgttt gttctcgaca 1140
gacggctctg ttgaaaagaa gaggatctct tattcaagtg ccagtttggg actggcccag 1200
gatgtcgcac atctcttgct gcgccttgga attacatctc aactccgttc gagagggcca 1260
cgggctcaca aggttcttat atcgggccgc gaggatattt tgcggtttgc tgaacttatc 1320
ggaccctacc tcttgggggc caagagggag agacttgcag cgctggaagc tgaggcccgc 1380
aggcgtttgc ctggacaggg atggcacttg cggcttgttc ttcctgccgt ggcgtacaga 1440
gtgagcgagg ctaaaaggcg ctcgggattt tcgtggagtg aagccggtcg gcgcgtcgca 1500
gttgcgggat cgtgtttgtc atctggactc aacctcaaat tgcccagacg ctacctttct 1560
cggcaccggt tgtcgctgct cggtgaggct tttgccgacc ctgggctgga agcgctcgcg 1620
gaaggccaag tgctctggga ccctattgtt gctgtcgaac cggccggtaa ggcgagaaca 1680
ttcgacttgc gcgttccacc ctttgcaaac ttcgtgagcg aggacctggt ggtgcataac 1740
tccattgtgg ggacagccac gttcgatcag tactggagcg tgcgcacctc taagcggact 1800
tcaggaacag tgaccgtgac cgatcacttc cgcgcctggg cgaaccgggg cctgaacctc 1860
ggcacaatag accaaattac attgtgcgtg gagggttacc aaagctctgg atcagccaac 1920
atcacccaga acaccttctc tcagggctct tcttccggca gttcgggtgg ctcatccggc 1980
tccacaacga ctactcgcat cgagtgtgag aacatgtcct tgtccggacc ctacgttagc 2040
aggatcacca atccctttaa tggtattgcg ctgtacgcca acggagacac agcccgcgct 2100
accgttaact tccccgcaag tcgcaactac aatttccgcc tgcggggttg cggcaacaac 2160
aataatcttg cccgtgtgga cctgaggatc gacggacgga ccgtcgggac cttttattac 2220
cagggcacat acccctggga ggccccaatt gacaatgttt atgtcagtgc ggggagtcat 2280
acagtcgaaa tcactgttac tgcggataac ggcacatggg acgtgtatgc cgactacctg 2340
gtgatacag 2349

<210> SEQ ID NO 38
<211> LENGTH: 2349
<212> TYPE: DNA
<213> ORGANISM: Artificial Sequence
<220> FEATURE:
<223> OTHER INFORMATION: Synthetic construct, S158-30 DNA sequence

<400> SEQUENCE: 38
atgttcctta agaaactgtc taagttgctg ctcgtcgtgc tccttgttgc cgtttacaca 60
caggtcaacg cgcaaacaag cattactctg acatccaacg catccggtac gtttgacggt 120
tactattacg aactctggaa ggatactggc aatacaacaa tgacggtcta cactcaaggt 180
cgcttttcct gccagtggtc gaacatcaat aacgcgttgt ttaggaccgg gaagaaatac 240
aaccagaatt ggcagtctct tggcacaatc cggatcacgt actctgcgac ttacaaccca 300
aacgggaact cctacttgtg tatctatggc tggtctacca acccattggt cgagttctac 360
atcgttgagt cctgggggaa ctggagaccg cctggtgcca cgtccctggg ccaagtgaca 420
atcgatggcg ggacctacga catctatagg acgacacgcg tcaaccagcc ttgcctggcc 480
gagggctcgc tcgtcttgga cgcggctacc gggcagaggg tccctatcga aaaggtgcgt 540
ccggggatgg aagttttctc cttgggacct gattacagac tgtatcgggt gcccgttttg 600
gaggtccttg agagcggggt tagggaagtt gtgcgcctca gaactcggtc agggagaacg 660
ctggtgttga caccagatca cccgcttttg acccccgaag gttggaaacc tctttgtgac 720
ctcccgcttg gaactccaat tgcagtcccc gcagaactgc ctgtggcggg ccacttggcc 780
ccacctgaag aacgtgttac gctcctggct cttctgttgg gggatgggaa cacaaagctg 840
tcgggtcgga gaggtacacg tcctaatgcc ttcttctaca gcaaagaccc cgaattgctc 900
gcggcttatc gccggtgtgc agaagccttg ggtgcaaagg tgaaagcata cgtccacccg 960
actacggggg tggttacact cgcaaccctc gctccacgtc ctggagctca agatcctgtc 1020

```
aaacgcctcg ttgtcgaggc gggaatggtt gctaaagccg aagagaagag ggtcccggag   1080

gaggtgtttc gttaccggcg tgaggcgttg gccctttttct tgggccgttt gttctcgaca   1140

gacggctctg ttgaaaagaa gaggatctct tattcaagtg ccagtttggg actggcccag   1200

gatgtcgcac atctcttgct gcgccttgga attacatctc aactccgttc gagagggcca   1260

cgggctcacg aggttcttat atcgggccgc gaggatattt tgcggtttgc tgaacttatc   1320

ggaccctacc tcttgggggc caagagggag agacttgcag cgctggaagc tgaggcccgc   1380

aggcgtttgc ctggacaggg atggcacttg cggcttgttc ttcctgccgt ggcgtacaga   1440

gtgagcgagg ctaaaaggcg ctcgggattt tcgtggagtg aagccggtcg gcgcgtcgca   1500

gttgcgggat cgtgtttgtc atctggactc aacctcaaat tgcccagacg ctacctttct   1560

cggcaccggt tgtcgatgct cggtgaggct tttgccgacc ctgggctgga agcgctcgcg   1620

gaaggccaag tgctctggga ccctattgtt gctgtcgaac cggccggtaa ggcgagaaca   1680

ttcgacttgc gcgttccacc ctttgcaaac ttcgtgagcg aggacctggt ggtgcataac   1740

tccattgtgg ggacagccac gttcgatcag tactggagcg tgcgcacctc taagcggact   1800

tcaggaacag tgaccgtgac cgatcacttc cgcgcctggg cgaaccgggg cctgaacctc   1860

ggcacaatag accaaattac attgtgcgtg gagggttacc aaagctctgg atcagccaac   1920

atcacccaga acaccttctc tcagggctct tcttccggca gttcgggtgg ctcatccggc   1980

tccacaacga ctactcgcat cgagtgtgag aacatgtcct tgtccggacc ctacgttagc   2040

aggatcacca atccctttaa tggtattgcg ctgtacgcca acggagacac agcccgcgct   2100

accgttaact tccccgcaag tcgcaactac aatttccgcc tgcggggttg cggcaacaac   2160

aataatcttg cccgtgtgga cctgaggatc gacggacgga ccgtcgggac cttttattac   2220

cagggcacat acccctggga ggccccaatt gacaatgttt atgtcagtgc ggggagtcat   2280

acagtcgaaa tcactgttac tgcggataac ggcacatggg acgtgtatgc cgactacctg   2340

gtgatacag                                                           2349
```

<210> SEQ ID NO 39
<211> LENGTH: 24
<212> TYPE: PRT
<213> ORGANISM: Dictyoglomus thermophilum

<400> SEQUENCE: 39

```
Met Phe Leu Lys Lys Leu Ser Lys Leu Leu Leu Val Val Leu Leu Val
1               5                   10                  15

Ala Val Tyr Thr Gln Val Asn Ala
            20
```

<210> SEQ ID NO 40
<211> LENGTH: 433
<212> TYPE: PRT
<213> ORGANISM: Artificial Sequence
<220> FEATURE:
<223> OTHER INFORMATION: Synthetic construct, Tth iXynB clone T134 protein

<400> SEQUENCE: 40

```
Arg Pro Pro Gly Ala Cys Leu Ala Glu Gly Ser Leu Val Leu Asp Ala
1               5                   10                  15

Ala Thr Gly Gln Arg Val Pro Ile Glu Lys Val Arg Pro Gly Met Glu
            20                  25                  30

Val Phe Ser Leu Gly Pro Asp Tyr Arg Leu Tyr Arg Val Pro Val Leu
        35                  40                  45
```

-continued

```
Glu Val Leu Glu Ser Gly Val Arg Glu Val Val Arg Leu Arg Thr Arg
    50                  55                  60

Ser Gly Arg Thr Leu Val Leu Thr Pro Asp His Pro Leu Leu Thr Pro
65                  70                  75                  80

Glu Gly Trp Lys Pro Leu Cys Asp Leu Pro Leu Gly Thr Pro Ile Ala
                85                  90                  95

Val Pro Ala Glu Leu Pro Val Ala Gly His Leu Ala Pro Pro Glu Glu
            100                 105                 110

Arg Val Thr Leu Leu Ala Leu Leu Leu Gly Asp Gly Asn Thr Lys Leu
        115                 120                 125

Ser Gly Arg Arg Gly Thr Arg Pro Asn Ala Phe Phe Tyr Ser Lys Asp
    130                 135                 140

Pro Glu Leu Leu Ala Ala Tyr Arg Arg Cys Ala Glu Ala Leu Gly Ala
145                 150                 155                 160

Lys Val Lys Ala Tyr Val His Pro Thr Thr Gly Val Val Thr Leu Ala
                165                 170                 175

Thr Leu Ala Pro Arg Pro Gly Ala Gln Asp Pro Val Lys Arg Leu Val
            180                 185                 190

Val Glu Ala Gly Met Val Ala Lys Ala Glu Glu Lys Arg Val Pro Glu
        195                 200                 205

Glu Val Phe Arg Tyr Arg Arg Glu Ala Leu Ala Leu Phe Leu Gly Arg
    210                 215                 220

Leu Phe Ser Thr Asp Gly Ser Val Glu Lys Lys Arg Ile Ser Tyr Ser
225                 230                 235                 240

Ser Ala Ser Leu Gly Leu Ala Gln Asp Val Ala His Leu Leu Leu Arg
                245                 250                 255

Leu Gly Ile Thr Ser Gln Leu Arg Ser Arg Gly Pro Arg Ala His Glu
            260                 265                 270

Val Leu Ile Ser Gly Arg Glu Asp Ile Leu Arg Phe Ala Glu Leu Ile
        275                 280                 285

Gly Pro Tyr Leu Leu Gly Ala Lys Arg Glu Arg Leu Ala Ala Leu Glu
    290                 295                 300

Ala Glu Ala Arg Arg Arg Leu Pro Gly Gln Gly Trp His Leu Arg Leu
305                 310                 315                 320

Val Leu Pro Ala Val Ala Tyr Arg Val Ser Glu Ala Lys Arg Arg Ser
                325                 330                 335

Gly Phe Ser Trp Ser Glu Ala Gly Arg Arg Val Ala Val Ala Gly Ser
            340                 345                 350

Cys Leu Ser Ser Gly Leu Asn Leu Lys Leu Pro Arg Arg Tyr Leu Ser
        355                 360                 365

Arg His Arg Leu Ser Leu Leu Gly Glu Ala Phe Ala Asp Pro Gly Leu
    370                 375                 380

Glu Ala Leu Ala Glu Gly Gln Val Leu Trp Asp Pro Ile Val Ala Val
385                 390                 395                 400

Glu Pro Ala Gly Lys Ala Arg Thr Phe Asp Leu Arg Val Pro Pro Phe
                405                 410                 415

Ala Asn Phe Val Ser Glu Asp Leu Val Val His Asn Thr Ser Leu Gly
            420                 425                 430

Gln
```

<210> SEQ ID NO 41
<211> LENGTH: 433
<212> TYPE: PRT

```
<213> ORGANISM: Artificial Sequence
<220> FEATURE:
<223> OTHER INFORMATION: Synthetic construct, Tth iXynB clone S158
      protein

<400> SEQUENCE: 41

Arg Val Asn Gln Pro Cys Leu Ala Glu Gly Ser Leu Val Leu Asp Ala
1               5                   10                  15

Ala Thr Gly Gln Arg Val Pro Ile Glu Lys Val Arg Pro Gly Met Glu
            20                  25                  30

Val Phe Ser Leu Gly Pro Asp Tyr Arg Leu Tyr Arg Val Pro Val Leu
        35                  40                  45

Glu Val Leu Glu Ser Gly Val Arg Glu Val Val Arg Leu Arg Thr Arg
    50                  55                  60

Ser Gly Arg Thr Leu Val Leu Thr Pro Asp His Pro Leu Leu Thr Pro
65                  70                  75                  80

Glu Gly Trp Lys Pro Leu Cys Asp Leu Pro Leu Gly Thr Pro Ile Ala
                85                  90                  95

Val Pro Ala Glu Leu Pro Val Ala Gly His Leu Ala Pro Pro Glu Glu
            100                 105                 110

Arg Val Thr Leu Leu Ala Leu Leu Leu Gly Asp Gly Asn Thr Lys Leu
        115                 120                 125

Ser Gly Arg Arg Gly Thr Arg Pro Asn Ala Phe Phe Tyr Ser Lys Asp
    130                 135                 140

Pro Glu Leu Leu Ala Ala Tyr Arg Arg Cys Ala Glu Ala Leu Gly Ala
145                 150                 155                 160

Lys Val Lys Ala Tyr Val His Pro Thr Thr Gly Val Val Thr Leu Ala
                165                 170                 175

Thr Leu Ala Pro Arg Pro Gly Ala Gln Asp Pro Val Lys Arg Leu Val
            180                 185                 190

Val Glu Ala Gly Met Val Ala Lys Ala Glu Glu Lys Arg Val Pro Glu
        195                 200                 205

Glu Val Phe Arg Tyr Arg Arg Glu Ala Leu Ala Leu Phe Leu Gly Arg
    210                 215                 220

Leu Phe Ser Thr Asp Gly Ser Val Glu Lys Lys Arg Ile Ser Tyr Ser
225                 230                 235                 240

Ser Ala Ser Leu Gly Leu Ala Gln Asp Val Ala His Leu Leu Leu Arg
                245                 250                 255

Leu Gly Ile Thr Ser Gln Leu Arg Ser Arg Gly Pro Arg Ala His Glu
            260                 265                 270

Val Leu Ile Ser Gly Arg Glu Asp Ile Leu Arg Phe Ala Glu Leu Ile
        275                 280                 285

Gly Pro Tyr Leu Leu Gly Ala Lys Arg Glu Arg Leu Ala Ala Leu Glu
    290                 295                 300

Ala Glu Ala Arg Arg Arg Leu Pro Gly Gln Gly Trp His Leu Arg Leu
305                 310                 315                 320

Val Leu Pro Ala Val Ala Tyr Arg Val Ser Glu Ala Lys Arg Arg Ser
                325                 330                 335

Gly Phe Ser Trp Ser Glu Ala Gly Arg Arg Val Ala Val Ala Gly Ser
            340                 345                 350

Cys Leu Ser Ser Gly Leu Asn Leu Lys Leu Pro Arg Arg Tyr Leu Ser
        355                 360                 365

Arg His Arg Leu Ser Leu Leu Gly Glu Ala Phe Ala Asp Pro Gly Leu
    370                 375                 380
```

```
Glu Ala Leu Ala Glu Gly Gln Val Leu Trp Asp Pro Ile Val Ala Val
385                 390                 395                 400

Glu Pro Ala Gly Lys Ala Arg Thr Phe Asp Leu Arg Val Pro Pro Phe
                405                 410                 415

Ala Asn Phe Val Ser Glu Asp Leu Val Val His Asn Ser Ile Val Gly
            420                 425                 430

Thr


<210> SEQ ID NO 42
<211> LENGTH: 57
<212> TYPE: PRT
<213> ORGANISM: Thermus thermophilus

<400> SEQUENCE: 42

Leu Ala Glu Gly Ser Leu Val Leu Asp Ala Ala Thr Gly Gln Arg Val
1               5                   10                  15

Pro Ile Glu Lys Val Arg Pro Gly Met Glu Val Phe Ser Leu Gly Pro
            20                  25                  30

Asp Tyr Arg Leu Tyr Arg Val Pro Val Leu Glu Val Leu Glu Ser Gly
        35                  40                  45

Val Arg Glu Val Val Arg Leu Arg Thr
    50                  55


<210> SEQ ID NO 43
<211> LENGTH: 4
<212> TYPE: PRT
<213> ORGANISM: Thermus thermophilus

<400> SEQUENCE: 43

Leu Ala Glu Gly
1


<210> SEQ ID NO 44
<211> LENGTH: 60
<212> TYPE: PRT
<213> ORGANISM: Mycobacterium tuberculosis

<400> SEQUENCE: 44

Leu Ala Glu Gly Thr Arg Ile Phe Asp Pro Val Thr Gly Thr Thr His
1               5                   10                  15

Arg Ile Glu Asp Val Val Asp Gly Arg Lys Pro Ile His Val Val Ala
            20                  25                  30

Ala Ala Lys Asp Gly Thr Leu His Ala Arg Pro Val Val Ser Trp Phe
        35                  40                  45

Asp Gln Gly Thr Arg Asp Val Ile Gly Leu Arg Ile
    50                  55                  60


<210> SEQ ID NO 45
<211> LENGTH: 60
<212> TYPE: PRT
<213> ORGANISM: Thermus thermophilus

<400> SEQUENCE: 45

Arg Ser Gly Arg Thr Leu Val Leu Thr Pro Asp His Pro Leu Leu Thr
1               5                   10                  15

Pro Glu Gly Trp Lys Pro Leu Cys Asp Leu Pro Leu Gly Thr Pro Ile
            20                  25                  30

Ala Val Pro Ala Glu Leu Pro Val Ala Gly His Leu Ala Pro Pro Glu
        35                  40                  45
```

```
Glu Arg Val Thr Leu Leu Ala Leu Leu Leu Gly Asp
    50                  55                  60


<210> SEQ ID NO 46
<211> LENGTH: 4
<212> TYPE: PRT
<213> ORGANISM: Thermus thermophilus

<400> SEQUENCE: 46

Thr Pro Asp His
1


<210> SEQ ID NO 47
<211> LENGTH: 60
<212> TYPE: PRT
<213> ORGANISM: Mycobacterium tuberculosis

<400> SEQUENCE: 47

Ala Gly Gly Ala Ile Leu Trp Ala Thr Pro Asp His Lys Val Leu Thr
1               5                   10                  15

Glu Tyr Gly Trp Arg Ala Ala Gly Glu Leu Arg Lys Gly Asp Arg Val
            20                  25                  30

Ala Gln Pro Arg Arg Phe Asp Gly Phe Gly Asp Ser Ala Pro Ile Pro
        35                  40                  45

Ala Arg Val Gln Ala Leu Ala Asp Ala Leu Asp Asp
    50                  55                  60


<210> SEQ ID NO 48
<211> LENGTH: 53
<212> TYPE: PRT
<213> ORGANISM: Thermus thermophilus

<400> SEQUENCE: 48

Leu Arg Leu Val Leu Pro Ala Val Ala Tyr Arg Val Ser Glu Ala Lys
1               5                   10                  15

Arg Arg Ser Gly Phe Ser Trp Ser Glu Ala Gly Arg Arg Val Ala Val
            20                  25                  30

Ala Gly Ser Cys Leu Ser Ser Gly Leu Asn Leu Lys Leu Pro Arg Arg
        35                  40                  45

Tyr Leu Ser Arg His
    50


<210> SEQ ID NO 49
<211> LENGTH: 52
<212> TYPE: PRT
<213> ORGANISM: Mycobacterium tuberculosis

<400> SEQUENCE: 49

Leu Arg Ile Ala Gly Gly Ala Ile Leu Trp Ala Thr Pro Asp His Lys
1               5                   10                  15

Val Leu Thr Glu Tyr Gly Trp Arg Ala Ala Gly Glu Leu Arg Lys Gly
            20                  25                  30

Asp Arg Val Ala Gln Pro Arg Arg Phe Asp Gly Phe Gly Asp Ser Ala
        35                  40                  45

Pro Ile Pro Ala
    50


<210> SEQ ID NO 50
<211> LENGTH: 57
<212> TYPE: PRT
<213> ORGANISM: Thermus thermophilus
```

<400> SEQUENCE: 50

Arg Leu Ser Leu Leu Gly Glu Ala Phe Ala Asp Pro Gly Leu Glu Ala
1               5                   10                  15

Leu Ala Glu Gly Gln Val Leu Trp Asp Pro Ile Val Ala Val Glu Pro
            20                  25                  30

Ala Gly Lys Ala Arg Thr Phe Asp Leu Arg Val Pro Pro Phe Ala Asn
        35                  40                  45

Phe Val Ser Glu Asp Leu Val Val His
    50                  55

<210> SEQ ID NO 51
<211> LENGTH: 6
<212> TYPE: PRT
<213> ORGANISM: Thermus thermophilus

<400> SEQUENCE: 51

Ala Arg Thr Phe Asp Leu
1               5

<210> SEQ ID NO 52
<211> LENGTH: 57
<212> TYPE: PRT
<213> ORGANISM: Mycobacterium tuberculosis

<400> SEQUENCE: 52

Arg Val Gln Ala Leu Ala Asp Ala Leu Asp Asp Lys Phe Leu His Asp
1               5                   10                  15

Met Leu Ala Glu Glu Leu Arg Tyr Ser Val Ile Arg Glu Val Leu Pro
            20                  25                  30

Thr Arg Arg Ala Arg Thr Phe Asp Leu Glu Val Glu Glu Leu His Thr
        35                  40                  45

Leu Val Ala Glu Gly Val Val Val His
    50                  55

<210> SEQ ID NO 53
<211> LENGTH: 46
<212> TYPE: PRT
<213> ORGANISM: Thermus thermophilus

<400> SEQUENCE: 53

Arg Ser Gly Arg Thr Leu Val Leu Thr Pro Asp His Pro Leu Leu Thr
1               5                   10                  15

Pro Glu Gly Trp Lys Pro Leu Cys Asp Leu Pro Leu Gly Thr Pro Ile
            20                  25                  30

Ala Val Pro Ala Glu Leu Pro Val Ala Gly His Leu Ala Asp
        35                  40                  45

<210> SEQ ID NO 54
<211> LENGTH: 46
<212> TYPE: PRT
<213> ORGANISM: Thermus thermophilus

<400> SEQUENCE: 54

Pro Gly Leu Glu Ala Leu Ala Glu Gly Gln Val Leu Trp Asp Pro Ile
1               5                   10                  15

Val Ala Val Glu Pro Ala Gly Lys Ala Arg Thr Phe Asp Leu Arg Val
            20                  25                  30

Pro Pro Phe Ala Asn Phe Val Ser Glu Asp Leu Val Val His
        35                  40                  45

<210> SEQ ID NO 55
<211> LENGTH: 46
<212> TYPE: PRT
<213> ORGANISM: Mycobacterium tuberculosis

<400> SEQUENCE: 55

Lys Phe Leu His Asp Met Leu Ala Glu Glu Leu Arg Tyr Ser Val Ile
1 5 10 15

Arg Glu Val Leu Pro Thr Arg Arg Ala Arg Thr Phe Asp Leu Glu Val
20 25 30

Glu Glu Leu His Thr Leu Val Ala Glu Gly Val Val Val His
35 40 45

<210> SEQ ID NO 56
<211> LENGTH: 9983
<212> TYPE: DNA
<213> ORGANISM: Artificial Sequence
<220> FEATURE:
<223> OTHER INFORMATION: Synthetic construct, pAG2004 vector

<400> SEQUENCE: 56
ccgatggccg agctgtggat gggcgcacat ccgaaaagca gttcacgagt gcagaatgcc 60
gccggagata tcgtttcact gcgtgatgtg attgagagtg ataaatcgac tctgctcgga 120
gaggccgttg ccaaacgctt tggcgaactg cctttcctgt tcaaagtatt atgcgcagca 180
cagccactct ccattcaggt tcatccaaac aaacacaatt ctgaaatcgg ttttgccaaa 240
gaaaatgccg caggtatccc gatggatgcc gccgagcgta actataaaga tcctaaccac 300
aagccggagc tggtttttgc gctgacgcct ttccttgcga tgaacgcgtt tcgtgaattt 360
tccgagattg tctccctact ccagccggtc gcaggtgcac atccggcgat tgctcacttt 420
ttacaacagc ctgatgccga acgtttaagc gaactgttcg ccagcctgtt gaatatgcag 480
ggtgaagaaa aatcccgcgc gctggcgatt ttaaaatcgg ccctcgatag ccagcagggt 540
gaaccgtggc aaacgattcg tttaatttct gaattttacc cggaagacag cggtctgttc 600
tccccgctat tgctgaatgt ggtgaaattg aaccctggcg aagcgatgtt cctgttcgct 660
gaaacaccgc acgcttacct gcaaggcgtg gcgctggaag tgatggcaaa ctccgataac 720
gtgctgcgtg cgggtctgac gcctaaatac attgatattc cggaactggt tgccaatgtg 780
aaattcgaag ccaaaccggc taaccagttg ttgacccagc cggtgaaaca aggtgcagaa 840
ctggacttcc cgattccagt ggatgatttt gccttctcgc tgcatgacct tagtgataaa 900
gaaaccacca ttagccagca gagtgccgcc attttgttct gcgtcgaagg cgatgcaacg 960
ttgtggaaag gttctcagca gttacagctt aaaccgggtg aatcagcgtt tattgccgcc 1020
aacgaatcac cggtgactgt caaaggccac ggccgtttag cgcgtgttta caacaagctg 1080
taagagctta ctgaaaaaat taacatctct tgctaagctg ggagctctag atccccgaat 1140
ttccccgatc gttcaaacat ttggcaataa agtttcttaa gattgaatcc tgttgccggt 1200
cttgcgatga ttatcatata atttctgttg aattacgtta agcatgtaat aattaacatg 1260
taatgcatga cgttatttat gagatgggtt tttatgatta gagtcccgca attatacatt 1320
taatacgcga tagaaaacaa aatatagcgc gcaaactagg ataaattatc gcgcgcggtg 1380
tcatctatgt tactagatcg ggaattggcg agctcgaatt aattcagtac attaaaaacg 1440
tccgcaatgt gttattaagt tgtctaagcg tcaatttgtt tacaccacaa tatatcctgc 1500
caccagccag ccaacagctc cccgaccggc agctcggcac aaaatcacca ctcgatacag 1560

```
gcagcccatc agtccgggac ggcgtcagcg ggagagccgt tgtaaggcgg cagactttgc   1620
tcatgttacc gatgctattc ggaagaacgg caactaagct gccgggtttg aaacacggat   1680
gatctcgcgg agggtagcat gttgattgta acgatgacag agcgttgctg cctgtgatca   1740
aatatcatct ccctcgcaga gatccgaatt atcagccttc ttattcattt ctcgcttaac   1800
cgtgacaggc tgtcgatctt gagaactatg ccgacataat aggaaatcgc tggataaagc   1860
cgctgaggaa gctgagtggc gctatttctt tagaagtgaa cgttgacgat cgtcgaccgt   1920
accccgatga attaattcgg acgtacgttc tgaacacagc tggatactta cttgggcgat   1980
tgtcatacat gacatcaaca atgtacccgt ttgtgtaacc gtctcttgga ggttcgtatg   2040
acactagtgg ttcccctcag cttgcgacta gatgttgagg cctaacattt tattagagag   2100
caggctagtt gcttagatac atgatcttca ggccgttatc tgtcagggca agcgaaaatt   2160
ggccatttat gacgaccaat gccccgcaga agctcccatc tttgccgcca tagacgccgc   2220
gcccccctt tggggtgtag aacatccttt tgccagatgt ggaaaagaag ttcgttgtcc   2280
cattgttggc aatgacgtag tagccggcga aagtgcgaga cccatttgcg ctatatataa   2340
gcctacgatt tccgttgcga ctattgtcgt aattggatga actattatcg tagttgctct   2400
cagagttgtc gtaatttgat ggactattgt cgtaattgct tatggagttg tcgtagttgc   2460
ttggagaaat gtcgtagttg gatggggagt agtcataggg aagacgagct tcatccacta   2520
aaacaattgg caggtcagca agtgcctgcc ccgatgccat cgcaagtacg aggcttagaa   2580
ccaccttcaa cagatcgcgc atagtcttcc ccagctctct aacgcttgag ttaagccgcg   2640
ccgcgaagcg gcgtcggctt gaacgaattg ttagacatta tttgccgact accttggtga   2700
tctcgccttt cacgtagtga acaaattctt ccaactgatc tgcgcgcgag gccaagcgat   2760
cttcttgtcc aagataagcc tgcctagctt caagtatgac gggctgatac tgggccggca   2820
ggcgctccat tgcccagtcg gcagcgacat ccttcggcgc gattttgccg gttactgcgc   2880
tgtaccaaat gcgggacaac gtaagcacta catttcgctc atcgccagcc cagtcgggcg   2940
gcgagttcca tagcgttaag gtttcattta gcgcctcaaa tagatcctgt tcaggaaccg   3000
gatcaaagag ttcctccgcc gctggaccta ccaaggcaac gctatgttct cttgcttttg   3060
tcagcaagat agccagatca atgtcgatcg tggctggctc gaagatacct gcaagaatgt   3120
cattgcgctg ccattctcca aattgcagtt cgcgcttagc tggataacgc cacggaatga   3180
tgtcgtcgtg cacaacaatg gtgacttcta cagcgcggag aatctcgctc tctccagggg   3240
aagccgaagt ttccaaaagg tcgttgatca aagctcgccg cgttgtttca tcaagcctta   3300
cggtcaccgt aaccagcaaa tcaatatcac tgtgtggctt caggccgcca tccactgcgg   3360
agccgtacaa atgtacggcc agcaacgtcg gttcgagatg gcgctcgatg acgccaacta   3420
cctctgatag ttgagtcgat acttcggcga tcaccgcttc cctcatgatg tttaactcct   3480
gaattaagcc gcgccgcgaa gcggtgtcgg cttgaatgaa ttgttaggcg tcatcctgtg   3540
ctcccgagaa ccagtaccag tacatcgctg tttcgttcga gacttgaggt ctagttttat   3600
acgtgaacag gtcaatgccg ccgagagtaa agccacattt tgcgtacaaa ttgcaggcag   3660
gtacattgtt cgtttgtgtc tctaatcgta tgccaaggag ctgtctgctt agtgcccact   3720
ttttcgcaaa ttcgatgaga ctgtgcgcga ctcctttgcc tcggtgcgtg tgcgacacaa   3780
caatgtgttc gatagaggct agatcgttcc atgttgagtt gagttcaatc ttcccgacaa   3840
gctcttggtc gatgaatgcg ccatagcaag cagagtcttc atcagagtca tcatccgaga   3900
```

-continued

```
tgtaatcctt ccggtagggg ctcacacttc tggtagatag ttcaaagcct tggtcggata   3960
ggtgcacatc gaacacttca cgaacaatga aatggttctc agcatccaat gtttccgcca   4020
cctgctcagg gatcaccgaa atcttcatat gacgcctaac gcctggcaca gcggatcgca   4080
aacctggcgc ggcttttggc acaaaaggcg tgacaggttt gcgaatccgt tgctgccact   4140
tgttaaccct tttgccagat ttggtaacta taatttatgt tagaggcgaa gtcttgggta   4200
aaaactggcc taaaattgct ggggatttca ggaaagtaaa catcaccttc cggctcgatg   4260
tctattgtag atatatgtag tgtatctact tgatcggggg atctgctgcc tcgcgcgttt   4320
cggtgatgac ggtgaaaacc tctgacacat gcagctcccg gagacggtca cagcttgtct   4380
gtaagcggat gccgggagca gacaagcccg tcagggcgcg tcagcgggtg ttggcgggtg   4440
tcggggcgca gccatgaccc agtcacgtag cgatagcgga gtgtatactg gcttaactat   4500
gcggcatcag agcagattgt actgagagtg caccatatgc ggtgtgaaat accgcacaga   4560
tgcgtaagga gaaaataccg catcaggcgc tcttccgctt cctcgctcac tgactcgctg   4620
cgctcggtcg ttcggctgcg gcgagcggta tcagctcact caaaggcggt aatacggtta   4680
tccacagaat caggggataa cgcaggaaag aacatgtgag caaaaggcca gcaaaaggcc   4740
aggaaccgta aaaaggccgc gttgctggcg tttttccata ggctccgccc ccctgacgag   4800
catcacaaaa atcgacgctc aagtcagagg tggcgaaacc cgacaggact ataaagatac   4860
caggcgtttc cccctggaag ctccctcgtg cgctctcctg ttccgaccct gccgcttacc   4920
ggatacctgt ccgcctttct cccttcggga agcgtggcgc tttctcatag ctcacgctgt   4980
aggtatctca gttcggtgta ggtcgttcgc tccaagctgg gctgtgtgca cgaacccccc   5040
gttcagcccg accgctgcgc cttatccggt aactatcgtc ttgagtccaa cccggtaaga   5100
cacgacttat cgccactggc agcagccact ggtaacagga ttagcagagc gaggtatgta   5160
ggcggtgcta cagagttctt gaagtggtgg cctaactacg gctacactag aaggacagta   5220
tttggtatct gcgctctgct gaagccagtt accttcggaa aaagagttgg tagctcttga   5280
tccggcaaac aaaccaccgc tggtagcggt ggtttttttg tttgcaagca gcagattacg   5340
cgcagaaaaa aaggatctca agaagatcct ttgatctttt ctacggggtc tgacgctcag   5400
tggaacgaaa actcacgtta agggattttg gtcatgagat tatcaaaaag gatcttcacc   5460
tagatccttt taaattaaaa atgaagtttt aaatcaatct aaagtatata tgagtaaact   5520
tggtctgaca gttaccaatg cttaatcagt gaggcaccta tctcagcgat ctgtctattt   5580
cgttcatcca tagttgcctg actccccgtc gtgtagataa ctacgatacg ggagggctta   5640
ccatctggcc ccagtgctgc aatgataccg cgagacccac gctcaccggc tccagattta   5700
tcagcaataa accagccagc cggaagggcc gagcgcagaa gtggtcctgc aactttatcc   5760
gcctccatcc agtctattaa ttgttgccgg gaagctagag taagtagttc gccagttaat   5820
agtttgcgca acgttgttgc cattgctgca gggggggggg ggggggggtt ccattgttca   5880
ttccacggac aaaaacagag aaaggaaacg acagaggcca aaaagctcgc tttcagcacc   5940
tgtcgtttcc tttcttttca gagggtattt taaataaaaa cattaagtta tgacgaagaa   6000
gaacggaaac gccttaaacc ggaaaatttt cataaatagc gaaaacccgc gaggtcgccg   6060
ccccgtaacc tgtcggatca ccggaaagga cccgtaaagt gataatgatt atcatctaca   6120
tatcacaacg tgcgtggagg ccatcaaacc acgtcaaata atcaattatg acgcaggtat   6180
cgtattaatt gatctgcatc aacttaacgt aaaaacaact tcagacaata caaatcagcg   6240
acactgaata cggggcaacc tcatgtcccc cccccccccc ccctgcaggc atcgtggtgt   6300
```

```
cacgctcgtc gtttggtatg gcttcattca gctccggttc ccaacgatca aggcgagtta   6360
catgatcccc catgttgtgc aaaaaagcgg ttagctcctt cggtcctccg atcgttgtca   6420
gaagtaagtt ggccgcagtg ttatcactca tggttatggc agcactgcat aattctctta   6480
ctgtcatgcc atccgtaaga tgcttttctg tgactggtga gtactcaacc aagtcattct   6540
gagaatagtg tatgcggcga ccgagttgct cttgcccggc gtcaacacgg gataataccg   6600
cgccacatag cagaacttta aaagtgctca tcattggaaa acgttcttcg gggcgaaaac   6660
tctcaaggat cttaccgctg ttgagatcca gttcgatgta acccactcgt gcacccaact   6720
gatcttcagc atcttttact ttcaccagcg tttctgggtg agcaaaaaca ggaaggcaaa   6780
atgccgcaaa aaagggaata agggcgacac ggaaatgttg aatactcata ctcttccttt   6840
ttcaatatta ttgaagcatt tatcagggtt attgtctcat gagcggatac atatttgaat   6900
gtatttagaa aaataaacaa ataggggttc cgcgcacatt tccccgaaaa gtgccacctg   6960
acgtctaaga aaccattatt atcatgacat taacctataa aaataggcgt atcacgaggc   7020
cctttcgtct tcaagaattg gtcgacgatc ttgctgcgtt cggatatttt cgtggagttc   7080
ccgccacaga cccggattga aggcgagatc cagcaactcg cgccagatca tcctgtgacg   7140
gaactttggc gcgtgatgac tggccaggac gtcggccgaa agagcgacaa gcagatcacg   7200
cttttcgaca gcgtcggatt tgcgatcgag gatttttcgg cgctgcgcta cgtccgcgac   7260
cgcgttgagg gatcaagcca cagcagccca ctcgaccttc tagccgaccc agacgagcca   7320
agggatcttt ttggaatgct gctccgtcgt caggctttcc gacgtttggg tggttgaaca   7380
gaagtcatta tcgcacggaa tgccaagcac tcccgagggg aaccctgtgg ttggcatgca   7440
catacaaatg gacgaacgga taaacctttt cacgcccttt taaatatccg attattctaa   7500
taaacgctct tttctcttag gtttacccgc caatatatcc tgtcaaacac tgatagttta   7560
aactgaaggc gggaaacgac aacctgatca tgagcggaga attaagggag tcacgttatg   7620
acccccgccg atgacgcggg acaagccgtt ttacgtttgg aactgacaga accgcaacgt   7680
tgaaggagcc actcagctta attaagtcta actcgagtta ctggtacgta ccaaatccat   7740
ggaatcaagg taccatcaat cccgggtatt catcctaggt atccaagaat tcatactaaa   7800
gcttgcatgc ctgcaggtcg actctagtaa cggccgccag tgtgctggaa ttaattcggc   7860
ttgtcgacca cccaacccca tatcgacaga ggatgtgaag aacaggtaaa tcacgcagaa   7920
gaacccatct ctgatagcag ctatcgatta gaacaacgaa tccatattgg gtccgtggga   7980
aatacttact gcacaggaag gggcgatct gacgaggccc cgccaccggc ctcgacccga    8040
ggccgaggcc gacgaagcgc cggcgagtac ggcgccgcgg cggcctctgc ccgtgccctc   8100
tgcgcgtggg agggagaggc cgcggtggtg gggcgcgcg cgcgcgcgcg cgcagctggt    8160
gcggcggcgc gggggtcagc cgccgagccg gcggcgacgg aggagcaggg cggcgtggac   8220
gcgaacttcc gatcggttgg tcagagtgcg cgagttgggc ttagccaatt aggtctcaac   8280
aatctattgg gccgtaaaat tcatgggccc tggtttgtct aggcccaata tcccgttcat   8340
ttcagcccac aaatatttcc ccagaggatt attaaggccc acacgcagct tatagcagat   8400
caagtacgat gtttcctgat cgttggatcg gaaacgtacg gtcttgatca ggcatgccga   8460
cttcgtcaaa gagaggcggc atgacctgac gcggagttgg ttccgggcac cgtctggatg   8520
gtcgtaccgg gaccggacac gtgtcgcgcc tccaactaca tggacacgtg tggtgctgcc   8580
attgggccgt acgcgtggcg gtgaccgcac cggatgctgc ctcgcaccgc cttgcccacg   8640
```

ctttatatag agaggttttc tctccattaa tcgcatagcg agtcgaatcg accgaagggg 8700
agggggagcg aagctttgcg ttctctaatc gcctcgtcaa ggtaactaat caatcacctc 8760
gtcctaatcc tcgaatctct cgtggtgccc gtctaatctc gcgattttga tgctcgtggt 8820
ggaaagcgta ggaggatccc gtgcgagtta gtctcaatct ctcagggttt cgtgcgattt 8880
tagggtgatc cacctcttaa tcgagttacg gtttcgtgcg attttagggt aatcctctta 8940
atctctcatt gatttagggt ttcgtgagaa tcgaggtagg gatctgtgtt atttatatcg 9000
atctaataga tggattggtt ttgagattgt tctgtcagat ggggattgtt tcgatatatt 9060
accctaatga tgtgtcagat ggggattgtt tcgatatatt accctaatga tgtgtcagat 9120
ggggattgtt tcgatatatt accctaatga tggataataa gagtagttca cagttatgtt 9180
ttgatcctgc cacatagttt gagttttgtg atcagattta gttttactta tttgtgctta 9240
gttcggatgg gattgttctg atattgttcc aatagatgaa tagctcgtta ggttaaaatc 9300
tttaggttga gttaggcgac acatagttta tttcctctgg atttggattg gaattgtgtt 9360
cttagttttt ttcccctgga tttggattgg aattgtgtgg agctgggtta gagaattaca 9420
tctgtatcgt gtacacctac ttgaactgta gagcttgggt tctaaggtca atttaatctg 9480
tattgtatct ggctctttgc ctagttgaac tgtagtgctg atgttgtact gtgttttttt 9540
acccgtttta tttgctttac tcgtgcaaat caaatctgtc agatgctaga actaggtggc 9600
tttattctgt gttcttacat agatctgttg tcctgtagtt acttatgtca gttttgttat 9660
tatctgaaga tatttttggt tgttgcttgt tgatgtggtg tgagctgtga gcagcgctct 9720
tatgattaat gatgctgtcc aattgtagtg tagtatgatg tgattgatat gttcatctat 9780
tttgagctga cagtaccgat atcgtaggat ctggtgccaa cttattctcc agctgctttt 9840
ttttacctat gttaattcca atcctttctt gcctcttcca gatccagata atgcagaaac 9900
tcattaactc agtgcaaaac tatgcctggg gcagcaaaac ggcgttgact gaactttatg 9960
gtatggaaaa tccgtccagc cag 9983

<210> SEQ ID NO 57
<211> LENGTH: 13393
<212> TYPE: DNA
<213> ORGANISM: Artificial Sequence
<220> FEATURE:
<223> OTHER INFORMATION: Synthetic construct, pAG2014 vector

<400> SEQUENCE: 57
aattcatact aaagcttgca tgcctgcagg tcgactctag taacggccgc cagtgtgctg 60
gaattaattc ggcttgtcga ccacccaacc ccatatcgac agaggatgtg aagaacaggt 120
aaatcacgca gaagaaccca tctctgatag cagctatcga ttagaacaac gaatccatat 180
tgggtccgtg ggaaatactt actgcacagg aagggggcga tctgacgagg ccccgccacc 240
ggcctcgacc cgaggccgag gccgacgaag cgccggcgag tacggcgccg cggcggcctc 300
tgcccgtgcc ctctgcgcgt gggagggaga ggccgcggtg gtgggggcgc gcgcgcgcgc 360
gcgcgcagct ggtgcggcgg cgcgggggtc agccgccgag ccggcggcga cggaggagca 420
gggcggcgtg gacgcgaact tccgatcggt tggtcagagt gcgcgagttg ggcttagcca 480
attaggtctc aacaatctat tgggccgtaa aattcatggg ccctggtttg tctaggccca 540
atatcccgtt catttcagcc cacaaatatt tccccagagg attattaagg cccacacgca 600
gcttatagca gatcaagtac gatgtttcct gatcgttgga tcggaaacgt acggtcttga 660
tcaggcatgc cgacttcgtc aaagagaggc ggcatgacct gacgcggagt tggttccggg 720
caccgtctgg atggtcgtac cgggaccgga cacgtgtcgc gcctccaact acatggacac 780
gtgtggtgct gccattgggc cgtacgcgtg gcggtgaccg caccggatgc tgcctcgcac 840
cgccttgccc acgctttata tagagaggtt ttctctccat taatcgcata gcgagtcgaa 900
tcgaccgaag gggaggggga gcgaagcttt gcgttctcta atcgcctcgt caaggtaact 960
aatcaatcac ctcgtcctaa tcctcgaatc tctcgtggtg cccgtctaat ctcgcgattt 1020
tgatgctcgt ggtggaaagc gtaggaggat cccgtgcgag ttagtctcaa tctctcaggg 1080
tttcgtgcga ttttagggtg atccacctct taatcgagtt acggtttcgt gcgattttag 1140
ggtaatcctc ttaatctctc attgatttag ggtttcgtga gaatcgaggt agggatctgt 1200
gttatttata tcgatctaat agatggattg gttttgagat tgttctgtca gatggggatt 1260
gtttcgatat attaccctaa tgatgtgtca gatggggatt gtttcgatat attaccctaa 1320
tgatgtgtca gatggggatt gtttcgatat attaccctaa tgatggataa taagagtagt 1380
tcacagttat gttttgatcc tgccacatag tttgagtttt gtgatcagat ttagttttac 1440
ttatttgtgc ttagttcgga tgggattgtt ctgatattgt tccaatagat gaatagctcg 1500
ttaggttaaa atctttaggt tgagttaggc gacacatagt ttatttcctc tggatttgga 1560
ttggaattgt gttcttagtt tttttcccct ggatttggat tggaattgtg tggagctggg 1620
ttagagaatt acatctgtat cgtgtacacc tacttgaact gtagagcttg ggttctaagg 1680
tcaatttaat ctgtattgta tctggctctt tgcctagttg aactgtagtg ctgatgttgt 1740
actgtgtttt tttacccgtt ttatttgctt tactcgtgca aatcaaatct gtcagatgct 1800
agaactaggt ggctttattc tgtgttctta catagatctg ttgtcctgta gttacttatg 1860
tcagttttgt tattatctga agatattttt ggttgttgct tgttgatgtg gtgtgagctg 1920
tgagcagcgc tcttatgatt aatgatgctg tccaattgta gtgtagtatg atgtgattga 1980
tatgttcatc tattttgagc tgacagtacc gatatcgtag gatctggtgc caacttattc 2040
tccagctgct ttttttacc tatgttaatt ccaatccttt cttgcctctt ccagatccag 2100
ataatgcaga aactcattaa ctcagtgcaa aactatgcct ggggcagcaa aacggcgttg 2160
actgaacttt atggtatgga aaatccgtcc agccagccga tggccgagct gtggatgggc 2220
gcacatccga aaagcagttc acgagtgcag aatgccgccg gagatatcgt ttcactgcgt 2280
gatgtgattg agagtgataa atcgactctg ctcggagagg ccgttgccaa acgctttggc 2340
gaactgcctt tcctgttcaa agtattatgc gcagcacagc cactctccat tcaggttcat 2400
ccaaacaaac acaattctga aatcggtttt gccaaagaaa atgccgcagg tatcccgatg 2460
gatgccgccg agcgtaacta taaagatcct aaccacaagc cggagctggt ttttgcgctg 2520
acgcctttcc ttgcgatgaa cgcgtttcgt gaattttccg agattgtctc cctactccag 2580
ccggtcgcag gtgcacatcc ggcgattgct cactttttac aacagcctga tgccgaacgt 2640
ttaagcgaac tgttcgccag cctgttgaat atgcagggtg aagaaaaatc ccgcgcgctg 2700
gcgattttaa aatcggccct cgatagccag cagggtgaac cgtggcaaac gattcgttta 2760
atttctgaat tttacccgga agacagcggt ctgttctccc cgctattgct gaatgtggtg 2820
aaattgaacc ctggcgaagc gatgttcctg ttcgctgaaa caccgcacgc ttacctgcaa 2880
ggcgtggcgc tggaagtgat ggcaaactcc gataacgtgc tgcgtgcggg tctgacgcct 2940
aaatacattg atattccgga actggttgcc aatgtgaaat tcgaagccaa accggctaac 3000
cagttgttga cccagccggt gaaacaaggt gcagaactgg acttcccgat tccagtggat 3060

-continued gattttgcct tctcgctgca tgaccttagt gataaagaaa ccaccattag ccagcagagt 3120
gccgccattt tgttctgcgt cgaaggcgat gcaacgttgt ggaaaggttc tcagcagtta 3180
cagcttaaac cgggtgaatc agcgtttatt gccgccaacg aatcaccggt gactgtcaaa 3240
ggccacggcc gtttagcgcg tgtttacaac aagctgtaag agcttactga aaaaattaac 3300
atctcttgct aagctgggag ctctagatcc ccgaatttcc ccgatcgttc aaacatttgg 3360
caataaagtt tcttaagatt gaatcctgtt gccggtcttg cgatgattat catataattt 3420
ctgttgaatt acgttaagca tgtaataatt aacatgtaat gcatgacgtt atttatgaga 3480
tgggttttta tgattagagt cccgcaatta tacatttaat acgcgataga aaacaaaata 3540
tagcgcgcaa actaggataa attatcgcgc gcggtgtcat ctatgttact agatcgggaa 3600
ttggcgagct cgaattaatt cagtacatta aaaacgtccg caatgtgtta ttaagttgtc 3660
taagcgtcaa tttgtttaca ccacaatata tcctgccacc agccagccaa cagctccccg 3720
accggcagct cggcacaaaa tcaccactcg atacaggcag cccatcagtc cgggacggcg 3780
tcagcgggag agccgttgta aggcggcaga ctttgctcat gttaccgatg ctattcggaa 3840
gaacggcaac taagctgccg ggtttgaaac acggatgatc tcgcggaggg tagcatgttg 3900
attgtaacga tgacagagcg ttgctgcctg tgatcaaata tcatctccct cgcagagatc 3960
cgaattatca gccttcttat tcatttctcg cttaaccgtg acaggctgtc gatcttgaga 4020
actatgccga cataatagga aatcgctgga taaagccgct gaggaagctg agtggcgcta 4080
tttctttaga agtgaacgtt gacgatcgtc gaccgtaccc cgatgaatta attcggacgt 4140
acgttctgaa cacagctgga tacttacttg ggcgattgtc atacatgaca tcaacaatgt 4200
acccgtttgt gtaaccgtct cttggaggtt cgtatgacac tagtggttcc cctcagcttg 4260
cgactagatg ttgaggccta acattttatt agagagcagg ctagttgctt agatacatga 4320
tcttcaggcc gttatctgtc agggcaagcg aaaattggcc atttatgacg accaatgccc 4380
cgcagaagct cccatctttg ccgccataga cgccgcgccc ccttttgggg gtgtagaaca 4440
tccttttgcc agatgtggaa aagaagttcg ttgtcccatt gttggcaatg acgtagtagc 4500
cggcgaaagt gcgagaccca tttgcgctat atataagcct acgatttccg ttgcgactat 4560
tgtcgtaatt ggatgaacta ttatcgtagt tgctctcaga gttgtcgtaa tttgatggac 4620
tattgtcgta attgcttatg gagttgtcgt agttgcttgg agaaatgtcg tagttggatg 4680
gggagtagtc atagggaaga cgagcttcat ccactaaaac aattggcagg tcagcaagtg 4740
cctgccccga tgccatcgca agtacgaggc ttagaaccac cttcaacaga tcgcgcatag 4800
tcttccccag ctctctaacg cttgagttaa gccgcgccgc gaagcggcgt cggcttgaac 4860
gaattgttag acattatttg ccgactacct tggtgatctc gcctttcacg tagtgaacaa 4920
attcttccaa ctgatctgcg cgcgaggcca agcgatcttc ttgtccaaga taagcctgcc 4980
tagcttcaag tatgacgggc tgatactggg ccggcaggcg ctccattgcc cagtcggcag 5040
cgacatcctt cggcgcgatt ttgccggtta ctgcgctgta ccaaatgcgg gacaacgtaa 5100
gcactacatt tcgctcatcg ccagcccagt cgggcggcga gttccatagc gttaaggttt 5160
catttagcgc ctcaaataga tcctgttcag gaaccggatc aaagagttcc tccgccgctg 5220
gacctaccaa ggcaacgcta tgttctcttg cttttgtcag caagatagcc agatcaatgt 5280
cgatcgtggc tggctcgaag atacctgcaa gaatgtcatt gcgctgccat tctccaaatt 5340
gcagttcgcg cttagctgga taacgccacg gaatgatgtc gtcgtgcaca acaatggtga 5400
cttctacagc gcggagaatc tcgctctctc caggggaagc cgaagtttcc aaaaggtcgt 5460

```
tgatcaaagc tcgccgcgtt gtttcatcaa gccttacggt caccgtaacc agcaaatcaa   5520
tatcactgtg tggcttcagg ccgccatcca ctgcggagcc gtacaaatgt acggccagca   5580
acgtcggttc gagatggcgc tcgatgacgc caactacctc tgatagttga gtcgatactt   5640
cggcgatcac cgcttccctc atgatgttta actcctgaat taagccgcgc cgcgaagcgg   5700
tgtcggcttg aatgaattgt taggcgtcat cctgtgctcc cgagaaccag taccagtaca   5760
tcgctgtttc gttcgagact tgaggtctag ttttatacgt gaacaggtca atgccgccga   5820
gagtaaagcc acattttgcg tacaaattgc aggcaggtac attgttcgtt tgtgtctcta   5880
atcgtatgcc aaggagctgt ctgcttagtg cccacttttt cgcaaattcg atgagactgt   5940
gcgcgactcc tttgcctcgg tgcgtgtgcg acacaacaat gtgttcgata gaggctagat   6000
cgttccatgt tgagttgagt tcaatcttcc cgacaagctc ttggtcgatg aatgcgccat   6060
agcaagcaga gtcttcatca gagtcatcat ccgagatgta atccttccgg taggggctca   6120
cacttctggt agatagttca aagccttggt cggataggtg cacatcgaac acttcacgaa   6180
caatgaaatg gttctcagca tccaatgttt ccgccacctg ctcagggatc accgaaatct   6240
tcatatgacg cctaacgcct ggcacagcgg atcgcaaacc tggcgcggct tttggcacaa   6300
aaggcgtgac aggtttgcga atccgttgct gccacttgtt aaccctttttg ccagatttgg   6360
taactataat ttatgttaga ggcgaagtct tgggtaaaaa ctggcctaaa attgctgggg   6420
atttcaggaa agtaaacatc accttccggc tcgatgtcta ttgtagatat atgtagtgta   6480
tctacttgat cgggggatct gctgcctcgc gcgtttcggt gatgacggtg aaaacctctg   6540
acacatgcag ctcccggaga cggtcacagc ttgtctgtaa gcggatgccg ggagcagaca   6600
agcccgtcag ggcgcgtcag cgggtgttgg cgggtgtcgg ggcgcagcca tgacccagtc   6660
acgtagcgat agcggagtgt atactggctt aactatgcgg catcagagca gattgtactg   6720
agagtgcacc atatgcggtg tgaaataccg cacagatgcg taaggagaaa ataccgcatc   6780
aggcgctctt ccgcttcctc gctcactgac tcgctgcgct cggtcgttcg gctgcggcga   6840
gcggtatcag ctcactcaaa ggcggtaata cggttatcca cagaatcagg ggataacgca   6900
ggaaagaaca tgtgagcaaa aggccagcaa aaggccagga accgtaaaaa ggccgcgttg   6960
ctggcgtttt tccataggct ccgcccccct gacgagcatc acaaaaatcg acgctcaagt   7020
cagaggtggc gaaacccgac aggactataa agataccagg cgtttccccc tggaagctcc   7080
ctcgtgcgct ctcctgttcc gaccctgccg cttaccggat acctgtccgc ctttctccct   7140
tcgggaagcg tggcgctttc tcatagctca cgctgtaggt atctcagttc ggtgtaggtc   7200
gttcgctcca agctgggctg tgtgcacgaa ccccccgttc agcccgaccg ctgcgcctta   7260
tccggtaact atcgtcttga gtccaacccg gtaagacacg acttatcgcc actggcagca   7320
gccactggta acaggattag cagagcgagg tatgtaggcg gtgctacaga gttcttgaag   7380
tggtggccta actacggcta cactagaagg acagtatttg gtatctgcgc tctgctgaag   7440
ccagttacct tcggaaaaag agttggtagc tcttgatccg gcaaacaaac caccgctggt   7500
agcggtggtt tttttgtttg caagcagcag attacgcgca gaaaaaaagg atctcaagaa   7560
gatcctttga tcttttctac ggggtctgac gctcagtgga acgaaaactc acgttaaggg   7620
attttggtca tgagattatc aaaaaggatc ttcacctaga tccttttaaa ttaaaaatga   7680
agttttaaat caatctaaag tatatatgag taaacttggt ctgacagtta ccaatgctta   7740
atcagtgagg cacctatctc agcgatctgt ctatttcgtt catccatagt tgcctgactc   7800
```

-continued

```
cccgtcgtgt agataactac gatacgggag ggcttaccat ctggccccag tgctgcaatg   7860
ataccgcgag acccacgctc accggctcca gatttatcag caataaacca gccagccgga   7920
agggccgagc gcagaagtgg tcctgcaact ttatccgcct ccatccagtc tattaattgt   7980
tgccgggaag ctagagtaag tagttcgcca gttaatagtt tgcgcaacgt tgttgccatt   8040
gctgcagggg gggggggggg ggggttccat tgttcattcc acggacaaaa acagagaaag   8100
gaaacgacag aggccaaaaa gctcgctttc agcacctgtc gtttcctttc ttttcagagg   8160
gtattttaaa taaaaacatt aagttatgac gaagaagaac ggaaacgcct taaaccggaa   8220
aattttcata aatagcgaaa acccgcgagg tcgccgcccc gtaacctgtc ggatcaccgg   8280
aaaggacccg taaagtgata atgattatca tctacatatc acaacgtgcg tggaggccat   8340
caaaccacgt caaataatca attatgacgc aggtatcgta ttaattgatc tgcatcaact   8400
taacgtaaaa acaacttcag acaatacaaa tcagcgacac tgaatacggg gcaacctcat   8460
gtcccccccc cccccccct gcaggcatcg tggtgtcacg ctcgtcgttt ggtatggctt   8520
cattcagctc cggttcccaa cgatcaaggc gagttacatg atcccccatg ttgtgcaaaa   8580
aagcggttag ctccttcggt cctccgatcg ttgtcagaag taagttggcc gcagtgttat   8640
cactcatggt tatggcagca ctgcataatt ctcttactgt catgccatcc gtaagatgct   8700
tttctgtgac tggtgagtac tcaaccaagt cattctgaga atagtgtatg cggcgaccga   8760
gttgctcttg cccggcgtca acacgggata ataccgcgcc acatagcaga actttaaaag   8820
tgctcatcat tggaaaacgt tcttcggggc gaaaactctc aaggatctta ccgctgttga   8880
gatccagttc gatgtaaccc actcgtgcac ccaactgatc ttcagcatct tttactttca   8940
ccagcgtttc tgggtgagca aaaacaggaa ggcaaaatgc cgcaaaaaag ggaataaggg   9000
cgacacggaa atgttgaata ctcatactct tcctttttca atattattga agcatttatc   9060
agggttattg tctcatgagc ggatacatat ttgaatgtat ttagaaaaat aaacaaatag   9120
gggttccgcg cacatttccc cgaaaagtgc cacctgacgt ctaagaaacc attattatca   9180
tgacattaac ctataaaaat aggcgtatca cgaggccctt tcgtcttcaa gaattggtcg   9240
acgatcttgc tgcgttcgga tattttcgtg gagttcccgc cacagacccg gattgaaggc   9300
gagatccagc aactcgcgcc agatcatcct gtgacggaac tttggcgcgt gatgactggc   9360
caggacgtcg gccgaaagag cgacaagcag atcacgcttt tcgacagcgt cggatttgcg   9420
atcgaggatt tttcggcgct gcgctacgtc cgcgaccgcg ttgagggatc aagccacagc   9480
agcccactcg accttctagc cgacccagac gagccaaggg atcttttttgg aatgctgctc   9540
cgtcgtcagg ctttccgacg tttgggtggt tgaacagaag tcattatcgc acggaatgcc   9600
aagcactccc gaggggaacc ctgtggttgg catgcacata caaatggacg aacggataaa   9660
ccttttcacg cccttttaaa tatccgatta ttctaataaa cgctcttttc tcttaggttt   9720
acccgccaat atatcctgtc aaacactgat agtttaaact gaaggcggga aacgacaacc   9780
tgatcatgag cggagaatta agggagtcac gttatgaccc ccgccgatga cgcgggacaa   9840
gccgttttac gtttggaact gacagaaccg caacgttgaa ggagccactc agcttaatta   9900
agtctaactc gagttactgg tacgtaccaa atccatggaa tcaaggtacc gtcgactcta   9960
gtaacggccg ccagtgtgct ggaattaatt cggcttgtcg accacccaac cccatatcga  10020
cagaggatgt gaagaacagg taaatcacgc agaagaaccc atctctgata gcagctatcg  10080
attagaacaa cgaatccata ttgggtccgt gggaaatact tactgcacag gaaggggcg   10140
atctgacgag gccccgccac cggcctcgac ccgaggccga ggccgacgaa gcgccggcga  10200
```

-continued

```
gtacggcgcc gcggcggcct ctgcccgtgc cctctgcgcg tgggagggag aggccgcggt  10260
ggtgggggcg cgcgcgcgcg cgcgcgcagc tggtgcggcg gcgcgggggt cagccgccga  10320
gccggcggcg acggaggagc agggcggcgt ggacgcgaac ttccgatcgg ttggtcagag  10380
tgcgcgagtt gggcttagcc aattaggtct caacaatcta ttgggccgta aaattcatgg  10440
gccctggttt gtctaggccc aatatcccgt tcatttcagc ccacaaatat ttccccagag  10500
gattattaag gcccacacgc agcttatagc agatcaagta cgatgtttcc tgatcgttgg  10560
atcggaaacg tacggtcttg atcaggcatg ccgacttcgt caaagagagg cggcatgacc  10620
tgacgcggag ttggttccgg gcaccgtctg gatggtcgta ccgggaccgg acacgtgtcg  10680
cgcctccaac tacatggaca cgtgtggtgc tgccattggg ccgtacgcgt ggcggtgacc  10740
gcaccggatg ctgcctcgca ccgccttgcc cacgctttat atagagaggt tttctctcca  10800
ttaatcgcat agcgagtcga atcgaccgaa ggggaggggg agcgaagctt tgcgttctct  10860
aatcgcctcg tcaaggtaac taatcaatca cctcgtccta atcctcgaat ctctcgtggt  10920
gcccgtctaa tctcgcgatt ttgatgctcg tggtggaaag cgtaggagga tcccgtgcga  10980
gttagtctca atctctcagg gtttcgtgcg attttagggt gatccacctc ttaatcgagt  11040
tacggtttcg tgcgatttta gggtaatcct cttaatctct cattgattta gggtttcgtg  11100
agaatcgagg tagggatctg tgttatttat atcgatctaa tagatggatt ggttttgaga  11160
ttgttctgtc agatggggat tgtttcgata tattacccta atgatgtgtc agatggggat  11220
tgtttcgata tattacccta atgatgtgtc agatggggat tgtttcgata tattacccta  11280
atgatggata ataagagtag ttcacagtta tgttttgatc ctgccacata gtttgagttt  11340
tgtgatcaga tttagtttta cttatttgtg cttagttcgg atgggattgt tctgatattg  11400
ttccaataga tgaatagctc gttaggttaa aatctttagg ttgagttagg cgacacatag  11460
tttatttcct ctggatttgg attggaattg tgttcttagt ttttttcccc tggatttgga  11520
ttggaattgt gtggagctgg gttagagaat tacatctgta tcgtgtacac ctacttgaac  11580
tgtagagctt gggttctaag gtcaatttaa tctgtattgt atctggctct ttgcctagtt  11640
gaactgtagt gctgatgttg tactgtgttt ttttacccgt tttatttgct ttactcgtgc  11700
aaatcaaatc tgtcagatgc tagaactagg tggctttatt ctgtgttctt acatagatct  11760
gttgtcctgt agttacttat gtcagttttg ttattatctg aagatatttt tggttgttgc  11820
ttgttgatgt ggtgtgagct gtgagcagcg ctcttatgat taatgatgct gtccaattgt  11880
agtgtagtat gatgtgattg atatgttcat ctattttgag ctgacagtac cgatatcgta  11940
ggatctggtg ccaacttatt ctccagctgc tttttttac ctatgttaat tccaatcctt  12000
tcttgcctct tccagatcca gataatggcg aacaaacatt tgtccctctc cctcttcctc  12060
gtcctccttg gcctgtcggc cagcttggcc tccgggcaac aaacaagcat tactctgaca  12120
tccaacgcat ccggtacgtt tgacggttac tattacgaac tctggaagga tactggcaat  12180
acaacaatga cggtctacac tcaaggtcgc ttttcctgcc agtggtcgaa catcaataac  12240
gcgttgttta ggaccgggaa gaaatacaac cagaattggc agtctcttgg cacaatccgg  12300
atcacgtact ctgcgactta caacccaaac gggaactcct acttgtgtat ctatggctgg  12360
tctaccaacc cattggtcga gttctacatc gttgagtcct gggggaactg gagaccgcct  12420
ggtgccacgt ccctgggcca agtgacaatc gatggcggga cctacgacat ctataggacg  12480
acacgcgtca accagccttc cattgtgggg acagccacgt tcgatcagta ctggagcgtg  12540
```

cgcacctcta agcggacttc aggaacagtg accgtgaccg atcacttccg cgcctgggcg 12600
aaccggggcc tgaacctcgg cacaatagac caaattacat tgtgcgtgga gggttaccaa 12660
agctctggat cagccaacat cacccagaac accttctctc agggctcttc ttccggcagt 12720
tcgggtggct catccggctc cacaacgact actcgcatcg agtgtgagaa catgtccttg 12780
tccggaccct acgttagcag gatcaccaat ccctttaatg gtattgcgct gtacgccaac 12840
ggagacacag cccgcgctac cgttaacttc cccgcaagtc gcaactacaa tttccgcctg 12900
cggggttgcg gcaacaacaa taatcttgcc cgtgtggacc tgaggatcga cggacggacc 12960
gtcgggacct tttattacca gggcacatac ccctgggagg ccccaattga caatgtttat 13020
gtcagtgcgg ggagtcatac agtcgaaatc actgttactg cggataacgg cacatgggac 13080
gtgtatgccg actacctggt gatacagtga cctaggtccc cgaatttccc cgatcgttca 13140
aacatttggc aataaagttt cttaagattg aatcctgttg ccggtcttgc gatgattatc 13200
atataatttc tgttgaatta cgttaagcat gtaataatta acatgtaatg catgacgtta 13260
tttatgagat gggtttttat gattagagtc ccgcaattat acatttaata cgcgatagaa 13320
aacaaaatat agcgcgcaaa ctaggataaa ttatcgcgcg cggtgtcatc tatgttacta 13380
gatcgggaat tgg 13393

<210> SEQ ID NO 58
<211> LENGTH: 14662
<212> TYPE: DNA
<213> ORGANISM: Artificial Sequence
<220> FEATURE:
<223> OTHER INFORMATION: Synthetic construct, pAG2029 vector

<400> SEQUENCE: 58
aattcatact aaagcttgca tgcctgcagg tcgactctag taacggccgc cagtgtgctg 60
gaattaattc ggcttgtcga ccacccaacc ccatatcgac agaggatgtg aagaacaggt 120
aaatcacgca gaagaaccca tctctgatag cagctatcga ttagaacaac gaatccatat 180
tgggtccgtg ggaaatactt actgcacagg aagggggcga tctgacgagg ccccgccacc 240
ggcctcgacc cgaggccgag gccgacgaag cgccggcgag tacggcgccg cggcggcctc 300
tgcccgtgcc ctctgcgcgt gggagggaga ggccgcggtg gtgggggcgc gcgcgcgcgc 360
gcgcgcagct ggtgcggcgg cgcgggggtc agccgccgag ccggcggcga cggaggagca 420
gggcggcgtg gacgcgaact tccgatcggt tggtcagagt gcgcgagttg ggcttagcca 480
attaggtctc aacaatctat tggccgtaa aattcatggg ccctggtttg tctaggccca 540
atatcccgtt catttcagcc cacaaatatt tccccagagg attattaagg cccacacgca 600
gcttatagca gatcaagtac gatgtttcct gatcgttgga tcggaaacgt acggtcttga 660
tcaggcatgc cgacttcgtc aaagagaggc ggcatgacct gacgcggagt tggttccggg 720
caccgtctgg atggtcgtac cgggaccgga cacgtgtcgc gcctccaact acatggacac 780
gtgtggtgct gccattgggc cgtacgcgtg gcggtgaccg caccggatgc tgcctcgcac 840
cgccttgccc acgctttata tagagaggtt ttctctccat taatcgcata gcgagtcgaa 900
tcgaccgaag gggagggga gcgaagcttt gcgttctcta atcgcctcgt caaggtaact 960
aatcaatcac ctcgtcctaa tcctcgaatc tctcgtggtg cccgtctaat ctcgcgattt 1020
tgatgctcgt ggtggaaagc gtaggaggat cccgtgcgag ttagtctcaa tctctcaggg 1080
tttcgtgcga ttttagggtg atccacctct taatcgagtt acggtttcgt gcgattttag 1140
ggtaatcctc ttaatctctc attgatttag ggtttcgtga gaatcgaggt agggatctgt 1200
gttatttata tcgatctaat agatggattg gttttgagat tgttctgtca gatggggatt 1260
gtttcgatat attaccctaa tgatgtgtca gatggggatt gtttcgatat attaccctaa 1320
tgatgtgtca gatggggatt gtttcgatat attaccctaa tgatggataa taagagtagt 1380
tcacagttat gttttgatcc tgccacatag tttgagtttt gtgatcagat ttagttttac 1440
ttatttgtgc ttagttcgga tgggattgtt ctgatattgt tccaatagat gaatagctcg 1500
ttaggttaaa atctttaggt tgagttaggc gacacatagt ttatttcctc tggatttgga 1560
ttggaattgt gttcttagtt tttttcccct ggatttggat tggaattgtg tggagctggg 1620
ttagagaatt acatctgtat cgtgtacacc tacttgaact gtagagcttg ggttctaagg 1680
tcaatttaat ctgtattgta tctggctctt tgcctagttg aactgtagtg ctgatgttgt 1740
actgtgtttt tttacccgtt ttatttgctt tactcgtgca aatcaaatct gtcagatgct 1800
agaactaggt ggctttattc tgtgttctta catagatctg ttgtcctgta gttacttatg 1860
tcagttttgt tattatctga agatattttt ggttgttgct tgttgatgtg gtgtgagctg 1920
tgagcagcgc tcttatgatt aatgatgctg tccaattgta gtgtagtatg atgtgattga 1980
tatgttcatc tattttgagc tgacagtacc gatatcgtag gatctggtgc caacttattc 2040
tccagctgct ttttttacc tatgttaatt ccaatccttt cttgcctctt ccagatccag 2100
ataatgcaga aactcattaa ctcagtgcaa aactatgcct ggggcagcaa aacggcgttg 2160
actgaacttt atggtatgga aaatccgtcc agccagccga tggccgagct gtggatgggc 2220
gcacatccga aaagcagttc acgagtgcag aatgccgccg gagatatcgt ttcactgcgt 2280
gatgtgattg agagtgataa atcgactctg ctcggagagg ccgttgccaa acgctttggc 2340
gaactgcctt tcctgttcaa agtattatgc gcagcacagc cactctccat tcaggttcat 2400
ccaaacaaac acaattctga aatcggtttt gccaaagaaa atgccgcagg tatcccgatg 2460
gatgccgccg agcgtaacta taaagatcct aaccacaagc cggagctggt tttgcgctg 2520
acgcctttcc ttgcgatgaa cgcgtttcgt gaattttccg agattgtctc cctactccag 2580
ccggtcgcag gtgcacatcc ggcgattgct cactttttac aacagcctga tgccgaacgt 2640
ttaagcgaac tgttcgccag cctgttgaat atgcagggtg aagaaaaatc ccgcgcgctg 2700
gcgattttaa aatcggccct cgatagccag cagggtgaac cgtggcaaac gattcgttta 2760
atttctgaat tttacccgga agacagcggt ctgttctccc cgctattgct gaatgtggtg 2820
aaattgaacc ctggcgaagc gatgttcctg ttcgctgaaa caccgcacgc ttacctgcaa 2880
ggcgtggcgc tggaagtgat ggcaaactcc gataacgtgc tgcgtgcggg tctgacgcct 2940
aaatacattg atattccgga actggttgcc aatgtgaaat tcgaagccaa accggctaac 3000
cagttgttga cccagccggt gaaacaaggt gcagaactgg acttcccgat tccagtggat 3060
gattttgcct tctcgctgca tgaccttagt gataaagaaa ccaccattag ccagcagagt 3120
gccgccattt tgttctgcgt cgaaggcgat gcaacgttgt ggaaaggttc tcagcagtta 3180
cagcttaaac cgggtgaatc agcgtttatt gccgccaacg aatcaccggt gactgtcaaa 3240
ggccacggcc gtttagcgcg tgtttacaac aagctgtaag agcttactga aaaaattaac 3300
atctcttgct aagctgggag ctctagatcc ccgaatttcc ccgatcgttc aaacatttgg 3360
caataaagtt tcttaagatt gaatcctgtt gccggtcttg cgatgattat catataattt 3420
ctgttgaatt acgttaagca tgtaataatt aacatgtaat gcatgacgtt atttatgaga 3480
tgggttttta tgattagagt cccgcaatta tacatttaat acgcgataga aaacaaaata 3540

-continued

```
tagcgcgcaa actaggataa attatcgcgc gcggtgtcat ctatgttact agatcgggaa   3600
ttggcgagct cgaattaatt cagtacatta aaaacgtccg caatgtgtta ttaagttgtc   3660
taagcgtcaa tttgtttaca ccacaatata tcctgccacc agccagccaa cagctccccg   3720
accggcagct cggcacaaaa tcaccactcg atacaggcag cccatcagtc cgggacggcg   3780
tcagcgggag agccgttgta aggcggcaga ctttgctcat gttaccgatg ctattcggaa   3840
gaacggcaac taagctgccg ggtttgaaac acggatgatc tcgcggaggg tagcatgttg   3900
attgtaacga tgacagagcg ttgctgcctg tgatcaaata tcatctccct cgcagagatc   3960
cgaattatca gccttcttat tcatttctcg cttaaccgtg acaggctgtc gatcttgaga   4020
actatgccga cataatagga aatcgctgga taaagccgct gaggaagctg agtggcgcta   4080
tttctttaga agtgaacgtt gacgatcgtc gaccgtaccc cgatgaatta attcggacgt   4140
acgttctgaa cacagctgga tacttacttg ggcgattgtc atacatgaca tcaacaatgt   4200
acccgtttgt gtaaccgtct cttggaggtt cgtatgacac tagtggttcc cctcagcttg   4260
cgactagatg ttgaggccta acattttatt agagagcagg ctagttgctt agatacatga   4320
tcttcaggcc gttatctgtc agggcaagcg aaaattggcc atttatgacg accaatgccc   4380
cgcagaagct cccatctttg ccgccataga cgccgcgccc ccttttgggg gtgtagaaca   4440
tccttttgcc agatgtggaa aagaagttcg ttgtcccatt gttggcaatg acgtagtagc   4500
cggcgaaagt gcgagaccca tttgcgctat atataagcct acgatttccg ttgcgactat   4560
tgtcgtaatt ggatgaacta ttatcgtagt tgctctcaga gttgtcgtaa tttgatggac   4620
tattgtcgta attgcttatg gagttgtcgt agttgcttgg agaaatgtcg tagttggatg   4680
gggagtagtc atagggaaga cgagcttcat ccactaaaac aattggcagg tcagcaagtg   4740
cctgccccga tgccatcgca agtacgaggc ttagaaccac cttcaacaga tcgcgcatag   4800
tcttccccag ctctctaacg cttgagttaa gccgcgccgc gaagcggcgt cggcttgaac   4860
gaattgttag acattatttg ccgactacct tggtgatctc gcctttcacg tagtgaacaa   4920
attcttccaa ctgatctgcg cgcgaggcca agcgatcttc ttgtccaaga taagcctgcc   4980
tagcttcaag tatgacgggc tgatactggg ccggcaggcg ctccattgcc cagtcggcag   5040
cgacatcctt cggcgcgatt ttgccggtta ctgcgctgta ccaaatgcgg gacaacgtaa   5100
gcactacatt tcgctcatcg ccagcccagt cgggcggcga gttccatagc gttaaggttt   5160
catttagcgc ctcaaataga tcctgttcag gaaccggatc aaagagttcc tccgccgctg   5220
gacctaccaa ggcaacgcta tgttctcttg cttttgtcag caagatagcc agatcaatgt   5280
cgatcgtggc tggctcgaag atacctgcaa gaatgtcatt gcgctgccat tctccaaatt   5340
gcagttcgcg cttagctgga taacgccacg gaatgatgtc gtcgtgcaca acaatggtga   5400
cttctacagc gcggagaatc tcgctctctc caggggaagc cgaagtttcc aaaaggtcgt   5460
tgatcaaagc tcgccgcgtt gtttcatcaa gccttacggt caccgtaacc agcaaatcaa   5520
tatcactgtg tggcttcagg ccgccatcca ctgcggagcc gtacaaatgt acggccagca   5580
acgtcggttc gagatggcgc tcgatgacgc caactacctc tgatagttga gtcgatactt   5640
cggcgatcac cgcttccctc atgatgttta actcctgaat taagccgcgc cgcgaagcgg   5700
tgtcggcttg aatgaattgt taggcgtcat cctgtgctcc cgagaaccag taccagtaca   5760
tcgctgtttc gttcgagact tgaggtctag ttttatacgt gaacaggtca atgccgccga   5820
gagtaaagcc acattttgcg tacaaattgc aggcaggtac attgttcgtt tgtgtctcta   5880
atcgtatgcc aaggagctgt ctgcttagtg cccacttttt cgcaaattcg atgagactgt   5940
```

```
gcgcgactcc tttgcctcgg tgcgtgtgcg acacaacaat gtgttcgata gaggctagat   6000
cgttccatgt tgagttgagt tcaatcttcc cgacaagctc ttggtcgatg aatgcgccat   6060
agcaagcaga gtcttcatca gagtcatcat ccgagatgta atccttccgg taggggctca   6120
cacttctggt agatagttca aagccttggt cggataggtg cacatcgaac acttcacgaa   6180
caatgaaatg gttctcagca tccaatgttt ccgccacctg ctcagggatc accgaaatct   6240
tcatatgacg cctaacgcct ggcacagcgg atcgcaaacc tggcgcggct tttggcacaa   6300
aaggcgtgac aggtttgcga atccgttgct gccacttgtt aaccctttttg ccagatttgg   6360
taactataat ttatgttaga ggcgaagtct tgggtaaaaa ctggcctaaa attgctgggg   6420
atttcaggaa agtaaacatc accttccggc tcgatgtcta ttgtagatat atgtagtgta   6480
tctacttgat cgggggatct gctgcctcgc gcgtttcggt gatgacggtg aaaacctctg   6540
acacatgcag ctcccggaga cggtcacagc ttgtctgtaa gcggatgccg ggagcagaca   6600
agcccgtcag ggcgcgtcag cgggtgttgg cgggtgtcgg ggcgcagcca tgacccagtc   6660
acgtagcgat agcggagtgt atactggctt aactatgcgg catcagagca gattgtactg   6720
agagtgcacc atatgcggtg tgaaataccg cacagatgcg taaggagaaa ataccgcatc   6780
aggcgctctt ccgcttcctc gctcactgac tcgctgcgct cggtcgttcg gctgcggcga   6840
gcggtatcag ctcactcaaa ggcggtaata cggttatcca cagaatcagg ggataacgca   6900
ggaaagaaca tgtgagcaaa aggccagcaa aaggccagga accgtaaaaa ggccgcgttg   6960
ctggcgtttt tccataggct ccgcccccct gacgagcatc acaaaaatcg acgctcaagt   7020
cagaggtggc gaaacccgac aggactataa agataccagg cgtttccccc tggaagctcc   7080
ctcgtgcgct ctcctgttcc gaccctgccg cttaccggat acctgtccgc ctttctccct   7140
tcgggaagcg tggcgctttc tcatagctca cgctgtaggt atctcagttc ggtgtaggtc   7200
gttcgctcca agctgggctg tgtgcacgaa ccccccgttc agcccgaccg ctgcgcctta   7260
tccggtaact atcgtcttga gtccaacccg gtaagacacg acttatcgcc actggcagca   7320
gccactggta acaggattag cagagcgagg tatgtaggcg gtgctacaga gttcttgaag   7380
tggtggccta actacggcta cactagaagg acagtatttg gtatctgcgc tctgctgaag   7440
ccagttacct tcggaaaaag agttggtagc tcttgatccg gcaaacaaac caccgctggt   7500
agcggtggtt tttttgtttg caagcagcag attacgcgca gaaaaaaagg atctcaagaa   7560
gatcctttga tcttttctac ggggtctgac gctcagtgga acgaaaactc acgttaaggg   7620
attttggtca tgagattatc aaaaaggatc ttcacctaga tccttttaaa ttaaaaatga   7680
agttttaaat caatctaaag tatatatgag taaacttggt ctgacagtta ccaatgctta   7740
atcagtgagg cacctatctc agcgatctgt ctatttcgtt catccatagt tgcctgactc   7800
cccgtcgtgt agataactac gatacgggag ggcttaccat ctggccccag tgctgcaatg   7860
ataccgcgag acccacgctc accggctcca gatttatcag caataaacca gccagccgga   7920
agggccgagc gcagaagtgg tcctgcaact ttatccgcct ccatccagtc tattaattgt   7980
tgccgggaag ctagagtaag tagttcgcca gttaatagtt tgcgcaacgt tgttgccatt   8040
gctgcagggg gggggggggg ggggttccat tgttcattcc acggacaaaa acagagaaag   8100
gaaacgacag aggccaaaaa gctcgctttc agcacctgtc gtttcctttc ttttcagagg   8160
gtattttaaa taaaaacatt aagttatgac gaagaagaac ggaaacgcct taaaccggaa   8220
aattttcata aatagcgaaa acccgcgagg tcgccgcccc gtaacctgtc ggatcaccgg   8280
```

```
aaaggacccg taaagtgata atgattatca tctacatatc acaacgtgcg tggaggccat   8340
caaaccacgt caaataatca attatgacgc aggtatcgta ttaattgatc tgcatcaact   8400
taacgtaaaa acaacttcag acaatacaaa tcagcgacac tgaatacggg gcaacctcat   8460
gtcccccccc cccccccct gcaggcatcg tggtgtcacg ctcgtcgttt ggtatggctt   8520
cattcagctc cggttcccaa cgatcaaggc gagttacatg atcccccatg ttgtgcaaaa   8580
aagcggttag ctccttcggt cctccgatcg ttgtcagaag taagttggcc gcagtgttat   8640
cactcatggt tatggcagca ctgcataatt ctcttactgt catgccatcc gtaagatgct   8700
tttctgtgac tggtgagtac tcaaccaagt cattctgaga atagtgtatg cggcgaccga   8760
gttgctcttg cccggcgtca acacgggata ataccgcgcc acatagcaga actttaaaag   8820
tgctcatcat tggaaaacgt tcttcggggc gaaaactctc aaggatctta ccgctgttga   8880
gatccagttc gatgtaaccc actcgtgcac ccaactgatc ttcagcatct tttactttca   8940
ccagcgtttc tgggtgagca aaaacaggaa ggcaaaatgc cgcaaaaaag ggaataaggg   9000
cgacacggaa atgttgaata ctcatactct tcctttttca atattattga agcatttatc   9060
agggttattg tctcatgagc ggatacatat ttgaatgtat ttagaaaaat aaacaaatag   9120
gggttccgcg cacatttccc cgaaaagtgc cacctgacgt ctaagaaacc attattatca   9180
tgacattaac ctataaaaat aggcgtatca cgaggccctt tcgtcttcaa gaattggtcg   9240
acgatcttgc tgcgttcgga tattttcgtg gagttcccgc cacagacccg gattgaaggc   9300
gagatccagc aactcgcgcc agatcatcct gtgacggaac tttggcgcgt gatgactggc   9360
caggacgtcg gccgaaagag cgacaagcag atcacgcttt tcgacagcgt cggatttgcg   9420
atcgaggatt tttcggcgct gcgctacgtc cgcgaccgcg ttgagggatc aagccacagc   9480
agcccactcg accttctagc cgacccagac gagccaaggg atctttttgg aatgctgctc   9540
cgtcgtcagg ctttccgacg tttgggtggt tgaacagaag tcattatcgc acggaatgcc   9600
aagcactccc gaggggaacc ctgtggttgg catgcacata caaatggacg aacggataaa   9660
ccttttcacg ccctttttaaa tatccgatta ttctaataaa cgctcttttc tcttaggttt   9720
acccgccaat atatcctgtc aaacactgat agtttaaact gaaggcggga aacgacaacc   9780
tgatcatgag cggagaatta agggagtcac gttatgaccc ccgccgatga cgcgggacaa   9840
gccgttttac gtttggaact gacagaaccg caacgttgaa ggagccactc agcttaatta   9900
agtctaactc gagttactgg tacgtaccaa atccatggaa tcaaggtacc gtcgactcta   9960
gtaacggccg ccagtgtgct ggaattaatt cggcttgtcg accacccaac cccatatcga   10020
cagaggatgt gaagaacagg taaatcacgc agaagaaccc atctctgata gcagctatcg   10080
attagaacaa cgaatccata ttgggtccgt gggaaatact tactgcacag gaagggggcg   10140
atctgacgag gccccgccac cggcctcgac ccgaggccga ggccgacgaa gcgccggcga   10200
gtacggcgcc gcggcggcct ctgcccgtgc cctctgcgcg tgggagggag aggccgcggt   10260
ggtgggggcg cgcgcgcgcg cgcgcgcagc tggtgcggcg gcgcgggggt cagccgccga   10320
gccggcggcg acggaggagc agggcggcgt ggacgcgaac ttccgatcgg ttggtcagag   10380
tgcgcgagtt gggcttagcc aattaggtct caacaatcta ttgggccgta aaattcatgg   10440
gccctggttt gtctaggccc aatatcccgt tcatttcagc ccacaaatat ttccccagag   10500
gattattaag gcccacacgc agcttatagc agatcaagta cgatgtttcc tgatcgttgg   10560
atcggaaacg tacggtcttg atcaggcatg ccgacttcgt caaagagagg cggcatgacc   10620
tgacgcggag ttggttccgg gcaccgtctg gatggtcgta ccgggaccgg acacgtgtcg   10680
```

cgcctccaac tacatggaca cgtgtggtgc tgccattggg ccgtacgcgt ggcggtgacc 10740
gcaccggatg ctgcctcgca ccgccttgcc cacgctttat atagagaggt tttctctcca 10800
ttaatcgcat agcgagtcga atcgaccgaa ggggaggggg agcgaagctt tgcgttctct 10860
aatcgcctcg tcaaggtaac taatcaatca cctcgtccta atcctcgaat ctctcgtggt 10920
gcccgtctaa tctcgcgatt ttgatgctcg tggtggaaag cgtaggagga tcccgtgcga 10980
gttagtctca atctctcagg gtttcgtgcg attttagggt gatccacctc ttaatcgagt 11040
tacggtttcg tgcgatttta gggtaatcct cttaatctct cattgattta gggtttcgtg 11100
agaatcgagg tagggatctg tgttatttat atcgatctaa tagatggatt ggttttgaga 11160
ttgttctgtc agatggggat tgtttcgata tattacccta atgatgtgtc agatggggat 11220
tgtttcgata tattacccta atgatgtgtc agatggggat tgtttcgata tattacccta 11280
atgatggata ataagagtag ttcacagtta tgttttgatc ctgccacata gtttgagttt 11340
tgtgatcaga tttagtttta cttatttgtg cttagttcgg atgggattgt tctgatattg 11400
ttccaataga tgaatagctc gttaggttaa aatctttagg ttgagttagg cgacacatag 11460
tttatttcct ctggatttgg attggaattg tgttcttagt ttttttcccc tggatttgga 11520
ttggaattgt gtggagctgg gttagagaat tacatctgta tcgtgtacac ctacttgaac 11580
tgtagagctt gggttctaag gtcaatttaa tctgtattgt atctggctct ttgcctagtt 11640
gaactgtagt gctgatgttg tactgtgttt ttttacccgt tttatttgct ttactcgtgc 11700
aaatcaaatc tgtcagatgc tagaactagg tggctttatt ctgtgttctt acatagatct 11760
gttgtcctgt agttacttat gtcagttttg ttattatctg aagatatttt tggttgttgc 11820
ttgttgatgt ggtgtgagct gtgagcagcg ctcttatgat taatgatgct gtccaattgt 11880
agtgtagtat gatgtgattg atatgttcat ctattttgag ctgacagtac cgatatcgta 11940
ggatctggtg ccaacttatt ctccagctgc tttttttttac ctatgttaat tccaatcctt 12000
tcttgcctct tccagatcca gataatggcg aacaaacatt tgtccctctc cctcttcctc 12060
gtcctccttg gcctgtcggc cagcttggcc tccgggcaac aaacaagcat tactctgaca 12120
tccaacgcat ccggtacgtt tgacggttac tattacgaac tctggaagga tactggcaat 12180
acaacaatga cggtctacac tcaaggtcgc ttttcctgcc agtggtcgaa catcaataac 12240
gcgttgttta ggaccgggaa gaaatacaac cagaattggc agtctcttgg cacaatccgg 12300
atcacgtact ctgcgactta caacccaaac gggaactcct acttgtgtat ctatggctgg 12360
tctaccaacc cattggtcga gttctacatc gttgagtcct gggggaactg gagaccgcct 12420
ggtgcctgcc tggccgaggg ctcgctcgtc ttggacgcgg ctaccgggca gagggtccct 12480
atcgaaaagg tgcgtccggg gatggaagtt ttctccttgg gacctgatta cagactgtat 12540
cgggtgcccg ttttggaggt ccttgagagc ggggttaggg aagttgtgcg cctcagaact 12600
cggtcaggga gaacgctggt gttgacacca gatcacccgc ttttgacccc cgaaggttgg 12660
aaacctcttt gtgacctccc gcttggaact ccaattgcag tccccgcaga actgcctgtg 12720
gcgggccact tggccccacc tgaagaacgt gttacgctcc tggctcttct gttgggggat 12780
gggaacacaa agctgtcggg tcggagaggt acacgtccta atgcctcctt ctacagcaaa 12840
gaccccgaat tgctcgcggc ttatcgccgg tgtgcagaag ccttgggtgc aaaggtgaaa 12900
gcatacgtcc acccgactac gggggtggtt acactcgcaa ccctcgctcc acgtcctgga 12960
gctcaagatc ctgtcaaacg cctcgttgtc gaggcgggaa tggttgctaa agccgaagag 13020
aagagggtcc cggaggaggt gtttcgttac cggcgtgagg cgttggccct tttcttgggc 13080
cgtttgttct cgacagacgg ctctgttgaa aagaagagga tctcttattc aagtgccagt 13140
ttgggactgg cccaggatgt cgcacatctc ttgctgcgcc ttggaattag atctcaactc 13200
cgttcgagag ggccacgggc tcacgaggtt cttatatcgg gccgcgagga tattttgcga 13260
tttgctgaac ttatcggacc ctacctcttg ggggccaaga gggagagact tgcagcgctg 13320
gaagctgagg cccgcaggcg tttgcctgga cagggatggc acttgcggct tgttcttcct 13380
gccgtggcgt acagagtgag cgaggctaaa aggcgctcgg gattttcgtg gagtgaagcc 13440
ggtcggcgcg tcgcagttgc gggatcgtgt ttgtcatctg gactcaacct caaattgccc 13500
agacgctacc tttctcggca ccggttgtcg ctgctcggtg aggcttttgc cgaccctggg 13560
ctggaagcgc tcgcggaagg ccaagtgctc tgggacccta ttgttgctgt cgaaccggcc 13620
ggtaaggcga gaacattcga cttgcgcgtt ccacccttg caaacttcgt gagcgaggac 13680
ctggtggtgc ataacacgtc cctgggccaa gtgacaatcg atggcgggac ctacgacatc 13740
tataggacga cacgcgtcaa ccagccttcc attgtgggga cagccacgtt cgatcagtac 13800
tggagcgtgc gcacctctaa gcggacttca ggaacagtga ccgtgaccga tcacttccgc 13860
gcctgggcga accggggcct gaacctcggc acaatagacc aaattacatt gtgcgtggag 13920
ggttaccaaa gctctggatc agccaacatc acccagaaca ccttctctca gggctcttct 13980
tccggcagtt cgggtggctc atccggctcc acaacgacta ctcgcatcga gtgtgagaac 14040
atgtccttgt ccggacccta cgttagcagg atcaccaatc cctttaatgg tattgcgctg 14100
tacgccaacg gagacacagc ccgcgctacc gttaacttcc ccgcaagtcg caactacaat 14160
ttccgcctgc ggggttgcgg caacaacaat aatcttgccc gtgtggacct gaggatcgac 14220
ggacggaccg tcgggacctt ttattaccag ggcacatacc cctgggaggc cccaattgac 14280
aatgtttatg tcagtgcggg gagtcataca gtcgaaatca ctgttactgc ggataacggc 14340
acatgggacg tgtatgccga ctacctggtg atacagtgac ctaggtcccc gaatttcccc 14400
gatcgttcaa acatttggca ataaagtttc ttaagattga atcctgttgc cggtcttgcg 14460
atgattatca tataatttct gttgaattac gttaagcatg taataattaa catgtaatgc 14520
atgacgttat ttatgagatg ggtttttatg attagagtcc cgcaattata catttaatac 14580
gcgatagaaa acaaaatata gcgcgcaaac taggataaat tatcgcgcgc ggtgtcatct 14640
atgttactag atcgggaatt gg 14662

<210> SEQ ID NO 59
<211> LENGTH: 2286
<212> TYPE: DNA
<213> ORGANISM: Artificial Sequence
<220> FEATURE:
<223> OTHER INFORMATION: Synthetic construct, P77T134-100-101 Nucleotide sequence

<400> SEQUENCE: 59
atgcaaacaa gcattactct gacatccaac gcatccggta cgtttgacgg ttactattac 60
gaactctgga aggatactgg caatacaaca atgacggtct acactcaagg tcgcttttcc 120
tgccagtggt cgaacatcaa taacgcgttg tttaggaccg ggaagaaata caaccagaat 180
tggcagtctc ttggcacaat ccggatcacg tactctgcga cttacaaccc aaacgggaac 240
tcctacttgt gtatctatgg ctggtctacc aacccattgg tcgagttcta catcgttgag 300
tcctggggga actggagacc gcctggtgcc tgcctggccg agggctcgct cgtcttggac 360

```
gcggctaccg ggcagagggt ccctatcgaa aaggtgcgtc cggggatgga agttttctcc    420

ttgggacctg attacagact gtatcgggtg cccgttttgg aggtccttga gagcggggtt    480

agggaagttg tgcgcctcag aactcggtca gggagaacgc tggtgttgac accagatcac    540

ccgcttttga cccccgaagg ttggaaacct ctttgtgacc tcccgcttgg aactccaatt    600

gcagtccccg cagaactgcc tgtggcgggc cacttggccc cacctgaaga acgtgttacg    660

ctcctggctc ttctgttggg ggatgggaac acaaagctgt cgggtcggag aggtacacgt    720

cctaatgcct tcttctacag caaaaacccc gaattgctcg cggcttatcg ccggtgtgca    780

gaagccttgg gtgcaaaggt gaaagcatac gtccacccga ctacgggggt ggttacactc    840

gcaaccctcg ctccacgtcc tggagctcaa gatcctgtca aacgcctcgt tgtcgaggcg    900

ggaatggttg ctaaagccga agagaagagg gtcccggagg aggtgtttcg ttaccggcgt    960

gaggcgttgg cccttttctt gggccgtttg ttctcgacag acggctctgt tgaaaagaag   1020

aggatctctt attcaagtgc cagtttggga ctggcccagg atgtcgcaca tctcttgctg   1080

cgccttggaa ttacatctca actccgttcg agagggccac gggctcacga ggttcttata   1140

tcgggccgcg aggatatttt gcggtttgct gaacttatcg gaccctacct cttgggggcc   1200

aagagggaga gacttgcagc gctggaagct gaggcccgca ggcgtttgcc tggacaggga   1260

tggcacttgc ggcttgttct tcctgccgtg gcgtacagag tgggcgaggc ggaaaggcgc   1320

tcgggatttt cgtggagtga agccggtcgg cgcgtcgcag ttgcgggatc gtgtttgtca   1380

tctggactca acctcaaatt gcccagacgc tacctttctc ggcaccggtt gtcgctgctc   1440

ggtgaggctt ttgccgaccc tgggctggaa gcgctcgcgg aaggccaagt gctctgggac   1500

cctattgttg ctgtcgaacc ggccggtaag gcgagaacat tcgacttgcg cgttccaccc   1560

tttgcaaact tcgtgagcga ggacctggtg gtgcataaca ccgtcccccct gggccaagtg  1620

acaatcgatg gcgggaccta cgacatctat aggacgacac gcgtcaacca gccttccatt   1680

gtggggacag ccacgttcga tcagtactgg agcgtgcgca cctctaagcg gacttcagga   1740

acagtgaccg tgaccgatca cttccgcgcc tgggcgaacc ggggcctgaa cctcggcaca   1800

atagaccaaa ttacattgtg cgtggagggt taccaaagct ctggatcagc caacatcacc   1860

cagaacacct tctctcaggg ctcttcttcc ggcagttcgg gtggctcatc cggctccaca   1920

acgactactc gcatcgagtg tgagaacatg tccttgtccg gaccctacgt tagcaggatc   1980

accaatccct ttaatggtat tgcgctgtac gccaacggag acacagcccg cgctaccgtt   2040

aacttccccg caagtcgcaa ctacaatttc cgcctgcggg gttgcggcaa caacaataat   2100

cttgcccgtg tggacctgag gatcgacgga cggaccgtcg ggacctttta ttaccagggc   2160

acatacccct gggaggcccc aattgacaat gtttatgtca gtgcggggag tcatacagtc   2220

gaaatcactg ttactgcgga taacggcaca tgggacgtgt atgccgacta cctggtgata   2280

cagtga                                                              2286
```

<210> SEQ ID NO 60
<211> LENGTH: 761
<212> TYPE: PRT
<213> ORGANISM: Artificial Sequence
<220> FEATURE:
<223> OTHER INFORMATION: Synthetic construct, P77T134-100-101 Amino acid sequence

<400> SEQUENCE: 60

```
Met Gln Thr Ser Ile Thr Leu Thr Ser Asn Ala Ser Gly Thr Phe Asp
1               5                   10                  15
```

Gly Tyr Tyr Tyr Glu Leu Trp Lys Asp Thr Gly Asn Thr Thr Met Thr
20 25 30

Val Tyr Thr Gln Gly Arg Phe Ser Cys Gln Trp Ser Asn Ile Asn Asn
35 40 45

Ala Leu Phe Arg Thr Gly Lys Lys Tyr Asn Gln Asn Trp Gln Ser Leu
50 55 60

Gly Thr Ile Arg Ile Thr Tyr Ser Ala Thr Tyr Asn Pro Asn Gly Asn
65 70 75 80

Ser Tyr Leu Cys Ile Tyr Gly Trp Ser Thr Asn Pro Leu Val Glu Phe
85 90 95

Tyr Ile Val Glu Ser Trp Gly Asn Trp Arg Pro Pro Gly Ala Cys Leu
100 105 110

Ala Glu Gly Ser Leu Val Leu Asp Ala Ala Thr Gly Gln Arg Val Pro
115 120 125

Ile Glu Lys Val Arg Pro Gly Met Glu Val Phe Ser Leu Gly Pro Asp
130 135 140

Tyr Arg Leu Tyr Arg Val Pro Val Leu Glu Val Leu Glu Ser Gly Val
145 150 155 160

Arg Glu Val Val Arg Leu Arg Thr Arg Ser Gly Arg Thr Leu Val Leu
165 170 175

Thr Pro Asp His Pro Leu Leu Thr Pro Glu Gly Trp Lys Pro Leu Cys
180 185 190

Asp Leu Pro Leu Gly Thr Pro Ile Ala Val Pro Ala Glu Leu Pro Val
195 200 205

Ala Gly His Leu Ala Pro Pro Glu Glu Arg Val Thr Leu Leu Ala Leu
210 215 220

Leu Leu Gly Asp Gly Asn Thr Lys Leu Ser Gly Arg Arg Gly Thr Arg
225 230 235 240

Pro Asn Ala Phe Phe Tyr Ser Lys Asn Pro Glu Leu Leu Ala Ala Tyr
245 250 255

Arg Arg Cys Ala Glu Ala Leu Gly Ala Lys Val Lys Ala Tyr Val His
260 265 270

Pro Thr Thr Gly Val Val Thr Leu Ala Thr Leu Ala Pro Arg Pro Gly
275 280 285

Ala Gln Asp Pro Val Lys Arg Leu Val Val Glu Ala Gly Met Val Ala
290 295 300

Lys Ala Glu Glu Lys Arg Val Pro Glu Glu Val Phe Arg Tyr Arg Arg
305 310 315 320

Glu Ala Leu Ala Leu Phe Leu Gly Arg Leu Phe Ser Thr Asp Gly Ser
325 330 335

Val Glu Lys Lys Arg Ile Ser Tyr Ser Ser Ala Ser Leu Gly Leu Ala
340 345 350

Gln Asp Val Ala His Leu Leu Leu Arg Leu Gly Ile Thr Ser Gln Leu
355 360 365

Arg Ser Arg Gly Pro Arg Ala His Glu Val Leu Ile Ser Gly Arg Glu
370 375 380

Asp Ile Leu Arg Phe Ala Glu Leu Ile Gly Pro Tyr Leu Leu Gly Ala
385 390 395 400

Lys Arg Glu Arg Leu Ala Ala Leu Glu Ala Glu Ala Arg Arg Arg Leu
405 410 415

Pro Gly Gln Gly Trp His Leu Arg Leu Val Leu Pro Ala Val Ala Tyr
420 425 430

```
Arg Val Gly Glu Ala Glu Arg Arg Ser Gly Phe Ser Trp Ser Glu Ala
        435                 440                 445

Gly Arg Arg Val Ala Val Ala Gly Ser Cys Leu Ser Ser Gly Leu Asn
    450                 455                 460

Leu Lys Leu Pro Arg Arg Tyr Leu Ser Arg His Arg Leu Ser Leu Leu
465                 470                 475                 480

Gly Glu Ala Phe Ala Asp Pro Gly Leu Glu Ala Leu Ala Glu Gly Gln
                485                 490                 495

Val Leu Trp Asp Pro Ile Val Ala Val Glu Pro Ala Gly Lys Ala Arg
            500                 505                 510

Thr Phe Asp Leu Arg Val Pro Pro Phe Ala Asn Phe Val Ser Glu Asp
        515                 520                 525

Leu Val Val His Asn Thr Val Pro Leu Gly Gln Val Thr Ile Asp Gly
    530                 535                 540

Gly Thr Tyr Asp Ile Tyr Arg Thr Thr Arg Val Asn Gln Pro Ser Ile
545                 550                 555                 560

Val Gly Thr Ala Thr Phe Asp Gln Tyr Trp Ser Val Arg Thr Ser Lys
                565                 570                 575

Arg Thr Ser Gly Thr Val Thr Val Thr Asp His Phe Arg Ala Trp Ala
            580                 585                 590

Asn Arg Gly Leu Asn Leu Gly Thr Ile Asp Gln Ile Thr Leu Cys Val
        595                 600                 605

Glu Gly Tyr Gln Ser Ser Gly Ser Ala Asn Ile Thr Gln Asn Thr Phe
    610                 615                 620

Ser Gln Gly Ser Ser Ser Gly Ser Ser Gly Gly Ser Ser Gly Ser Thr
625                 630                 635                 640

Thr Thr Thr Arg Ile Glu Cys Glu Asn Met Ser Leu Ser Gly Pro Tyr
                645                 650                 655

Val Ser Arg Ile Thr Asn Pro Phe Asn Gly Ile Ala Leu Tyr Ala Asn
            660                 665                 670

Gly Asp Thr Ala Arg Ala Thr Val Asn Phe Pro Ala Ser Arg Asn Tyr
        675                 680                 685

Asn Phe Arg Leu Arg Gly Cys Gly Asn Asn Asn Asn Leu Ala Arg Val
    690                 695                 700

Asp Leu Arg Ile Asp Gly Arg Thr Val Gly Thr Phe Tyr Tyr Gln Gly
705                 710                 715                 720

Thr Tyr Pro Trp Glu Ala Pro Ile Asp Asn Val Tyr Val Ser Ala Gly
                725                 730                 735

Ser His Thr Val Glu Ile Thr Val Thr Ala Asp Asn Gly Thr Trp Asp
            740                 745                 750

Val Tyr Ala Asp Tyr Leu Val Ile Gln
        755                 760
```

<210> SEQ ID NO 61
<211> LENGTH: 2358
<212> TYPE: DNA
<213> ORGANISM: Artificial Sequence
<220> FEATURE:
<223> OTHER INFORMATION: Synthetic construct, BAASS:P77T134-100-101
      Nucleotide sequence

<400> SEQUENCE: 61

```
atggcgaaca aacatttgtc cctctccctc ttcctcgtcc tccttggcct gtcggccagc      60

ttggcctccg ggcaacaaac aagcattact ctgacatcca acgcatccgg tacgtttgac     120

ggttactatt acgaactctg gaaggatact ggcaatacaa caatgacggt ctacactcaa     180
```

```
ggtcgctttt cctgccagtg gtcgaacatc aataacgcgt tgtttaggac cgggaagaaa    240
tacaaccaga attggcagtc tcttggcaca atccggatca cgtactctgc gacttacaac    300
ccaaacggga actcctactt gtgtatctat ggctggtcta ccaacccatt ggtcgagttc    360
tacatcgttg agtcctgggg gaactggaga ccgcctggtg cctgcctggc cgagggctcg    420
ctcgtcttgg acgcggctac cggcagaggg gtccctatcg aaaaggtgcg tccggggatg    480
gaagttttct ccttgggacc tgattacaga ctgtatcggg tgcccgtttt ggaggtcctt    540
gagagcgggg ttagggaagt tgtgcgcctc agaactcggt cagggagaac gctggtgttg    600
acaccagatc acccgctttt gacccccgaa ggttggaaac ctctttgtga cctcccgctt    660
ggaactccaa ttgcagtccc cgcagaactg cctgtggcgg gccacttggc ccccacctgaa   720
gaacgtgtta cgctcctggc tcttctgttg gggatggga acacaaagct gtcgggtcgg    780
agaggtacac gtcctaatgc cttcttctac agcaaaaacc ccgaattgct cgcggcttat    840
cgccggtgtg cagaagcctt gggtgcaaag gtgaaagcat acgtccaccc gactacgggg    900
gtggttacac tcgcaaccct cgctccacgt cctggagctc aagatcctgt caaacgcctc    960
gttgtcgagg cgggaatggt tgctaaagcc gaagagaaga gggtcccgga ggaggtgttt   1020
cgttaccggc gtgaggcgtt ggcccttttc ttgggccgtt tgttctcgac agacggctct   1080
gttgaaaaga agaggatctc ttattcaagt gccagtttgg gactggccca ggatgtcgca   1140
catctcttgc tgcgccttgg aattacatct caactccgtt cgagagggcc acgggctcac   1200
gaggttctta tatcgggccg cgaggatatt ttgcggtttg ctgaacttat cggaccctac   1260
ctcttggggg ccaagaggga gagacttgca gcgctggaag ctgaggcccg caggcgtttg   1320
cctggacagg gatggcactt gcggcttgtt cttcctgccg tggcgtacag agtgggcgag   1380
gcggaaaggc gctcgggatt ttcgtggagt gaagccggtc ggcgcgtcgc agttgcggga   1440
tcgtgtttgt catctggact caacctcaaa ttgcccagac gctacctttc tcggcaccgg   1500
ttgtcgctgc tcggtgaggc ttttgccgac cctgggctgg aagcgctcgc ggaaggccaa   1560
gtgctctggg accctattgt tgctgtcgaa ccggccggta aggcgagaac attcgacttg   1620
cgcgttccac cctttgcaaa cttcgtgagc gaggacctgg tggtgcataa caccgtcccc   1680
ctgggccaag tgacaatcga tggcgggacc tacgacatct ataggacgac acgcgtcaac   1740
cagccttcca ttgtggggac agccacgttc gatcagtact ggagcgtgcg cacctctaag   1800
cggacttcag gaacagtgac cgtgaccgat cacttccgcg cctgggcgaa ccggggcctg   1860
aacctcggca caatagacca aattacattg tgcgtggagg gttaccaaag ctctggatca   1920
gccaacatca cccagaacac cttctctcag ggctcttctt ccggcagttc gggtggctca   1980
tccggctcca caacgactac tcgcatcgag tgtgagaaca tgtccttgtc cggaccctac   2040
gttagcagga tcaccaatcc ctttaatggt attgcgctgt acgccaacgg agacacagcc   2100
cgcgctaccg ttaacttccc cgcaagtcgc aactacaatt tccgcctgcg ggttgcggc    2160
aacaacaata atcttgcccg tgtggacctg aggatcgacg gacggaccgt cgggaccttt   2220
tattaccagg gcacataccc ctgggaggcc ccaattgaca atgtttatgt cagtgcgggg   2280
agtcatacag tcgaaatcac tgttactgcg gataacggca catgggacgt gtatgccgac   2340
tacctggtga tacagtga                                                 2358
```

<210> SEQ ID NO 62
<211> LENGTH: 785
<212> TYPE: PRT

<213> ORGANISM: Artificial Sequence
<220> FEATURE:
<223> OTHER INFORMATION: Synthetic construct, BAASS:P77T134-100-101
Amino acid sequence

<400> SEQUENCE: 62

```
Met Ala Asn Lys His Leu Ser Leu Ser Leu Phe Leu Val Leu Leu Gly
1               5                   10                  15

Leu Ser Ala Ser Leu Ala Ser Gly Gln Gln Thr Ser Ile Thr Leu Thr
            20                  25                  30

Ser Asn Ala Ser Gly Thr Phe Asp Gly Tyr Tyr Tyr Glu Leu Trp Lys
        35                  40                  45

Asp Thr Gly Asn Thr Thr Met Thr Val Tyr Thr Gln Gly Arg Phe Ser
    50                  55                  60

Cys Gln Trp Ser Asn Ile Asn Asn Ala Leu Phe Arg Thr Gly Lys Lys
65                  70                  75                  80

Tyr Asn Gln Asn Trp Gln Ser Leu Gly Thr Ile Arg Ile Thr Tyr Ser
                85                  90                  95

Ala Thr Tyr Asn Pro Asn Gly Asn Ser Tyr Leu Cys Ile Tyr Gly Trp
            100                 105                 110

Ser Thr Asn Pro Leu Val Glu Phe Tyr Ile Val Glu Ser Trp Gly Asn
        115                 120                 125

Trp Arg Pro Pro Gly Ala Cys Leu Ala Glu Gly Ser Leu Val Leu Asp
    130                 135                 140

Ala Ala Thr Gly Gln Arg Val Pro Ile Glu Lys Val Arg Pro Gly Met
145                 150                 155                 160

Glu Val Phe Ser Leu Gly Pro Asp Tyr Arg Leu Tyr Arg Val Pro Val
                165                 170                 175

Leu Glu Val Leu Glu Ser Gly Val Arg Glu Val Val Arg Leu Arg Thr
            180                 185                 190

Arg Ser Gly Arg Thr Leu Val Leu Thr Pro Asp His Pro Leu Leu Thr
        195                 200                 205

Pro Glu Gly Trp Lys Pro Leu Cys Asp Leu Pro Leu Gly Thr Pro Ile
    210                 215                 220

Ala Val Pro Ala Glu Leu Pro Val Ala Gly His Leu Ala Pro Pro Glu
225                 230                 235                 240

Glu Arg Val Thr Leu Leu Ala Leu Leu Leu Gly Asp Gly Asn Thr Lys
                245                 250                 255

Leu Ser Gly Arg Arg Gly Thr Arg Pro Asn Ala Phe Phe Tyr Ser Lys
            260                 265                 270

Asn Pro Glu Leu Leu Ala Ala Tyr Arg Arg Cys Ala Glu Ala Leu Gly
        275                 280                 285

Ala Lys Val Lys Ala Tyr Val His Pro Thr Thr Gly Val Val Thr Leu
    290                 295                 300

Ala Thr Leu Ala Pro Arg Pro Gly Ala Gln Asp Pro Val Lys Arg Leu
305                 310                 315                 320

Val Val Glu Ala Gly Met Val Ala Lys Ala Glu Glu Lys Arg Val Pro
                325                 330                 335

Glu Glu Val Phe Arg Tyr Arg Arg Glu Ala Leu Ala Leu Phe Leu Gly
            340                 345                 350

Arg Leu Phe Ser Thr Asp Gly Ser Val Glu Lys Lys Arg Ile Ser Tyr
        355                 360                 365

Ser Ser Ala Ser Leu Gly Leu Ala Gln Asp Val Ala His Leu Leu Leu
    370                 375                 380
```

-continued

```
Arg Leu Gly Ile Thr Ser Gln Leu Arg Ser Arg Gly Pro Arg Ala His
385                 390                 395                 400

Glu Val Leu Ile Ser Gly Arg Glu Asp Ile Leu Arg Phe Ala Glu Leu
                405                 410                 415

Ile Gly Pro Tyr Leu Leu Gly Ala Lys Arg Glu Arg Leu Ala Ala Leu
            420                 425                 430

Glu Ala Glu Ala Arg Arg Arg Leu Pro Gly Gln Gly Trp His Leu Arg
        435                 440                 445

Leu Val Leu Pro Ala Val Ala Tyr Arg Val Gly Glu Ala Glu Arg Arg
    450                 455                 460

Ser Gly Phe Ser Trp Ser Glu Ala Gly Arg Arg Val Ala Val Ala Gly
465                 470                 475                 480

Ser Cys Leu Ser Ser Gly Leu Asn Leu Lys Leu Pro Arg Arg Tyr Leu
                485                 490                 495

Ser Arg His Arg Leu Ser Leu Leu Gly Glu Ala Phe Ala Asp Pro Gly
            500                 505                 510

Leu Glu Ala Leu Ala Glu Gly Gln Val Leu Trp Asp Pro Ile Val Ala
        515                 520                 525

Val Glu Pro Ala Gly Lys Ala Arg Thr Phe Asp Leu Arg Val Pro Pro
    530                 535                 540

Phe Ala Asn Phe Val Ser Glu Asp Leu Val Val His Asn Thr Val Pro
545                 550                 555                 560

Leu Gly Gln Val Thr Ile Asp Gly Gly Thr Tyr Asp Ile Tyr Arg Thr
                565                 570                 575

Thr Arg Val Asn Gln Pro Ser Ile Val Gly Thr Ala Thr Phe Asp Gln
            580                 585                 590

Tyr Trp Ser Val Arg Thr Ser Lys Arg Thr Ser Gly Thr Val Thr Val
        595                 600                 605

Thr Asp His Phe Arg Ala Trp Ala Asn Arg Gly Leu Asn Leu Gly Thr
    610                 615                 620

Ile Asp Gln Ile Thr Leu Cys Val Glu Gly Tyr Gln Ser Ser Gly Ser
625                 630                 635                 640

Ala Asn Ile Thr Gln Asn Thr Phe Ser Gln Gly Ser Ser Ser Gly Ser
                645                 650                 655

Ser Gly Gly Ser Ser Gly Ser Thr Thr Thr Thr Arg Ile Glu Cys Glu
            660                 665                 670

Asn Met Ser Leu Ser Gly Pro Tyr Val Ser Arg Ile Thr Asn Pro Phe
        675                 680                 685

Asn Gly Ile Ala Leu Tyr Ala Asn Gly Asp Thr Ala Arg Ala Thr Val
    690                 695                 700

Asn Phe Pro Ala Ser Arg Asn Tyr Asn Phe Arg Leu Arg Gly Cys Gly
705                 710                 715                 720

Asn Asn Asn Asn Leu Ala Arg Val Asp Leu Arg Ile Asp Gly Arg Thr
                725                 730                 735

Val Gly Thr Phe Tyr Tyr Gln Gly Thr Tyr Pro Trp Glu Ala Pro Ile
            740                 745                 750

Asp Asn Val Tyr Val Ser Ala Gly Ser His Thr Val Glu Ile Thr Val
        755                 760                 765

Thr Ala Asp Asn Gly Thr Trp Asp Val Tyr Ala Asp Tyr Leu Val Ile
    770                 775                 780

Gln
785
```

<210> SEQ ID NO 63
<211> LENGTH: 2376
<212> TYPE: DNA
<213> ORGANISM: Artificial Sequence
<220> FEATURE:
<223> OTHER INFORMATION: Synthetic construct,
BAASS:P77T134-100-101:SEKDEL Nucleotide sequence

<400> SEQUENCE: 63

```
atggcgaaca aacatttgtc cctctccctc ttcctcgtcc tccttggcct gtcggccagc     60
ttggcctccg ggcaacaaac aagcattact ctgacatcca acgcatccgg tacgtttgac    120
ggttactatt acgaactctg gaaggatact ggcaatacaa caatgacggt ctacactcaa    180
ggtcgctttt cctgccagtg gtcgaacatc aataacgcgt tgtttaggac cgggaagaaa    240
tacaaccaga attggcagtc tcttggcaca atccggatca cgtactctgc gacttacaac    300
ccaaacggga actcctactt gtgtatctat ggctggtcta ccaacccatt ggtcgagttc    360
tacatcgttg agtcctgggg gaactggaga ccgcctggtg cctgcctggc cgagggctcg    420
ctcgtcttgg acgcggctac cggcagagg gtccctatcg aaaaggtgcg tccggggatg    480
gaagttttct ccttgggacc tgattacaga ctgtatcggg tgcccgtttt ggaggtcctt    540
gagagcgggg ttagggaagt tgtgcgcctc agaactcggt cagggagaac gctggtgttg    600
acaccagatc acccgctttt gacccccgaa ggttggaaac ctctttgtga cctcccgctt    660
ggaactccaa ttgcagtccc cgcagaactg cctgtggcgg gccacttggc cccacctgaa    720
gaacgtgtta cgctcctggc tcttctgttg ggggatggga acacaaagct gtcgggtcgg    780
agaggtacac gtcctaatgc cttcttctac agcaaaaacc ccgaattgct cgcggcttat    840
cgccggtgtg cagaagcctt gggtgcaaag gtgaaagcat acgtccaccc gactacgggg    900
gtggttacac tcgcaaccct cgctccacgt cctggagctc aagatcctgt caaacgcctc    960
gttgtcgagg cgggaatggt tgctaaagcc gaagagaaga gggtcccgga ggaggtgttt   1020
cgttaccggc gtgaggcgtt ggccctttc ttgggccgtt tgttctcgac agacggctct   1080
gttgaaaaga agaggatctc ttattcaagt gccagtttgg gactggccca ggatgtcgca   1140
catctcttgc tgcgccttgg aattacatct caactccgtt cgagagggcc acgggctcac   1200
gaggttctta tatcgggccg cgaggatatt ttgcggtttg ctgaacttat cggaccctac   1260
ctcttggggg ccaagaggga gagacttgca gcgctggaag ctgaggcccg caggcgtttg   1320
cctggacagg gatggcactt gcggcttgtt cttcctgccg tggcgtacag agtgggcgag   1380
gcggaaaggc gctcgggatt ttcgtggagt gaagccggtc ggcgcgtcgc agttgcggga   1440
tcgtgtttgt catctggact caacctcaaa ttgcccagac gctacctttc tcggcaccgg   1500
ttgtcgctgc tcggtgaggc ttttgccgac cctgggctgg aagcgctcgc ggaaggccaa   1560
gtgctctggg accctattgt tgctgtcgaa ccggccggta aggcgagaac attcgacttg   1620
cgcgttccac cctttgcaaa cttcgtgagc gaggacctgg tggtgcataa caccgtcccc   1680
ctgggccaag tgacaatcga tggcgggacc tacgacatct ataggacgac acgcgtcaac   1740
cagccttcca ttgtggggac agccacgttc gatcagtact ggagcgtgcg cacctctaag   1800
cggacttcag gaacagtgac cgtgaccgat cacttccgcg cctgggcgaa ccggggcctg   1860
aacctcggca caatagacca aattacattg tgcgtggagg gttaccaaag ctctggatca   1920
gccaacatca cccagaacac cttctctcag ggctcttctt ccggcagttc gggtggctca   1980
tccggctcca caacgactac tcgcatcgag tgtgagaaca tgtccttgtc cggaccctac   2040
gttagcagga tcaccaatcc ctttaatggt attgcgctgt acgccaacgg agacacagcc   2100
```

```
cgcgctaccg ttaacttccc cgcaagtcgc aactacaatt tccgcctgcg ggttgcggc   2160

aacaacaata atcttgcccg tgtggacctg aggatcgacg gacggaccgt cgggaccttt   2220

tattaccagg gcacataccc ctgggaggcc ccaattgaca atgtttatgt cagtgcgggg   2280

agtcatacag tcgaaatcac tgttactgcg gataacggca catgggacgt gtatgccgac   2340

tacctggtga tacagagcga gaaggacgag ctgtga                             2376


<210> SEQ ID NO 64
<211> LENGTH: 791
<212> TYPE: PRT
<213> ORGANISM: Artificial Sequence
<220> FEATURE:
<223> OTHER INFORMATION: Synthetic construct,
      BAASS:P77T134-100-101:SEKDEL Amino acid sequence

<400> SEQUENCE: 64

Met Ala Asn Lys His Leu Ser Leu Ser Leu Phe Leu Val Leu Leu Gly
1               5                   10                  15

Leu Ser Ala Ser Leu Ala Ser Gly Gln Gln Thr Ser Ile Thr Leu Thr
            20                  25                  30

Ser Asn Ala Ser Gly Thr Phe Asp Gly Tyr Tyr Tyr Glu Leu Trp Lys
        35                  40                  45

Asp Thr Gly Asn Thr Thr Met Thr Val Tyr Thr Gln Gly Arg Phe Ser
    50                  55                  60

Cys Gln Trp Ser Asn Ile Asn Asn Ala Leu Phe Arg Thr Gly Lys Lys
65                  70                  75                  80

Tyr Asn Gln Asn Trp Gln Ser Leu Gly Thr Ile Arg Ile Thr Tyr Ser
                85                  90                  95

Ala Thr Tyr Asn Pro Asn Gly Asn Ser Tyr Leu Cys Ile Tyr Gly Trp
            100                 105                 110

Ser Thr Asn Pro Leu Val Glu Phe Tyr Ile Val Glu Ser Trp Gly Asn
        115                 120                 125

Trp Arg Pro Pro Gly Ala Cys Leu Ala Glu Gly Ser Leu Val Leu Asp
    130                 135                 140

Ala Ala Thr Gly Gln Arg Val Pro Ile Glu Lys Val Arg Pro Gly Met
145                 150                 155                 160

Glu Val Phe Ser Leu Gly Pro Asp Tyr Arg Leu Tyr Arg Val Pro Val
                165                 170                 175

Leu Glu Val Leu Glu Ser Gly Val Arg Glu Val Val Arg Leu Arg Thr
            180                 185                 190

Arg Ser Gly Arg Thr Leu Val Leu Thr Pro Asp His Pro Leu Leu Thr
        195                 200                 205

Pro Glu Gly Trp Lys Pro Leu Cys Asp Leu Pro Leu Gly Thr Pro Ile
    210                 215                 220

Ala Val Pro Ala Glu Leu Pro Val Ala Gly His Leu Ala Pro Pro Glu
225                 230                 235                 240

Glu Arg Val Thr Leu Leu Ala Leu Leu Leu Gly Asp Gly Asn Thr Lys
                245                 250                 255

Leu Ser Gly Arg Arg Gly Thr Arg Pro Asn Ala Phe Phe Tyr Ser Lys
            260                 265                 270

Asn Pro Glu Leu Leu Ala Ala Tyr Arg Arg Cys Ala Glu Ala Leu Gly
        275                 280                 285

Ala Lys Val Lys Ala Tyr Val His Pro Thr Thr Gly Val Val Thr Leu
    290                 295                 300
```

-continued

```
Ala Thr Leu Ala Pro Arg Pro Gly Ala Gln Asp Pro Val Lys Arg Leu
305                 310                 315                 320

Val Val Glu Ala Gly Met Val Ala Lys Ala Glu Glu Lys Arg Val Pro
                325                 330                 335

Glu Glu Val Phe Arg Tyr Arg Arg Glu Ala Leu Ala Leu Phe Leu Gly
            340                 345                 350

Arg Leu Phe Ser Thr Asp Gly Ser Val Glu Lys Lys Arg Ile Ser Tyr
        355                 360                 365

Ser Ser Ala Ser Leu Gly Leu Ala Gln Asp Val Ala His Leu Leu Leu
    370                 375                 380

Arg Leu Gly Ile Thr Ser Gln Leu Arg Ser Arg Gly Pro Arg Ala His
385                 390                 395                 400

Glu Val Leu Ile Ser Gly Arg Glu Asp Ile Leu Arg Phe Ala Glu Leu
                405                 410                 415

Ile Gly Pro Tyr Leu Leu Gly Ala Lys Arg Glu Arg Leu Ala Ala Leu
            420                 425                 430

Glu Ala Glu Ala Arg Arg Arg Leu Pro Gly Gln Gly Trp His Leu Arg
        435                 440                 445

Leu Val Leu Pro Ala Val Ala Tyr Arg Val Gly Glu Ala Glu Arg Arg
    450                 455                 460

Ser Gly Phe Ser Trp Ser Glu Ala Gly Arg Arg Val Ala Val Ala Gly
465                 470                 475                 480

Ser Cys Leu Ser Ser Gly Leu Asn Leu Lys Leu Pro Arg Arg Tyr Leu
                485                 490                 495

Ser Arg His Arg Leu Ser Leu Leu Gly Glu Ala Phe Ala Asp Pro Gly
            500                 505                 510

Leu Glu Ala Leu Ala Glu Gly Gln Val Leu Trp Asp Pro Ile Val Ala
        515                 520                 525

Val Glu Pro Ala Gly Lys Ala Arg Thr Phe Asp Leu Arg Val Pro Pro
    530                 535                 540

Phe Ala Asn Phe Val Ser Glu Asp Leu Val Val His Asn Thr Val Pro
545                 550                 555                 560

Leu Gly Gln Val Thr Ile Asp Gly Gly Thr Tyr Asp Ile Tyr Arg Thr
                565                 570                 575

Thr Arg Val Asn Gln Pro Ser Ile Val Gly Thr Ala Thr Phe Asp Gln
            580                 585                 590

Tyr Trp Ser Val Arg Thr Ser Lys Arg Thr Ser Gly Thr Val Thr Val
        595                 600                 605

Thr Asp His Phe Arg Ala Trp Ala Asn Arg Gly Leu Asn Leu Gly Thr
    610                 615                 620

Ile Asp Gln Ile Thr Leu Cys Val Glu Gly Tyr Gln Ser Ser Gly Ser
625                 630                 635                 640

Ala Asn Ile Thr Gln Asn Thr Phe Ser Gln Gly Ser Ser Ser Gly Ser
                645                 650                 655

Ser Gly Gly Ser Ser Gly Ser Thr Thr Thr Thr Arg Ile Glu Cys Glu
            660                 665                 670

Asn Met Ser Leu Ser Gly Pro Tyr Val Ser Arg Ile Thr Asn Pro Phe
        675                 680                 685

Asn Gly Ile Ala Leu Tyr Ala Asn Gly Asp Thr Ala Arg Ala Thr Val
    690                 695                 700

Asn Phe Pro Ala Ser Arg Asn Tyr Asn Phe Arg Leu Arg Gly Cys Gly
705                 710                 715                 720

Asn Asn Asn Asn Leu Ala Arg Val Asp Leu Arg Ile Asp Gly Arg Thr
```

```
                725                 730                 735

Val Gly Thr Phe Tyr Tyr Gln Gly Thr Tyr Pro Trp Glu Ala Pro Ile
            740                 745                 750

Asp Asn Val Tyr Val Ser Ala Gly Ser His Thr Val Glu Ile Thr Val
        755                 760                 765

Thr Ala Asp Asn Gly Thr Trp Asp Val Tyr Ala Asp Tyr Leu Val Ile
    770                 775                 780

Gln Ser Glu Lys Asp Glu Leu
785                 790


<210> SEQ ID NO 65
<211> LENGTH: 4654
<212> TYPE: DNA
<213> ORGANISM: Artificial Sequence
<220> FEATURE:
<223> OTHER INFORMATION: Synthetic construct, expression cassette in
      pAG2227

<400> SEQUENCE: 65

ggtaccgtcg actctagtaa cggccgccag tgtgctggaa ttaattcggc ttgtcgacca      60

cccaacccca tatcgacaga ggatgtgaag aacaggtaaa tcacgcagaa gaacccatct     120

ctgatagcag ctatcgatta gaacaacgaa tccatattgg gtccgtggga aatacttact     180

gcacaggaag gggcgatct gacgaggccc cgccaccggc ctcgacccga ggccgaggcc     240

gacgaagcgc cggcgagtac ggcgccgcgg cggcctctgc ccgtgccctc tgcgcgtggg     300

agggagaggc cgcggtggtg ggggcgcgcg cgcgcgcgcg cgcagctggt gcggcggcgc     360

gggggtcagc cgccgagccg gcggcgacgg aggagcaggg cggcgtggac gcgaacttcc     420

gatcggttgg tcagagtgcg cgagttgggc ttagccaatt aggtctcaac aatctattgg     480

gccgtaaaat tcatgggccc tggtttgtct aggcccaata tcccgttcat ttcagcccac     540

aaatatttcc ccagaggatt attaaggccc acacgcagct tatagcagat caagtacgat     600

gtttcctgat cgttggatcg gaaacgtacg gtcttgatca ggcatgccga cttcgtcaaa     660

gagaggcggc atgacctgac gcggagttgg ttccgggcac cgtctggatg gtcgtaccgg     720

gaccggacac gtgtcgcgcc tccaactaca tggacacgtg tggtgctgcc attgggccgt     780

acgcgtggcg gtgaccgcac cggatgctgc ctcgcaccgc cttgcccacg ctttatatag     840

agaggttttc tctccattaa tcgcatagcg agtcgaatcg accgaagggg agggggagcg     900

aagctttgcg ttctctaatc gcctcgtcaa ggtaactaat caatcacctc gtcctaatcc     960

tcgaatctct cgtggtgccc gtctaatctc gcgattttga tgctcgtggt ggaaagcgta    1020

ggaggatccc gtgcgagtta gtctcaatct ctcagggttt cgtgcgattt tagggtgatc    1080

cacctcttaa tcgagttacg gtttcgtgcg attttagggt aatcctctta atctctcatt    1140

gatttagggt ttcgtgagaa tcgaggtagg gatctgtgtt atttatatcg atctaataga    1200

tggattggtt ttgagattgt tctgtcagat ggggattgtt tcgatatatt accctaatga    1260

tgtgtcagat ggggattgtt tcgatatatt accctaatga tgtgtcagat ggggattgtt    1320

tcgatatatt accctaatga tggataataa gagtagttca cagttatgtt ttgatcctgc    1380

cacatagttt gagttttgtg atcagattta gttttactta tttgtgctta gttcggatgg    1440

gattgttctg atattgttcc aatagatgaa tagctcgtta ggttaaaatc tttaggttga    1500

gttaggcgac acatagttta tttcctctgg atttggattg gaattgtgtt cttagttttt    1560

ttcccctgga tttggattgg aattgtgtgg agctgggtta gagaattaca tctgtatcgt    1620
```

-continued

```
gtacacctac ttgaactgta gagcttgggt tctaaggtca atttaatctg tattgtatct   1680
ggctctttgc ctagttgaac tgtagtgctg atgttgtact gtgttttttt acccgtttta   1740
tttgctttac tcgtgcaaat caaatctgtc agatgctaga actaggtggc tttattctgt   1800
gttcttacat agatctgttg tcctgtagtt acttatgtca gttttgttat tatctgaaga   1860
tatttttggt tgttgcttgt tgatgtggtg tgagctgtga gcagcgctct tatgattaat   1920
gatgctgtcc aattgtagtg tagtatgatg tgattgatat gttcatctat tttgagctga   1980
cagtaccgat atcgtaggat ctggtgccaa cttattctcc agctgctttt ttttacctat   2040
gttaattcca atcctttctt gcctcttcca gatccagata atgcaaacaa gcattactct   2100
gacatccaac gcatccggta cgtttgacgg ttactattac gaactctgga aggatactgg   2160
caatacaaca atgacggtct acactcaagg tcgcttttcc tgccagtggt cgaacatcaa   2220
taacgcgttg tttaggaccg ggaagaaata caaccagaat tggcagtctc ttggcacaat   2280
ccggatcacg tactctgcga cttacaaccc aaacgggaac tcctacttgt gtatctatgg   2340
ctggtctacc aacccattgg tcgagttcta catcgttgag tcctggggga actggagacc   2400
gcctggtgcc tgcctggccg agggctcgct cgtcttggac gcggctaccg ggcagagggt   2460
ccctatcgaa aaggtgcgtc cggggatgga agttttctcc ttgggacctg attacagact   2520
gtatcgggtg cccgttttgg aggtccttga gagcggggtt agggaagttg tgcgcctcag   2580
aactcggtca gggagaacgc tggtgttgac accagatcac ccgcttttga cccccgaagg   2640
ttggaaacct ctttgtgacc tcccgcttgg aactccaatt gcagtccccg cagaactgcc   2700
tgtggcgggc cacttggccc cacctgaaga acgtgttacg ctcctggctc ttctgttggg   2760
ggatgggaac acaaagctgt cgggtcggag aggtacacgt cctaatgcct tcttctacag   2820
caaaaacccc gaattgctcg cggcttatcg ccggtgtgca gaagccttgg gtgcaaaggt   2880
gaaagcatac gtccacccga ctacgggggt ggttacactc gcaaccctcg ctccacgtcc   2940
tggagctcaa gatcctgtca aacgcctcgt tgtcgaggcg ggaatggttg ctaaagccga   3000
agagaagagg gtcccggagg aggtgtttcg ttaccggcgt gaggcgttgg ccctttttctt   3060
gggccgtttg ttctcgacag acggctctgt tgaaaagaag aggatctctt attcaagtgc   3120
cagtttggga ctggcccagg atgtcgcaca tctcttgctg cgccttggaa ttacatctca   3180
actccgttcg agagggccac gggctcacga ggttcttata tcgggccgcg aggatatttt   3240
gcggtttgct gaacttatcg gaccctacct cttgggggcc aagagggaga gacttgcagc   3300
gctggaagct gaggcccgca ggcgtttgcc tggacaggga tggcacttgc ggcttgttct   3360
tcctgccgtg gcgtacagag tgggcgaggc ggaaaggcgc tcgggatttt cgtggagtga   3420
agccggtcgg cgcgtcgcag ttgcgggatc gtgtttgtca tctggactca acctcaaatt   3480
gcccagacgc tacctttctc ggcaccggtt gtcgctgctc ggtgaggctt ttgccgaccc   3540
tgggctggaa gcgctcgcgg aaggccaagt gctctgggac cctattgttg ctgtcgaacc   3600
ggccggtaag gcgagaacat tcgacttgcg cgttccaccc tttgcaaact tcgtgagcga   3660
ggacctggtg gtgcataaca ccgtcccccct gggccaagtg acaatcgatg gcgggaccta   3720
cgacatctat aggacgacac gcgtcaacca gccttccatt gtggggacag ccacgttcga   3780
tcagtactgg agcgtgcgca cctctaagcg gacttcagga acagtgaccg tgaccgatca   3840
cttccgcgcc tgggcgaacc ggggcctgaa cctcggcaca atagaccaaa ttacattgtg   3900
cgtggagggt taccaaagct ctggatcagc caacatcacc cagaacacct tctctcaggg   3960
ctcttcttcc ggcagttcgg gtggctcatc cggctccaca acgactactc gcatcgagtg   4020
```

tgagaacatg tccttgtccg gaccctacgt tagcaggatc accaatccct ttaatggtat 4080
tgcgctgtac gccaacggag acacagcccg cgctaccgtt aacttccccg caagtcgcaa 4140
ctacaatttc cgcctgcggg gttgcggcaa caacaataat cttgcccgtg tggacctgag 4200
gatcgacgga cggaccgtcg ggacctttta ttaccagggc acataccccct gggaggcccc 4260 aattgacaat gtttatgtca gtgcggggag tcatacagtc gaaatcactg ttactgcgga 4320
taacggcaca tgggacgtgt atgccgacta cctggtgata cagtgaccta ggtccccgaa 4380
tttccccgat cgttcaaaca tttggcaata aagtttctta agattgaatc ctgttgccgg 4440
tcttgcgatg attatcatat aatttctgtt gaattacgtt aagcatgtaa taattaacat 4500
gtaatgcatg acgttattta tgagatgggt ttttatgatt agagtcccgc aattatacat 4560
ttaatacgcg atagaaaaca aaatatagcg cgcaaactag gataaattat cgcgcgcggt 4620
gtcatctatg ttactagatc gggaattgga attc 4654

<210> SEQ ID NO 66
<211> LENGTH: 4726
<212> TYPE: DNA
<213> ORGANISM: Artificial Sequence
<220> FEATURE:
<223> OTHER INFORMATION: Synthetic construct, expression cassette in pAG2228

<400> SEQUENCE: 66
ggtaccgtcg actctagtaa cggccgccag tgtgctggaa ttaattcggc ttgtcgacca 60
cccaacccca tatcgacaga ggatgtgaag aacaggtaaa tcacgcagaa gaacccatct 120
ctgatagcag ctatcgatta gaacaacgaa tccatattgg gtccgtggga aatacttact 180
gcacaggaag gggcgatct gacgaggccc cgccaccggc ctcgacccga ggccgaggcc 240
gacgaagcgc cggcgagtac ggcgccgcgg cggcctctgc ccgtgccctc tgcgcgtggg 300
agggagaggc cgcggtggtg ggggcgcgcg cgcgcgcgcg cgcagctggt gcggcggcgc 360
gggggtcagc cgccgagccg gcggcgacgg aggagcaggg cggcgtggac gcgaacttcc 420
gatcggttgg tcagagtgcg cgagttgggc ttagccaatt aggtctcaac aatctattgg 480
gccgtaaaat tcatgggccc tggtttgtct aggcccaata tcccgttcat ttcagcccac 540
aaatatttcc ccagaggatt attaaggccc acacgcagct tatagcagat caagtacgat 600
gtttcctgat cgttggatcg gaaacgtacg gtcttgatca ggcatgccga cttcgtcaaa 660
gagaggcggc atgacctgac gcggagttgg ttccgggcac cgtctggatg gtcgtaccgg 720
gaccggacac gtgtcgcgcc tccaactaca tggacacgtg tggtgctgcc attgggccgt 780
acgcgtggcg gtgaccgcac cggatgctgc ctcgcaccgc cttgcccacg ctttatatag 840
agaggttttc tctccattaa tcgcatagcg agtcgaatcg accgaagggg agggggagcg 900
aagctttgcg ttctctaatc gcctcgtcaa ggtaactaat caatcacctc gtcctaatcc 960
tcgaatctct cgtggtgccc gtctaatctc gcgattttga tgctcgtggt ggaaagcgta 1020
ggaggatccc gtgcgagtta gtctcaatct ctcagggttt cgtgcgattt tagggtgatc 1080
cacctcttaa tcgagttacg gtttcgtgcg attttagggt aatcctctta atctctcatt 1140
gatttagggt ttcgtgagaa tcgaggtagg gatctgtgtt atttatatcg atctaataga 1200
tggattggtt ttgagattgt tctgtcagat ggggattgtt tcgatatatt accctaatga 1260
tgtgtcagat ggggattgtt tcgatatatt accctaatga tgtgtcagat ggggattgtt 1320
tcgatatatt accctaatga tggataataa gagtagttca cagttatgtt ttgatcctgc 1380

```
cacatagttt gagttttgtg atcagattta gttttactta tttgtgctta gttcggatgg   1440

gattgttctg atattgttcc aatagatgaa tagctcgtta ggttaaaatc tttaggttga   1500

gttaggcgac acatagttta tttcctctgg atttggattg gaattgtgtt cttagttttt   1560

ttcccctgga tttggattgg aattgtgtgg agctgggtta gagaattaca tctgtatcgt   1620

gtacacctac ttgaactgta gagcttgggt tctaaggtca atttaatctg tattgtatct   1680

ggctctttgc ctagttgaac tgtagtgctg atgttgtact gtgttttttt acccgtttta   1740

tttgctttac tcgtgcaaat caaatctgtc agatgctaga actaggtggc tttattctgt   1800

gttcttacat agatctgttg tcctgtagtt acttatgtca gttttgttat tatctgaaga   1860

tatttttggt tgttgcttgt tgatgtggtg tgagctgtga gcagcgctct tatgattaat   1920

gatgctgtcc aattgtagtg tagtatgatg tgattgatat gttcatctat tttgagctga   1980

cagtaccgat atcgtaggat ctggtgccaa cttattctcc agctgctttt ttttacctat   2040

gttaattcca atcctttctt gcctcttcca gatccagata atggcgaaca aacatttgtc   2100

cctctccctc ttcctcgtcc tccttggcct gtcggccagc ttggcctccg ggcaacaaac   2160

aagcattact ctgacatcca acgcatccgg tacgtttgac ggttactatt acgaactctg   2220

gaaggatact ggcaatacaa caatgacggt ctacactcaa ggtcgctttt cctgccagtg   2280

gtcgaacatc aataacgcgt tgtttaggac cgggaagaaa tacaaccaga attggcagtc   2340

tcttggcaca atccggatca cgtactctgc gacttacaac ccaaacggga actcctactt   2400

gtgtatctat ggctggtcta ccaacccatt ggtcgagttc tacatcgttg agtcctgggg   2460

gaactggaga ccgcctggtg cctgcctggc cgagggctcg ctcgtcttgg acgcggctac   2520

cgggcagagg gtccctatcg aaaaggtgcg tccggggatg gaagttttct ccttgggacc   2580

tgattacaga ctgtatcggg tgcccgtttt ggaggtcctt gagagcgggg ttagggaagt   2640

tgtgcgcctc agaactcggt cagggagaac gctggtgttg acaccagatc acccgctttt   2700

gacccccgaa ggttggaaac ctctttgtga cctcccgctt ggaactccaa ttgcagtccc   2760

cgcagaactg cctgtggcgg gccacttggc cccacctgaa gaacgtgtta cgctcctggc   2820

tcttctgttg ggggatggga acacaaagct gtcgggtcgg agaggtacac gtcctaatgc   2880

cttcttctac agcaaaaacc ccgaattgct cgcggcttat cgccggtgtg cagaagcctt   2940

gggtgcaaag gtgaaagcat acgtccaccc gactacgggg gtggttacac tcgcaaccct   3000

cgctccacgt cctggagctc aagatcctgt caaacgcctc gttgtcgagg cgggaatggt   3060

tgctaaagcc gaagagaaga gggtcccgga ggaggtgttt cgttaccggc gtgaggcgtt   3120

ggccctttc ttgggccgtt tgttctcgac agacggctct gttgaaaaga agaggatctc   3180

ttattcaagt gccagtttgg gactggccca ggatgtcgca catctcttgc tgcgccttgg   3240

aattacatct caactccgtt cgagagggcc acgggctcac gaggttctta tatcgggccg   3300

cgaggatatt ttgcggtttg ctgaacttat cggaccctac ctcttggggg ccaagaggga   3360

gagacttgca gcgctggaag ctgaggcccg caggcgtttg cctggacagg gatggcactt   3420

gcggcttgtt cttcctgccg tggcgtacag agtgggcgag gcggaaaggc gctcgggatt   3480

ttcgtggagt gaagccggtc ggcgcgtcgc agttgcggga tcgtgtttgt catctggact   3540

caacctcaaa ttgcccagac gctacctttc tcggcaccgg ttgtcgctgc tcggtgaggc   3600

ttttgccgac cctgggctgg aagcgctcgc ggaaggccaa gtgctctggg accctattgt   3660

tgctgtcgaa ccggccggta aggcgagaac attcgacttg cgcgttccac cctttgcaaa   3720
```

```
cttcgtgagc gaggacctgg tggtgcataa caccgtcccc ctgggccaag tgacaatcga   3780

tggcgggacc tacgacatct ataggacgac acgcgtcaac cagccttcca ttgtggggac   3840

agccacgttc gatcagtact ggagcgtgcg cacctctaag cggacttcag gaacagtgac   3900

cgtgaccgat cacttccgcg cctgggcgaa ccggggcctg aacctcggca caatagacca   3960

aattacattg tgcgtggagg gttaccaaag ctctggatca gccaacatca cccagaacac   4020

cttctctcag ggctcttctt ccggcagttc gggtggctca tccggctcca caacgactac   4080

tcgcatcgag tgtgagaaca tgtccttgtc cggaccctac gttagcagga tcaccaatcc   4140

ctttaatggt attgcgctgt acgccaacgg agacacagcc cgcgctaccg ttaacttccc   4200

cgcaagtcgc aactacaatt tccgcctgcg gggttgcggc aacaacaata atcttgcccg   4260

tgtggacctg aggatcgacg gacggaccgt cgggaccttt tattaccagg gcacataccc   4320

ctgggaggcc ccaattgaca atgtttatgt cagtgcgggg agtcatacag tcgaaatcac   4380

tgttactgcg gataacggca catgggacgt gtatgccgac tacctggtga tacagtgacc   4440

taggtccccg aatttccccg atcgttcaaa catttggcaa taaagtttct taagattgaa   4500

tcctgttgcc ggtcttgcga tgattatcat ataatttctg ttgaattacg ttaagcatgt   4560

aataattaac atgtaatgca tgacgttatt tatgagatgg gtttttatga ttagagtccc   4620

gcaattatac atttaatacg cgatagaaaa caaaatatag cgcgcaaact aggataaatt   4680

atcgcgcgcg gtgtcatcta tgttactaga tcgggaattg gaattc                 4726
```

<210> SEQ ID NO 67
<211> LENGTH: 4744
<212> TYPE: DNA
<213> ORGANISM: Artificial Sequence
<220> FEATURE:
<223> OTHER INFORMATION: Synthetic construct, expression cassette in pAG2229

<400> SEQUENCE: 67

```
ggtaccgtcg actctagtaa cggccgccag tgtgctggaa ttaattcggc ttgtcgacca     60

cccaacccca tatcgacaga ggatgtgaag aacaggtaaa tcacgcagaa gaacccatct    120

ctgatagcag ctatcgatta gaacaacgaa tccatattgg gtccgtggga aatacttact    180

gcacaggaag gggcgatct gacgaggccc cgccaccggc ctcgacccga ggccgaggcc    240

gacgaagcgc cggcgagtac ggcgccgcgg cggcctctgc ccgtgccctc tgcgcgtggg    300

agggagaggc cgcggtggtg ggggcgcgcg cgcgcgcgcg cgcagctggt gcggcggcgc    360

gggggtcagc cgccgagccg gcggcgacgg aggagcaggg cggcgtggac gcgaacttcc    420

gatcggttgg tcagagtgcg cgagttgggc ttagccaatt aggtctcaac aatctattgg    480

gccgtaaaat tcatgggccc tggtttgtct aggcccaata tcccgttcat ttcagcccac    540

aaatatttcc ccagaggatt attaaggccc acacgcagct tatagcagat caagtacgat    600

gtttcctgat cgttggatcg gaaacgtacg gtcttgatca ggcatgccga cttcgtcaaa    660

gagaggcggc atgacctgac gcggagttgg ttccgggcac cgtctggatg gtcgtaccgg    720

gaccggacac gtgtcgcgcc tccaactaca tggacacgtg tggtgctgcc attgggccgt    780

acgcgtggcg gtgaccgcac cggatgctgc ctcgcaccgc cttgcccacg ctttatatag    840

agaggttttc tctccattaa tcgcatagcg agtcgaatcg accgaagggg agggggagcg    900

aagctttgcg ttctctaatc gcctcgtcaa ggtaactaat caatcacctc gtcctaatcc    960

tcgaatctct cgtggtgccc gtctaatctc gcgattttga tgctcgtggt ggaaagcgta   1020
```

-continued

```
ggaggatccc gtgcgagtta gtctcaatct ctcagggttt cgtgcgattt tagggtgatc   1080
cacctcttaa tcgagttacg gtttcgtgcg attttagggt aatcctctta atctctcatt   1140
gatttagggt ttcgtgagaa tcgaggtagg gatctgtgtt atttatatcg atctaataga   1200
tggattggtt ttgagattgt tctgtcagat ggggattgtt tcgatatatt accctaatga   1260
tgtgtcagat ggggattgtt tcgatatatt accctaatga tgtgtcagat ggggattgtt   1320
tcgatatatt accctaatga tggataataa gagtagttca cagttatgtt ttgatcctgc   1380
cacatagttt gagttttgtg atcagattta gttttactta tttgtgctta gttcggatgg   1440
gattgttctg atattgttcc aatagatgaa tagctcgtta ggttaaaatc tttaggttga   1500
gttaggcgac acatagttta tttcctctgg atttggattg gaattgtgtt cttagttttt   1560
ttcccctgga tttggattgg aattgtgtgg agctgggtta gagaattaca tctgtatcgt   1620
gtacacctac ttgaactgta gagcttgggt tctaaggtca atttaatctg tattgtatct   1680
ggctctttgc ctagttgaac tgtagtgctg atgttgtact gtgttttttt acccgtttta   1740
tttgctttac tcgtgcaaat caaatctgtc agatgctaga actaggtggc tttattctgt   1800
gttcttacat agatctgttg tcctgtagtt acttatgtca gttttgttat tatctgaaga   1860
tatttttggt tgttgcttgt tgatgtggtg tgagctgtga gcagcgctct tatgattaat   1920
gatgctgtcc aattgtagtg tagtatgatg tgattgatat gttcatctat tttgagctga   1980
cagtaccgat atcgtaggat ctggtgccaa cttattctcc agctgctttt ttttacctat   2040
gttaattcca atcctttctt gcctcttcca gatccagata atggcgaaca aacatttgtc   2100
cctctccctc ttcctcgtcc tccttggcct gtcggccagc ttggcctccg ggcaacaaac   2160
aagcattact ctgacatcca acgcatccgg tacgtttgac ggttactatt acgaactctg   2220
gaaggatact ggcaatacaa caatgacggt ctacactcaa ggtcgctttt cctgccagtg   2280
gtcgaacatc aataacgcgt tgtttaggac cgggaagaaa tacaaccaga attggcagtc   2340
tcttggcaca atccggatca cgtactctgc gacttacaac ccaaacggga actcctactt   2400
gtgtatctat ggctggtcta ccaacccatt ggtcgagttc tacatcgttg agtcctgggg   2460
gaactggaga ccgcctggtg cctgcctggc cgagggctcg ctcgtcttgg acgcggctac   2520
cgggcagagg gtccctatcg aaaaggtgcg tccggggatg gaagttttct ccttgggacc   2580
tgattacaga ctgtatcggg tgcccgtttt ggaggtcctt gagagcgggg ttagggaagt   2640
tgtgcgcctc agaactcggt cagggagaac gctggtgttg acaccagatc acccgctttt   2700
gacccccgaa ggttggaaac ctctttgtga cctcccgctt ggaactccaa ttgcagtccc   2760
cgcagaactg cctgtggcgg gccacttggc cccacctgaa gaacgtgtta cgctcctggc   2820
tcttctgttg ggggatggga acacaaagct gtcgggtcgg agaggtacac gtcctaatgc   2880
cttcttctac agcaaaaacc ccgaattgct cgcggcttat cgccggtgtg cagaagcctt   2940
gggtgcaaag gtgaaagcat acgtccaccc gactacgggg gtggttacac tcgcaaccct   3000
cgctccacgt cctggagctc aagatcctgt caaacgcctc gttgtcgagg cgggaatggt   3060
tgctaaagcc gaagagaaga gggtcccgga ggaggtgttt cgttaccggc gtgaggcgtt   3120
ggccctttc ttgggccgtt tgttctcgac agacggctct gttgaaaaga agaggatctc   3180
ttattcaagt gccagtttgg gactggccca ggatgtcgca catctcttgc tgcgccttgg   3240
aattacatct caactccgtt cgagagggcc acgggctcac gaggttctta tatcgggccg   3300
cgaggatatt ttgcggtttg ctgaacttat cggaccctac ctcttggggg ccaagaggga   3360
gagacttgca gcgctggaag ctgaggcccg caggcgtttg cctggacagg gatggcactt   3420
```

gcggcttgtt cttcctgccg tggcgtacag agtgggcgag gcggaaaggc gctcgggatt 3480
ttcgtggagt gaagccggtc ggcgcgtcgc agttgcggga tcgtgtttgt catctggact 3540
caacctcaaa ttgcccagac gctacctttc tcggcaccgg ttgtcgctgc tcggtgaggc 3600
ttttgccgac cctgggctgg aagcgctcgc ggaaggccaa gtgctctggg accctattgt 3660
tgctgtcgaa ccggccggta aggcgagaac attcgacttg cgcgttccac cctttgcaaa 3720
cttcgtgagc gaggacctgg tggtgcataa caccgtcccc ctgggccaag tgacaatcga 3780
tggcgggacc tacgacatct ataggacgac acgcgtcaac cagccttcca ttgtggggac 3840
agccacgttc gatcagtact ggagcgtgcg cacctctaag cggacttcag gaacagtgac 3900
cgtgaccgat cacttccgcg cctgggcgaa ccggggcctg aacctcggca caatagacca 3960
aattacattg tgcgtggagg gttaccaaag ctctggatca gccaacatca cccagaacac 4020
cttctctcag ggctcttctt ccggcagttc gggtggctca tccggctcca caacgactac 4080
tcgcatcgag tgtgagaaca tgtccttgtc cggaccctac gttagcagga tcaccaatcc 4140
ctttaatggt attgcgctgt acgccaacgg agacacagcc cgcgctaccg ttaacttccc 4200
cgcaagtcgc aactacaatt tccgcctgcg gggttgcggc aacaacaata atcttgcccg 4260
tgtggacctg aggatcgacg gacggaccgt cgggaccttt tattaccagg gcacataccc 4320
ctgggaggcc ccaattgaca atgtttatgt cagtgcgggg agtcatacag tcgaaatcac 4380
tgttactgcg gataacggca catgggacgt gtatgccgac tacctggtga tacagagcga 4440
gaaggacgag ctgtgaccta ggtccccgaa tttccccgat cgttcaaaca tttggcaata 4500
aagtttctta agattgaatc ctgttgccgg tcttgcgatg attatcatat aatttctgtt 4560
gaattacgtt aagcatgtaa taattaacat gtaatgcatg acgttattta tgagatgggt 4620
ttttatgatt agagtcccgc aattatacat ttaatacgcg atagaaaaca aaatatagcg 4680
cgcaaactag gataaattat cgcgcgcggt gtcatctatg ttactagatc gggaattgga 4740
attc 4744

<210> SEQ ID NO 68
<211> LENGTH: 4683
<212> TYPE: DNA
<213> ORGANISM: Artificial Sequence
<220> FEATURE:
<223> OTHER INFORMATION: Synthetic construct, expression cassette in pAG2361 and pAG4004

<400> SEQUENCE: 68
ggtaccctgc agtgcagcgt gacccggtcg tgcccctctc tagagataat gagcattgca 60
tgtctaagtt ataaaaaatt accacatatt ttttttgtca cacttgtttg aagtgcagtt 120
tatctatctt tatacatata tttaaacttt actctacgaa taatataatc tatagtacta 180
caataatatc agtgttttag agaatcatat aaatgaacag ttagacatgg tctaaaggac 240
aattgagtat tttgacaaca ggactctaca gttttatctt tttagtgtgc atgtgttctc 300
cttttttttt gcaaatagct tcacctatat aatacttcat ccattttatt agtacatcca 360
tttagggttt agggttaatg gtttttatag actaattttt ttagtacatc tattttattc 420
tattttagcc tctaaattaa gaaaactaaa actctatttt agttttttta tttaataatt 480
tagatataaa atagaataaa ataaagtgac taaaaattaa acaaataccc tttaagaaat 540
taaaaaaact aaggaaacat ttttcttgtt tcgagtagat aatgccagcc tgttaaacgc 600
cgtcgacgag tctaacggac accaaccagc gaaccagcag cgtcgcgtcg ggccaagcga 660

```
agcagacggc acggcatctc tgtcgctgcc tctggacccc tctcgagagt tccgctccac    720
cgttggactt gctccgctgt cggcatccag aaattgcgtg gcggagcggc agacgtgagc    780
cggcacggca ggcggcctcc tcctcctctc acggcacggc agctacgggg gattcctttc    840
ccaccgctcc ttcgctttcc cttcctcgcc cgccgtaata aatagacacc ccctccacac    900
cctctttccc caacctcgtg ttgttcggag cgcacacaca cacaaccaga tctcccccaa    960
atccacccgt cggcacctcc gcttcaaggt acgccgctcg tcctcccccc cccccccctct   1020
ctaccttctc tagatcggcg ttccggtcca tggttagggc ccggtagttc tacttctgtt   1080
catgtttgtg ttagatccgt gtttgtgtta gatccgtgct gctagcgttc gtacacggat   1140
gcgacctgta cgtcagacac gttctgattg ctaacttgcc agtgtttctc tttggggaat   1200
cctgggatgg ctctagccgt tccgcagacg ggatcgattt catgattttt tttgtttcgt   1260
tgcatagggt ttggtttgcc cttttccttt atttcaatat atgccgtgca cttgtttgtc   1320
gggtcatctt ttcatgcttt tttttgtctt ggttgtgatg atgtggtctg gttgggcggt   1380
cgttctagat cggagtagaa ttctgtttca aactacctgg tggatttatt aattttggat   1440
ctgtatgtgt gtgccataca tattcatagt tacgaattga agatgatgga tggaaatatc   1500
gatctaggat aggtatacat gttgatgcgg gttttactga tgcatataca gagatgcttt   1560
ttgttcgctt ggttgtgatg atgtggtgtg gttgggcggt cgttcattcg ttctagatcg   1620
gagtagaata ctgtttcaaa ctacctggtg tatttattaa ttttggaact gtatgtgtgt   1680
gtcatacatc ttcatagtta cgagtttaag atggatggaa atatcgatct aggataggta   1740
tacatgttga tgtgggtttt actgatgcat atacatgatg gcatatgcag catctattca   1800
tatgctctaa ccttgagtac ctatctatta taataaacaa gtatgtttta taattatttt   1860
gatcttgata tacttggatg atggcatatg cagcagctat atgtggattt ttttagccct   1920
gccttcatac gctatttatt tgcttggtac tgtttctttt gtcgatgctc accctgttgt   1980
ttggtgttac ttctgcagat ccagatcgga tcctaaacca tggcgaacaa acatttgtcc   2040
ctctccctct tcctcgtcct ccttggcctg tcggccagct tggcctccgg gcaacaaaca   2100
agcattactc tgacatccaa cgcatccggt acgtttgacg gttactatta cgaactctgg   2160
aaggatactg gcaatacaac aatgacggtc tacactcaag gtcgcttttc ctgccagtgg   2220
tcgaacatca ataacgcgtt gtttaggacc gggaagaaat acaaccagaa ttggcagtct   2280
cttggcacaa tccggatcac gtactctgcg acttacaacc caaacgggaa ctcctacttg   2340
tgtatctatg gctggtctac caacccattg gtcgagttct acatcgttga gtcctggggg   2400
aactggagac cgcctggtgc ctgcctggcc gagggctcgc tcgtcttgga cgcggctacc   2460
gggcagaggg tccctatcga aaaggtgcgt ccggggatgg aagttttctc cttgggacct   2520
gattacagac tgtatcgggt gcccgttttg gaggtccttg agagcggggt tagggaagtt   2580
gtgcgcctca gaactcggtc agggagaacg ctggtgttga caccagatca cccgcttttg   2640
acccccgaag gttggaaacc tctttgtgac ctcccgcttg gaactccaat tgcagtcccc   2700
gcagaactgc ctgtggcggg ccacttggcc ccacctgaag aacgtgttac gctcctggct   2760
cttctgttgg gggatgggaa cacaaagctg tcgggtcgga gaggtacacg tcctaatgcc   2820
ttcttctaca gcaaaaaccc cgaattgctc gcggcttatc gccggtgtgc agaagccttg   2880
ggtgcaaagg tgaaagcata cgtccacccg actacggggg tggttacact cgcaaccctc   2940
gctccacgtc ctggagctca agatcctgtc aaacgcctcg ttgtcgaggc gggaatggtt   3000
```

```
gctaaagccg aagagaagag ggtcccggag gaggtgtttc gttaccggcg tgaggcgttg   3060
gcccttttct tgggccgttt gttctcgaca gacggctctg ttgaaaagaa gaggatctct   3120
tattcaagtg ccagtttggg actggcccag gatgtcgcac atctcttgct gcgccttgga   3180
attacatctc aactccgttc gagagggcca cgggctcacg aggttcttat atcgggccgc   3240
gaggatattt tgcggtttgc tgaacttatc ggaccctacc tcttgggggc caagagggag   3300
agacttgcag cgctggaagc tgaggcccgc aggcgtttgc ctggacaggg atggcacttg   3360
cggcttgttc ttcctgccgt ggcgtacaga gtgggcgagg ctgaaaggcg ctcgggattt   3420
tcgtggagtg aagccggtcg gcgcgtcgca gttgcgggat cgtgtttgtc atctggactc   3480
aacctcaaat tgcccagacg ctacctttct cggcaccggt tgtcgctgct cggtgaggct   3540
tttgccgacc ctgggctgga agcgctcgcg gaaggccaag tgctctggga ccctattgtt   3600
gctgtcgaac cggccggtaa ggcgagaaca ttcgacttgc gcgttccacc ctttgcaaac   3660
ttcgtgagcg aggacctggt ggtgcataac accgtccccc tgggccaagt gacaatcgat   3720
ggcgggacct acgacatcta taggacgaca cgcgtcaacc agccttccat tgtggggaca   3780
gccacgttcg atcagtactg gagcgtgcgc acctctaagc ggacttcagg aacagtgacc   3840
gtgaccgatc acttccgcgc ctgggcgaac cggggcctga acctcggcac aatagaccaa   3900
attacattgt gcgtggaggg ttaccaaagc tctggatcag ccaacatcac ccagaacacc   3960
ttctctcagg gctcttcttc cggcagttcg ggtggctcat ccggctccac aacgactact   4020
cgcatcgagt gtgagaacat gtccttgtcc ggaccctacg ttagcaggat caccaatccc   4080
tttaatggta ttgcgctgta cgccaacgga gacacagccc gcgctaccgt taacttcccc   4140
gcaagtcgca actacaattt ccgcctgcgg ggttgcggca acaacaataa tcttgcccgt   4200
gtggacctga ggatcgacgg acggaccgtc gggacctttt attaccaggg cacatacccc   4260
tgggaggccc caattgacaa tgtttatgtc agtgcgggga gtcatacagt cgaaatcact   4320
gttactgcgg ataacggcac atgggacgtg tatgccgact acctggtgat acagagcgag   4380
aaggacgagc tgtgacctag gtccccgaat ttccccgatc gttcaaacat ttggcaataa   4440
agtttcttaa gattgaatcc tgttgccggt cttgcgatga ttatcatata atttctgttg   4500
aattacgtta agcatgtaat aattaacatg taatgcatga cgttatttat gagatgggtt   4560
tttatgatta gagtcccgca attatacatt taatacgcga tagaaaacaa aatatagcgc   4620
gcaaactagg ataaattatc gcgcgcggtg tcatctatgt tactagatcg ggaattggaa   4680
ttc                                                                 4683
```

<210> SEQ ID NO 69
<211> LENGTH: 10146
<212> TYPE: DNA
<213> ORGANISM: Artificial Sequence
<220> FEATURE:
<223> OTHER INFORMATION: Synthetic construct, pAG4000 vector

<400> SEQUENCE: 69

```
aattcctgca gtgcagcgtg acccggtcgt gcccctctct agagataatg agcattgcat     60
gtctaagtta taaaaaatta ccacatattt tttttgtcac acttgtttga agtgcagttt    120
atctatcttt atacatatat ttaaacttta ctctacgaat aatataatct atagtactac    180
aataatatca gtgttttaga gaatcatata aatgaacagt tagacatggt ctaaaggaca    240
attgagtatt ttgacaacag gactctacag ttttatcttt ttagtgtgca tgtgttctcc    300
tttttttttg caaatagctt cacctatata atacttcatc cattttatta gtacatccat    360
```

```
ttagggttta gggttaatgg tttttataga ctaatttttt tagtacatct attttattct    420
attttagcct ctaaattaag aaaactaaaa ctctatttta gtttttttat ttaataattt    480
agatataaaa tagaataaaa taaagtgact aaaaattaaa caaataccct ttaagaaatt    540
aaaaaaacta aggaaacatt tttcttgttt cgagtagata atgccagcct gttaaacgcc    600
gtcgacgagt ctaacggaca ccaaccagcg aaccagcagc gtcgcgtcgg gccaagcgaa    660
gcagacggca cggcatctct gtcgctgcct ctggacccct ctcgagagtt ccgctccacc    720
gttggacttg ctccgctgtc ggcatccaga aattgcgtgg cggagcggca gacgtgagcc    780
ggcacggcag gcggcctcct cctcctctca cggcacggca gctacggggg attcctttcc    840
caccgctcct tcgctttccc ttcctcgccc gccgtaataa atagacaccc cctccacacc    900
ctctttcccc aacctcgtgt tgttcggagc gcacacacac acaaccagat ctcccccaaa    960
tccacccgtc ggcacctccg cttcaaggta cgccgctcgt cctccccccc cccccctctc   1020
taccttctct agatcggcgt tccggtccat ggttagggcc cggtagttct acttctgttc   1080
atgtttgtgt tagatccgtg tttgtgttag atccgtgctg ctagcgttcg tacacggatg   1140
cgacctgtac gtcagacacg ttctgattgc taacttgcca gtgtttctct ttggggaatc   1200
ctgggatggc tctagccgtt ccgcagacgg gatcgatttc atgatttttt ttgtttcgtt   1260
gcatagggtt tggtttgccc ttttccttta tttcaatata tgccgtgcac ttgtttgtcg   1320
ggtcatcttt tcatgctttt ttttgtcttg gttgtgatga tgtggtctgg ttgggcggtc   1380
gttctagatc ggagtagaat tctgtttcaa actacctggt ggatttatta attttggatc   1440
tgtatgtgtg tgccatacat attcatagtt acgaattgaa gatgatggat ggaaatatcg   1500
atctaggata ggtatacatg ttgatgcggg ttttactgat gcatatacag agatgctttt   1560
tgttcgcttg gttgtgatga tgtggtgtgg ttgggcggtc gttcattcgt tctagatcgg   1620
agtagaatac tgtttcaaac tacctggtgt atttattaat tttggaactg tatgtgtgtg   1680
tcatacatct tcatagttac gagtttaaga tggatggaaa tatcgatcta ggataggtat   1740
acatgttgat gtgggtttta ctgatgcata tacatgatgg catatgcagc atctattcat   1800
atgctctaac cttgagtacc tatctattat aataaacaag tatgttttat aattattttg   1860
atcttgatat acttggatga tggcatatgc agcagctata tgtggatttt tttagccctg   1920
ccttcatacg ctatttattt gcttggtact gtttcttttg tcgatgctca ccctgttgtt   1980
tggtgttact tctgcagatg cagaaactca ttaactcagt gcaaaactat gcctggggca   2040
gcaaaacggc gttgactgaa ctttatggta tggaaaatcc gtccagccag ccgatggccg   2100
agctgtggat gggcgcacat ccgaaaagca gttcacgagt gcagaatgcc gccggagata   2160
tcgtttcact gcgtgatgtg attgagagtg ataaatcgac tctgctcgga gaggccgttg   2220
ccaaacgctt tggcgaactg cctttcctgt tcaaagtatt atgcgcagca cagccactct   2280
ccattcaggt tcatccaaac aaacacaatt ctgaaatcgg ttttgccaaa gaaaatgccg   2340
caggtatccc gatggatgcc gccgagcgta actataaaga tcctaaccac aagccggagc   2400
tggtttttgc gctgacgcct ttccttgcga tgaacgcgtt tcgtgaattt tccgagattg   2460
tctccctact ccagccggtc gcaggtgcac atccggcgat tgctcacttt ttacaacagc   2520
ctgatgccga acgtttaagc gaactgttcg ccagcctgtt gaatatgcag ggtgaagaaa   2580
aatcccgcgc gctggcgatt ttaaaatcgg ccctcgatag ccagcagggt gaaccgtggc   2640
aaacgattcg tttaatttct gaattttacc cggaagacag cggtctgttc tccccgctat   2700
```

-continued

```
tgctgaatgt ggtgaaattg aaccctggcg aagcgatgtt cctgttcgct gaaacaccgc   2760
acgcttacct gcaaggcgtg gcgctggaag tgatggcaaa ctccgataac gtgctgcgtg   2820
cgggtctgac gcctaaatac attgatattc cggaactggt tgccaatgtg aaattcgaag   2880
ccaaaccggc taaccagttg ttgacccagc cggtgaaaca aggtgcagaa ctggacttcc   2940
cgattccagt ggatgatttt gccttctcgc tgcatgacct tagtgataaa gaaaccacca   3000
ttagccagca gagtgccgcc attttgttct gcgtcgaagg cgatgcaacg ttgtggaaag   3060
gttctcagca gttacagctt aaaccgggtg aatcagcgtt tattgccgcc aacgaatcac   3120
cggtgactgt caaaggccac ggccgtttag cgcgtgttta caacaagctg taagagctta   3180
ctgaaaaaat taacatctct tgctaagctg ggagctctag atccccgaat ttccccgatc   3240
gttcaaacat ttggcaataa agtttcttaa gattgaatcc tgttgccggt cttgcgatga   3300
ttatcatata atttctgttg aattacgtta agcatgtaat aattaacatg taatgcatga   3360
cgttatttat gagatgggtt tttatgatta gagtcccgca attatacatt taatacgcga   3420
tagaaaacaa aatatagcgc gcaaactagg ataaattatc gcgcgcggtg tcatctatgt   3480
tactagatcg ggaattggcg agctcgaatt aattcagtac attaaaaacg tccgcaatgt   3540
gttattaagt tgtctaagcg tcaatttgtt tacaccacaa tatatcctgc caccagccag   3600
ccaacagctc cccgaccggc agctcggcac aaaatcacca ctcgatacag gcagcccatc   3660
agtccgggac ggcgtcagcg ggagagccgt tgtaaggcgg cagactttgc tcatgttacc   3720
gatgctattc ggaagaacgg caactaagct gccgggtttg aaacacggat gatctcgcgg   3780
agggtagcat gttgattgta acgatgacag agcgttgctg cctgtgatca aatatcatct   3840
ccctcgcaga gatccgaatt atcagccttc ttattcattt ctcgcttaac cgtgacaggc   3900
tgtcgatctt gagaactatg ccgacataat aggaaatcgc tggataaagc cgctgaggaa   3960
gctgagtggc gctatttctt tagaagtgaa cgttgacgat cgtcgaccgt accccgatga   4020
attaattcgg acgtacgttc tgaacacagc tggatactta cttgggcgat tgtcatacat   4080
gacatcaaca atgtacccgt ttgtgtaacc gtctcttgga ggttcgtatg acactagtgg   4140
ttcccctcag cttgcgacta gatgttgagg cctaacattt tattagagag caggctagtt   4200
gcttagatac atgatcttca ggccgttatc tgtcagggca agcgaaaatt ggccatttat   4260
gacgaccaat gccccgcaga agctcccatc tttgccgcca tagacgccgc gccccccttt   4320
tggggtgtag aacatccttt tgccagatgt ggaaaagaag ttcgttgtcc cattgttggc   4380
aatgacgtag tagccggcga aagtgcgaga cccatttgcg ctatatataa gcctacgatt   4440
tccgttgcga ctattgtcgt aattggatga actattatcg tagttgctct cagagttgtc   4500
gtaatttgat ggactattgt cgtaattgct tatggagttg tcgtagttgc ttggagaaat   4560
gtcgtagttg gatggggagt agtcataggg aagacgagct tcatccacta aaacaattgg   4620
caggtcagca agtgcctgcc ccgatgccat cgcaagtacg aggcttagaa ccaccttcaa   4680
cagatcgcgc atagtcttcc ccagctctct aacgcttgag ttaagccgcg ccgcgaagcg   4740
gcgtcggctt gaacgaattg ttagacatta tttgccgact accttggtga tctcgccttt   4800
cacgtagtga acaaattctt ccaactgatc tgcgcgcgag gccaagcgat cttcttgtcc   4860
aagataagcc tgcctagctt caagtatgac gggctgatac tgggccggca ggcgctccat   4920
tgcccagtcg gcagcgacat ccttcggcgc gattttgccg gttactgcgc tgtaccaaat   4980
gcgggacaac gtaagcacta catttcgctc atcgccagcc cagtcgggcg gcgagttcca   5040
tagcgttaag gtttcattta gcgcctcaaa tagatcctgt tcaggaaccg gatcaaagag   5100
```

-continued

```
ttcctccgcc gctggaccta ccaaggcaac gctatgttct cttgcttttg tcagcaagat   5160
agccagatca atgtcgatcg tggctggctc gaagatacct gcaagaatgt cattgcgctg   5220
ccattctcca aattgcagtt cgcgcttagc tggataacgc cacggaatga tgtcgtcgtg   5280
cacaacaatg gtgacttcta cagcgcggag aatctcgctc tctccagggg aagccgaagt   5340
ttccaaaagg tcgttgatca aagctcgccg cgttgtttca tcaagcctta cggtcaccgt   5400
aaccagcaaa tcaatatcac tgtgtggctt caggccgcca tccactgcgg agccgtacaa   5460
atgtacggcc agcaacgtcg gttcgagatg gcgctcgatg acgccaacta cctctgatag   5520
ttgagtcgat acttcggcga tcaccgcttc cctcatgatg tttaactcct gaattaagcc   5580
gcgccgcgaa gcggtgtcgg cttgaatgaa ttgttaggcg tcatcctgtg ctcccgagaa   5640
ccagtaccag tacatcgctg tttcgttcga gacttgaggt ctagttttat acgtgaacag   5700
gtcaatgccg ccgagagtaa agccacattt tgcgtacaaa ttgcaggcag gtacattgtt   5760
cgtttgtgtc tctaatcgta tgccaaggag ctgtctgctt agtgcccact tttcgcaaa    5820
ttcgatgaga ctgtgcgcga ctcctttgcc tcggtgcgtg tgcgacacaa caatgtgttc   5880
gatagaggct agatcgttcc atgttgagtt gagttcaatc ttcccgacaa gctcttggtc   5940
gatgaatgcg ccatagcaag cagagtcttc atcagagtca tcatccgaga tgtaatcctt   6000
ccggtagggg ctcacacttc tggtagatag ttcaaagcct tggtcggata ggtgcacatc   6060
gaacacttca cgaacaatga aatggttctc agcatccaat gtttccgcca cctgctcagg   6120
gatcaccgaa atcttcatat gacgcctaac gcctggcaca gcggatcgca aacctggcgc   6180
ggcttttggc acaaaaggcg tgacaggttt gcgaatccgt tgctgccact tgttaaccct   6240
tttgccagat ttggtaacta taatttatgt tagaggcgaa gtcttgggta aaaactggcc   6300
taaaattgct ggggatttca ggaaagtaaa catcaccttc cggctcgatg tctattgtag   6360
atatatgtag tgtatctact tgatcggggg atctgctgcc tcgcgcgttt cggtgatgac   6420
ggtgaaaacc tctgacacat gcagctcccg gagacggtca cagcttgtct gtaagcggat   6480
gccgggagca gacaagcccg tcagggcgcg tcagcgggtg ttggcgggtg tcggggcgca   6540
gccatgaccc agtcacgtag cgatagcgga gtgtatactg gcttaactat gcggcatcag   6600
agcagattgt actgagagtg caccatatgc ggtgtgaaat accgcacaga tgcgtaagga   6660
gaaaataccg catcaggcgc tcttccgctt cctcgctcac tgactcgctg cgctcggtcg   6720
ttcggctgcg gcgagcggta tcagctcact caaaggcggt aatacggtta tccacagaat   6780
caggggataa cgcaggaaag aacatgtgag caaaaggcca gcaaaaggcc aggaaccgta   6840
aaaaggccgc gttgctggcg tttttccata ggctccgccc ccctgacgag catcacaaaa   6900
atcgacgctc aagtcagagg tggcgaaacc cgacaggact ataaagatac caggcgtttc   6960
cccctggaag ctccctcgtg cgctctcctg ttccgaccct gccgcttacc ggatacctgt   7020
ccgcctttct cccttcggga agcgtggcgc tttctcatag ctcacgctgt aggtatctca   7080
gttcggtgta ggtcgttcgc tccaagctgg gctgtgtgca cgaacccccc gttcagcccg   7140
accgctgcgc cttatccggt aactatcgtc ttgagtccaa cccggtaaga cacgacttat   7200
cgccactggc agcagccact ggtaacagga ttagcagagc gaggtatgta ggcggtgcta   7260
cagagttctt gaagtggtgg cctaactacg gctacactag aaggacagta tttggtatct   7320
gcgctctgct gaagccagtt accttcggaa aaagagttgg tagctcttga tccggcaaac   7380
aaaccaccgc tggtagcggt ggtttttttg tttgcaagca gcagattacg cgcagaaaaa   7440
```

aaggatctca agaagatcct ttgatctttt ctacggggtc tgacgctcag tggaacgaaa 7500
actcacgtta agggattttg gtcatgagat tatcaaaaag gatcttcacc tagatccttt 7560
taaattaaaa atgaagtttt aaatcaatct aaagtatata tgagtaaact tggtctgaca 7620
gttaccaatg cttaatcagt gaggcaccta tctcagcgat ctgtctattt cgttcatcca 7680
tagttgcctg actccccgtc gtgtagataa ctacgatacg ggagggctta ccatctggcc 7740
ccagtgctgc aatgataccg cgagacccac gctcaccggc tccagattta tcagcaataa 7800
accagccagc cggaagggcc gagcgcagaa gtggtcctgc aactttatcc gcctccatcc 7860
agtctattaa ttgttgccgg gaagctagag taagtagttc gccagttaat agtttgcgca 7920
acgttgttgc cattgctgca gggggggggg gggggggggtt ccattgttca ttccacggac 7980
aaaaacagag aaaggaaacg acagaggcca aaaagctcgc tttcagcacc tgtcgtttcc 8040
tttcttttca gagggtattt taaataaaaa cattaagtta tgacgaagaa gaacggaaac 8100
gccttaaacc ggaaaatttt cataaatagc gaaaacccgc gaggtcgccg ccccgtaacc 8160
tgtcggatca ccggaaagga cccgtaaagt gataatgatt atcatctaca tatcacaacg 8220
tgcgtggagg ccatcaaacc acgtcaaata atcaattatg acgcaggtat cgtattaatt 8280
gatctgcatc aacttaacgt aaaaacaact tcagacaata caaatcagcg acactgaata 8340
cggggcaacc tcatgtcccc cccccccccc ccctgcaggc atcgtggtgt cacgctcgtc 8400
gtttggtatg gcttcattca gctccggttc ccaacgatca aggcgagtta catgatcccc 8460
catgttgtgc aaaaaagcgg ttagctcctt cggtcctccg atcgttgtca gaagtaagtt 8520
ggccgcagtg ttatcactca tggttatggc agcactgcat aattctctta ctgtcatgcc 8580
atccgtaaga tgcttttctg tgactggtga gtactcaacc aagtcattct gagaatagtg 8640
tatgcggcga ccgagttgct cttgcccggc gtcaacacgg gataataccg cgccacatag 8700
cagaacttta aaagtgctca tcattggaaa acgttcttcg gggcgaaaac tctcaaggat 8760
cttaccgctg ttgagatcca gttcgatgta acccactcgt gcacccaact gatcttcagc 8820
atcttttact ttcaccagcg tttctgggtg agcaaaaaca ggaaggcaaa atgccgcaaa 8880
aaagggaata agggcgacac ggaaatgttg aatactcata ctcttccttt ttcaatatta 8940
ttgaagcatt tatcagggtt attgtctcat gagcggatac atatttgaat gtatttagaa 9000
aaataaacaa ataggggttc cgcgcacatt tccccgaaaa gtgccacctg acgtctaaga 9060
aaccattatt atcatgacat taacctataa aaataggcgt atcacgaggc cctttcgtct 9120
tcaagaattg gtcgacgatc ttgctgcgtt cggatatttt cgtggagttc ccgccacaga 9180
cccggattga aggcgagatc cagcaactcg cgccagatca tcctgtgacg gaactttggc 9240
gcgtgatgac tggccaggac gtcggccgaa agagcgacaa gcagatcacg cttttcgaca 9300
gcgtcggatt tgcgatcgag gatttttcgg cgctgcgcta cgtccgcgac cgcgttgagg 9360
gatcaagcca cagcagccca ctcgaccttc tagccgaccc agacgagcca agggatcttt 9420
ttggaatgct gctccgtcgt caggctttcc gacgtttggg tggttgaaca gaagtcatta 9480
tcgcacggaa tgccaagcac tcccgagggg aaccctgtgg ttggcatgca catacaaatg 9540
gacgaacgga taaacctttt cacgcccttt taaatatccg attattctaa taaacgctct 9600
tttctcttag gtttacccgc caatatatcc tgtcaaacac tgatagttta aactgaaggc 9660
gggaaacgac aacctgatca tgagcggaga attaagggag tcacgttatg acccccgccg 9720
atgacgcggg acaagccgtt ttacgtttgg aactgacaga accgcaacgt tgaaggagcc 9780
actcagctta attaagtcta actcgagtta ctggtacgta ccaaatccat ggaatcaagg 9840
taccatcaat cccgggtatt catcctaggt ccccgaattt ccccgatcgt tcaaacattt 9900
ggcaataaag tttcttaaga ttgaatcctg ttgccggtct tgcgatgatt atcatataat 9960
ttctgttgaa ttacgttaag catgtaataa ttaacatgta atgcatgacg ttatttatga 10020
gatgggtttt tatgattaga gtcccgcaat tatacattta atacgcgata gaaaacaaaa 10080
tatagcgcgc aaactaggat aaattatcgc gcgcggtgtc atctatgtta ctagatcggg 10140
aattgg 10146

<210> SEQ ID NO 70
<211> LENGTH: 14622
<212> TYPE: DNA
<213> ORGANISM: Artificial Sequence
<220> FEATURE:
<223> OTHER INFORMATION: Synthetic construct, pAG2361 vector

<400> SEQUENCE: 70
ctaggtcccc gaatttcccc gatcgttcaa acatttggca ataaagtttc ttaagattga 60
atcctgttgc cggtcttgcg atgattatca tataatttct gttgaattac gttaagcatg 120
taataattaa catgtaatgc atgacgttat ttatgagatg ggtttttatg attagagtcc 180
cgcaattata catttaatac gcgatagaaa acaaaatata gcgcgcaaac taggataaat 240
tatcgcgcgc ggtgtcatct atgttactag atcgggaatt ggaattcata ctaaagcttg 300
catgcctgca ggtcgactct agtaacggcc gccagtgtgc tggaattaat tcggcttgtc 360
gaccacccaa ccccatatcg acagaggatg tgaagaacag gtaaatcacg cagaagaacc 420
catctctgat agcagctatc gattagaaca acgaatccat attgggtccg tgggaaatac 480
ttactgcaca ggaagggggc gatctgacga ggccccgcca ccggcctcga cccgaggccg 540
aggccgacga agcgccggcg agtacggcgc cgcggcggcc tctgcccgtg ccctctgcgc 600
gtgggaggga gaggccgcgg tggtgggggc gcgcgcgcgc gcgcgcgcag ctggtgcggc 660
ggcgcggggg tcagccgccg agccggcggc gacggaggag cagggcggcg tggacgcgaa 720
cttccgatcg gttggtcaga gtgcgcgagt tgggcttagc caattaggtc tcaacaatct 780
attgggccgt aaaattcatg ggccctggtt tgtctaggcc caatatcccg ttcatttcag 840
cccacaaata tttccccaga ggattattaa ggcccacacg cagcttatag cagatcaagt 900
acgatgtttc ctgatcgttg gatcggaaac gtacggtctt gatcaggcat gccgacttcg 960
tcaaagagag gcggcatgac ctgacgcgga gttggttccg ggcaccgtct ggatggtcgt 1020
accgggaccg gacacgtgtc gcgcctccaa ctacatggac acgtgtggtg ctgccattgg 1080
gccgtacgcg tggcggtgac cgcaccggat gctgcctcgc accgccttgc ccacgcttta 1140
tatagagagg ttttctctcc attaatcgca tagcgagtcg aatcgaccga aggggagggg 1200
gagcgaagct ttgcgttctc taatcgcctc gtcaaggtaa ctaatcaatc acctcgtcct 1260
aatcctcgaa tctctcgtgg tgcccgtcta atctcgcgat tttgatgctc gtggtggaaa 1320
gcgtaggagg atcccgtgcg agttagtctc aatctctcag ggtttcgtgc gattttaggg 1380
tgatccacct cttaatcgag ttacggtttc gtgcgatttt agggtaatcc tcttaatctc 1440
tcattgattt agggtttcgt gagaatcgag gtagggatct gtgttattta tatcgatcta 1500
atagatggat tggttttgag attgttctgt cagatgggga ttgtttcgat atattaccct 1560
aatgatgtgt cagatgggga ttgtttcgat atattaccct aatgatgtgt cagatgggga 1620
ttgtttcgat atattaccct aatgatggat aataagagta gttcacagtt atgttttgat 1680

-continued

```
cctgccacat agtttgagtt ttgtgatcag atttagtttt acttatttgt gcttagttcg   1740
gatgggattg ttctgatatt gttccaatag atgaatagct cgttaggtta aaatctttag   1800
gttgagttag gcgacacata gtttatttcc tctggatttg gattggaatt gtgttcttag   1860
tttttttccc ctggatttgg attggaattg tgtggagctg ggttagagaa ttacatctgt   1920
atcgtgtaca cctacttgaa ctgtagagct tgggttctaa ggtcaattta atctgtattg   1980
tatctggctc tttgcctagt tgaactgtag tgctgatgtt gtactgtgtt tttttacccg   2040
ttttatttgc tttactcgtg caaatcaaat ctgtcagatg ctagaactag gtggctttat   2100
tctgtgttct tacatagatc tgttgtcctg tagttactta tgtcagtttt gttattatct   2160
gaagatattt ttggttgttg cttgttgatg tggtgtgagc tgtgagcagc gctcttatga   2220
ttaatgatgc tgtccaattg tagtgtagta tgatgtgatt gatatgttca tctattttga   2280
gctgacagta ccgatatcgt aggatctggt gccaacttat tctccagctg cttttttttta   2340
cctatgttaa ttccaatcct ttcttgcctc ttccagatcc agataatgca gaaactcatt   2400
aactcagtgc aaaactatgc ctggggcagc aaaacggcgt tgactgaact ttatggtatg   2460
gaaaatccgt ccagccagcc gatggccgag ctgtggatgg gcgcacatcc gaaaagcagt   2520
tcacgagtgc agaatgccgc cggagatatc gtttcactgc gtgatgtgat tgagagtgat   2580
aaatcgactc tgctcggaga ggccgttgcc aaacgctttg gcgaactgcc tttcctgttc   2640
aaagtattat gcgcagcaca gccactctcc attcaggttc atccaaacaa acacaattct   2700
gaaatcggtt ttgccaaaga aaatgccgca ggtatcccga tggatgccgc cgagcgtaac   2760
tataaagatc ctaaccacaa gccggagctg gtttttgcgc tgacgccttt ccttgcgatg   2820
aacgcgtttc gtgaattttc cgagattgtc tccctactcc agccggtcgc aggtgcacat   2880
ccggcgattg ctcacttttt acaacagcct gatgccgaac gtttaagcga actgttcgcc   2940
agcctgttga atatgcaggg tgaagaaaaa tcccgcgcgc tggcgatttt aaaatcggcc   3000
ctcgatagcc agcagggtga accgtggcaa acgattcgtt taatttctga attttacccg   3060
gaagacagcg gtctgttctc cccgctattg ctgaatgtgg tgaaattgaa ccctggcgaa   3120
gcgatgttcc tgttcgctga aacaccgcac gcttacctgc aaggcgtggc gctggaagtg   3180
atggcaaact ccgataacgt gctgcgtgcg ggtctgacgc ctaaatacat tgatattccg   3240
gaactggttg ccaatgtgaa attcgaagcc aaaccggcta accagttgtt gacccagccg   3300
gtgaaacaag gtgcagaact ggacttcccg attccagtgg atgattttgc cttctcgctg   3360
catgacctta gtgataaaga aaccaccatt agccagcaga gtgccgccat tttgttctgc   3420
gtcgaaggcg atgcaacgtt gtggaaaggt tctcagcagt tacagcttaa accgggtgaa   3480
tcagcgttta ttgccgccaa cgaatcaccg gtgactgtca aaggccacgg ccgtttagcg   3540
cgtgtttaca acaagctgta agagcttact gaaaaaatta acatctcttg ctaagctggg   3600
agctctagat ccccgaattt ccccgatcgt tcaaacattt ggcaataaag tttcttaaga   3660
ttgaatcctg ttgccggtct tgcgatgatt atcatataat ttctgttgaa ttacgttaag   3720
catgtaataa ttaacatgta atgcatgacg ttatttatga gatgggtttt tatgattaga   3780
gtcccgcaat tatacattta atacgcgata gaaaacaaaa tatagcgcgc aaactaggat   3840
aaattatcgc gcgcggtgtc atctatgtta ctagatcggg aattggcgag ctcgaattaa   3900
ttcagtacat taaaaacgtc cgcaatgtgt tattaagttg tctaagcgtc aatttgttta   3960
caccacaata tatcctgcca ccagccagcc aacagctccc cgaccggcag ctcggcacaa   4020
aatcaccact cgatacaggc agcccatcag tccgggacgg cgtcagcggg agagccgttg   4080
```

-continued

```
taaggcggca gactttgctc atgttaccga tgctattcgg aagaacggca actaagctgc   4140
cgggtttgaa acacggatga tctcgcggag ggtagcatgt tgattgtaac gatgacagag   4200
cgttgctgcc tgtgatcaaa tatcatctcc ctcgcagaga tccgaattat cagccttctt   4260
attcatttct cgcttaaccg tgacaggctg tcgatcttga gaactatgcc gacataatag   4320
gaaatcgctg gataaagccg ctgaggaagc tgagtggcgc tatttcttta gaagtgaacg   4380
ttgacgatcg tcgaccgtac cccgatgaat taattcggac gtacgttctg aacacagctg   4440
gatacttact tgggcgattg tcatacatga catcaacaat gtacccgttt gtgtaaccgt   4500
ctcttggagg ttcgtatgac actagtggtt cccctcagct tgcgactaga tgttgaggcc   4560
taacatttta ttagagagca ggctagttgc ttagatacat gatcttcagg ccgttatctg   4620
tcagggcaag cgaaaattgg ccatttatga cgaccaatgc cccgcagaag ctcccatctt   4680
tgccgccata gacgccgcgc ccccttttg gggtgtagaa catccttttg ccagatgtgg   4740
aaaagaagtt cgttgtccca ttgttggcaa tgacgtagta gccggcgaaa gtgcgagacc   4800
catttgcgct atatataagc ctacgatttc cgttgcgact attgtcgtaa ttggatgaac   4860
tattatcgta gttgctctca gagttgtcgt aatttgatgg actattgtcg taattgctta   4920
tggagttgtc gtagttgctt ggagaaatgt cgtagttgga tggggagtag tcatagggaa   4980
gacgagcttc atccactaaa acaattggca ggtcagcaag tgcctgcccc gatgccatcg   5040
caagtacgag gcttagaacc accttcaaca gatcgcgcat agtcttcccc agctctctaa   5100
cgcttgagtt aagccgcgcc gcgaagcggc gtcggcttga acgaattgtt agacattatt   5160
tgccgactac cttggtgatc tcgcctttca cgtagtgaac aaattcttcc aactgatctg   5220
cgcgcgaggc caagcgatct tcttgtccaa gataagcctg cctagcttca agtatgacgg   5280
gctgatactg ggccggcagg cgctccattg cccagtcggc agcgacatcc ttcggcgcga   5340
ttttgccggt tactgcgctg taccaaatgc gggacaacgt aagcactaca tttcgctcat   5400
cgccagccca gtcgggcggc gagttccata gcgttaaggt ttcatttagc gcctcaaata   5460
gatcctgttc aggaaccgga tcaaagagtt cctccgccgc tggacctacc aaggcaacgc   5520
tatgttctct tgcttttgtc agcaagatag ccagatcaat gtcgatcgtg gctggctcga   5580
agatacctgc aagaatgtca ttgcgctgcc attctccaaa ttgcagttcg cgcttagctg   5640
gataacgcca cggaatgatg tcgtcgtgca caacaatggt gacttctaca gcgcggagaa   5700
tctcgctctc tccaggggaa gccgaagttt ccaaaaggtc gttgatcaaa gctcgccgcg   5760
ttgtttcatc aagccttacg gtcaccgtaa ccagcaaatc aatatcactg tgtggcttca   5820
ggccgccatc cactgcggag ccgtacaaat gtacggccag caacgtcggt tcgagatggc   5880
gctcgatgac gccaactacc tctgatagtt gagtcgatac ttcggcgatc accgcttccc   5940
tcatgatgtt taactcctga attaagccgc gccgcgaagc ggtgtcggct tgaatgaatt   6000
gttaggcgtc atcctgtgct cccgagaacc agtaccagta catcgctgtt tcgttcgaga   6060
cttgaggtct agttttatac gtgaacaggt caatgccgcc gagagtaaag ccacattttg   6120
cgtacaaatt gcaggcaggt acattgttcg tttgtgtctc taatcgtatg ccaaggagct   6180
gtctgcttag tgcccacttt ttcgcaaatt cgatgagact gtgcgcgact cctttgcctc   6240
ggtgcgtgtg cgacacaaca atgtgttcga tagaggctag atcgttccat gttgagttga   6300
gttcaatctt cccgacaagc tcttggtcga tgaatgcgcc atagcaagca gagtcttcat   6360
cagagtcatc atccgagatg taatccttcc ggtagggct cacacttctg gtagatagtt    6420
```

-continued caaagccttg gtcggatagg tgcacatcga acacttcacg aacaatgaaa tggttctcag 6480
catccaatgt ttccgccacc tgctcaggga tcaccgaaat cttcatatga cgcctaacgc 6540
ctggcacagc ggatcgcaaa cctggcgcgg cttttggcac aaaaggcgtg acaggtttgc 6600
gaatccgttg ctgccacttg ttaacccttt tgccagattt ggtaactata atttatgtta 6660
gaggcgaagt cttgggtaaa aactggccta aaattgctgg ggatttcagg aaagtaaaca 6720
tcaccttccg gctcgatgtc tattgtagat atatgtagtg tatctacttg atcgggggat 6780
ctgctgcctc gcgcgtttcg gtgatgacgg tgaaaacctc tgacacatgc agctcccgga 6840
gacggtcaca gcttgtctgt aagcggatgc cgggagcaga caagcccgtc agggcgcgtc 6900
agcgggtgtt ggcgggtgtc ggggcgcagc catgacccag tcacgtagcg atagcggagt 6960
gtatactggc ttaactatgc ggcatcagag cagattgtac tgagagtgca ccatatgcgg 7020
tgtgaaatac cgcacagatg cgtaaggaga aaataccgca tcaggcgctc ttccgcttcc 7080
tcgctcactg actcgctgcg ctcggtcgtt cggctgcggc gagcggtatc agctcactca 7140
aaggcggtaa tacggttatc cacagaatca ggggataacg caggaaagaa catgtgagca 7200
aaaggccagc aaaaggccag gaaccgtaaa aaggccgcgt tgctggcgtt tttccatagg 7260
ctccgccccc ctgacgagca tcacaaaaat cgacgctcaa gtcagaggtg gcgaaacccg 7320
acaggactat aaagatacca ggcgtttccc cctggaagct ccctcgtgcg ctctcctgtt 7380
ccgaccctgc cgcttaccgg atacctgtcc gcctttctcc cttcgggaag cgtggcgctt 7440
tctcatagct cacgctgtag gtatctcagt tcggtgtagg tcgttcgctc caagctgggc 7500
tgtgtgcacg aaccccccgt tcagcccgac cgctgcgcct tatccggtaa ctatcgtctt 7560
gagtccaacc cggtaagaca cgacttatcg ccactggcag cagccactgg taacaggatt 7620
agcagagcga ggtatgtagg cggtgctaca gagttcttga agtggtggcc taactacggc 7680
tacactagaa ggacagtatt tggtatctgc gctctgctga agccagttac cttcggaaaa 7740
agagttggta gctcttgatc cggcaaacaa accaccgctg gtagcggtgg tttttttgtt 7800
tgcaagcagc agattacgcg cagaaaaaaa ggatctcaag aagatccttt gatcttttct 7860
acggggtctg acgctcagtg gaacgaaaac tcacgttaag ggattttggt catgagatta 7920
tcaaaaagga tcttcaccta gatcctttta aattaaaaat gaagttttaa atcaatctaa 7980
agtatatatg agtaaacttg gtctgacagt taccaatgct taatcagtga ggcacctatc 8040
tcagcgatct gtctatttcg ttcatccata gttgcctgac tccccgtcgt gtagataact 8100
acgatacggg agggcttacc atctggcccc agtgctgcaa tgataccgcg agacccacgc 8160
tcaccggctc cagatttatc agcaataaac cagccagccg gaagggccga gcgcagaagt 8220
ggtcctgcaa ctttatccgc ctccatccag tctattaatt gttgccggga agctagagta 8280
agtagttcgc cagttaatag tttgcgcaac gttgttgcca ttgctgcagg gggggggggg 8340
ggggggttcc attgttcatt ccacggacaa aaacagagaa aggaaacgac agaggccaaa 8400
aagctcgctt tcagcacctg tcgtttcctt tcttttcaga gggtatttta aataaaaaca 8460
ttaagttatg acgaagaaga acggaaacgc cttaaaccgg aaaattttca taaatagcga 8520
aaacccgcga ggtcgccgcc ccgtaacctg tcggatcacc ggaaaggacc cgtaaagtga 8580
taatgattat catctacata tcacaacgtg cgtggaggcc atcaaaccac gtcaaataat 8640
caattatgac gcaggtatcg tattaattga tctgcatcaa cttaacgtaa aaacaacttc 8700
agacaataca aatcagcgac actgaatacg ggcaacctc atgtcccccc cccccccccc 8760
ctgcaggcat cgtggtgtca cgctcgtcgt ttggtatggc ttcattcagc tccggttccc 8820
aacgatcaag gcgagttaca tgatccccca tgttgtgcaa aaaagcggtt agctccttcg 8880
gtcctccgat cgttgtcaga agtaagttgg ccgcagtgtt atcactcatg gttatggcag 8940
cactgcataa ttctcttact gtcatgccat ccgtaagatg cttttctgtg actggtgagt 9000
actcaaccaa gtcattctga gaatagtgta tgcggcgacc gagttgctct tgcccggcgt 9060
caacacggga taataccgcg ccacatagca gaactttaaa agtgctcatc attggaaaac 9120
gttcttcggg gcgaaaactc tcaaggatct taccgctgtt gagatccagt tcgatgtaac 9180
ccactcgtgc acccaactga tcttcagcat cttttacttt caccagcgtt tctgggtgag 9240
caaaaacagg aaggcaaaat gccgcaaaaa agggaataag ggcgacacgg aaatgttgaa 9300
tactcatact cttccttttt caatattatt gaagcattta tcagggttat tgtctcatga 9360
gcggatacat atttgaatgt atttagaaaa ataaacaaat aggggttccg cgcacatttc 9420
cccgaaaagt gccacctgac gtctaagaaa ccattattat catgacatta acctataaaa 9480
ataggcgtat cacgaggccc tttcgtcttc aagaattggt cgacgatctt gctgcgttcg 9540
gatattttcg tggagttccc gccacagacc cggattgaag gcgagatcca gcaactcgcg 9600
ccagatcatc ctgtgacgga actttggcgc gtgatgactg gccaggacgt cggccgaaag 9660
agcgacaagc agatcacgct tttcgacagc gtcggatttg cgatcgagga tttttcggcg 9720
ctgcgctacg tccgcgaccg cgttgaggga tcaagccaca gcagcccact cgaccttcta 9780
gccgacccag acgagccaag ggatcttttt ggaatgctgc tccgtcgtca ggctttccga 9840
cgtttgggtg gttgaacaga agtcattatc gcacggaatg ccaagcactc ccgaggggaa 9900
ccctgtggtt ggcatgcaca tacaaatgga cgaacggata aaccttttca cgccctttta 9960
aatatccgat tattctaata aacgctcttt tctcttaggt ttacccgcca atatatcctg 10020
tcaaacactg atagtttaaa ctgaaggcgg gaaacgacaa cctgatcatg agcggagaat 10080
taagggagtc acgttatgac ccccgccgat gacgcgggac aagccgtttt acgtttggaa 10140
ctgacagaac cgcaacgttg aaggagccac tcagcttaat taagtctaac tcgagttact 10200
ggtacgtacc aaatccatgg aatcaaggta ccctgcagtg cagcgtgacc cggtcgtgcc 10260
cctctctaga gataatgagc attgcatgtc taagttataa aaaattacca catatttttt 10320
ttgtcacact tgtttgaagt gcagtttatc tatctttata catatattta aactttactc 10380
tacgaataat ataatctata gtactacaat aatatcagtg ttttagagaa tcatataaat 10440
gaacagttag acatggtcta aaggacaatt gagtattttg acaacaggac tctacagttt 10500
tatcttttta gtgtgcatgt gttctccttt ttttttgcaa atagcttcac ctatataata 10560
cttcatccat tttattagta catccattta gggtttaggg ttaatggttt ttatagacta 10620 attttttag tacatctatt ttattctatt ttagcctcta aattaagaaa actaaaactc 10680
tattttagtt tttttattta ataatttaga tataaaatag aataaaataa agtgactaaa 10740
aattaaacaa ataccettta agaaattaaa aaaactaagg aaacattttt cttgtttcga 10800
gtagataatg ccagcctgtt aaacgccgtc gacgagtcta acggacacca accagcgaac 10860
cagcagcgtc gcgtcgggcc aagcgaagca gacggcacgg catctctgtc gctgcctctg 10920
gacccctctc gagagttccg ctccaccgtt ggacttgctc cgctgtcggc atccagaaat 10980
tgcgtggcgg agcggcagac gtgagccggc acggcaggcg gcctcctcct cctctcacgg 11040
cacggcagct acgggggatt cctttcccac cgctccttcg ctttcccttc ctcgcccgcc 11100
gtaataaata gacacccct ccacaccctc tttccccaac ctcgtgttgt tcggagcgca 11160

-continued cacacacaca accagatctc ccccaaatcc acccgtcggc acctccgctt caaggtacgc 11220
cgctcgtcct cccccccccc ccctctctac cttctctaga tcggcgttcc ggtccatggt 11280
tagggcccgg tagttctact tctgttcatg tttgtgttag atccgtgttt gtgttagatc 11340
cgtgctgcta gcgttcgtac acggatgcga cctgtacgtc agacacgttc tgattgctaa 11400
cttgccagtg tttctctttg gggaatcctg ggatggctct agccgttccg cagacgggat 11460
cgatttcatg attttttttg tttcgttgca tagggtttgg tttgcccttt tcctttattt 11520
caatatatgc cgtgcacttg tttgtcgggt catcttttca tgcttttttt tgtcttggtt 11580
gtgatgatgt ggtctggttg ggcggtcgtt ctagatcgga gtagaattct gtttcaaact 11640
acctggtgga tttattaatt ttggatctgt atgtgtgtgc catacatatt catagttacg 11700
aattgaagat gatggatgga aatatcgatc taggataggt atacatgttg atgcgggttt 11760
tactgatgca tatacagaga tgctttttgt tcgcttggtt gtgatgatgt ggtgtggttg 11820
ggcggtcgtt cattcgttct agatcggagt agaatactgt ttcaaactac ctggtgtatt 11880
tattaatttt ggaactgtat gtgtgtgtca tacatcttca tagttacgag tttaagatgg 11940
atggaaatat cgatctagga taggtataca tgttgatgtg ggttttactg atgcatatac 12000
atgatggcat atgcagcatc tattcatatg ctctaacctt gagtacctat ctattataat 12060
aaacaagtat gttttataat tattttgatc ttgatatact tggatgatgg catatgcagc 12120
agctatatgt ggattttttt agccctgcct tcatacgcta tttatttgct tggtactgtt 12180
tcttttgtcg atgctcaccc tgttgtttgg tgttacttct gcagatccag atcggatcct 12240
aaaccatggc gaacaaacat ttgtccctct ccctcttcct cgtcctcctt ggcctgtcgg 12300
ccagcttggc ctccgggcaa caaacaagca ttactctgac atccaacgca tccggtacgt 12360
ttgacggtta ctattacgaa ctctggaagg atactggcaa tacaacaatg acggtctaca 12420
ctcaaggtcg cttttcctgc cagtggtcga acatcaataa cgcgttgttt aggaccggga 12480
agaaatacaa ccagaattgg cagtctcttg gcacaatccg gatcacgtac tctgcgactt 12540
acaacccaaa cgggaactcc tacttgtgta tctatggctg gtctaccaac ccattggtcg 12600
agttctacat cgttgagtcc tgggggaact ggagaccgcc tggtgcctgc ctggccgagg 12660
gctcgctcgt cttggacgcg gctaccgggc agagggtccc tatcgaaaag gtgcgtccgg 12720
ggatggaagt tttctccttg ggacctgatt acagactgta tcgggtgccc gttttggagg 12780
tccttgagag cggggttagg gaagttgtgc gcctcagaac tcggtcaggg agaacgctgg 12840
tgttgacacc agatcacccg cttttgaccc ccgaaggttg gaaacctctt tgtgacctcc 12900
cgcttggaac tccaattgca gtccccgcag aactgcctgt ggcgggccac ttggccccac 12960
ctgaagaacg tgttacgctc ctggctcttc tgttggggga tgggaacaca aagctgtcgg 13020
gtcggagagg tacacgtcct aatgccttct tctacagcaa aaaccccgaa ttgctcgcgg 13080
cttatcgccg gtgtgcagaa gccttgggtg caaaggtgaa agcatacgtc cacccgacta 13140
cgggggtggt tacactcgca accctcgctc cacgtcctgg agctcaagat cctgtcaaac 13200
gcctcgttgt cgaggcggga atggttgcta aagccgaaga gaagagggtc ccggaggagg 13260
tgtttcgtta ccggcgtgag gcgttggccc ttttcttggg ccgtttgttc tcgacagacg 13320
gctctgttga aaagaagagg atctcttatt caagtgccag tttgggactg gcccaggatg 13380
tcgcacatct cttgctgcgc cttggaatta catctcaact ccgttcgaga gggccacggg 13440
ctcacgaggt tcttatatcg ggccgcgagg atattttgcg gtttgctgaa cttatcggac 13500
cctacctctt gggggccaag agggagagac ttgcagcgct ggaagctgag gcccgcaggc 13560

```
gtttgcctgg acagggatgg cacttgcggc ttgttcttcc tgccgtggcg tacagagtgg  13620

gcgaggctga aaggcgctcg ggattttcgt ggagtgaagc cggtcggcgc gtcgcagttg  13680

cgggatcgtg tttgtcatct ggactcaacc tcaaattgcc cagacgctac ctttctcggc  13740

accggttgtc gctgctcggt gaggcttttg ccgaccctgg gctggaagcg ctcgcggaag  13800

gccaagtgct ctgggaccct attgttgctg tcgaaccggc cggtaaggcg agaacattcg  13860

acttgcgcgt tccacccttt gcaaacttcg tgagcgagga cctggtggtg cataacaccg  13920

tccccctggg ccaagtgaca atcgatggcg ggacctacga catctatagg acgacacgcg  13980

tcaaccagcc ttccattgtg ggacagccca cgttcgatca gtactggagc gtgcgcacct  14040

ctaagcggac ttcaggaaca gtgaccgtga ccgatcactt ccgcgcctgg gcgaaccggg  14100

gcctgaacct cggcacaata gaccaaatta cattgtgcgt ggagggttac caaagctctg  14160

gatcagccaa catcacccag aacaccttct ctcagggctc ttcttccggc agttcgggtg  14220

gctcatccgg ctccacaacg actactcgca tcgagtgtga gaacatgtcc ttgtccggac  14280

cctacgttag caggatcacc aatcccttta atggtattgc gctgtacgcc aacggagaca  14340

cagcccgcgc taccgttaac ttccccgcaa gtcgcaacta caatttccgc ctgcggggtt  14400

gcggcaacaa caataatctt gcccgtgtgg acctgaggat cgacggacgg accgtcggga  14460

ccttttatta ccagggcaca taccccctggg aggccccaat tgacaatgtt tatgtcagtg  14520

cggggagtca tacagtcgaa atcactgtta ctgcggataa cggcacatgg gacgtgtatg  14580

ccgactacct ggtgatacag agcgagaagg acgagctgtg ac                     14622
```

<210> SEQ ID NO 71
<211> LENGTH: 14531
<212> TYPE: DNA
<213> ORGANISM: Artificial Sequence
<220> FEATURE:
<223> OTHER INFORMATION: Synthetic construct, pAG4004 vector

<400> SEQUENCE: 71

```
ctaggtcccc gaatttcccc gatcgttcaa acatttggca ataaagtttc ttaagattga     60

atcctgttgc cggtcttgcg atgattatca tataatttct gttgaattac gttaagcatg    120

taataattaa catgtaatgc atgacgttat ttatgagatg ggtttttatg attagagtcc    180

cgcaattata catttaatac gcgatagaaa acaaaatata gcgcgcaaac taggataaat    240

tatcgcgcgc ggtgtcatct atgttactag atcgggaatt ggaattcctg cagtgcagcg    300

tgacccggtc gtgcccctct ctagagataa tgagcattgc atgtctaagt tataaaaaat    360

taccacatat ttttttgtc acacttgttt gaagtgcagt ttatctatct ttatacatat    420

atttaaactt tactctacga ataatataat ctatagtact acaataatat cagtgtttta    480

gagaatcata taaatgaaca gttagacatg gtctaaagga caattgagta ttttgacaac    540

aggactctac agttttatct ttttagtgtg catgtgttct cctttttttt tgcaaatagc    600

ttcacctata taatacttca tccattttat tagtacatcc atttagggtt tagggttaat    660

ggtttttata gactaatttt tttagtacat ctattttatt ctattttagc ctctaaatta    720

agaaaactaa aactctattt tagttttttt atttaataat ttagatataa aatagaataa    780

aataaagtga ctaaaaatta aacaaatacc ctttaagaaa ttaaaaaaac taaggaaaca    840

tttttcttgt ttcgagtaga taatgccagc ctgttaaacg ccgtcgacga gtctaacgga    900

caccaaccag cgaaccagca gcgtcgcgtc gggccaagcg aagcagacgg cacggcatct    960
```

-continued

```
ctgtcgctgc ctctggaccc ctctcgagag ttccgctcca ccgttggact tgctccgctg   1020
tcggcatcca gaaattgcgt ggcggagcgg cagacgtgag ccggcacggc aggcggcctc   1080
ctcctcctct cacggcacgg cagctacggg ggattccttt cccaccgctc cttcgctttc   1140
ccttcctcgc ccgccgtaat aaatagacac cccctccaca ccctctttcc ccaacctcgt   1200
gttgttcgga gcgcacacac acacaaccag atctccccca aatccacccg tcggcacctc   1260
cgcttcaagg tacgccgctc gtcctccccc cccccccctc tctaccttct ctagatcggc   1320
gttccggtcc atggttaggg cccggtagtt ctacttctgt tcatgtttgt gttagatccg   1380
tgtttgtgtt agatccgtgc tgctagcgtt cgtacacgga tgcgacctgt acgtcagaca   1440
cgttctgatt gctaacttgc cagtgtttct ctttggggaa tcctgggatg gctctagccg   1500
ttccgcagac gggatcgatt tcatgatttt ttttgtttcg ttgcataggg tttggtttgc   1560
ccttttcctt tatttcaata tatgccgtgc acttgtttgt cgggtcatct tttcatgctt   1620
tttttgtctt ggttgtgatg atgtggtctg gttgggcggt cgttctagat cggagtagaa   1680
ttctgtttca aactacctgg tggatttatt aattttggat ctgtatgtgt gtgccataca   1740
tattcatagt tacgaattga agatgatgga tggaaatatc gatctaggat aggtatacat   1800
gttgatgcgg gttttactga tgcatataca gagatgcttt ttgttcgctt ggttgtgatg   1860
atgtggtgtg gttgggcggt cgttcattcg ttctagatcg gagtagaata ctgtttcaaa   1920
ctacctggtg tatttattaa ttttggaact gtatgtgtgt gtcatacatc ttcatagtta   1980
cgagtttaag atggatggaa atatcgatct aggataggta tacatgttga tgtgggtttt   2040
actgatgcat atacatgatg gcatatgcag catctattca tatgctctaa ccttgagtac   2100
ctatctatta taataaacaa gtatgtttta taattatttt gatcttgata tacttggatg   2160
atggcatatg cagcagctat atgtggattt ttttagccct gccttcatac gctatttatt   2220
tgcttggtac tgtttctttt gtcgatgctc accctgttgt ttggtgttac ttctgcagat   2280
ccagatctaa accatgcaga aactcattaa ctcagtgcaa aactatgcct ggggcagcaa   2340
aacggcgttg actgaacttt atggtatgga aaatccgtcc agccagccga tggccgagct   2400
gtggatgggc gcacatccga aaagcagttc acgagtgcag aatgccgccg gagatatcgt   2460
ttcactgcgt gatgtgattg agagtgataa atcgactctg ctcggagagg ccgttgccaa   2520
acgctttggc gaactgcctt tcctgttcaa agtattatgc gcagcacagc cactctccat   2580
tcaggttcat ccaaacaaac acaattctga aatcggtttt gccaaagaaa atgccgcagg   2640
tatcccgatg gatgccgccg agcgtaacta taaagatcct aaccacaagc cggagctggt   2700
ttttgcgctg acgcctttcc ttgcgatgaa cgcgtttcgt gaattttccg agattgtctc   2760
cctactccag ccggtcgcag gtgcacatcc ggcgattgct cactttttac aacagcctga   2820
tgccgaacgt ttaagcgaac tgttcgccag cctgttgaat atgcagggtg aagaaaaatc   2880
ccgcgcgctg gcgatttaaa atcggccctc gatagccagc agggtgaacc gtggcaaacg   2940
attcgtttaa tttctgaatt ttacccggaa gacagcggtc tgttctcccc gctattgctg   3000
aatgtggtga aattgaaccc tggcgaagcg atgttcctgt tcgctgaaac accgcacgct   3060
tacctgcaag gcgtggcgct ggaagtgatg gcaaactccg ataacgtgct gcgtgcgggt   3120
ctgacgccta aatacattga tattccggaa ctggttgcca atgtgaaatt cgaagccaaa   3180
ccggctaacc agttgttgac ccagccggtg aaacaaggtg cagaactgga cttcccgatt   3240
ccagtggatg attttgcctt ctcgctgcat gaccttagtg ataaagaaac caccattagc   3300
cagcagagtg ccgccatttt gttctgcgtc gaaggcgatg caacgttgtg gaaaggtt     3360
```

```
ctcagcagtt acagcttaaa ccgggtgaat cagcgtttat tgccgccaac gaatcaccgg   3420
tgactgtcaa aggccacggc cgtttagcgc gtgtttacaa caagctgtaa gagcttactg   3480
aaaaaattaa catctcttgc taagctggga gctctagatc cccgaatttc cccgatcgtt   3540
caaacatttg gcaataaagt ttcttaagat tgaatcctgt tgccggtctt gcgatgatta   3600
tcatataatt tctgttgaat tacgttaagc atgtaataat taacatgtaa tgcatgacgt   3660
tatttatgag atgggttttt atgattagag tcccgcaatt atacatttaa tacgcgatag   3720
aaaacaaaat atagcgcgca aactaggata aattatcgcg cgcggtgtca tctatgttac   3780
tagatcggga attggcgagc tcgaattaat tcagtacatt aaaaacgtcc gcaatgtgtt   3840
attaagttgt ctaagcgtca atttgtttac accacaatat atcctgccac cagccagcca   3900
acagctcccc gaccggcagc tcggcacaaa atcaccactc gatacaggca gcccatcagt   3960
ccgggacggc gtcagcggga gagccgttgt aaggcggcag actttgctca tgttaccgat   4020
gctattcgga agaacggcaa ctaagctgcc gggtttgaaa cacggatgat ctcgcggagg   4080
gtagcatgtt gattgtaacg atgacagagc gttgctgcct gtgatcaaat atcatctccc   4140
tcgcagagat ccgaattatc agccttctta ttcatttctc gcttaaccgt gacaggctgt   4200
cgatcttgag aactatgccg acataatagg aaatcgctgg ataaagccgc tgaggaagct   4260
gagtggcgct atttctttag aagtgaacgt tgacgatcgt cgaccgtacc ccgatgaatt   4320
aattcggacg tacgttctga acacagctgg atacttactt gggcgattgt catacatgac   4380
atcaacaatg tacccgtttg tgtaaccgtc tcttggaggt tcgtatgaca ctagtggttc   4440
ccctcagctt gcgactagat gttgaggcct aacattttat tagagagcag gctagttgct   4500
tagatacatg atcttcaggc cgttatctgt cagggcaagc gaaaattggc catttatgac   4560
gaccaatgcc ccgcagaagc tcccatcttt gccgccatag acgccgcgcc cccttttgg   4620
ggtgtagaac atccttttgc cagatgtgga aaagaagttc gttgtcccat tgttggcaat   4680
gacgtagtag ccggcgaaag tgcgagaccc atttgcgcta tatataagcc tacgatttcc   4740
gttgcgacta ttgtcgtaat tggatgaact attatcgtag ttgctctcag agttgtcgta   4800
atttgatgga ctattgtcgt aattgcttat ggagttgtcg tagttgcttg gagaaatgtc   4860
gtagttggat ggggagtagt catagggaag acgagcttca tccactaaaa caattggcag   4920
gtcagcaagt gcctgccccg atgccatcgc aagtacgagg cttagaacca ccttcaacag   4980
atcgcgcata gtcttcccca gctctctaac gcttgagtta agccgcgccg cgaagcggcg   5040
tcggcttgaa cgaattgtta gacattattt gccgactacc ttggtgatct cgcctttcac   5100
gtagtgaaca aattcttcca actgatctgc gcgcgaggcc aagcgatctt cttgtccaag   5160
ataagcctgc ctagcttcaa gtatgacggg ctgatactgg gccggcaggc gctccattgc   5220
ccagtcggca gcgacatcct tcggcgcgat tttgccggtt actgcgctgt accaaatgcg   5280
ggacaacgta agcactacat ttcgctcatc gccagcccag tcgggcggcg agttccatag   5340
cgttaaggtt tcatttagcg cctcaaatag atcctgttca ggaaccggat caaagagttc   5400
ctccgccgct ggacctacca aggcaacgct atgttctctt gcttttgtca gcaagatagc   5460
cagatcaatg tcgatcgtgg ctggctcgaa gatacctgca agaatgtcat tgcgctgcca   5520
ttctccaaat tgcagttcgc gcttagctgg ataacgccac ggaatgatgt cgtcgtgcac   5580
aacaatggtg acttctacag cgcggagaat ctcgctctct ccaggggaag ccgaagtttc   5640
caaaaggtcg ttgatcaaag ctcgccgcgt tgtttcatca agccttacgg tcaccgtaac   5700
```

-continued

```
cagcaaatca atatcactgt gtggcttcag gccgccatcc actgcggagc cgtacaaatg   5760
tacggccagc aacgtcggtt cgagatggcg ctcgatgacg ccaactacct ctgatagttg   5820
agtcgatact tcggcgatca ccgcttccct catgatgttt aactcctgaa ttaagccgcg   5880
ccgcgaagcg gtgtcggctt gaatgaattg ttaggcgtca tcctgtgctc ccgagaacca   5940
gtaccagtac atcgctgttt cgttcgagac ttgaggtcta gttttatacg tgaacaggtc   6000
aatgccgccg agagtaaagc cacattttgc gtacaaattg caggcaggta cattgttcgt   6060
ttgtgtctct aatcgtatgc caaggagctg tctgcttagt gcccactttt tcgcaaattc   6120
gatgagactg tgcgcgactc ctttgcctcg gtgcgtgtgc gacacaacaa tgtgttcgat   6180
agaggctaga tcgttccatg ttgagttgag ttcaatcttc ccgacaagct cttggtcgat   6240
gaatgcgcca tagcaagcag agtcttcatc agagtcatca tccgagatgt aatccttccg   6300
gtaggggctc acacttctgg tagatagttc aaagccttgg tcggataggt gcacatcgaa   6360
cacttcacga acaatgaaat ggttctcagc atccaatgtt tccgccacct gctcagggat   6420
caccgaaatc ttcatatgac gcctaacgcc tggcacagcg gatcgcaaac ctggcgcggc   6480
ttttggcaca aaaggcgtga caggtttgcg aatccgttgc tgccacttgt taaccctttt   6540
gccagatttg gtaactataa tttatgttag aggcgaagtc ttgggtaaaa actggcctaa   6600
aattgctggg gatttcagga aagtaaacat caccttccgg ctcgatgtct attgtagata   6660
tatgtagtgt atctacttga tcgggggatc tgctgcctcg cgcgtttcgg tgatgacggt   6720
gaaaacctct gacacatgca gctcccggag acggtcacag cttgtctgta agcggatgcc   6780
gggagcagac aagcccgtca gggcgcgtca gcgggtgttg gcgggtgtcg gggcgcagcc   6840
atgacccagt cacgtagcga tagcggagtg tatactggct taactatgcg gcatcagagc   6900
agattgtact gagagtgcac catatgcggt gtgaaatacc gcacagatgc gtaaggagaa   6960
aataccgcat caggcgctct tccgcttcct cgctcactga ctcgctgcgc tcggtcgttc   7020
ggctgcggcg agcggtatca gctcactcaa aggcggtaat acggttatcc acagaatcag   7080
gggataacgc aggaaagaac atgtgagcaa aaggccagca aaaggccagg aaccgtaaaa   7140
aggccgcgtt gctggcgttt ttccataggc tccgcccccc tgacgagcat cacaaaaatc   7200
gacgctcaag tcagaggtgg cgaaacccga caggactata aagataccag gcgtttcccc   7260
ctggaagctc cctcgtgcgc tctcctgttc cgaccctgcc gcttaccgga tacctgtccg   7320
cctttctccc ttcgggaagc gtggcgcttt ctcatagctc acgctgtagg tatctcagtt   7380
cggtgtaggt cgttcgctcc aagctgggct gtgtgcacga accccccgtt cagcccgacc   7440
gctgcgcctt atccggtaac tatcgtcttg agtccaaccc ggtaagacac gacttatcgc   7500
cactggcagc agccactggt aacaggatta gcagagcgag gtatgtaggc ggtgctacag   7560
agttcttgaa gtggtggcct aactacggct acactagaag gacagtattt ggtatctgcg   7620
ctctgctgaa gccagttacc ttcggaaaaa gagttggtag ctcttgatcc ggcaaacaaa   7680
ccaccgctgg tagcggtggt ttttttgttt gcaagcagca gattacgcgc agaaaaaaag   7740
gatctcaaga agatcctttg atcttttcta cggggtctga cgctcagtgg aacgaaaact   7800
cacgttaagg gattttggtc atgagattat caaaaaggat cttcacctag atccttttaa   7860
attaaaaatg aagttttaaa tcaatctaaa gtatatatga gtaaacttgg tctgacagtt   7920
accaatgctt aatcagtgag gcacctatct cagcgatctg tctatttcgt tcatccatag   7980
ttgcctgact ccccgtcgtg tagataacta cgatacggga gggcttacca tctggcccca   8040
gtgctgcaat gataccgcga gacccacgct caccggctcc agatttatca gcaataaacc   8100
```

-continued

```
agccagccgg aagggccgag cgcagaagtg gtcctgcaac tttatccgcc tccatccagt   8160
ctattaattg ttgccgggaa gctagagtaa gtagttcgcc agttaatagt ttgcgcaacg   8220
ttgttgccat tgctgcaggg gggggggggg gggggttcca ttgttcattc cacggacaaa   8280
aacagagaaa ggaaacgaca gaggccaaaa agctcgcttt cagcacctgt cgtttccttt   8340
cttttcagag ggtattttaa ataaaaacat taagttatga cgaagaagaa cggaaacgcc   8400
ttaaaccgga aaattttcat aaatagcgaa aacccgcgag gtcgccgccc cgtaacctgt   8460
cggatcaccg gaaaggaccc gtaaagtgat aatgattatc atctacatat cacaacgtgc   8520
gtggaggcca tcaaaccacg tcaaataatc aattatgacg caggtatcgt attaattgat   8580
ctgcatcaac ttaacgtaaa aacaacttca gacaatacaa atcagcgaca ctgaatacgg   8640
ggcaacctca tgtccccccc cccccccccc tgcaggcatc gtggtgtcac gctcgtcgtt   8700
tggtatggct tcattcagct ccggttccca acgatcaagg cgagttacat gatcccccat   8760
gttgtgcaaa aaagcggtta gctccttcgg tcctccgatc gttgtcagaa gtaagttggc   8820
cgcagtgtta tcactcatgg ttatggcagc actgcataat tctcttactg tcatgccatc   8880
cgtaagatgc ttttctgtga ctggtgagta ctcaaccaag tcattctgag aatagtgtat   8940
gcggcgaccg agttgctctt gcccggcgtc aacacgggat aataccgcgc cacatagcag   9000
aactttaaaa gtgctcatca ttggaaaacg ttcttcgggg cgaaaactct caaggatctt   9060
accgctgttg agatccagtt cgatgtaacc cactcgtgca cccaactgat cttcagcatc   9120
ttttactttc accagcgttt ctgggtgagc aaaaacagga aggcaaaatg ccgcaaaaaa   9180
gggaataagg gcgacacgga aatgttgaat actcatactc ttcctttttc aatattattg   9240
aagcatttat cagggttatt gtctcatgag cggatacata tttgaatgta tttagaaaaa   9300
taaacaaata ggggttccgc gcacatttcc ccgaaaagtg ccacctgacg tctaagaaac   9360
cattattatc atgacattaa cctataaaaa taggcgtatc acgaggccct ttcgtcttca   9420
agaattggtc gacgatcttg ctgcgttcgg atattttcgt ggagttcccg ccacagaccc   9480
ggattgaagg cgagatccag caactcgcgc cagatcatcc tgtgacggaa ctttggcgcg   9540
tgatgactgg ccaggacgtc ggccgaaaga gcgacaagca gatcacgctt ttcgacagcg   9600
tcggatttgc gatcgaggat ttttcggcgc tgcgctacgt ccgcgaccgc gttgagggat   9660
caagccacag cagcccactc gaccttctag ccgacccaga cgagccaagg gatctttttg   9720
gaatgctgct ccgtcgtcag gctttccgac gtttgggtgg ttgaacagaa gtcattatcg   9780
cacggaatgc caagcactcc cgaggggaac cctgtggttg gcatgcacat acaaatggac   9840
gaacggataa accttttcac gcccttttaa atatccgatt attctaataa acgctctttt   9900
ctcttaggtt tacccgccaa tatatcctgt caaacactga tagtttaaac tgaaggcggg   9960
aaacgacaac ctgatcatga gcggagaatt aagggagtca cgttatgacc cccgccgatg  10020
acgcgggaca agccgtttta cgtttggaac tgacagaacc gcaacgttga aggagccact  10080
cagcttaatt aagtctaact cgagttactg gtacgtacca aatccatgga atcaaggtac  10140
cctgcagtgc agcgtgaccc ggtcgtgccc ctctctagag ataatgagca ttgcatgtct  10200
aagttataaa aaattaccac atattttttt tgtcacactt gtttgaagtg cagtttatct  10260
atctttatac atatatttaa actttactct acgaataata taatctatag tactacaata  10320
atatcagtgt tttagagaat catataaatg aacagttaga catggtctaa aggacaattg  10380
agtattttga caacaggact ctacagtttt atctttttag tgtgcatgtg ttctcctttt  10440
```

-continued

```
tttttgcaaa tagcttcacc tatataatac ttcatccatt ttattagtac atccatttag  10500
ggtttagggt taatggtttt tatagactaa ttttttagt acatctattt tattctattt  10560
tagcctctaa attaagaaaa ctaaaactct attttagttt ttttatttaa taatttagat  10620
ataaaataga ataaaataaa gtgactaaaa attaaacaaa taccctttaa gaaattaaaa  10680
aaactaagga aacattttc ttgtttcgag tagataatgc cagcctgtta aacgccgtcg  10740
acgagtctaa cggacaccaa ccagcgaacc agcagcgtcg cgtcgggcca agcgaagcag  10800
acggcacggc atctctgtcg ctgcctctgg acccctctcg agagttccgc tccaccgttg  10860
gacttgctcc gctgtcggca tccagaaatt gcgtggcgga gcggcagacg tgagccggca  10920
cggcaggcgg cctcctcctc ctctcacggc acggcagcta cgggggattc ctttcccacc  10980
gctccttcgc tttcccttcc tcgcccgccg taataaatag acaccccctc cacaccctct  11040
ttccccaacc tcgtgttgtt cggagcgcac acacacacaa ccagatctcc cccaaatcca  11100
cccgtcggca cctccgcttc aaggtacgcc gctcgtcctc cccccccccc cctctctacc  11160
ttctctagat cggcgttccg gtccatggtt agggcccggt agttctactt ctgttcatgt  11220
ttgtgttaga tccgtgtttg tgttagatcc gtgctgctag cgttcgtaca cggatgcgac  11280
ctgtacgtca gacacgttct gattgctaac ttgccagtgt ttctctttgg ggaatcctgg  11340
gatggctcta gccgttccgc agacgggatc gatttcatga ttttttttgt ttcgttgcat  11400
agggtttggt ttgccctttt cctttatttc aatatatgcc gtgcacttgt ttgtcgggtc  11460
atcttttcat gcttttttt gtcttggttg tgatgatgtg gtctggttgg gcggtcgttc  11520
tagatcggag tagaattctg tttcaaacta cctggtggat ttattaattt tggatctgta  11580
tgtgtgtgcc atacatattc atagttacga attgaagatg atggatggaa atatcgatct  11640
aggataggta tacatgttga tgcgggtttt actgatgcat atacagagat gctttttgtt  11700
cgcttggttg tgatgatgtg gtgtggttgg gcggtcgttc attcgttcta gatcggagta  11760
gaatactgtt tcaaactacc tggtgtattt attaattttg gaactgtatg tgtgtgtcat  11820
acatcttcat agttacgagt ttaagatgga tggaaatatc gatctaggat aggtatacat  11880
gttgatgtgg gttttactga tgcatataca tgatggcata tgcagcatct attcatatgc  11940
tctaaccttg agtacctatc tattataata aacaagtatg ttttataatt attttgatct  12000
tgatatactt ggatgatggc atatgcagca gctatatgtg gattttttta gccctgcctt  12060
catacgctat ttatttgctt ggtactgttt cttttgtcga tgctcaccct gttgtttggt  12120
gttacttctg cagatccaga tcggatccta aaccatggcg aacaaacatt tgtccctctc  12180
cctcttcctc gtcctccttg gcctgtcggc cagcttggcc tccgggcaac aaacaagcat  12240
tactctgaca tccaacgcat ccggtacgtt tgacggttac tattacgaac tctggaagga  12300
tactggcaat acaacaatga cggtctacac tcaaggtcgc ttttcctgcc agtggtcgaa  12360
catcaataac gcgttgttta ggaccgggaa gaaatacaac cagaattggc agtctcttgg  12420
cacaatccgg atcacgtact ctgcgactta caacccaaac gggaactcct acttgtgtat  12480
ctatggctgg tctaccaacc cattggtcga gttctacatc gttgagtcct gggggaactg  12540
gagaccgcct ggtgcctgcc tggccgaggg ctcgctcgtc ttggacgcgg ctaccgggca  12600
gagggtccct atcgaaaagg tgcgtccggg gatggaagtt ttctccttgg gacctgatta  12660
cagactgtat cgggtgcccg ttttggaggt ccttgagagc ggggttaggg aagttgtgcg  12720
cctcagaact cggtcaggga gaacgctggt gttgacacca gatcacccgc ttttgacccc  12780
cgaaggttgg aaacctcttt gtgacctccc gcttggaact ccaattgcag tccccgcaga  12840
```

actgcctgtg gcgggccact tggccccacc tgaagaacgt gttacgctcc tggctcttct 12900
gttgggggat gggaacacaa agctgtcggg tcggagaggt acacgtccta atgccttctt 12960
ctacagcaaa aaccccgaat tgctcgcggc ttatcgccgg tgtgcagaag ccttgggtgc 13020
aaaggtgaaa gcatacgtcc acccgactac gggggtggtt acactcgcaa ccctcgctcc 13080
acgtcctgga gctcaagatc ctgtcaaacg cctcgttgtc gaggcgggaa tggttgctaa 13140
agccgaagag aagagggtcc cggaggaggt gtttcgttac cggcgtgagg cgttggccct 13200
tttcttgggc cgtttgttct cgacagacgg ctctgttgaa aagaagagga tctcttattc 13260
aagtgccagt ttgggactgg cccaggatgt cgcacatctc ttgctgcgcc ttggaattac 13320
atctcaactc cgttcgagag ggccacgggc tcacgaggtt cttatatcgg gccgcgagga 13380
tattttgcgg tttgctgaac ttatcggacc ctacctcttg gggggccaaga gggagagact 13440 tgcagcgctg gaagctgagg cccgcaggcg tttgcctgga cagggatggc acttgcggct 13500
tgttcttcct gccgtggcgt acagagtggg cgaggctgaa aggcgctcgg gattttcgtg 13560
gagtgaagcc ggtcggcgcg tcgcagttgc gggatcgtgt ttgtcatctg gactcaacct 13620
caaattgccc agacgctacc tttctcggca ccggttgtcg ctgctcggtg aggcttttgc 13680
cgaccctggg ctggaagcgc tcgcggaagg ccaagtgctc tgggacccta ttgttgctgt 13740
cgaaccggcc ggtaaggcga gaacattcga cttgcgcgtt ccaccctttg caaacttcgt 13800
gagcgaggac ctggtggtgc ataacaccgt ccccctgggc caagtgacaa tcgatggcgg 13860
gacctacgac atctatagga cgacacgcgt caaccagcct tccattgtgg ggacagccac 13920
gttcgatcag tactggagcg tgcgcacctc taagcggact tcaggaacag tgaccgtgac 13980
cgatcacttc cgcgcctggg cgaaccgggg cctgaacctc ggcacaatag accaaattac 14040
attgtgcgtg gagggttacc aaagctctgg atcagccaac atcacccaga acaccttctc 14100
tcagggctct tcttccggca gttcgggtgg ctcatccggc tccacaacga ctactcgcat 14160
cgagtgtgag aacatgtcct tgtccggacc ctacgttagc aggatcacca atccctttaa 14220
tggtattgcg ctgtacgcca acggagacac agcccgcgct accgttaact tccccgcaag 14280
tcgcaactac aatttccgcc tgcggggttg cggcaacaac aataatcttg cccgtgtgga 14340
cctgaggatc gacggacgga ccgtcgggac cttttattac cagggcacat accccctggga 14400 ggccccaatt gacaatgttt atgtcagtgc ggggagtcat acagtcgaaa tcactgttac 14460
tgcggataac ggcacatggg acgtgtatgc cgactacctg gtgatacaga gcgagaagga 14520
cgagctgtga c 14531

<210> SEQ ID NO 72
<211> LENGTH: 14593
<212> TYPE: DNA
<213> ORGANISM: Artificial Sequence
<220> FEATURE:
<223> OTHER INFORMATION: Synthetic construct, pAG2227 vector

<400> SEQUENCE: 72
aattcatact aaagcttgca tgcctgcagg tcgactctag taacggccgc cagtgtgctg 60
gaattaattc ggcttgtcga ccacccaacc ccatatcgac agaggatgtg aagaacaggt 120
aaatcacgca gaagaaccca tctctgatag cagctatcga ttagaacaac gaatccatat 180
tgggtccgtg ggaaatactt actgcacagg aagggggcga tctgacgagg ccccgccacc 240
ggcctcgacc cgaggccgag gccgacgaag cgccggcgag tacggcgccg cggcggcctc 300

```
tgcccgtgcc ctctgcgcgt gggagggaga ggccgcggtg gtgggggcgc gcgcgcgcgc    360
gcgcgcagct ggtgcggcgg cgcgggggtc agccgccgag ccggcggcga cggaggagca    420
gggcggcgtg gacgcgaact tccgatcggt tggtcagagt gcgcgagttg ggcttagcca    480
attaggtctc aacaatctat tgggccgtaa aattcatggg ccctggtttg tctaggccca    540
atatcccgtt catttcagcc cacaaatatt tccccagagg attattaagg cccacacgca    600
gcttatagca gatcaagtac gatgtttcct gatcgttgga tcggaaacgt acggtcttga    660
tcaggcatgc cgacttcgtc aaagagaggc ggcatgacct gacgcggagt tggttccggg    720
caccgtctgg atggtcgtac cgggaccgga cacgtgtcgc gcctccaact acatggacac    780
gtgtggtgct gccattgggc cgtacgcgtg gcggtgaccg caccggatgc tgcctcgcac    840
cgccttgccc acgctttata tagagaggtt ttctctccat taatcgcata gcgagtcgaa    900
tcgaccgaag gggaggggga gcgaagcttt gcgttctcta atcgcctcgt caaggtaact    960
aatcaatcac ctcgtcctaa tcctcgaatc tctcgtggtg cccgtctaat ctcgcgattt   1020
tgatgctcgt ggtggaaagc gtaggaggat cccgtgcgag ttagtctcaa tctctcaggg   1080
tttcgtgcga ttttagggtg atccacctct taatcgagtt acggtttcgt gcgattttag   1140
ggtaatcctc ttaatctctc attgatttag ggtttcgtga gaatcgaggt agggatctgt   1200
gttatttata tcgatctaat agatggattg gttttgagat tgttctgtca gatggggatt   1260
gtttcgatat attaccctaa tgatgtgtca gatggggatt gtttcgatat attaccctaa   1320
tgatgtgtca gatggggatt gtttcgatat attaccctaa tgatggataa taagagtagt   1380
tcacagttat gttttgatcc tgccacatag tttgagtttt gtgatcagat ttagttttac   1440
ttatttgtgc ttagttcgga tgggattgtt ctgatattgt tccaatagat gaatagctcg   1500
ttaggttaaa atctttaggt tgagttaggc gacacatagt ttatttcctc tggatttgga   1560
ttggaattgt gttcttagtt tttttcccct ggatttggat tggaattgtg tggagctggg   1620
ttagagaatt acatctgtat cgtgtacacc tacttgaact gtagagcttg ggttctaagg   1680
tcaatttaat ctgtattgta tctggctctt tgcctagttg aactgtagtg ctgatgttgt   1740
actgtgtttt tttacccgtt ttatttgctt tactcgtgca aatcaaatct gtcagatgct   1800
agaactaggt ggctttattc tgtgttctta catagatctg ttgtcctgta gttacttatg   1860
tcagttttgt tattatctga agatattttt ggttgttgct tgttgatgtg gtgtgagctg   1920
tgagcagcgc tcttatgatt aatgatgctg tccaattgta gtgtagtatg atgtgattga   1980
tatgttcatc tattttgagc tgacagtacc gatatcgtag gatctggtgc caacttattc   2040
tccagctgct ttttttacc tatgttaatt ccaatccttt cttgcctctt ccagatccag   2100
ataatgcaga aactcattaa ctcagtgcaa aactatgcct ggggcagcaa aacggcgttg   2160
actgaacttt atggtatgga aaatccgtcc agccagccga tggccgagct gtggatgggc   2220
gcacatccga aaagcagttc acgagtgcag aatgccgccg gagatatcgt ttcactgcgt   2280
gatgtgattg agagtgataa atcgactctg ctcggagagg ccgttgccaa acgctttggc   2340
gaactgcctt tcctgttcaa agtattatgc gcagcacagc cactctccat tcaggttcat   2400
ccaaacaaac acaattctga aatcggtttt gccaaagaaa atgccgcagg tatcccgatg   2460
gatgccgccg agcgtaacta taaagatcct aaccacaagc cggagctggt tttgcgctg    2520
acgcctttcc ttgcgatgaa cgcgtttcgt gaattttccg agattgtctc cctactccag   2580
ccggtcgcag gtgcacatcc ggcgattgct cactttttac aacagcctga tgccgaacgt   2640
ttaagcgaac tgttcgccag cctgttgaat atgcagggtg aagaaaaatc ccgcgcgctg   2700
```

```
gcgattttaa aatcggccct cgatagccag cagggtgaac cgtggcaaac gattcgttta   2760
atttctgaat tttacccgga agacagcggt ctgttctccc cgctattgct gaatgtggtg   2820
aaattgaacc ctggcgaagc gatgttcctg ttcgctgaaa caccgcacgc ttacctgcaa   2880
ggcgtggcgc tggaagtgat ggcaaactcc gataacgtgc tgcgtgcggg tctgacgcct   2940
aaatacattg atattccgga actggttgcc aatgtgaaat tcgaagccaa accggctaac   3000
cagttgttga cccagccggt gaaacaaggt gcagaactgg acttcccgat tccagtggat   3060
gattttgcct tctcgctgca tgaccttagt gataaagaaa ccaccattag ccagcagagt   3120
gccgccattt tgttctgcgt cgaaggcgat gcaacgttgt ggaaaggttc tcagcagtta   3180
cagcttaaac cgggtgaatc agcgtttatt gccgccaacg aatcaccggt gactgtcaaa   3240
ggccacggcc gtttagcgcg tgtttacaac aagctgtaag agcttactga aaaaattaac   3300
atctcttgct aagctgggag ctctagatcc ccgaatttcc ccgatcgttc aaacatttgg   3360
caataaagtt tcttaagatt gaatcctgtt gccggtcttg cgatgattat catataattt   3420
ctgttgaatt acgttaagca tgtaataatt aacatgtaat gcatgacgtt atttatgaga   3480
tgggttttta tgattagagt cccgcaatta tacatttaat acgcgataga aaacaaaata   3540
tagcgcgcaa actaggataa attatcgcgc gcggtgtcat ctatgttact agatcgggaa   3600
ttggcgagct cgaattaatt cagtacatta aaaacgtccg caatgtgtta ttaagttgtc   3660
taagcgtcaa tttgtttaca ccacaatata tcctgccacc agccagccaa cagctccccg   3720
accggcagct cggcacaaaa tcaccactcg atacaggcag cccatcagtc cgggacggcg   3780
tcagcgggag agccgttgta aggcggcaga ctttgctcat gttaccgatg ctattcggaa   3840
gaacggcaac taagctgccg ggtttgaaac acggatgatc tcgcggaggg tagcatgttg   3900
attgtaacga tgacagagcg ttgctgcctg tgatcaaata tcatctccct cgcagagatc   3960
cgaattatca gccttcttat tcatttctcg cttaaccgtg acaggctgtc gatcttgaga   4020
actatgccga cataatagga aatcgctgga taaagccgct gaggaagctg agtggcgcta   4080
tttctttaga agtgaacgtt gacgatcgtc gaccgtaccc cgatgaatta attcggacgt   4140
acgttctgaa cacagctgga tacttacttg ggcgattgtc atacatgaca tcaacaatgt   4200
acccgtttgt gtaaccgtct cttggaggtt cgtatgacac tagtggttcc cctcagcttg   4260
cgactagatg ttgaggccta acattttatt agagagcagg ctagttgctt agatacatga   4320
tcttcaggcc gttatctgtc agggcaagcg aaaattggcc atttatgacg accaatgccc   4380
cgcagaagct cccatctttg ccgccataga cgccgcgccc ccttttgggg gtgtagaaca   4440
tccttttgcc agatgtggaa aagaagttcg ttgtcccatt gttggcaatg acgtagtagc   4500
cggcgaaagt gcgagaccca tttgcgctat atataagcct acgatttccg ttgcgactat   4560
tgtcgtaatt ggatgaacta ttatcgtagt tgctctcaga gttgtcgtaa tttgatggac   4620
tattgtcgta attgcttatg gagttgtcgt agttgcttgg agaaatgtcg tagttggatg   4680
gggagtagtc atagggaaga cgagcttcat ccactaaaac aattggcagg tcagcaagtg   4740
cctgccccga tgccatcgca agtacgaggc ttagaaccac cttcaacaga tcgcgcatag   4800
tcttccccag ctctctaacg cttgagttaa gccgcgccgc gaagcggcgt cggcttgaac   4860
gaattgttag acattatttg ccgactacct tggtgatctc gcctttcacg tagtgaacaa   4920
attcttccaa ctgatctgcg cgcgaggcca agcgatcttc ttgtccaaga taagcctgcc   4980
tagcttcaag tatgacgggc tgatactggg ccggcaggcg ctccattgcc cagtcggcag   5040
```

cgacatcctt cggcgcgatt ttgccggtta ctgcgctgta ccaaatgcgg gacaacgtaa 5100
gcactacatt tcgctcatcg ccagcccagt cgggcggcga gttccatagc gttaaggttt 5160
catttagcgc ctcaaataga tcctgttcag gaaccggatc aaagagttcc tccgccgctg 5220
gacctaccaa ggcaacgcta tgttctcttg cttttgtcag caagatagcc agatcaatgt 5280
cgatcgtggc tggctcgaag atacctgcaa gaatgtcatt gcgctgccat tctccaaatt 5340
gcagttcgcg cttagctgga taacgccacg gaatgatgtc gtcgtgcaca acaatggtga 5400
cttctacagc gcggagaatc tcgctctctc caggggaagc cgaagtttcc aaaaggtcgt 5460
tgatcaaagc tcgccgcgtt gtttcatcaa gccttacggt caccgtaacc agcaaatcaa 5520
tatcactgtg tggcttcagg ccgccatcca ctgcggagcc gtacaaatgt acggccagca 5580
acgtcggttc gagatggcgc tcgatgacgc caactacctc tgatagttga gtcgatactt 5640
cggcgatcac cgcttccctc atgatgttta actcctgaat taagccgcgc cgcgaagcgg 5700
tgtcggcttg aatgaattgt taggcgtcat cctgtgctcc cgagaaccag taccagtaca 5760
tcgctgtttc gttcgagact tgaggtctag ttttatacgt gaacaggtca atgccgccga 5820
gagtaaagcc acattttgcg tacaaattgc aggcaggtac attgttcgtt tgtgtctcta 5880
atcgtatgcc aaggagctgt ctgcttagtg cccacttttt cgcaaattcg atgagactgt 5940
gcgcgactcc tttgcctcgg tgcgtgtgcg acacaacaat gtgttcgata gaggctagat 6000
cgttccatgt tgagttgagt tcaatcttcc cgacaagctc ttggtcgatg aatgcgccat 6060
agcaagcaga gtcttcatca gagtcatcat ccgagatgta atccttccgg taggggctca 6120
cacttctggt agatagttca aagccttggt cggataggtg cacatcgaac acttcacgaa 6180
caatgaaatg gttctcagca tccaatgttt ccgccacctg ctcagggatc accgaaatct 6240
tcatatgacg cctaacgcct ggcacagcgg atcgcaaacc tggcgcggct tttggcacaa 6300
aaggcgtgac aggtttgcga atccgttgct gccacttgtt aacccttttg ccagatttgg 6360
taactataat ttatgttaga ggcgaagtct tgggtaaaaa ctggcctaaa attgctgggg 6420
atttcaggaa agtaaacatc accttccggc tcgatgtcta ttgtagatat atgtagtgta 6480
tctacttgat cgggggatct gctgcctcgc gcgtttcggt gatgacggtg aaaacctctg 6540
acacatgcag ctcccggaga cggtcacagc ttgtctgtaa gcggatgccg ggagcagaca 6600
agcccgtcag ggcgcgtcag cgggtgttgg cgggtgtcgg ggcgcagcca tgacccagtc 6660
acgtagcgat agcggagtgt atactggctt aactatgcgg catcagagca gattgtactg 6720
agagtgcacc atatgcggtg tgaaataccg cacagatgcg taaggagaaa ataccgcatc 6780
aggcgctctt ccgcttcctc gctcactgac tcgctgcgct cggtcgttcg gctgcggcga 6840
gcggtatcag ctcactcaaa ggcggtaata cggttatcca cagaatcagg ggataacgca 6900
ggaaagaaca tgtgagcaaa aggccagcaa aaggccagga accgtaaaaa ggccgcgttg 6960
ctggcgtttt tccataggct ccgcccccct gacgagcatc acaaaaatcg acgctcaagt 7020
cagaggtggc gaaacccgac aggactataa agataccagg cgtttccccc tggaagctcc 7080
ctcgtgcgct ctcctgttcc gaccctgccg cttaccggat acctgtccgc ctttctccct 7140
tcgggaagcg tggcgctttc tcatagctca cgctgtaggt atctcagttc ggtgtaggtc 7200
gttcgctcca agctgggctg tgtgcacgaa ccccccgttc agcccgaccg ctgcgcctta 7260
tccggtaact atcgtcttga gtccaacccg gtaagacacg acttatcgcc actggcagca 7320
gccactggta acaggattag cagagcgagg tatgtaggcg gtgctacaga gttcttgaag 7380
tggtggccta actacggcta cactagaagg acagtatttg gtatctgcgc tctgctgaag 7440
ccagttacct tcggaaaaag agttggtagc tcttgatccg gcaaacaaac caccgctggt 7500
agcggtggtt tttttgtttg caagcagcag attacgcgca gaaaaaaagg atctcaagaa 7560
gatcctttga tcttttctac ggggtctgac gctcagtgga acgaaaactc acgttaaggg 7620
attttggtca tgagattatc aaaaaggatc ttcacctaga tccttttaaa ttaaaaatga 7680
agttttaaat caatctaaag tatatatgag taaacttggt ctgacagtta ccaatgctta 7740
atcagtgagg cacctatctc agcgatctgt ctatttcgtt catccatagt tgcctgactc 7800
cccgtcgtgt agataactac gatacgggag ggcttaccat ctggccccag tgctgcaatg 7860
ataccgcgag acccacgctc accggctcca gatttatcag caataaacca gccagccgga 7920
agggccgagc gcagaagtgg tcctgcaact ttatccgcct ccatccagtc tattaattgt 7980
tgccgggaag ctagagtaag tagttcgcca gttaatagtt tgcgcaacgt tgttgccatt 8040
gctgcagggg gggggggggg ggggttccat tgttcattcc acggacaaaa acagagaaag 8100
gaaacgacag aggccaaaaa gctcgctttc agcacctgtc gtttcctttc ttttcagagg 8160
gtattttaaa taaaaacatt aagttatgac gaagaagaac ggaaacgcct taaaccggaa 8220
aattttcata aatagcgaaa acccgcgagg tcgccgcccc gtaacctgtc ggatcaccgg 8280
aaaggacccg taaagtgata atgattatca tctacatatc acaacgtgcg tggaggccat 8340
caaaccacgt caaataatca attatgacgc aggtatcgta ttaattgatc tgcatcaact 8400
taacgtaaaa acaacttcag acaatacaaa tcagcgacac tgaatacggg gcaacctcat 8460
gtcccccccc cccccccct gcaggcatcg tggtgtcacg ctcgtcgttt ggtatggctt 8520
cattcagctc cggttcccaa cgatcaaggc gagttacatg atcccccatg ttgtgcaaaa 8580
aagcggttag ctccttcggt cctccgatcg ttgtcagaag taagttggcc gcagtgttat 8640
cactcatggt tatggcagca ctgcataatt ctcttactgt catgccatcc gtaagatgct 8700
tttctgtgac tggtgagtac tcaaccaagt cattctgaga atagtgtatg cggcgaccga 8760
gttgctcttg cccggcgtca acacgggata ataccgcgcc acatagcaga actttaaaag 8820
tgctcatcat tggaaaacgt tcttcggggc gaaaactctc aaggatctta ccgctgttga 8880
gatccagttc gatgtaaccc actcgtgcac ccaactgatc ttcagcatct tttactttca 8940
ccagcgtttc tgggtgagca aaaacaggaa ggcaaaatgc cgcaaaaaag ggaataaggg 9000
cgacacggaa atgttgaata ctcatactct tcctttttca atattattga agcatttatc 9060
agggttattg tctcatgagc ggatacatat ttgaatgtat ttagaaaaat aaacaaatag 9120
gggttccgcg cacatttccc cgaaaagtgc cacctgacgt ctaagaaacc attattatca 9180
tgacattaac ctataaaaat aggcgtatca cgaggccctt tcgtcttcaa gaattggtcg 9240
acgatcttgc tgcgttcgga tattttcgtg gagttcccgc cacagacccg gattgaaggc 9300
gagatccagc aactcgcgcc agatcatcct gtgacggaac tttggcgcgt gatgactggc 9360
caggacgtcg gccgaaagag cgacaagcag atcacgcttt tcgacagcgt cggatttgcg 9420
atcgaggatt tttcggcgct gcgctacgtc cgcgaccgcg ttgagggatc aagccacagc 9480
agcccactcg accttctagc cgacccagac gagccaaggg atcttttttgg aatgctgctc 9540
cgtcgtcagg ctttccgacg tttgggtggt tgaacagaag tcattatcgc acggaatgcc 9600
aagcactccc gaggggaacc ctgtggttgg catgcacata caaatggacg aacggataaa 9660
ccttttcacg cccttttaaa tatccgatta ttctaataaa cgctcttttc tcttaggttt 9720
acccgccaat atatcctgtc aaacactgat agtttaaact gaaggcggga aacgacaacc 9780

-continued

```
tgatcatgag cggagaatta agggagtcac gttatgaccc ccgccgatga cgcgggacaa   9840
gccgttttac gtttggaact gacagaaccg caacgttgaa ggagccactc agcttaatta   9900
agtctaactc gagttactgg tacgtaccaa atccatggaa tcaaggtacc gtcgactcta   9960
gtaacggccg ccagtgtgct ggaattaatt cggcttgtcg accacccaac cccatatcga  10020
cagaggatgt gaagaacagg taaatcacgc agaagaaccc atctctgata gcagctatcg  10080
attagaacaa cgaatccata ttgggtccgt gggaaatact tactgcacag gaagggggcg  10140
atctgacgag gccccgccac cggcctcgac ccgaggccga ggccgacgaa gcgccggcga  10200
gtacggcgcc gcggcggcct ctgcccgtgc cctctgcgcg tgggagggag aggccgcggt  10260
ggtgggggcg cgcgcgcgcg cgcgcgcagc tggtgcggcg gcgcgggggt cagccgccga  10320
gccggcggcg acggaggagc agggcggcgt ggacgcgaac ttccgatcgg ttggtcagag  10380
tgcgcgagtt gggcttagcc aattaggtct caacaatcta ttgggccgta aaattcatgg  10440
gccctggttt gtctaggccc aatatcccgt tcatttcagc ccacaaatat ttccccagag  10500
gattattaag gcccacacgc agcttatagc agatcaagta cgatgtttcc tgatcgttgg  10560
atcggaaacg tacggtcttg atcaggcatg ccgacttcgt caaagagagg cggcatgacc  10620
tgacgcggag ttggttccgg gcaccgtctg gatggtcgta ccgggaccgg acacgtgtcg  10680
cgcctccaac tacatggaca cgtgtggtgc tgccattggg ccgtacgcgt ggcggtgacc  10740
gcaccggatg ctgcctcgca ccgccttgcc cacgctttat atagagaggt tttctctcca  10800
ttaatcgcat agcgagtcga atcgaccgaa ggggaggggg agcgaagctt tgcgttctct  10860
aatcgcctcg tcaaggtaac taatcaatca cctcgtccta atcctcgaat ctctcgtggt  10920
gcccgtctaa tctcgcgatt ttgatgctcg tggtggaaag cgtaggagga tcccgtgcga  10980
gttagtctca atctctcagg gtttcgtgcg attttagggt gatccacctc ttaatcgagt  11040
tacggtttcg tgcgatttta gggtaatcct cttaatctct cattgattta gggtttcgtg  11100
agaatcgagg tagggatctg tgttatttat atcgatctaa tagatggatt ggttttgaga  11160
ttgttctgtc agatggggat tgtttcgata tattacccta atgatgtgtc agatggggat  11220
tgtttcgata tattacccta atgatgtgtc agatggggat tgtttcgata tattacccta  11280
atgatggata ataagagtag ttcacagtta tgttttgatc ctgccacata gtttgagttt  11340
tgtgatcaga tttagtttta cttatttgtg cttagttcgg atgggattgt tctgatattg  11400
ttccaataga tgaatagctc gttaggttaa aatctttagg ttgagttagg cgacacatag  11460
tttatttcct ctggatttgg attggaattg tgttcttagt ttttttcccc tggatttgga  11520
ttggaattgt gtggagctgg gttagagaat tacatctgta tcgtgtacac ctacttgaac  11580
tgtagagctt gggttctaag gtcaatttaa tctgtattgt atctggctct ttgcctagtt  11640
gaactgtagt gctgatgttg tactgtgttt ttttacccgt tttatttgct ttactcgtgc  11700
aaatcaaatc tgtcagatgc tagaactagg tggctttatt ctgtgttctt acatagatct  11760
gttgtcctgt agttacttat gtcagttttg ttattatctg aagatatttt tggttgttgc  11820
ttgttgatgt ggtgtgagct gtgagcagcg ctcttatgat taatgatgct gtccaattgt  11880
agtgtagtat gatgtgattg atatgttcat ctattttgag ctgacagtac cgatatcgta  11940
ggatctggtg ccaacttatt ctccagctgc tttttttac ctatgttaat tccaatcctt  12000
tcttgcctct tccagatcca gataatgcaa acaagcatta ctctgacatc caacgcatcc  12060
ggtacgtttg acggttacta ttacgaactc tggaaggata ctggcaatac aacaatgacg  12120
gtctacactc aaggtcgctt ttcctgccag tggtcgaaca tcaataacgc gttgtttagg  12180
```

accgggaaga aatacaacca gaattggcag tctcttggca caatccggat cacgtactct 12240
gcgacttaca acccaaacgg gaactcctac ttgtgtatct atggctggtc taccaaccca 12300
ttggtcgagt tctacatcgt tgagtcctgg gggaactgga gaccgcctgg tgcctgcctg 12360
gccgagggct cgctcgtctt ggacgcggct accgggcaga gggtccctat cgaaaaggtg 12420
cgtccgggga tggaagtttt ctccttggga cctgattaca gactgtatcg ggtgcccgtt 12480
ttggaggtcc ttgagagcgg ggttagggaa gttgtgcgcc tcagaactcg gtcagggaga 12540
acgctggtgt tgacaccaga tcacccgctt ttgacccccg aaggttggaa acctctttgt 12600
gacctcccgc ttggaactcc aattgcagtc cccgcagaac tgcctgtggc gggccacttg 12660
gccccacctg aagaacgtgt tacgctcctg gctcttctgt tgggggatgg gaacacaaag 12720
ctgtcgggtc ggagaggtac acgtcctaat gccttcttct acagcaaaaa ccccgaattg 12780
ctcgcggctt atcgccggtg tgcagaagcc ttgggtgcaa aggtgaaagc atacgtccac 12840
ccgactacgg gggtggttac actcgcaacc ctcgctccac gtcctggagc tcaagatcct 12900
gtcaaacgcc tcgttgtcga ggcgggaatg gttgctaaag ccgaagagaa gagggtcccg 12960
gaggaggtgt ttcgttaccg gcgtgaggcg ttggcccttt tcttgggccg tttgttctcg 13020
acagacggct ctgttgaaaa gaagaggatc tcttattcaa gtgccagttt gggactggcc 13080
caggatgtcg cacatctctt gctgcgcctt ggaattacat ctcaactccg ttcgagaggg 13140
ccacgggctc acgaggttct tatatcgggc cgcgaggata ttttgcggtt tgctgaactt 13200
atcggaccct acctcttggg ggccaagagg gagagacttg cagcgctgga agctgaggcc 13260
cgcaggcgtt tgcctggaca gggatggcac ttgcggcttg ttcttcctgc cgtggcgtac 13320
agagtgggcg aggcggaaag gcgctcggga ttttcgtgga gtgaagccgg tcggcgcgtc 13380
gcagttgcgg gatcgtgttt gtcatctgga ctcaacctca aattgcccag acgctacctt 13440
tctcggcacc ggttgtcgct gctcggtgag gcttttgccg accctgggct ggaagcgctc 13500
gcggaaggcc aagtgctctg ggaccctatt gttgctgtcg aaccggccgg taaggcgaga 13560
acattcgact tgcgcgttcc accctttgca aacttcgtga gcgaggacct ggtggtgcat 13620
aacaccgtcc ccctgggcca agtgacaatc gatggcggga cctacgacat ctataggacg 13680
acacgcgtca accagccttc cattgtgggg acagccacgt tcgatcagta ctggagcgtg 13740
cgcacctcta agcggacttc aggaacagtg accgtgaccg atcacttccg cgcctgggcg 13800
aaccggggcc tgaacctcgg cacaatagac caaattacat tgtgcgtgga gggttaccaa 13860
agctctggat cagccaacat cacccagaac accttctctc agggctcttc ttccggcagt 13920
tcgggtggct catccggctc cacaacgact actcgcatcg agtgtgagaa catgtccttg 13980
tccggaccct acgttagcag gatcaccaat ccctttaatg gtattgcgct gtacgccaac 14040
ggagacacag cccgcgctac cgttaacttc cccgcaagtc gcaactacaa tttccgcctg 14100
cggggttgcg gcaacaacaa taatcttgcc cgtgtggacc tgaggatcga cggacggacc 14160
gtcgggacct tttattacca gggcacatac ccctgggagg ccccaattga caatgtttat 14220
gtcagtgcgg ggagtcatac agtcgaaatc actgttactg cggataacgg cacatgggac 14280
gtgtatgccg actacctggt gatacagtga cctaggtccc cgaatttccc cgatcgttca 14340
aacatttggc aataaagttt cttaagattg aatcctgttg ccggtcttgc gatgattatc 14400
atataatttc tgttgaatta cgttaagcat gtaataatta acatgtaatg catgacgtta 14460
tttatgagat gggtttttat gattagagtc ccgcaattat acatttaata cgcgatagaa 14520
aacaaaatat agcgcgcaaa ctaggataaa ttatcgcgcg cggtgtcatc tatgttacta 14580
gatcgggaat tgg 14593

<210> SEQ ID NO 73
<211> LENGTH: 14665
<212> TYPE: DNA
<213> ORGANISM: Artificial Sequence
<220> FEATURE:
<223> OTHER INFORMATION: Synthetic construct, pAG2228 vector

<400> SEQUENCE: 73
aattcatact aaagcttgca tgcctgcagg tcgactctag taacggccgc cagtgtgctg 60
gaattaattc ggcttgtcga ccacccaacc ccatatcgac agaggatgtg aagaacaggt 120
aaatcacgca gaagaaccca tctctgatag cagctatcga ttagaacaac gaatccatat 180
tgggtccgtg ggaaatactt actgcacagg aagggggcga tctgacgagg ccccgccacc 240
ggcctcgacc cgaggccgag gccgacgaag cgccggcgag tacggcgccg cggcggcctc 300
tgcccgtgcc ctctgcgcgt gggagggaga ggccgcggtg gtgggggcgc gcgcgcgcgc 360
gcgcgcagct ggtgcggcgg cgcgggggtc agccgccgag ccggcggcga cggaggagca 420
gggcggcgtg gacgcgaact tccgatcggt tggtcagagt gcgcgagttg ggcttagcca 480
attaggtctc aacaatctat tgggccgtaa aattcatggg ccctggtttg tctaggccca 540
atatcccgtt catttcagcc cacaaatatt tccccagagg attattaagg cccacacgca 600
gcttatagca gatcaagtac gatgtttcct gatcgttgga tcggaaacgt acggtcttga 660
tcaggcatgc cgacttcgtc aaagagaggc ggcatgacct gacgcggagt tggttccggg 720
caccgtctgg atggtcgtac cgggaccgga cacgtgtcgc gcctccaact acatggacac 780
gtgtggtgct gccattgggc cgtacgcgtg gcggtgaccg caccggatgc tgcctcgcac 840
cgccttgccc acgctttata tagagaggtt ttctctccat taatcgcata gcgagtcgaa 900
tcgaccgaag gggagggggga gcgaagcttt gcgttctcta atcgcctcgt caaggtaact 960
aatcaatcac ctcgtcctaa tcctcgaatc tctcgtggtg cccgtctaat ctcgcgattt 1020
tgatgctcgt ggtggaaagc gtaggaggat cccgtgcgag ttagtctcaa tctctcaggg 1080
tttcgtgcga ttttagggtg atccacctct taatcgagtt acggtttcgt gcgattttag 1140
ggtaatcctc ttaatctctc attgatttag ggtttcgtga gaatcgaggt agggatctgt 1200
gttatttata tcgatctaat agatggattg gttttgagat tgttctgtca gatggggatt 1260
gtttcgatat attaccctaa tgatgtgtca gatggggatt gtttcgatat attaccctaa 1320
tgatgtgtca gatggggatt gtttcgatat attaccctaa tgatggataa taagagtagt 1380
tcacagttat gttttgatcc tgccacatag tttgagtttt gtgatcagat ttagttttac 1440
ttatttgtgc ttagttcgga tgggattgtt ctgatattgt tccaatagat gaatagctcg 1500
ttaggttaaa atctttaggt tgagttaggc gacacatagt ttatttcctc tggatttgga 1560
ttggaattgt gttcttagtt tttttccccct ggatttggat tggaattgtg tggagctggg 1620
ttagagaatt acatctgtat cgtgtacacc tacttgaact gtagagcttg ggttctaagg 1680
tcaatttaat ctgtattgta tctggctctt tgcctagttg aactgtagtg ctgatgttgt 1740
actgtgtttt tttacccgtt ttatttgctt tactcgtgca aatcaaatct gtcagatgct 1800
agaactaggt ggctttattc tgtgttctta catagatctg ttgtcctgta gttacttatg 1860
tcagttttgt tattatctga agatattttt ggttgttgct tgttgatgtg gtgtgagctg 1920
tgagcagcgc tcttatgatt aatgatgctg tccaattgta gtgtagtatg atgtgattga 1980

-continued

```
tatgttcatc tattttgagc tgacagtacc gatatcgtag gatctggtgc caacttattc   2040
tccagctgct ttttttacc tatgttaatt ccaatccttt cttgcctctt ccagatccag   2100
ataatgcaga aactcattaa ctcagtgcaa aactatgcct ggggcagcaa aacggcgttg   2160
actgaacttt atggtatgga aaatccgtcc agccagccga tggccgagct gtggatgggc   2220
gcacatccga aaagcagttc acgagtgcag aatgccgccg gagatatcgt ttcactgcgt   2280
gatgtgattg agagtgataa atcgactctg ctcggagagg ccgttgccaa acgctttggc   2340
gaactgcctt tcctgttcaa agtattatgc gcagcacagc cactctccat tcaggttcat   2400
ccaaacaaac acaattctga aatcggtttt gccaaagaaa atgccgcagg tatcccgatg   2460
gatgccgccg agcgtaacta taaagatcct aaccacaagc cggagctggt tttgcgctg   2520
acgcctttcc ttgcgatgaa cgcgtttcgt gaattttccg agattgtctc cctactccag   2580
ccggtcgcag gtgcacatcc ggcgattgct cactttttac aacagcctga tgccgaacgt   2640
ttaagcgaac tgttcgccag cctgttgaat atgcagggtg aagaaaaatc ccgcgcgctg   2700
gcgattttaa aatcggccct cgatagccag cagggtgaac cgtggcaaac gattcgttta   2760
atttctgaat tttacccgga agacagcggt ctgttctccc cgctattgct gaatgtggtg   2820
aaattgaacc ctggcgaagc gatgttcctg ttcgctgaaa caccgcacgc ttacctgcaa   2880
ggcgtggcgc tggaagtgat ggcaaactcc gataacgtgc tgcgtgcggg tctgacgcct   2940
aaatacattg atattccgga actggttgcc aatgtgaaat tcgaagccaa accggctaac   3000
cagttgttga cccagccggt gaaacaaggt gcagaactgg acttcccgat tccagtggat   3060
gattttgcct tctcgctgca tgaccttagt gataaagaaa ccaccattag ccagcagagt   3120
gccgccattt tgttctgcgt cgaaggcgat gcaacgttgt ggaaaggttc tcagcagtta   3180
cagcttaaac cgggtgaatc agcgtttatt gccgccaacg aatcaccggt gactgtcaaa   3240
ggccacggcc gtttagcgcg tgtttacaac aagctgtaag agcttactga aaaaattaac   3300
atctcttgct aagctgggag ctctagatcc ccgaatttcc ccgatcgttc aaacatttgg   3360
caataaagtt tcttaagatt gaatcctgtt gccggtcttg cgatgattat catataattt   3420
ctgttgaatt acgttaagca tgtaataatt aacatgtaat gcatgacgtt atttatgaga   3480
tgggttttta tgattagagt cccgcaatta tacatttaat acgcgataga aaacaaaata   3540
tagcgcgcaa actaggataa attatcgcgc gcggtgtcat ctatgttact agatcgggaa   3600
ttggcgagct cgaattaatt cagtacatta aaaacgtccg caatgtgtta ttaagttgtc   3660
taagcgtcaa tttgtttaca ccacaatata tcctgccacc agccagccaa cagctccccg   3720
accggcagct cggcacaaaa tcaccactcg atacaggcag cccatcagtc cgggacggcg   3780
tcagcgggag agccgttgta aggcggcaga ctttgctcat gttaccgatg ctattcggaa   3840
gaacggcaac taagctgccg ggtttgaaac acggatgatc tcgcggaggg tagcatgttg   3900
attgtaacga tgacagagcg ttgctgcctg tgatcaaata tcatctccct cgcagagatc   3960
cgaattatca gccttcttat tcatttctcg cttaaccgtg acaggctgtc gatcttgaga   4020
actatgccga cataatagga aatcgctgga taaagccgct gaggaagctg agtggcgcta   4080
tttctttaga agtgaacgtt gacgatcgtc gaccgtaccc cgatgaatta attcggacgt   4140
acgttctgaa cacagctgga tacttacttg ggcgattgtc atacatgaca tcaacaatgt   4200
acccgtttgt gtaaccgtct cttggaggtt cgtatgacac tagtggttcc cctcagcttg   4260
cgactagatg ttgaggccta acattttatt agagagcagg ctagttgctt agatacatga   4320
```

tcttcaggcc gttatctgtc agggcaagcg aaaattggcc atttatgacg accaatgccc 4380
cgcagaagct cccatctttg ccgccataga cgccgcgccc cccttttggg gtgtagaaca 4440
tccttttgcc agatgtggaa aagaagttcg ttgtcccatt gttggcaatg acgtagtagc 4500
cggcgaaagt gcgagaccca tttgcgctat atataagcct acgatttccg ttgcgactat 4560
tgtcgtaatt ggatgaacta ttatcgtagt tgctctcaga gttgtcgtaa tttgatggac 4620
tattgtcgta attgcttatg gagttgtcgt agttgcttgg agaaatgtcg tagttggatg 4680
gggagtagtc atagggaaga cgagcttcat ccactaaaac aattggcagg tcagcaagtg 4740
cctgccccga tgccatcgca agtacgaggc ttagaaccac cttcaacaga tcgcgcatag 4800
tcttccccag ctctctaacg cttgagttaa gccgcgccgc gaagcggcgt cggcttgaac 4860
gaattgttag acattatttg ccgactacct tggtgatctc gcctttcacg tagtgaacaa 4920
attcttccaa ctgatctgcg cgcgaggcca agcgatcttc ttgtccaaga taagcctgcc 4980
tagcttcaag tatgacgggc tgatactggg ccggcaggcg ctccattgcc cagtcggcag 5040
cgacatcctt cggcgcgatt ttgccggtta ctgcgctgta ccaaatgcgg gacaacgtaa 5100
gcactacatt tcgctcatcg ccagcccagt cgggcggcga gttccatagc gttaaggttt 5160
catttagcgc ctcaaataga tcctgttcag gaaccggatc aaagagttcc tccgccgctg 5220
gacctaccaa ggcaacgcta tgttctcttg cttttgtcag caagatagcc agatcaatgt 5280
cgatcgtggc tggctcgaag atacctgcaa gaatgtcatt gcgctgccat tctccaaatt 5340
gcagttcgcg cttagctgga taacgccacg gaatgatgtc gtcgtgcaca acaatggtga 5400
cttctacagc gcggagaatc tcgctctctc caggggaagc cgaagtttcc aaaaggtcgt 5460
tgatcaaagc tcgccgcgtt gtttcatcaa gccttacggt caccgtaacc agcaaatcaa 5520
tatcactgtg tggcttcagg ccgccatcca ctgcggagcc gtacaaatgt acggccagca 5580
acgtcggttc gagatggcgc tcgatgacgc caactacctc tgatagttga gtcgatactt 5640
cggcgatcac cgcttccctc atgatgttta actcctgaat taagccgcgc cgcgaagcgg 5700
tgtcggcttg aatgaattgt taggcgtcat cctgtgctcc cgagaaccag taccagtaca 5760
tcgctgtttc gttcgagact tgaggtctag ttttatacgt gaacaggtca atgccgccga 5820
gagtaaagcc acattttgcg tacaaattgc aggcaggtac attgttcgtt tgtgtctcta 5880
atcgtatgcc aaggagctgt ctgcttagtg cccacttttt cgcaaattcg atgagactgt 5940
gcgcgactcc tttgcctcgg tgcgtgtgcg acacaacaat gtgttcgata gaggctagat 6000
cgttccatgt tgagttgagt tcaatcttcc cgacaagctc ttggtcgatg aatgcgccat 6060
agcaagcaga gtcttcatca gagtcatcat ccgagatgta atccttccgg taggggctca 6120
cacttctggt agatagttca aagccttggt cggataggtg cacatcgaac acttcacgaa 6180
caatgaaatg gttctcagca tccaatgttt ccgccacctg ctcagggatc accgaaatct 6240
tcatatgacg cctaacgcct ggcacagcgg atcgcaaacc tggcgcggct tttggcacaa 6300
aaggcgtgac aggtttgcga atccgttgct gccacttgtt aacccttttg ccagatttgg 6360
taactataat ttatgttaga ggcgaagtct tgggtaaaaa ctggcctaaa attgctgggg 6420
atttcaggaa agtaaacatc accttccggc tcgatgtcta ttgtagatat atgtagtgta 6480
tctacttgat cgggggatct gctgcctcgc gcgtttcggt gatgacggtg aaaacctctg 6540
acacatgcag ctcccggaga cggtcacagc ttgtctgtaa gcggatgccg ggagcagaca 6600
agcccgtcag ggcgcgtcag cgggtgttgg cgggtgtcgg ggcgcagcca tgacccagtc 6660
acgtagcgat agcggagtgt atactggctt aactatgcgg catcagagca gattgtactg 6720

```
agagtgcacc atatgcggtg tgaaataccg cacagatgcg taaggagaaa ataccgcatc   6780

aggcgctctt ccgcttcctc gctcactgac tcgctgcgct cggtcgttcg gctgcggcga   6840

gcggtatcag ctcactcaaa ggcggtaata cggttatcca cagaatcagg ggataacgca   6900

ggaaagaaca tgtgagcaaa aggccagcaa aaggccagga accgtaaaaa ggccgcgttg   6960

ctggcgtttt tccataggct ccgcccccct gacgagcatc acaaaaatcg acgctcaagt   7020

cagaggtggc gaaacccgac aggactataa agataccagg cgtttccccc tggaagctcc   7080

ctcgtgcgct ctcctgttcc gaccctgccg cttaccggat acctgtccgc ctttctccct   7140

tcgggaagcg tggcgctttc tcatagctca cgctgtaggt atctcagttc ggtgtaggtc   7200

gttcgctcca agctgggctg tgtgcacgaa ccccccgttc agcccgaccg ctgcgcctta   7260

tccggtaact atcgtcttga gtccaacccg gtaagacacg acttatcgcc actggcagca   7320

gccactggta acaggattag cagagcgagg tatgtaggcg gtgctacaga gttcttgaag   7380

tggtggccta actacggcta cactagaagg acagtatttg gtatctgcgc tctgctgaag   7440

ccagttacct tcggaaaaag agttggtagc tcttgatccg gcaaacaaac caccgctggt   7500

agcggtggtt tttttgtttg caagcagcag attacgcgca gaaaaaaagg atctcaagaa   7560

gatcctttga tcttttctac ggggtctgac gctcagtgga acgaaaactc acgttaaggg   7620

attttggtca tgagattatc aaaaaggatc ttcacctaga tccttttaaa ttaaaaatga   7680

agttttaaat caatctaaag tatatatgag taaacttggt ctgacagtta ccaatgctta   7740

atcagtgagg cacctatctc agcgatctgt ctatttcgtt catccatagt tgcctgactc   7800

cccgtcgtgt agataactac gatacgggag ggcttaccat ctggccccag tgctgcaatg   7860

ataccgcgag acccacgctc accggctcca gatttatcag caataaacca gccagccgga   7920

agggccgagc gcagaagtgg tcctgcaact ttatccgcct ccatccagtc tattaattgt   7980

tgccgggaag ctagagtaag tagttcgcca gttaatagtt tgcgcaacgt tgttgccatt   8040

gctgcagggg gggggggggg ggggttccat tgttcattcc acggacaaaa acagagaaag   8100

gaaacgacag aggccaaaaa gctcgctttc agcacctgtc gtttcctttc ttttcagagg   8160

gtattttaaa taaaaacatt aagttatgac gaagaagaac ggaaacgcct taaaccggaa   8220

aattttcata aatagcgaaa acccgcgagg tcgccgcccc gtaacctgtc ggatcaccgg   8280

aaaggacccg taaagtgata atgattatca tctacatatc acaacgtgcg tggaggccat   8340

caaaccacgt caaataatca attatgacgc aggtatcgta ttaattgatc tgcatcaact   8400

taacgtaaaa acaacttcag acaatacaaa tcagcgacac tgaatacggg gcaacctcat   8460

gtcccccccc ccccccccct gcaggcatcg tggtgtcacg ctcgtcgttt ggtatggctt   8520

cattcagctc cggttcccaa cgatcaaggc gagttacatg atcccccatg ttgtgcaaaa   8580

aagcggttag ctccttcggt cctccgatcg ttgtcagaag taagttggcc gcagtgttat   8640

cactcatggt tatggcagca ctgcataatt ctcttactgt catgccatcc gtaagatgct   8700

tttctgtgac tggtgagtac tcaaccaagt cattctgaga atagtgtatg cggcgaccga   8760

gttgctcttg cccggcgtca acacgggata ataccgcgcc acatagcaga actttaaaag   8820

tgctcatcat tggaaaacgt tcttcggggc gaaaactctc aaggatctta ccgctgttga   8880

gatccagttc gatgtaaccc actcgtgcac ccaactgatc ttcagcatct tttactttca   8940

ccagcgtttc tgggtgagca aaaacaggaa ggcaaaatgc cgcaaaaaag ggaataaggg   9000

cgacacggaa atgttgaata ctcatactct tcctttttca atattattga agcatttatc   9060
```

-continued

```
agggttattg tctcatgagc ggatacatat ttgaatgtat ttagaaaaat aaacaaatag   9120
gggttccgcg cacatttccc cgaaaagtgc cacctgacgt ctaagaaacc attattatca   9180
tgacattaac ctataaaaat aggcgtatca cgaggccctt tcgtcttcaa gaattggtcg   9240
acgatcttgc tgcgttcgga tattttcgtg gagttcccgc cacagacccg gattgaaggc   9300
gagatccagc aactcgcgcc agatcatcct gtgacggaac tttggcgcgt gatgactggc   9360
caggacgtcg gccgaaagag cgacaagcag atcacgcttt tcgacagcgt cggatttgcg   9420
atcgaggatt tttcggcgct gcgctacgtc cgcgaccgcg ttgagggatc aagccacagc   9480
agcccactcg accttctagc cgacccagac gagccaaggg atctttttgg aatgctgctc   9540
cgtcgtcagg ctttccgacg tttgggtggt tgaacagaag tcattatcgc acggaatgcc   9600
aagcactccc gaggggaacc ctgtggttgg catgcacata caaatggacg aacggataaa   9660
ccttttcacg cccttttaaa tatccgatta ttctaataaa cgctcttttc tcttaggttt   9720
acccgccaat atatcctgtc aaacactgat agtttaaact gaaggcggga aacgacaacc   9780
tgatcatgag cggagaatta agggagtcac gttatgaccc ccgccgatga cgcgggacaa   9840
gccgttttac gtttggaact gacagaaccg caacgttgaa ggagccactc agcttaatta   9900
agtctaactc gagttactgg tacgtaccaa atccatggaa tcaaggtacc gtcgactcta   9960
gtaacggccg ccagtgtgct ggaattaatt cggcttgtcg accacccaac cccatatcga  10020
cagaggatgt gaagaacagg taaatcacgc agaagaaccc atctctgata gcagctatcg  10080
attagaacaa cgaatccata ttgggtccgt gggaaatact tactgcacag gaagggggcg  10140
atctgacgag gccccgccac cggcctcgac ccgaggccga ggccgacgaa gcgccggcga  10200
gtacggcgcc gcggcggcct ctgcccgtgc cctctgcgcg tgggagggag aggccgcggt  10260
ggtgggggcg cgcgcgcgcg cgcgcgcagc tggtgcggcg gcgcgggggt cagccgccga  10320
gccggcggcg acggaggagc agggcggcgt ggacgcgaac ttccgatcgg ttggtcagag  10380
tgcgcgagtt gggcttagcc aattaggtct caacaatcta ttgggccgta aaattcatgg  10440
gccctggttt gtctaggccc aatatcccgt tcatttcagc ccacaaatat ttccccagag  10500
gattattaag gcccacacgc agcttatagc agatcaagta cgatgtttcc tgatcgttgg  10560
atcggaaacg tacggtcttg atcaggcatg ccgacttcgt caaagagagg cggcatgacc  10620
tgacgcggag ttggttccgg gcaccgtctg gatggtcgta ccgggaccgg acacgtgtcg  10680
cgcctccaac tacatggaca cgtgtggtgc tgccattggg ccgtacgcgt ggcggtgacc  10740
gcaccggatg ctgcctcgca ccgccttgcc cacgctttat atagagaggt tttctctcca  10800
ttaatcgcat agcgagtcga atcgaccgaa ggggaggggg agcgaagctt tgcgttctct  10860
aatcgcctcg tcaaggtaac taatcaatca cctcgtccta atcctcgaat ctctcgtggt  10920
gcccgtctaa tctcgcgatt ttgatgctcg tggtggaaag cgtaggagga tcccgtgcga  10980
gttagtctca atctctcagg gtttcgtgcg attttagggt gatccacctc ttaatcgagt  11040
tacggtttcg tgcgatttta gggtaatcct cttaatctct cattgattta gggtttcgtg  11100
agaatcgagg tagggatctg tgttatttat atcgatctaa tagatggatt ggttttgaga  11160
ttgttctgtc agatggggat tgtttcgata tattacccta atgatgtgtc agatggggat  11220
tgtttcgata tattacccta atgatgtgtc agatggggat tgtttcgata tattacccta  11280
atgatggata ataagagtag ttcacagtta tgttttgatc ctgccacata gtttgagttt  11340
tgtgatcaga tttagtttta cttatttgtg cttagttcgg atgggattgt tctgatattg  11400
ttccaataga tgaatagctc gttaggttaa aatctttagg ttgagttagg cgacacatag  11460
```

tttatttcct ctggatttgg attggaattg tgttcttagt ttttttcccc tggatttgga 11520
ttggaattgt gtggagctgg gttagagaat tacatctgta tcgtgtacac ctacttgaac 11580
tgtagagctt gggttctaag gtcaatttaa tctgtattgt atctggctct ttgcctagtt 11640
gaactgtagt gctgatgttg tactgtgttt ttttacccgt tttatttgct ttactcgtgc 11700
aaatcaaatc tgtcagatgc tagaactagg tggctttatt ctgtgttctt acatagatct 11760
gttgtcctgt agttacttat gtcagttttg ttattatctg aagatatttt tggttgttgc 11820
ttgttgatgt ggtgtgagct gtgagcagcg ctcttatgat taatgatgct gtccaattgt 11880
agtgtagtat gatgtgattg atatgttcat ctattttgag ctgacagtac cgatatcgta 11940
ggatctggtg ccaacttatt ctccagctgc tttttttttac ctatgttaat tccaatcctt 12000
tcttgcctct tccagatcca gataatggcg aacaaacatt tgtccctctc cctcttcctc 12060
gtcctccttg gcctgtcggc cagcttggcc tccgggcaac aaacaagcat tactctgaca 12120
tccaacgcat ccggtacgtt tgacggttac tattacgaac tctggaagga tactggcaat 12180
acaacaatga cggtctacac tcaaggtcgc ttttcctgcc agtggtcgaa catcaataac 12240
gcgttgttta ggaccgggaa gaaatacaac cagaattggc agtctcttgg cacaatccgg 12300
atcacgtact ctgcgactta caacccaaac gggaactcct acttgtgtat ctatggctgg 12360
tctaccaacc cattggtcga gttctacatc gttgagtcct gggggaactg gagaccgcct 12420
ggtgcctgcc tggccgaggg ctcgctcgtc ttggacgcgg ctaccgggca gagggtccct 12480
atcgaaaagg tgcgtccggg gatggaagtt ttctccttgg gacctgatta cagactgtat 12540
cgggtgcccg ttttggaggt ccttgagagc ggggttaggg aagttgtgcg cctcagaact 12600
cggtcaggga gaacgctggt gttgacacca gatcacccgc ttttgacccc cgaaggttgg 12660
aaacctcttt gtgacctccc gcttggaact ccaattgcag tccccgcaga actgcctgtg 12720
gcgggccact tggccccacc tgaagaacgt gttacgctcc tggctcttct gttgggggat 12780
gggaacacaa agctgtcggg tcggagaggt acacgtccta atgccttctt ctacagcaaa 12840
aaccccgaat tgctcgcggc ttatcgccgg tgtgcagaag ccttgggtgc aaaggtgaaa 12900
gcatacgtcc acccgactac gggggtggtt acactcgcaa ccctcgctcc acgtcctgga 12960
gctcaagatc ctgtcaaacg cctcgttgtc gaggcgggaa tggttgctaa agccgaagag 13020
aagagggtcc cggaggaggt gtttcgttac cggcgtgagg cgttggccct tttcttgggc 13080
cgtttgttct cgacagacgg ctctgttgaa aagaagagga tctcttattc aagtgccagt 13140
ttgggactgg cccaggatgt cgcacatctc ttgctgcgcc ttggaattac atctcaactc 13200
cgttcgagag ggccacgggc tcacgaggtt cttatatcgg gccgcgagga tattttgcgg 13260
tttgctgaac ttatcggacc ctacctcttg gggggccaaga gggagagact tgcagcgctg 13320
gaagctgagg cccgcaggcg tttgcctgga cagggatggc acttgcggct tgttcttcct 13380
gccgtggcgt acagagtggg cgaggcggaa aggcgctcgg gattttcgtg gagtgaagcc 13440
ggtcggcgcg tcgcagttgc gggatcgtgt ttgtcatctg gactcaacct caaattgccc 13500
agacgctacc tttctcggca ccggttgtcg ctgctcggtg aggcttttgc cgaccctggg 13560
ctggaagcgc tcgcggaagg ccaagtgctc tgggacccta ttgttgctgt cgaaccggcc 13620
ggtaaggcga gaacattcga cttgcgcgtt ccacccttttg caaacttcgt gagcgaggac 13680
ctggtggtgc ataacaccgt ccccctgggc caagtgacaa tcgatggcgg gacctacgac 13740
atctatagga cgacacgcgt caaccagcct tccattgtgg ggacagccac gttcgatcag 13800
tactggagcg tgcgcacctc taagcggact tcaggaacag tgaccgtgac cgatcacttc 13860
cgcgcctggg cgaaccgggg cctgaacctc ggcacaatag accaaattac attgtgcgtg 13920
gagggttacc aaagctctgg atcagccaac atcacccaga acaccttctc tcagggctct 13980
tcttccggca gttcgggtgg ctcatccggc tccacaacga ctactcgcat cgagtgtgag 14040
aacatgtcct tgtccggacc ctacgttagc aggatcacca atccctttaa tggtattgcg 14100
ctgtacgcca acggagacac agcccgcgct accgttaact tccccgcaag tcgcaactac 14160
aatttccgcc tgcggggttg cggcaacaac aataatcttg cccgtgtgga cctgaggatc 14220
gacggacgga ccgtcgggac cttttattac cagggcacat acccctggga ggccccaatt 14280
gacaatgttt atgtcagtgc ggggagtcat acagtcgaaa tcactgttac tgcggataac 14340
ggcacatggg acgtgtatgc cgactacctg gtgatacagt gacctaggtc cccgaatttc 14400
cccgatcgtt caaacatttg gcaataaagt ttcttaagat tgaatcctgt tgccggtctt 14460
gcgatgatta tcatataatt tctgttgaat tacgttaagc atgtaataat taacatgtaa 14520
tgcatgacgt tatttatgag atgggttttt atgattagag tcccgcaatt atacatttaa 14580
tacgcgatag aaaacaaaat atagcgcgca aactaggata aattatcgcg cgcggtgtca 14640
tctatgttac tagatcggga attgg 14665

<210> SEQ ID NO 74
<211> LENGTH: 14683
<212> TYPE: DNA
<213> ORGANISM: Artificial Sequence
<220> FEATURE:
<223> OTHER INFORMATION: Synthetic construct, pAG2229 vector

<400> SEQUENCE: 74
aattcatact aaagcttgca tgcctgcagg tcgactctag taacggccgc cagtgtgctg 60
gaattaattc ggcttgtcga ccacccaacc ccatatcgac agaggatgtg aagaacaggt 120
aaatcacgca gaagaaccca tctctgatag cagctatcga ttagaacaac gaatccatat 180
tgggtccgtg ggaaatactt actgcacagg aagggggcga tctgacgagg ccccgccacc 240
ggcctcgacc cgaggccgag gccgacgaag cgccggcgag tacggcgccg cggcggcctc 300
tgcccgtgcc ctctgcgcgt gggagggaga ggccgcggtg gtgggggcgc gcgcgcgcgc 360
gcgcgcagct ggtgcggcgg cgcgggggtc agccgccgag ccggcggcga cggaggagca 420
gggcggcgtg gacgcgaact tccgatcggt tggtcagagt gcgcgagttg ggcttagcca 480
attaggtctc aacaatctat tggccgtaa aattcatggg ccctggtttg tctaggccca 540
atatcccgtt catttcagcc cacaaatatt tccccagagg attattaagg cccacacgca 600
gcttatagca gatcaagtac gatgtttcct gatcgttgga tcggaaacgt acggtcttga 660
tcaggcatgc cgacttcgtc aaagagaggc ggcatgacct gacgcggagt tggttccggg 720
caccgtctgg atggtcgtac cgggaccgga cacgtgtcgc gcctccaact acatggacac 780
gtgtggtgct gccattgggc cgtacgcgtg gcggtgaccg caccggatgc tgcctcgcac 840
cgccttgccc acgctttata tagagaggtt ttctctccat taatcgcata gcgagtcgaa 900
tcgaccgaag gggaggggga gcgaagcttt gcgttctcta atcgcctcgt caaggtaact 960
aatcaatcac ctcgtcctaa tcctcgaatc tctcgtggtg cccgtctaat ctcgcgattt 1020
tgatgctcgt ggtggaaagc gtaggaggat cccgtgcgag ttagtctcaa tctctcaggg 1080
tttcgtgcga ttttagggtg atccacctct taatcgagtt acggtttcgt gcgattttag 1140
ggtaatcctc ttaatctctc attgatttag ggtttcgtga gaatcgaggt agggatctgt 1200

```
gttatttata tcgatctaat agatggattg gttttgagat tgttctgtca gatggggatt   1260
gtttcgatat attaccctaa tgatgtgtca gatggggatt gtttcgatat attaccctaa   1320
tgatgtgtca gatggggatt gtttcgatat attaccctaa tgatggataa taagagtagt   1380
tcacagttat gttttgatcc tgccacatag tttgagtttt gtgatcagat ttagttttac   1440
ttatttgtgc ttagttcgga tgggattgtt ctgatattgt tccaatagat gaatagctcg   1500
ttaggttaaa atctttaggt tgagttaggc gacacatagt ttatttcctc tggatttgga   1560
ttggaattgt gttcttagtt tttttcccct ggatttggat tggaattgtg tggagctggg   1620
ttagagaatt acatctgtat cgtgtacacc tacttgaact gtagagcttg ggttctaagg   1680
tcaatttaat ctgtattgta tctggctctt tgcctagttg aactgtagtg ctgatgttgt   1740
actgtgtttt tttacccgtt ttatttgctt tactcgtgca aatcaaatct gtcagatgct   1800
agaactaggt ggctttattc tgtgttctta catagatctg ttgtcctgta gttacttatg   1860
tcagttttgt tattatctga agatattttt ggttgttgct tgttgatgtg gtgtgagctg   1920
tgagcagcgc tcttatgatt aatgatgctg tccaattgta gtgtagtatg atgtgattga   1980
tatgttcatc tattttgagc tgacagtacc gatatcgtag gatctggtgc caacttattc   2040
tccagctgct ttttttacc tatgttaatt ccaatccttt cttgcctctt ccagatccag    2100
ataatgcaga aactcattaa ctcagtgcaa aactatgcct ggggcagcaa aacggcgttg   2160
actgaacttt atggtatgga aaatccgtcc agccagccga tggccgagct gtggatgggc   2220
gcacatccga aaagcagttc acgagtgcag aatgccgccg gagatatcgt ttcactgcgt   2280
gatgtgattg agagtgataa atcgactctg ctcggagagg ccgttgccaa acgctttggc   2340
gaactgcctt tcctgttcaa agtattatgc gcagcacagc cactctccat tcaggttcat   2400
ccaaacaaac acaattctga aatcggtttt gccaaagaaa atgccgcagg tatcccgatg   2460
gatgccgccg agcgtaacta taaagatcct aaccacaagc cggagctggt ttttgcgctg   2520
acgcctttcc ttgcgatgaa cgcgtttcgt gaattttccg agattgtctc cctactccag   2580
ccggtcgcag gtgcacatcc ggcgattgct cactttttac aacagcctga tgccgaacgt   2640
ttaagcgaac tgttcgccag cctgttgaat atgcagggtg aagaaaaatc ccgcgcgctg   2700
gcgattttaa aatcggccct cgatagccag cagggtgaac cgtggcaaac gattcgttta   2760
atttctgaat tttacccgga agacagcggt ctgttctccc cgctattgct gaatgtggtg   2820
aaattgaacc ctggcgaagc gatgttcctg ttcgctgaaa caccgcacgc ttacctgcaa   2880
ggcgtggcgc tggaagtgat ggcaaactcc gataacgtgc tgcgtgcggg tctgacgcct   2940
aaatacattg atattccgga actggttgcc aatgtgaaat tcgaagccaa accggctaac   3000
cagttgttga cccagccggt gaaacaaggt gcagaactgg acttcccgat tccagtggat   3060
gattttgcct tctcgctgca tgaccttagt gataaagaaa ccaccattag ccagcagagt   3120
gccgccattt tgttctgcgt cgaaggcgat gcaacgttgt ggaaaggttc tcagcagtta   3180
cagcttaaac cgggtgaatc agcgtttatt gccgccaacg aatcaccggt gactgtcaaa   3240
ggccacggcc gtttagcgcg tgtttacaac aagctgtaag agcttactga aaaaattaac   3300
atctcttgct aagctgggag ctctagatcc ccgaatttcc ccgatcgttc aaacatttgg   3360
caataaagtt tcttaagatt gaatcctgtt gccggtcttg cgatgattat catataattt   3420
ctgttgaatt acgttaagca tgtaataatt aacatgtaat gcatgacgtt atttatgaga   3480
tgggttttta tgattagagt cccgcaatta tacatttaat acgcgataga aaacaaaata   3540
```

-continued

```
tagcgcgcaa actaggataa attatcgcgc gcggtgtcat ctatgttact agatcgggaa   3600
ttggcgagct cgaattaatt cagtacatta aaaacgtccg caatgtgtta ttaagttgtc   3660
taagcgtcaa tttgtttaca ccacaatata tcctgccacc agccagccaa cagctccccg   3720
accggcagct cggcacaaaa tcaccactcg atacaggcag cccatcagtc cgggacggcg   3780
tcagcgggag agccgttgta aggcggcaga ctttgctcat gttaccgatg ctattcggaa   3840
gaacggcaac taagctgccg ggtttgaaac acggatgatc tcgcggaggg tagcatgttg   3900
attgtaacga tgacagagcg ttgctgcctg tgatcaaata tcatctccct cgcagagatc   3960
cgaattatca gccttcttat tcatttctcg cttaaccgtg acaggctgtc gatcttgaga   4020
actatgccga cataatagga aatcgctgga taaagccgct gaggaagctg agtggcgcta   4080
tttctttaga agtgaacgtt gacgatcgtc gaccgtaccc cgatgaatta attcggacgt   4140
acgttctgaa cacagctgga tacttacttg ggcgattgtc atacatgaca tcaacaatgt   4200
acccgtttgt gtaaccgtct cttggaggtt cgtatgacac tagtggttcc cctcagcttg   4260
cgactagatg ttgaggccta acattttatt agagagcagg ctagttgctt agatacatga   4320
tcttcaggcc gttatctgtc agggcaagcg aaaattggcc atttatgacg accaatgccc   4380
cgcagaagct cccatctttg ccgccataga cgccgcgccc cccttttggg gtgtagaaca   4440
tccttttgcc agatgtggaa aagaagttcg ttgtcccatt gttggcaatg acgtagtagc   4500
cggcgaaagt gcgagaccca tttgcgctat atataagcct acgatttccg ttgcgactat   4560
tgtcgtaatt ggatgaacta ttatcgtagt tgctctcaga gttgtcgtaa tttgatggac   4620
tattgtcgta attgcttatg gagttgtcgt agttgcttgg agaaatgtcg tagttggatg   4680
gggagtagtc atagggaaga cgagcttcat ccactaaaac aattggcagg tcagcaagtg   4740
cctgccccga tgccatcgca agtacgaggc ttagaaccac cttcaacaga tcgcgcatag   4800
tcttccccag ctctctaacg cttgagttaa gccgcgccgc gaagcggcgt cggcttgaac   4860
gaattgttag acattatttg ccgactacct tggtgatctc gcctttcacg tagtgaacaa   4920
attcttccaa ctgatctgcg cgcgaggcca agcgatcttc ttgtccaaga taagcctgcc   4980
tagcttcaag tatgacgggc tgatactggg ccggcaggcg ctccattgcc cagtcggcag   5040
cgacatcctt cggcgcgatt ttgccggtta ctgcgctgta ccaaatgcgg gacaacgtaa   5100
gcactacatt tcgctcatcg ccagcccagt cgggcggcga gttccatagc gttaaggttt   5160
catttagcgc ctcaaataga tcctgttcag gaaccggatc aaagagttcc tccgccgctg   5220
gacctaccaa ggcaacgcta tgttctcttg cttttgtcag caagatagcc agatcaatgt   5280
cgatcgtggc tggctcgaag atacctgcaa gaatgtcatt gcgctgccat tctccaaatt   5340
gcagttcgcg cttagctgga taacgccacg gaatgatgtc gtcgtgcaca acaatggtga   5400
cttctacagc gcggagaatc tcgctctctc caggggaagc cgaagtttcc aaaaggtcgt   5460
tgatcaaagc tcgccgcgtt gtttcatcaa gccttacggt caccgtaacc agcaaatcaa   5520
tatcactgtg tggcttcagg ccgccatcca ctgcggagcc gtacaaatgt acggccagca   5580
acgtcggttc gagatggcgc tcgatgacgc caactacctc tgatagttga gtcgatactt   5640
cggcgatcac cgcttccctc atgatgttta actcctgaat taagccgcgc cgcgaagcgg   5700
tgtcggcttg aatgaattgt taggcgtcat cctgtgctcc cgagaaccag taccagtaca   5760
tcgctgtttc gttcgagact tgaggtctag ttttatacgt gaacaggtca atgccgccga   5820
gagtaaagcc acattttgcg tacaaattgc aggcaggtac attgttcgtt tgtgtctcta   5880
atcgtatgcc aaggagctgt ctgcttagtg cccacttttt cgcaaattcg atgagactgt   5940
```

-continued

```
gcgcgactcc tttgcctcgg tgcgtgtgcg acacaacaat gtgttcgata gaggctagat   6000
cgttccatgt tgagttgagt tcaatcttcc cgacaagctc ttggtcgatg aatgcgccat   6060
agcaagcaga gtcttcatca gagtcatcat ccgagatgta atccttccgg taggggctca   6120
cacttctggt agatagttca aagccttggt cggataggtg cacatcgaac acttcacgaa   6180
caatgaaatg gttctcagca tccaatgttt ccgccacctg ctcagggatc accgaaatct   6240
tcatatgacg cctaacgcct ggcacagcgg atcgcaaacc tggcgcggct tttggcacaa   6300
aaggcgtgac aggtttgcga atccgttgct gccacttgtt aaccctttttg ccagatttgg   6360
taactataat ttatgttaga ggcgaagtct tgggtaaaaa ctggcctaaa attgctgggg   6420
atttcaggaa agtaaacatc accttccggc tcgatgtcta ttgtagatat atgtagtgta   6480
tctacttgat cgggggatct gctgcctcgc gcgtttcggt gatgacggtg aaaacctctg   6540
acacatgcag ctcccggaga cggtcacagc ttgtctgtaa gcggatgccg ggagcagaca   6600
agcccgtcag ggcgcgtcag cgggtgttgg cgggtgtcgg ggcgcagcca tgacccagtc   6660
acgtagcgat agcggagtgt atactggctt aactatgcgg catcagagca gattgtactg   6720
agagtgcacc atatgcggtg tgaaataccg cacagatgcg taaggagaaa ataccgcatc   6780
aggcgctctt ccgcttcctc gctcactgac tcgctgcgct cggtcgttcg gctgcggcga   6840
gcggtatcag ctcactcaaa ggcggtaata cggttatcca cagaatcagg ggataacgca   6900
ggaaagaaca tgtgagcaaa aggccagcaa aaggccagga accgtaaaaa ggccgcgttg   6960
ctggcgtttt tccataggct ccgcccccct gacgagcatc acaaaaatcg acgctcaagt   7020
cagaggtggc gaaacccgac aggactataa agataccagg cgtttccccc tggaagctcc   7080
ctcgtgcgct ctcctgttcc gaccctgccg cttaccggat acctgtccgc ctttctccct   7140
tcgggaagcg tggcgctttc tcatagctca cgctgtaggt atctcagttc ggtgtaggtc   7200
gttcgctcca agctgggctg tgtgcacgaa ccccccgttc agcccgaccg ctgcgcctta   7260
tccggtaact atcgtcttga gtccaacccg gtaagacacg acttatcgcc actggcagca   7320
gccactggta acaggattag cagagcgagg tatgtaggcg gtgctacaga gttcttgaag   7380
tggtggccta actacggcta cactagaagg acagtatttg gtatctgcgc tctgctgaag   7440
ccagttacct tcggaaaaag agttggtagc tcttgatccg gcaaacaaac caccgctggt   7500
agcggtggtt tttttgtttg caagcagcag attacgcgca gaaaaaaagg atctcaagaa   7560
gatcctttga tcttttctac ggggtctgac gctcagtgga acgaaaactc acgttaaggg   7620
attttggtca tgagattatc aaaaaggatc ttcacctaga tccttttaaa ttaaaaatga   7680
agttttaaat caatctaaag tatatatgag taaacttggt ctgacagtta ccaatgctta   7740
atcagtgagg cacctatctc agcgatctgt ctatttcgtt catccatagt tgcctgactc   7800
cccgtcgtgt agataactac gatacgggag ggcttaccat ctggccccag tgctgcaatg   7860
ataccgcgag acccacgctc accggctcca gatttatcag caataaacca gccagccgga   7920
agggccgagc gcagaagtgg tcctgcaact ttatccgcct ccatccagtc tattaattgt   7980
tgccgggaag ctagagtaag tagttcgcca gttaatagtt tgcgcaacgt tgttgccatt   8040
gctgcagggg gggggggggg ggggttccat tgttcattcc acggacaaaa acagagaaag   8100
gaaacgacag aggccaaaaa gctcgctttc agcacctgtc gtttcctttc ttttcagagg   8160
gtattttaaa taaaaacatt aagttatgac gaagaagaac ggaaacgcct taaaccggaa   8220
aattttcata aatagcgaaa acccgcgagg tcgccgcccc gtaacctgtc ggatcaccgg   8280
```

```
aaaggacccg taaagtgata atgattatca tctacatatc acaacgtgcg tggaggccat   8340
caaaccacgt caaataatca attatgacgc aggtatcgta ttaattgatc tgcatcaact   8400
taacgtaaaa acaacttcag acaatacaaa tcagcgacac tgaatacggg gcaacctcat   8460
gtcccccccc cccccccct gcaggcatcg tggtgtcacg ctcgtcgttt ggtatggctt   8520
cattcagctc cggttcccaa cgatcaaggc gagttacatg atcccccatg ttgtgcaaaa   8580
aagcggttag ctccttcggt cctccgatcg ttgtcagaag taagttggcc gcagtgttat   8640
cactcatggt tatggcagca ctgcataatt ctcttactgt catgccatcc gtaagatgct   8700
tttctgtgac tggtgagtac tcaaccaagt cattctgaga atagtgtatg cggcgaccga   8760
gttgctcttg cccggcgtca acacgggata ataccgcgcc acatagcaga actttaaaag   8820
tgctcatcat tggaaaacgt tcttcggggc gaaaactctc aaggatctta ccgctgttga   8880
gatccagttc gatgtaaccc actcgtgcac ccaactgatc ttcagcatct tttactttca   8940
ccagcgtttc tgggtgagca aaaacaggaa ggcaaaatgc cgcaaaaaag ggaataaggg   9000
cgacacggaa atgttgaata ctcatactct tcctttttca atattattga agcatttatc   9060
agggttattg tctcatgagc ggatacatat ttgaatgtat ttagaaaaat aaacaaatag   9120
gggttccgcg cacatttccc cgaaaagtgc cacctgacgt ctaagaaacc attattatca   9180
tgacattaac ctataaaaat aggcgtatca cgaggccctt tcgtcttcaa gaattggtcg   9240
acgatcttgc tgcgttcgga tattttcgtg gagttcccgc cacagacccg gattgaaggc   9300
gagatccagc aactcgcgcc agatcatcct gtgacggaac tttggcgcgt gatgactggc   9360
caggacgtcg gccgaaagag cgacaagcag atcacgcttt tcgacagcgt cggatttgcg   9420
atcgaggatt tttcggcgct gcgctacgtc cgcgaccgcg ttgagggatc aagccacagc   9480
agcccactcg accttctagc cgacccagac gagccaaggg atctttttgg aatgctgctc   9540
cgtcgtcagg ctttccgacg tttgggtggt tgaacagaag tcattatcgc acggaatgcc   9600
aagcactccc gaggggaacc ctgtggttgg catgcacata caaatggacg aacggataaa   9660
ccttttcacg cccttttaaa tatccgatta ttctaataaa cgctcttttc tcttaggttt   9720
acccgccaat atatcctgtc aaacactgat agtttaaact gaaggcggga aacgacaacc   9780
tgatcatgag cggagaatta agggagtcac gttatgaccc ccgccgatga cgcgggacaa   9840
gccgttttac gtttggaact gacagaaccg caacgttgaa ggagccactc agcttaatta   9900
agtctaactc gagttactgg tacgtaccaa atccatggaa tcaaggtacc gtcgactcta   9960
gtaacggccg ccagtgtgct ggaattaatt cggcttgtcg accacccaac cccatatcga  10020
cagaggatgt gaagaacagg taaatcacgc agaagaaccc atctctgata gcagctatcg  10080
attagaacaa cgaatccata ttgggtccgt gggaaatact tactgcacag gaagggggcg  10140
atctgacgag gccccgccac cggcctcgac ccgaggccga ggccgacgaa gcgccggcga  10200
gtacggcgcc gcggcggcct ctgcccgtgc cctctgcgcg tgggagggag aggccgcggt  10260
ggtgggggcg cgcgcgcgcg cgcgcgcagc tggtgcggcg gcgcgggggt cagccgccga  10320
gccggcggcg acggaggagc agggcggcgt ggacgcgaac ttccgatcgg ttggtcagag  10380
tgcgcgagtt gggcttagcc aattaggtct caacaatcta ttgggccgta aaattcatgg  10440
gccctggttt gtctaggccc aatatcccgt tcatttcagc ccacaaatat ttccccagag  10500
gattattaag gcccacacgc agcttatagc agatcaagta cgatgtttcc tgatcgttgg  10560
atcggaaacg tacggtcttg atcaggcatg ccgacttcgt caaagagagg cggcatgacc  10620
tgacgcggag ttggttccgg gcaccgtctg gatggtcgta ccgggaccgg acacgtgtcg  10680
```

```
cgcctccaac tacatggaca cgtgtggtgc tgccattggg ccgtacgcgt ggcggtgacc  10740
gcaccggatg ctgcctcgca ccgccttgcc cacgctttat atagagaggt tttctctcca  10800
ttaatcgcat agcgagtcga atcgaccgaa ggggaggggg agcgaagctt tgcgttctct  10860
aatcgcctcg tcaaggtaac taatcaatca cctcgtccta atcctcgaat ctctcgtggt  10920
gcccgtctaa tctcgcgatt ttgatgctcg tggtggaaag cgtaggagga tcccgtgcga  10980
gttagtctca atctctcagg gtttcgtgcg attttagggt gatccacctc ttaatcgagt  11040
tacggtttcg tgcgatttta gggtaatcct cttaatctct cattgattta gggtttcgtg  11100
agaatcgagg tagggatctg tgttatttat atcgatctaa tagatggatt ggttttgaga  11160
ttgttctgtc agatggggat tgtttcgata tattacccta atgatgtgtc agatggggat  11220
tgtttcgata tattacccta atgatgtgtc agatggggat tgtttcgata tattacccta  11280
atgatggata ataagagtag ttcacagtta tgttttgatc ctgccacata gtttgagttt  11340
tgtgatcaga tttagtttta cttatttgtg cttagttcgg atgggattgt tctgatattg  11400
ttccaataga tgaatagctc gttaggttaa aatctttagg ttgagttagg cgacacatag  11460
tttatttcct ctggatttgg attggaattg tgttcttagt ttttttcccc tggatttgga  11520
ttggaattgt gtggagctgg gttagagaat tacatctgta tcgtgtacac ctacttgaac  11580
tgtagagctt gggttctaag gtcaatttaa tctgtattgt atctggctct ttgcctagtt  11640
gaactgtagt gctgatgttg tactgtgttt ttttacccgt tttatttgct ttactcgtgc  11700
aaatcaaatc tgtcagatgc tagaactagg tggctttatt ctgtgttctt acatagatct  11760
gttgtcctgt agttacttat gtcagttttg ttattatctg aagatatttt tggttgttgc  11820
ttgttgatgt ggtgtgagct gtgagcagcg ctcttatgat taatgatgct gtccaattgt  11880
agtgtagtat gatgtgattg atatgttcat ctattttgag ctgacagtac cgatatcgta  11940
ggatctggtg ccaacttatt ctccagctgc tttttttttac ctatgttaat tccaatcctt  12000
tcttgcctct tccagatcca gataatggcg aacaaacatt tgtccctctc cctcttcctc  12060
gtcctccttg gcctgtcggc cagcttggcc tccgggcaac aaacaagcat tactctgaca  12120
tccaacgcat ccggtacgtt tgacggttac tattacgaac tctggaagga tactggcaat  12180
acaacaatga cggtctacac tcaaggtcgc ttttcctgcc agtggtcgaa catcaataac  12240
gcgttgttta ggaccgggaa gaaatacaac cagaattggc agtctcttgg cacaatccgg  12300
atcacgtact ctgcgactta caacccaaac gggaactcct acttgtgtat ctatggctgg  12360
tctaccaacc cattggtcga gttctacatc gttgagtcct gggggaactg gagaccgcct  12420
ggtgcctgcc tggccgaggg ctcgctcgtc ttggacgcgg ctaccgggca gagggtccct  12480
atcgaaaagg tgcgtccggg gatggaagtt ttctccttgg gacctgatta cagactgtat  12540
cgggtgcccg ttttggaggt ccttgagagc ggggttaggg aagttgtgcg cctcagaact  12600
cggtcaggga gaacgctggt gttgacacca gatcacccgc ttttgacccc cgaaggttgg  12660
aaacctcttt gtgacctccc gcttggaact ccaattgcag tccccgcaga actgcctgtg  12720
gcgggccact tggccccacc tgaagaacgt gttacgctcc tggctcttct gttgggggat  12780
gggaacacaa agctgtcggg tcggagaggt acacgtccta atgccttctt ctacagcaaa  12840
```

-continued

```
aaccccgaat tgctcgcggc ttatcgccgg tgtgcagaag ccttgggtgc aaaggtgaaa  12900

gcatacgtcc acccgactac gggggtggtt acactcgcaa ccctcgctcc acgtcctgga  12960

gctcaagatc ctgtcaaacg cctcgttgtc gaggcgggaa tggttgctaa agccgaagag  13020

aagagggtcc cggaggaggt gtttcgttac cggcgtgagg cgttggccct tttcttgggc  13080

cgtttgttct cgacagacgg ctctgttgaa aagaagagga tctcttattc aagtgccagt  13140

ttgggactgg cccaggatgt cgcacatctc ttgctgcgcc ttggaattac atctcaactc  13200

cgttcgagag ggccacgggc tcacgaggtt cttatatcgg gccgcgagga tattttgcgg  13260

tttgctgaac ttatcggacc ctacctcttg gggggccaaga gggagagact tgcagcgctg  13320

gaagctgagg cccgcaggcg tttgcctgga cagggatggc acttgcggct tgttcttcct  13380

gccgtggcgt acagagtggg cgaggcggaa aggcgctcgg gattttcgtg gagtgaagcc  13440

ggtcggcgcg tcgcagttgc gggatcgtgt ttgtcatctg gactcaacct caaattgccc  13500

agacgctacc tttctcggca ccggttgtcg ctgctcggtg aggcttttgc cgaccctggg  13560

ctggaagcgc tcgcggaagg ccaagtgctc tgggacccta ttgttgctgt cgaaccggcc  13620

ggtaaggcga gaacattcga cttgcgcgtt ccacccctttg caaacttcgt gagcgaggac  13680

ctggtggtgc ataacaccgt ccccctgggc caagtgacaa tcgatggcgg gacctacgac  13740

atctatagga cgacacgcgt caaccagcct tccattgtgg ggacagccac gttcgatcag  13800

tactggagcg tgcgcacctc taagcggact tcaggaacag tgaccgtgac cgatcacttc  13860

cgcgcctggg cgaaccgggg cctgaacctc ggcacaatag accaaattac attgtgcgtg  13920

gagggttacc aaagctctgg atcagccaac atcacccaga acaccttctc tcagggctct  13980

tcttccggca gttcgggtgg ctcatccggc tccacaacga ctactcgcat cgagtgtgag  14040

aacatgtcct tgtccggacc ctacgttagc aggatcacca atccctttaa tggtattgcg  14100

ctgtacgcca acggagacac agcccgcgct accgttaact tccccgcaag tcgcaactac  14160

aatttccgcc tgcggggttg cggcaacaac aataatcttg cccgtgtgga cctgaggatc  14220

gacggacgga ccgtcgggac cttttattac cagggcacat accccctggga ggccccaatt  14280

gacaatgttt atgtcagtgc ggggagtcat acagtcgaaa tcactgttac tgcggataac  14340

ggcacatggg acgtgtatgc cgactacctg gtgatacaga gcgagaagga cgagctgtga  14400

cctaggtccc cgaatttccc cgatcgttca aacatttggc aataaagttt cttaagattg  14460

aatcctgttg ccggtcttgc gatgattatc atataatttc tgttgaatta cgttaagcat  14520

gtaataatta acatgtaatg catgacgtta tttatgagat gggtttttat gattagagtc  14580

ccgcaattat acatttaata cgcgatagaa aacaaaatat agcgcgcaaa ctaggataaa  14640

ttatcgcgcg cggtgtcatc tatgttacta gatcgggaat tgg                    14683
```

<210> SEQ ID NO 75
<211> LENGTH: 24
<212> TYPE: PRT
<213> ORGANISM: Thermus thermophilus

<400> SEQUENCE: 75

```
Leu Ala Glu Gly Ser Leu Val Leu Asp Ala Ala Thr Gly Gln Arg Val
1               5                   10                  15

Pro Ile Glu Lys Val Arg Pro Gly
            20
```

<210> SEQ ID NO 76
<211> LENGTH: 33

<212> TYPE: PRT
<213> ORGANISM: Thermus thermophilus

<400> SEQUENCE: 76

Met Glu Val Phe Ser Leu Gly Pro Asp Tyr Arg Leu Tyr Arg Val Pro
1               5                   10                  15

Val Leu Glu Val Leu Glu Ser Gly Val Arg Glu Val Val Arg Leu Arg
            20                  25                  30

Thr

<210> SEQ ID NO 77
<211> LENGTH: 52
<212> TYPE: PRT
<213> ORGANISM: Thermus thermophilus

<400> SEQUENCE: 77

Leu Arg Leu Val Leu Pro Ala Val Ala Tyr Arg Val Ser Glu Ala Lys
1               5                   10                  15

Arg Arg Ser Gly Phe Ser Trp Ser Glu Ala Gly Arg Arg Val Ala Val
            20                  25                  30

Ala Gly Ser Cys Leu Ser Ser Gly Leu Asn Leu Lys Leu Pro Arg Arg
        35                  40                  45

Tyr Leu Ser Arg
    50

<210> SEQ ID NO 78
<211> LENGTH: 28
<212> TYPE: PRT
<213> ORGANISM: Mycobacterium tuberculosis

<400> SEQUENCE: 78

Leu Arg Ile Ala Gly Gly Ala Ile Leu Trp Ala Thr Pro Asp His Lys
1               5                   10                  15

Val Leu Thr Glu Tyr Gly Trp Arg Ala Ala Gly Glu
            20                  25

<210> SEQ ID NO 79
<211> LENGTH: 24
<212> TYPE: PRT
<213> ORGANISM: Mycobacterium tuberculosis

<400> SEQUENCE: 79

Leu Arg Lys Gly Asp Arg Val Ala Gln Pro Arg Arg Phe Asp Gly Phe
1               5                   10                  15

Gly Asp Ser Ala Pro Ile Pro Ala
            20

<210> SEQ ID NO 80
<211> LENGTH: 38
<212> TYPE: PRT
<213> ORGANISM: Thermus thermophilus

<400> SEQUENCE: 80

Arg Ser Gly Arg Thr Leu Val Leu Thr Pro Asp His Pro Leu Leu Thr
1               5                   10                  15

Pro Glu Gly Trp Lys Pro Leu Cys Asp Leu Pro Leu Gly Thr Pro Ile
            20                  25                  30

Ala Val Pro Ala Glu Leu
        35

-continued

```
<210> SEQ ID NO 81
<211> LENGTH: 8
<212> TYPE: PRT
<213> ORGANISM: Thermus thermophilus

<400> SEQUENCE: 81

Pro Val Ala Gly His Leu Ala Asp
1               5
```